US007741026B2

(12) United States Patent
Jestin et al.

(10) Patent No.: US 7,741,026 B2
(45) **Date of Patent: *Jun. 22, 2010**

(54) CIRCOVIRUS SEQUENCES ASSOCIATED WITH PIGLET WEIGHT LOSS DISEASE (PWD)

(75) Inventors: André Jestin, Saint-Brieuc (FR); Emmanuel Albina, Tréguex (FR); Pierre Le Cann, Plédran (FR); Philippe Blanchard, Plérin (FR); Evelyne Hutet, Plérin (FR); Claire Arnauld, Saint-Brieuc (FR); Catherine Truong, Saint-Brieuc (FR); Dominique Mahe, Saint-Carreuc (FR); Roland Cariolet, Ploufragan (FR); François Madec, Saint-Brieuc (FR)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/003,188

(22) Filed: Dec. 20, 2007

(65) Prior Publication Data

US 2008/0233147 A1 Sep. 25, 2008

Related U.S. Application Data

(63) Continuation of application No. 11/488,904, filed on Jul. 19, 2006, now Pat. No. 7,314,628, which is a continuation of application No. 10/682,420, filed on Oct. 10, 2003, now abandoned, which is a continuation of application No. 10/637,011, filed on Aug. 8, 2003, now Pat. No. 7,223,594, which is a continuation of application No. 09/514,245, filed on Feb. 28, 2000, now Pat. No. 6,703,023, which is a continuation-in-part of application No. PCT/FR98/02634, filed on Dec. 4, 1998, now abandoned.

(30) Foreign Application Priority Data

Dec. 5, 1997 (FR) .................................. 97 15396

(51) Int. Cl.
*C12Q 1/70* (2006.01)

(52) U.S. Cl. ............................ 435/5; 435/6; 435/320.1

(58) Field of Classification Search ....................... None
See application file for complete search history.

(56) References Cited

U.S. PATENT DOCUMENTS

| | | | |
|---|---|---|---|
| 4,946,787 | A | 8/1990 | Eppstein et al. |
| 5,106,733 | A | 4/1992 | Baker et al. |
| 5,322,774 | A | 6/1994 | Peakman et al. |
| 5,382,425 | A | 1/1995 | Cochran et al. |
| 5,459,127 | A | 10/1995 | Felgner et al. |
| 5,498,413 | A | 3/1996 | Casel Alvarez et al. |
| 5,545,412 | A | 8/1996 | Eppstein et al. |
| 5,565,205 | A | 10/1996 | Petersen |
| 5,580,557 | A | 12/1996 | Kramer |
| 5,580,859 | A | 12/1996 | Felgner et al. |
| 5,587,164 | A | 12/1996 | Sanderson et al. |
| 5,703,055 | A | 12/1997 | Felgner et al. |
| 5,705,385 | A | 1/1998 | Bally et al. |
| 5,719,131 | A | 2/1998 | Harris et al. |
| 5,733,555 | A | 3/1998 | Chu |
| 5,756,103 | A | 5/1998 | Paoletti et al. |
| 5,770,212 | A | 6/1998 | Falkner et al. |
| 5,795,872 | A | 8/1998 | Ricigliano et al. |
| 5,811,103 | A | 9/1998 | Meyers et al. |
| 5,820,869 | A | 10/1998 | Wasmoen et al. |
| 5,833,975 | A | 11/1998 | Paoletti et al. |
| 5,885,823 | A | 3/1999 | Knittel et al. |
| 5,888,513 | A | 3/1999 | Plana Duran et al. |
| 5,910,488 | A | 6/1999 | Nabel et al. |
| 5,925,359 | A | 7/1999 | Van Woensel et al. |
| 5,968,525 | A | 10/1999 | Fitzgerald et al. |
| 5,990,091 | A | 11/1999 | Tartaglia et al. |
| 6,004,777 | A | 12/1999 | Tartaglia et al. |
| 6,015,694 | A | 1/2000 | Dubensky, Jr. et al. |
| 6,019,980 | A | 2/2000 | Li et al. |
| 6,033,904 | A | 3/2000 | Cochran et al. |
| 6,143,734 | A | 11/2000 | Garvey et al. |

(Continued)

FOREIGN PATENT DOCUMENTS

| | | |
|---|---|---|
| DE | 10044648 | 3/2002 |

(Continued)

OTHER PUBLICATIONS

U.S. Appl. No. 60/069,750, filed Dec. 16, 1997, Wang et al.

(Continued)

*Primary Examiner*—Ali R. Salimi
(74) *Attorney, Agent, or Firm*—Buchanan, Ingersoll & Rooney, PC

(57) ABSTRACT

The genome sequences and the nucleotide sequences coding for the PWD circovirus polypeptides, such as the circovirus structural and non-structural polypeptides, vectors including the sequences, and cells and animals transformed by the vectors are provided. Methods for detecting the nucleic acids or polypeptides, and kits for diagnosing infection by a PWD circovirus, also are provided. Method for selecting compounds capable of modulating the viral infection are further provided. Pharmaceutical, including vaccines, compositions for preventing and/or treating viral infections caused by PWD circovirus and the use of vectors for preventing and/or treating diseases also are provided.

27 Claims, 29 Drawing Sheets

U.S. PATENT DOCUMENTS

| | | | |
|---|---|---|---|
| 6,165,493 | A | 12/2000 | Neurath et al. |
| 6,207,165 | B1 | 3/2001 | Audonnet et al. |
| 6,217,883 | B1 | 4/2001 | Allan et al. |
| 6,287,856 | B1 | 9/2001 | Poet et al. |
| 6,294,176 | B1 | 9/2001 | Cochran et al. |
| 6,368,601 | B1 | 4/2002 | Allan et al. |
| 6,391,314 | B1 | 5/2002 | Allan et al. |
| 6,475,779 | B2 | 11/2002 | Mathiowitz et al. |
| 6,497,883 | B1 | 12/2002 | Bublot et al. |
| 6,517,843 | B1 | 2/2003 | Ellis et al. |
| 6,573,081 | B2 | 6/2003 | Bernhardt et al. |
| 6,660,272 | B2 | 12/2003 | Allan et al. |
| 6,703,023 | B1 | 3/2004 | Jestin et al. |
| 6,794,163 | B2 | 9/2004 | Liu et al. |
| 6,943,152 | B1 | 9/2005 | Audonnet et al. |
| 6,953,581 | B2 | 10/2005 | Allan et al. |
| 7,109,025 | B1 | 9/2006 | Eloit et al. |
| 7,122,192 | B2 | 10/2006 | Allan et al. |
| 7,144,698 | B2 | 12/2006 | Wang et al. |
| 7,148,015 | B2 | 12/2006 | Jestin et al. |
| 7,179,472 | B2 | 2/2007 | Jestin et al. |
| 7,192,594 | B2 | 3/2007 | Haines et al. |
| 7,223,407 | B2 | 5/2007 | Jestin et al. |
| 7,223,594 | B2 | 5/2007 | Jestin et al. |
| 7,244,433 | B2 | 7/2007 | Jestin et al. |
| 7,258,865 | B2 | 8/2007 | Jestin et al. |
| 7,261,898 | B2 | 8/2007 | Jestin et al. |
| 7,279,166 | B2 | 10/2007 | Meng et al. |
| 7,297,537 | B2 | 11/2007 | Jestin et al. |
| 7,314,628 | B2 | 1/2008 | Jestin et al. |
| 7,323,330 | B2 * | 1/2008 | Jestin et al. .............. 435/320.1 |
| 7,368,117 | B2 | 5/2008 | Fetzer et al. |
| 7,390,494 | B2 | 6/2008 | Jestin et al. |
| 7,405,075 | B2 | 7/2008 | Jestin et al. |
| 7,407,803 | B2 | 8/2008 | Jestin et al. |
| 7,425,444 | B2 | 9/2008 | Jestin et al. |
| 7,604,808 | B2 | 10/2009 | Jestin et al. |
| 2002/0055189 | A1 | 5/2002 | Bernhardt et al. |
| 2002/0106639 | A1 | 8/2002 | Wang et al. |
| 2002/0177216 | A1 | 11/2002 | Liu et al. |
| 2003/0170270 | A1 | 9/2003 | Meng et al. |
| 2003/0170616 | A1 | 9/2003 | Wang et al. |
| 2003/0215455 | A1 | 11/2003 | Reynolds et al. |
| 2004/0062775 | A1 | 4/2004 | Jestin et al. |
| 2004/0076635 | A1 | 4/2004 | Jestin et al. |
| 2004/0091502 | A1 | 5/2004 | Jestin et al. |
| 2004/0253270 | A1 | 12/2004 | Meng et al. |
| 2005/0008651 | A1 | 1/2005 | Jestin et al. |
| 2005/0031647 | A1 | 2/2005 | Roof et al. |
| 2005/0058653 | A1 | 3/2005 | Ellis et al. |
| 2005/0279889 | A1 | 12/2005 | Greene |
| 2006/0246425 | A1 | 11/2006 | Allibert et al. |
| 2006/0286123 | A1 | 12/2006 | Fetzer et al. |
| 2007/0059325 | A1 | 3/2007 | Jestin et al. |
| 2007/0065925 | A1 | 3/2007 | Jestin et al. |
| 2008/0112980 | A1 | 5/2008 | Roof et al. |
| 2008/0181910 | A1 | 7/2008 | Roof et al. |
| 2008/0233147 | A1 | 9/2008 | Jestin et al. |
| 2008/0261887 | A1 | 10/2008 | Roof et al. |
| 2008/0267995 | A1 | 10/2008 | Roof et al. |
| 2008/0279875 | A1 | 11/2008 | Roof et al. |
| 2008/0279876 | A1 | 11/2008 | Roof et al. |
| 2008/0279889 | A1 | 11/2008 | Roof et al. |
| 2009/0042245 | A1 | 2/2009 | Eichmeyer et al. |
| 2009/0123490 | A1 | 5/2009 | Jestin et al. |
| 2009/0162918 | A1 | 6/2009 | Jestin et al. |

FOREIGN PATENT DOCUMENTS

| | | | |
|---|---|---|---|
| EP | 0 737 750 | | 10/1996 |
| EP | 1 386 617 | | 3/2008 |
| FR | 2 422 956 | | 11/1979 |
| FR | 2 518 755 | | 6/1983 |
| FR | 2769322 | | 4/1999 |
| FR | 2772047 | | 6/1999 |
| SU | 1 538 305 | | 12/1994 |
| WO | WO 89/06972 | A1 | 8/1989 |
| WO | WO 90/07935 | A1 | 7/1990 |
| WO | WO 90/11092 | | 10/1990 |
| WO | WO 91/18627 | A1 | 12/1991 |
| WO | WO 92/03157 | A1 | 3/1992 |
| WO | WO 92/05255 | | 4/1992 |
| WO | WO 93/16726 | A2 | 9/1993 |
| WO | WO 94/01133 | | 1/1994 |
| WO | WO 94/21797 | | 9/1994 |
| WO | WO 94/27238 | | 11/1994 |
| WO | WO 94/27435 | | 12/1994 |
| WO | WO 95/11307 | | 4/1995 |
| WO | WO 95/30437 | A1 | 11/1995 |
| WO | WO 96/34109 | | 10/1996 |
| WO | WO 96/40931 | | 12/1996 |
| WO | WO 96/40945 | | 12/1996 |
| WO | WO 98/40499 | | 9/1998 |
| WO | WO 99/18214 | | 4/1999 |
| WO | WO 99/29717 | | 6/1999 |
| WO | WO 99/29871 | | 6/1999 |
| WO | WO 00/01409 | | 1/2000 |
| WO | WO 00/24428 | | 5/2000 |
| WO | WO 00/47756 | A1 | 8/2000 |
| WO | WO 00/77188 | | 12/2000 |
| WO | WO 00/77188 | A2 | 12/2000 |
| WO | WO 00/77216 | | 12/2000 |
| WO | WO 01/96377 | | 6/2002 |
| WO | WO 02/10299 | | 12/2002 |

OTHER PUBLICATIONS

U.S. Appl. No. 60/069,233, filed Dec. 11, 1997, Wang et al.

Derwent Abstract of French Patent Appl. No. 2 422 956, 1979.

Derwent Abstract of French Patent Appl. No. 2 518 755, 1983.

Derwent Abstract of German Patent Appl. No. 10044648, 2002.

DMRIE structure, Printed from PubChem Compund Summary 2008.

ABI-Prism , "Automated DNA Sequencing, Chemistry Guide", Applied Biosystems, product manual, applicable to automated sequencers ABI PRISM 310, 377 and 373 (2000).

Adams, Mark D. et al. "Complementary DNA Sequencing: Expressed Sequence Tags and Human Genome Project," *Science*, 1651-1656. (1991).

Albina et al., "Premiers résultats du CNEVA sur le dépérissement fatal du porcelet en fin de post-sevrage" *La Semaine Veterinaire des Filieres*, 26:1-2, Nov. 30, 1996.

Allan et al., "Porcine Circoviruses: A Review," *J Vet Diagn Invest.* 12: 3-14 (2000).

Allan et al., "Immunostimulation, PCV-2 and PMWS," *Veterinary Record* (2000); 147(6):170-171.

Allan, G.M., et al., "Production, preliminary characterisation and applications of monoclonal antibodies to porcine circovirus," *Veterinary Immunology and Immunopathology*, 43 (1994) 357-371.

Allan, G.M. et al., "Pathogenesis of porcine circovirus;experimental infections of colostrum deprived piglets and examination of pig fetal material," *Vet. Microbiol.*, (1995) 44: 49-64.

Allan, G. M. et al., "Isolation of Procine Circovirus-like Viruses from Pigs with a Wasting Disease in the USA and Europe", *Journal of Veterinary Diagnostic Investigation*, vol. 10, pp. 3-10, Jan. 1998, XP 002068503.

Altmann, Curtis R. et al. "Microarray-Based Analysis of Early Development in Xenopus laevis," *Developmental Biology*, 236:64-75 (2001).

Author Unknown, GenBank info on AF027217 (Revised Jul. 5, 2002).

Author Unknown, NCBI Sequence Revision History of AF027217 (Revised Jul. 5, 2002).

Bantle, John A. et al. "Phase III Interlaboratory Study of FETAX Part 3. Fetax Validation using 12 Compounds with and without an Exogenous Metabolic Activation System," *Journal of Applied Toxicology*, 19:447-472 (1999).
Barany, F., PNAS. USA, (1991) 88: 189-193.
Behr, J.P., "Gene Transfer with Synthetic Cationic Amphiphiles: Prospects for Gene Therapy" *Bioconjugate Chem.* 5(5):382-389 (1994).
Bei, R. et al., "The Use of a Cationic Liposome Formulation (DOTAP) Mixed with a Recombinant Tumor-Associated Antigen to Induce Immune Responses and Protective Immunity in Mice," *Journal of Immunotherapy*, 21(3):159-169 (1998).
Blanchard et al., "An ORF2 Protein-Based ELISA for Procine Circovirus Type 2 Antibodies in Post-Weaning Multisystemic Wasting Syndrome", *Veterinary Microbiology*, (2003) 94:183-184.
Blanchard et al., "Protection of Swine Against Post-Weaning Multisystemic Wasting Syndrome (PMWS) by Porcine Circovirus Type 2 (PCV2) Proteins", *Vaccine* (2003) 21:4565-4575.
Buckholz, R.G., "Yeast systems for the expression of heterologous gene products." *Curr. Op. Biotechnology* (1993) 4:538-542.
Burg, J.L. et al., "Single molecule detection of RNA reporter probes by amplification with QB replicase," *Mol. and Cell. Probes*, (1996) 10: 257-271.
Cho et al., "Enhanced cellular immunity of hepatitis C virus nonstructural proteins by codelivery of granulocyte macrophage-colony stimulating factor gene in intramuscular DNA immunization," *Vaccine* 17:1136-1144 (1999).
Chu, B.C.F. et al., "Synthesis of an amplifiable reporter RNA for bioassays," *NAR*, (1986) 14: 5591-5603.
Chu, P.W.G. et al., "Putative full length clones of the genomic DNA segments of subterranean cover stunt virus and identification of the segment coding for the viral coat protein," *Virus Research*, (1993) 27: 161-171.
Chu, Te-hua Terina et al., "Toward Highly Efficient Cell-Type-Specific Gene Transfer with Retroviral Vectors Displaying Single-Chain Antibodies", *J. Virol.*, (1997) 71(1):720-725.
Clark, E.G., "Post-weaning multisystemic wasting syndrome," American Association of Swine Practitioners, (1997) 499-501.
Cosset, Francois-Loic et al., "Retroviral Retargeting by Envelopes Expressing an N-Terminal Binding Domain", *J. Virol.*, (1995) 69:6314-6322.
Cruse et al., "The Illustrated Dictionary of Immunology," Boca Raton: CRC Press (1995) p. 156.
Cruse et al., "The Illustrated Dictionary of Immunology," 2nd edition. Boca Raton: CRC Press (2003) p. 613.
Daft, B. et al., "Interstitial Pneumonia and Lymphadenopathy Associated with Circovirus Infection in a Six-Week Old Pig," *American Association of Veterinary Laboratory Diagnosticians*, (1996) 32.
Dedet, V., "Seule certitude: un maladie à part entière," *La Semaine Veterinaire* p. 54, May 24, 1997.
Derse, D. et al., *J. Virol.*,(1995) 69(3): 1907-1912.
Dialog Inpadoc Family and Legal Status Search for German Patent Appl. No. 10044648.
Dialog Inpadoc Family and Legal Status Search for U.S. Patent Appl. Pub. No. 2002/0177216.
Dialog Inpadoc Family and Legal Status Search for U.S. Patent Appl. Pub. No. 2002/0106639.
Dialog Inpadoc Family and Legal Status Search for U.S. Appl. No. 2002/0055189.
Dialog Inpadoc Family and Legal Status Search for U.S. Appl. No. 6,517,843.
Dialog Inpadoc Family and Legal Status Search for U.S. Patent No. 6,143,334 (2001).
Dialog Inpadoc Family and Legal Status Search for U.S. Patent No. 6,287,856 (2001).
Dialog Inpadoc Family and Legal Status Search for U.S. Patent No. 6,217,883 (2001).
Dialog Inpadoc Family and Legal Status Search for US Patent No. 6,497,883 (2002).
Dialog Inpadoc Family and Legal Status Search for WO 01/96377 (2001).
Dialog Inpadoc Family and Legal Status Search for WO 02/102999 (2002).
Donnelly, John J. et al., "Immunization with DNA" *Journal of Immunological Methods*, 176:145-152 (1994).
Dorland's Illustrated Medical Dictionary, 28th edition. Philadelphia. WB Saunders p. 1787 (1994).
Duck, P. et al., "Probe amplifier system based on Chimeric Cycling Oligonucleotides," *Biotechniques*, (1990) 9:142-147.
Dulac, G.C. et al., *Can. J. Vet. Res.*, (1989) 53:431-433.
Edwards, C.P. et al., "Current applications of COS cell based transient expression systems." *Curr, Op. Biotechnology* (1993) 4:558-563.
Edwards, S. et al., "Evidence of Circovirus Infection in Brittish pigs," *Vet. Rec.*, (1994) 134:680-681.
Ellis et al., "Reproduction of lesions of Post eaning multisystemic wasting syndrome in gnotobiotic piglets," *J. Vet. Diagn. Invest.* 11:3-14 (1999).
Ellis et al., "Coinfection by porcine circoviruses and porcine parvovirus in pigs with naturally acquired postweaning multisystemic wasting syndrome" *J. Vet. Diagn. Invest.* 12(1):21-27 (2000).
Ellis, J. et al., "Isolation of Circovirus from legions of Pigs with Postweaning Multisystemic Wasting Syndrome", *Canadian Veterinary Journal*, col. 39, pp. 44-51, Jan. 1998, XP-002068502.
Erlich, H.A., "PCR Technology. Principles and Applications for DNA Amplification." (1989) New York: Stockton Press.
Ertl, H.C.J. et al., "Genetic Immunization" *Viral Immunology*, 9(1):1-9 (1996).
Felgner, et al., "Lipofection: a highly efficient, lipid-mediated DNA-transfection procedure," *Proc. Natl. Acad. Sci.*, (1987) 84: 7413-7417.
Felgner J.H. et al., "Enhanced gene delivery and mechanism studies with a novel series of cationic lipid formulations," *The journal of biological chemistry*, 269(4)2550-2561 (1994).
Fenaux, M. et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2," *Journal of Clinical Microbiology*, Jul. 2000, 38(7):2494-2503.
Fontes, E.P.B. et al., "Interaction between a Geminivirus Replication Protein and Origin DNA is Essential for Viral Replication," *J. Biol. Chem.*, (1994) vol. 269, No. 11:8459-8465.
Fort, Douglas J. et al. "Evaluation of the Developmental Toxicity of Thalidomide Using Frog Embryo Teratogenesis Assay—Xenopus (FETAX): Biotransformation and Detoxification," *Teratogensis, Carcinogenesis, and Mutagenesis*, 20:35-47 (2000).
Fraley et al., "Introduction of Liposome-encapsulated SV40 DNA into cells," *J. Biol. Chem.*, (1980) 255:10431-10435.
GenBank Accession No. AF027217; May 14, 1998.
Gregoriadis G. et al., "Liposome-mediated DNA vaccination" FEBS Letters, Feb. 3, 1997; 402:107-110.
Gregoriadis, Gregory, "Genetic vaccines: strategies for optimization" *Pharmaceutical Research*, 15( 5):661-670 (1998).
Grierson, S.S., et al., "Genome sequence analysis of 10 Dutch porcine circovirus type 2 (PCV-2) isolates from a PMWS case-control study," *Research in Veterinary Science*, 77 (2004) pp. 265-268.
Guateli, J.C. et al., "isothermal, in vitro amplification of nucleic acids by a multienzyme reaction modeled after retroviral replication," *Proc. Nat'l Acad. Sci., USA*, (1990) 87: 1874-1878.
Hackland, A.F. et al., "Coat protein-mediated resistance in transgenic plants," *Arch. Virol.*, (1994) 139: 1-22.
Haddad, D. et al., "Comparative study of DNA-based immunization vectors: effect of secretion signals on the antibody responses in mice," *FEMS Immunology and Medical Microbiology*, 18(3):193-202 (1997).
Hamel et al., "Porcine Circovirus," (Sequence Alignments for SEQ ID NO:s 1-4 and 6) Genbank Acc No: 027217, Dec. 19, 1997.
Hamel, A. et al., "Nucleotide Sequence of Procine Circovirus Associated with Postweaning Multisystemic Wasting Syndrome in Pigs", *Journal of Virology*, col. 72, No. 6, pp. 5262-5267, Jun 1998, XP-002078783.

Hanson, S.F. et al., "Mutational Analysis of a putative NTP-Binding Domain in the Replication-Associated Protein (ACI) of Bean Golden Mosaic Geminivirus," *Virology*, (1995) 211: 1-9.
Harding, J.C. et al., "Recognizing and diagnosing post-weaning multisystemic wasting syndrome (PMWS),"*Swine Health and Production*, (1997) vol. 5, No. 5: 201-203.
Harding, J.C., "Post-weaning Multisystemic Wasting Syndrome (PMWS): Preliminary Epidemiology and Clinical Presentation," *American Association of Swine Practitioners*, (1997) 503.
Harding, R.M. et al., "Nucleotide sequence of one compartment of the banana bunchy top virus genome contains a putative replicase gene," *Journal of General Virology*, (1993) 74: 323-328.
Heyraud-Nitschke, F. et al., "Determination of the origin cleavage and joining domain of geminivirus rep proteins," *Nucleic Acids Research*, (1995) vol. 23, No. 6: 910-916.
Homer, G.W., "Pig Circovirus Antibodies present in New Zealand pigs," *Surveillance* (1991) 18(5): 23.
Huygen, K. et al., "Immunogenicity and protective efficacy of a tuberculosis DNA vaccine," *Nature Medicine*, (1996) 2(8): 893-898.
Innis, M.A. et al., "A guide to Methods and Applications," *PCR Protocols* (1990) San Diego, Academic Press.
Inumaru, S. et al., "cDNA Cloning of Porcine Granulocyte-Macrophage Colony-Stimulating Factor"*Immunology and Cell Biology*, 73:474-476, XP-000946635 (1995).
Ishii N. et al., "Cationic liposomes are a strong adjuvant for a DNA vaccine of human immunodeficiency virus type 1" *AIDS Res Hum Retroviruses*, Nov. 1, 1997 13(6):1421-1428.
Izumida, et al., "Establishment of the Attenuated Strain of Porcine Parvovirus of the Live Vaccine and its Biological-Immunological Characteristics," *Japanese Veterinary Science*, 48(2):293-303 (1996).
Kaneda, et al., "Increased Expression of DNA Cointroduced with Nuclear Protein in Adult Rat Liver,"*Science*, (1989) 243: 375-378.
Kasahara, N. et al., "Tissue-Specific Targeting of Retroviral Vectors Through Ligan-Receptor Interactions", *Science*, (1994) 266: 1373-1376.
Kessler, C., "Overview of Amplification on Systems in Non-radioactive Labeling and Detection of Biomolecules," (1992), Springer Verlag, Berlin, New-York: 197-205.
Kievitis, T. et al., "NASBA™ isothermal enzymatic in vitro nucleic acid amplification optimized for the diagnosis of HIV-1 infection," *J. Virol. Methods*, (1991) 35: 273-286.
Klavinskis, Linda S. et al., "Intranasal Immunization with Plasmid DNA-Lipid Complexes Elicits Mucosal Immunity in the Female Genital and Rectal Tracts" *J. Immunol* 1999, pp. 254-262.
Knell, S. et al., "Comparative genetic characterization of Porcine Circovirus type 2 samples from German wild boar populations," *Veterinary Microbiology*, 109 (2005) pp. 169-177.
Kohler, G. et al., "Continuous cultures of fused cells secreting antibody of predefined specificity," *Nature*, (1975) 256(5517): 495-497.
Krakowka et al., "Activation of the Immune System in the Pivotal Event in the Production of Wasting Disease in Pigs Infected with Porcine Circovirus-2 (PCV-2)," *Vet Pathology*. 38:31-42 (2001).
Krakowka et al., "Immunologic Features of Porcine Circovirus Type-2 Infection," *Viral Immunology*. 15 (4): 567-582 (2002).
Kwoh, D.Y. et al., "Transcription-based amplification system and detection of amplified human immunodeficiency virus type I with a bead-based sandwich hybridization format," *Proc. Nat'l Acad. Sci., USA*, (1989) 86: 1173-1177.
Ladany, S. et al., "Enzyme immunoassay to determine exposure to Chlamydia pneumoniae (strain TWAR)," *J. Clin. Microbiol.* (1989) 27: 2778-2783.
Lazarowitz, S.G. et al., "Maize streak virus genes essential for systemic spread and symptom development," *The EMBO Journal*, (1989) vol. 8 No. 4:1023-1032.
LeCann et al., "Piglet Wasting disease," *Veterinary Record*, p. 660, Dec. 20/27 1997.
Lekcharoensuk, P. et al., "Epitope Mapping of the Major Capsid Protein of Type 2 Porcine Circovirus (PCV2) by Using Chimeric PCV1 and PCV2," *Journal of Virology*, vol. 78, No. 15, Aug. 2004, pp. 8135-8145.
Liu et al., "Maize streak virus coat protein binds single- and double-stranded DNA in vitro," *J. Gen. Virol.*, (1997) 78 (Pt 6), 1265-1270.
Luckow, V.A., "Baculovirus systems for the expression of human gene products." *Curr. Op. Biotechnol.* (1993) 4:564-572.
Mahé et al., "Differential Recognition of ORF 2 Protein from Type 1 and Type 2 Porcine Circoviruses and Identification of Immunorelevant Epitopes", *Journal of General Virology* 81:1815-1824 (2000).
Mankertz et al., "Porcine Circovirus Complete Genome", EMBL Sequence Database XP-002104869 May 22, 1997.
Mankertz, A. et al., "Mapping and Characterization of the Origin of DNA Replication of Porcine Circovirus.", *Journal of Virology* vol. 71, No. 3, pp. 2562-2566, Mar. 1997, XP-002078782.
Marglin, A. et al., "The Synthesis of Bovine Insulin by the Solid Phase Method," *J. Am. Chem. Soc.*, (1966) 88(21): 5051-5052.
Matthews, J.A. et al., "Analystical Strategies for the Use of DNA Probes," *Anal. Biochem.*, (1988) 169: 1-25.
McCluskie, Michael J. et al., "Route and Method of Delivery of DNA Vaccine Influence Immune Responses in Mice and Non-Human Primates" *Molecular Medicine* 5:287-300 (1999).
McInnes, C.J. et al., "Cloning and Expression of a cDNA Encoding Ovine Granulocyte-Macrophage Colony-Stimulating Factor" *Gene*, 105: 275-279, XP-002148815 (1991).
McNeilly, F. et al., "Effect of porcine circovirus infection on porcine alveolar macrophage function," *Vet. Immunol. Immunopathol.*, (1996) 49: 295-306.
Meehan, B.M. et al., "Sequence of porcine circovirus DNA: affinities with plant circoviruses,", *Journal of General Virology*, vol. 78, No. 1, pp. 221-227, Jan. 1997.
Meehan et al., "Putative PCV Replication-Associated Protein (REP)", EMBL Sequence Database XP 002104867 (1997).
Meehan et al., "Porcine Circovirus Complete Genome", EMBL Sequence Database XP-002104868 (1997).
Meehan, B.M. et al., "Characterization of noval circovirus DNAs associated with wasting syndromes in pigs.", *Journal of General Virology*, vol. 79, No. 9, pp. 2171-2179, Sep. 1998, XP-002090386.
Midoux, P. et al., "Specific gene transfer mediated by lactosylated poly-L-lysine into hepatoma cells," *Nucleic Acids Research*, (1993) 21: 871-878.
Miele, E.A. et al., "Autocatalytic Replication of a Recombinant RNA," *J. Mol. Biol.*, (1983) 171: 281-295.
Miller, J.S. et al., "The nucleotide sequence of RNA-1 of Indian peanut clump furovirus" *Arch. Virol.* 141:2301-2312, (1996).
Morozov, I. et al., "Detection of a Novel Strain of Procine Circovirus in Pigs with Postweaning Multisystemic Wasting Syndrome", *Journal of Clinical Microbiology*, col. 36, No. 9, pp. 2535-2541, Sep. 1998, XP-002090921.
Müller, "In Methode der Organischen Chemie, E. Wunsch Ed.," (1974) vol. 15-I and 15-II, Thieme, Stuttgart.
Mumford J. A. et al. "Antigenicity and immunogenicity of equine infleuenza vaccines containing a Carbomer adjuvant," *Epidemiot Infect.* 112: 421-437 (1994).
Murphy, F.A. et al., "Virus Taxonomy," (1995) *Sixth Report of the International Committee on Taxonomy of Viruses*, Springer-Verlag Wien New York.
Nakakura, Norihiko et al. "Synthesis of Heterogeneous mRNA-like RNA and Low-Molecular-Weight RNA before the Midblastula Transition in Embryos of *Xenopus laevis," Developmental Biology*, 123:421-429 (1987).
Nash Ra et al., "Molecular cloning and in vivo evaluation of canine granulocyte-macrophage colony-stimulating factor" *Blood* 78(4):930-937, XP 002133949 (1991).
Nawagtigul et al., "Open Reading Frame 2 of Porcine Circovirus Type 2 Encodes a Major Capsid Protein", *Journal of General Virology* 81:2281-2287 (2000).
Nayer et al., "Detection and Characterization of Porcine Circovirus Associated With Postweaving Multisystemic Wasting Syndrome Pigs", *Can Vet. J.* 38(6):385-386 (1997).
Neddleman, S.B. et al., "A General Method Applicable to the Search for Similarities in the Amino Acid Sequence of Two Proteins", *J. Mol. Biol.*, (1970) 48(3):443-453.
Newport, John et al. "Major Developmental Transition in Early Xenopus Embryos: I. Characterization and Timing of Cellular Changes at the Midblastula Stage," *Cell* 30:675-686 (1982).

Newport, John et al. "A Major Developmental Transition in Early Xenopus Embryos: II. Control of the Onset of Transcription," *Cell* 30:687-696 (1982).
Nieuwkoop and Faber "Normal Table of Xenopus laevis (Daudin)—A Systematic and chronological survey of the development from the fertilized egg to the end of metamorposis," Chapter VII, 162-188 Garland Publishing(1994).
Norman, JA et al., "Development of Improved Vectors for DNA-Based Immunization and other Gene Therapy Applications," *Vaccine*, 15(8): 801-803 (1997).
Nuwaysir, Emile F. et al. "Microarrays and Toxicology: The Advent of Toxicogenomics," *Molecular Carcinogenesis*, 24:153-159 (1999).
Okada, E. et al., "Intranasal immunization of a DNA vaccine with IL-I2- and Granulocyte-macrophage colony-stimulating Factor (GM-(SF))—expressing plasmids in Liposomes Induces Strong Mucosal and Cell-Mediated immune responses against HIV-1 antigens," *The Journal of Immunology*, 159:3638-3647 (1997).
Olins, P.O. et al., "Recent advances in heterologous gene expression in *Escherichia coli," Curr. Op. Biotechnol.* (1993) 4:520-525.
Pagano et al., "Factors Influencing the Enhancement of the Infectivity of Poliovirus Ribonucleic Acid by Diethylaminoethyl-Dextran," *J. Virol.*, (1967) 1: 891-897.
Parker, SE et al., " Plasmid DNA gene therapy: Studies with the human interleukin-2 gene in tumor cells in vitro and in the murine B16 melanoma model in vivo," *Cancer Gene Therapy*, 3(3):175-185 (1996).
Pearson, W.R. et al., "Improved Tools for Biological Sequence Comparison", *Proc. Nat'l Acad, Sci., USA*, (1988) 85: 2444-2448.
Restifo, N P et al. "The promises of nucleic acid vaccines,", *Gene Therapy*, 7:89-92 (2000).
Rolfs, A. et al., "PCR Topics: Usage of Polymerase Chain Reaction in Genetic and Infectious Disease" (1991), Springer-Verlag, Berlin.
Rose, N. et al., "Risk Factors for Porcine Post-Weaning Multisystemic Wasting Syndrome (PMWS) in 149 French Farrow-to-Finish Herds", *Preventive Veterinary Microbiology*, (2002) 61: 209-225.
Ruitenberg, K. M. et al., "DNA-Mediated Immunization with Glycoprotein D of Equine Herpesvirus 1 (EHV-1) in a Murine Model of EHV-1 Respiratory Infection," *Vaccine*, 17:237-244 (1999).
Sambrook, J. et al., "Molecular cloning: A Laboratory Manual." Cold Spring Harbor, NY: Cold Spring Harbor Laboratory Press (1989).
Sanchez-Pescador, R., "Rapid chemiluminescent nucleic assays for detection of TEM-1 beta-lactamase-mediated penicillin resistance in Neisseria gororrhoeae and other bacteria," *J. Clin. Microbiol.*, (1988) 26(10): 1934-1938.
Schena, Mark, et al. "Quantitative Monitoring of Gene Expression Patterns with a Complementary DNA Microarray," *Science*, 270:467-470 (1995).
Schena, Mark et al. "Parallel human genome analysis: Microarray-based expression monitoring of 1000 genes," *Proc. Natl. Acad. Sci. USA*, 93:10614-10619 (1996).
Schultz, J et al., "Update on Antiviral DNA Vaccine Research (1998-2000)," *Intervirology*; 43:197-217 (2000).
Ségales, J. et al., "First Report of Post-Weaning Multisystemic Wasting Syndrome in Pigs in Spain", *Beterinary Record*, col. 141, No. 23, pp. 600-601, Dec. 1997, XP-002068504.
Shiver, J.W., "Immune Responses to HIV gp120 Elicited by DNA Vaccination," *Vaccines*, (1995), eds Chanock, et al., pp. 95-98, Cold Spring Harbor Laboratory Press, Cold Spring Harbor, New York.
Sin, J-I et al., "Protective Immunity Against Heterologous Challenge with Encephalomyocarditis Virus by VP1 DNA Vaccination: Effect of Coinjection with a Granulocyte-Macrophage Colony Stimulating Factor Gene," *Vaccine* 15:1827-1833 (1997).
Smith, T.F. et al., "Comparison of Biosequences", *Advances in Applied Mathematics*, (1981) 2:482-489.
Somasundaram, C. et al., "Enhanced Protective Response and Immuno-Adjuvant Effects of Porcine GM-CSF on DNA Vaccination of Pigs against Aujeszky's Disease Virus," *Veterinary Immunology and Immunopathology* 70:277-287 (1999).
Tascon, R.E. et al., "Vaccination against tuberculosis by DNA injection," *Nature Medicine*, (1996) 2(8):888-892.
Terpestra et al., "Potentcy control of modified live viral vaccines for veterinary use," *Vaccine* 14(6):570-575 (1996).
Tischer, I. et al., "A very small porcine virus with circular single-stranded DNA," *Nature*, (1982) 295:64-66.
Tischer, I. et al., "Studies on Epideniology and Pathologenicity of Porcine Circovirus," *Arch. Virol.*, (1986) 91:271-276.
Tischer, I. et al., "Viral DNA from Cells Infected With Porcine Circovirus," *Zentralbl Baktetiol Mikrobiol Hyg [A]* (1988) 270:280-287.
Tischer, I. et al., "Distribution of antibodies to porcine circovirus in swing populations of different breeding farms.", *Archives of Virology*, vol. 140, No. 4, pp. 737-743, 1995, XP-002104704.
Todd et al., "Comparision of Three Animal Viruses with Circular Single-Stranded DNA Genomes," *Arch Virol.*, 117:129-135 (1991).
Urdea, M.S., "A comparison of non-radioisotopic hybridization assay methods using fluorescent chemiluminescent and enzyme labeled synthetic oligodeooxyribonucleotide probes," *Nucleic Acids Research*, (1988) 11:4937-4957.
Valsesia-Whittmann, S. et al., "Improvement of Retroviral Retargeting by Using Amino Acid Spacers between an Additional Binding Domain and the N Terminus of Moloney Nurine Leukemia Virus SU", *J. Virol*, (1996) 70(3):2059-2064.
Vannier, et al., "Study of the Efficacy of an Inactivated Virus Vaccine Against Porcine Parvovirus," *Ann. Rech. Vet.* 17(4):425-432 (1986).
Vogel, et al., "Nucleic Acid Vaccines," *Clinical Microbiology Reviews* 8(3):406-410 (1995).
Walker, G.T. et al., "Strand displacement amplification—an isothermal, in vitro DNA amplification technique," *Nucleic Acids Res.* (1992) 20: 1691-1696.
Walker, G.T. et al., "Isothermal in vitro amplification of DNA by a restriction enzyme/DNA polymerase system," *Proc. Nat'l Acad. Sci., USA*, (1992) 89: 392-396.
Watanabe, Y et al., "Highly Efficient Transfection into Primary Cultured Mouse Hepatocytes by Use of Cation-Liposomes: An Application for Immunization," *J. Biochem.* 116:1220-1226 (1994).
Wen, L. et al., "Genotyping of porcine circovirus type 2 from a variety of clinical conditions in China," *Veterinary Microbiology*, 110 (2005) pp. 141-146.
West et al., "Myocarditis and abortion associated with intrauterine infection of sows with porcine circovirus 2" *J Vet Diagn Invest.* 11: 530-532 (1999).
Wheeler, C.J. et al., "Converting an alcohol to an amine in a cationic lipid dramatically alters the co-lipid requirement, cellular transfection activity and the ultrastructure of DNA-cytofectin complexes," *Biochemica et Biophysica Acta* 1280:1-11, XP 002035803 (1996).
White, B.A. et al. Eds, "PCR Cloning Protocol" *Methods in Molecular Biology*, 67, Humana Press, Towota, (1997).
Xiang Z. et al., "Manipulation of the immune response to a plasmid-encoded viral antigen by coinoculation with plasmids expressing cytokines," *Immunity*, 2:129-135 (1995).
Yokoyama et al. "DNA immunization: Effects of vehicle and route of administration on the induction of protective antiviral immunity," *FEMS Immunology and Medical Microbiology*, 14:221-230 (1996).
Young, "Fields Virology" 3rd ed. Philadelphia: Lippencott-Raven Publishers Chapter 70- Parvoviruses; vol. 2, p. 2199-2220 (1996).
Young, John A. T. et al., "Efficient Incorporation of Human CD4 Protein into Avian Leukosis Virus Particles", *Science*, (1990) 250(4986):1421-1423.
Zhang, Michael Q. "Large-Scale Gene Expression Data Analysis: A New Challenge to Computational Biologists," *Genome Research*, 9(8):681-688 (1999).
Zhao, T.M. et al., "Infectivity of chimeric human T-cell leukemia virus type I molecular clones assessed by naked DNA inoculation," *Proc. Natl. Acad. Sci., USA* (1996) 93(13): 6653-6648.
Nawagitgul et al., Modified Indirect Porcine Circovirus (PCV) Type 2-Based and Recombiant Capsid Protein (ORF2)-Based Enzyme-Linked Immunosorbent Assays for Detection of Antibodies to PCV, Clinical and Diagnostic Laboratory Immunology, Jan. 2002, vol. 9, No. 1, pp. 33-40, see the abstract.
Walker IW, et al., (J Vet Diagn Invest. 2000; 12:400-5).
Liu Q, et al., (Protein Expr Purif. 2001; 21:115-20).
G. Allan et al., "Novel porcine circoviruses from pigs with wasting disease syndrome," 142(17) Veterinary Record 467-468 (Apr. 25, 1998).

G. Allan et al., "Isolation and characterisation of circoviruses from pigs with wasting syndromes in Spain, Denmark and Northern Ireland," 66 Vet. Microbiology 115-123 (1999).
A. Hamel et al., "PCR detection and characterization of type-2 porcine circovirus," 64 Can. Journal of Vet. Research 44-52 (2000).
John C.S. Harding, "The clinical expression and emergence of porcine circovirus 2," 98 Veterinary Microbiology 131-135 (2004).
S. Krakowka et al., "Viral Wasting Syndrome of Swine: Experimental Reproduction . . . ," 37 Vet. Pathol. 254-263 (2000).
G. Nayar et al., "Detection and characterization of porcine circovirus associated with postweaning . . . ," 38 Can. Vet. J. 385-386 (Jun. 1997).
I. Tischer et al., "Replication of porcine circovirus: induction by glucosamine and cell cycle dependence," 96 Arch Virol 39-57 (1987).
D. Todd et al., "Purification and biochemical characterization of chicken anaemia agent," 71 Journal of General Virology 819-823 (1990).
D. Todd et al., "Dot Blot Hybridization Assay for Chicken Anemia Agent Using a Cloned DNA Probe," 29(5) Journal of Clinical Microbiology 933-939 (May 1991).
I. Walker et al., "Development and application of a competitive enzyme-linked immunosorbent assay . . . ," 12 J Vet Diagn Invest 400-405 (2000).
GenBank Accession No. AF027217, Dec. 17, 1997.
H.-J. Buhk et al., "Cloning and Sequencing of the Porcine Circovirus (PCV) Genome," Series A 260(4) Zentralblatt fur Bakteriologie Mikrobiologie und Hygiene 465 (Dec. 1985).
S. Inumaru et al., "Expression of biologically active recombinant porcine GM-CSF by baculovirus gene expression system," 76 Immunology and Cell Biology 195-201 (1998).
Opposition against EP 1 036 180 B1 filed by Boehringer Ingelheim on Jul. 24, 2009 ("Opposition") (57 pages).
Notification of Opposition against EP 1 036 180 B1 dated Aug. 11, 2009 (1 page).
"D2" from Opposition—"Submission of the Proprietor to the EPO dated Apr. 11, 2008" (4 pages).
"D13a" from Opposition—"U.S. Appl. No. 60/069,750 (priority document dated Dec. 16, 1997 of D13)" (46 pages).
"D15" from Opposition—"Hamel, A., et al., J. Virol., Jun. 1998, pp. 5262-5267" (6 pages).
"D19" from Opposition—"Meehan et al., J. Gen. Virol., Sep. 1998, 79, 2171-2179" (9 pages).
"D20" from Opposition—"Morozov et al., J. Clin. Microbiol., Sep. 1998, pp. 2535-2541" (7 pages).
"D23" from Opposition—"Ellis et al., Canadian Veterinarian Journal, vol. 39, Jan. 1998" (8 pages).
"D24" from Opposition—"Allan et al., Journal of Veterinary Diagnostic Investigation, 10:3-10 (1998)" (8 pages).
"D25" from Opposition—"Allan et al.; Veterinary Record, 1998, p. 467 to 468" (2 pages).
D. Tood et al., "Dot Blot Hybridization Assay for Chicken Anemia Agent Using a Cloned DNA Probe," 29(5) Journal of Clinical Microbiology 933-939 (May 1991).
AF086834 (including GenBank revision histories), Sep. 29, 1998.
AF086835 (including GenBank revision histories), Sep. 29, 1998.
AF086836 (including GenBank revision histories), Sep. 29, 1998.
AF085695 (Including GenBank revision histories), Sep. 30, 1998.
AJ223185 (including GenBank revision histories), Jul. 7, 1998.
"D1" from Opposition—"WO 99/18214 (English translation)" (38 pages), Apr. 15, 1999 translated in 2009.
"D3" from Opposition—"Translation of SEQ ID No. 4 of WO 99/18214 (PCV IMP 1010)" (5 pages), Jul. 24, 2009.
"D4" from Opposition—"Printout of SEQ ID No. 4 from Patent WO 99/18214 (GenBank A97281.1)" (1 page), Apr. 15, 1999.
"D5" from Opposition—"Translation of SEQ ID No. 1 of WO 99/18214" (5 pages), Jul. 24, 2009.
"D6" from Opposition—"Translation of SEQ ID No. 2 of WO 99/18214" (5 pages), Jul. 24, 2009.
"D7" from Opposition—"Printout of SEQ ID No. 1 from Patent WO 99/18214 (GenBank A97278.1)" (1 page), Apr. 15, 1999.
"D8" from Opposition—"Printout of SEQ ID No. 2 from Patent WO 99/18214 (GenBank A97279.1)" (1 page), Apr. 15, 1999.
"D9" from Opposition—"Translation of SEQ ID No. 3 of WO 99/18214" (5 pages), Jul. 24, 2009.
"D10" from Opposition—"Printout of SEQ ID No. 3 from Patent WO 99/18214 (GenBank A97280.1)" (1 page), Apr. 15, 1999.
"D11" from Opposition—"Translation of SEQ ID No. 6 from Patent WO 99/18214" (5 pages), Jul. 24, 2009.
"D12" from Opposition—"Printout of SEQ ID No. 6 from Patent WO 99/18214 (GenBank A97283.1)" (1 page), 2 Apr. 15, 2009.
"D13" from Opposition—"WO 99/29717" (82 pages), Jun. 17, 1999.
"D13a" from Opposition—"U.S. Appl. No. 60/069,750 (priority document dated (filed) Dec. 16, 1997 of D13)" (46 page).
"D14" from Opposition—"Marked Figures pp. 3/12, 4/12 and 6/12 of D13" (3 pages), Jul. 24, 2009.
"D16" from Opposition—"Enlarged excerpt of p. 5265 of D15" (1 page), Jun. 1998.
"D17" from Opposition—"Translation of pmws nucleotide sequence in D15" (5 pages), Jul. 24, 2009.
"D18" from Opposition—"Printout of nucleotide sequence in D15 retrieved from GenBank (AF27217.1)" (3 pages), Jun. 1998.
"D19a" from Opposition—"Sequence alignments—Sequences in the opposed patent and in D1" (8 pages), Jul. 24, 2009.
"D19b" from Opposition—"Sequence alignments—Sequences in the opposed patent and in D19" (26 pages),Jul. 24, 2009.
"D19c" from Opposition—"Sequence alignments—Sequences in the opposed patent and in D15" (3 pages), Jul. 24, 2009.
"D21" from Opposition—"Nucleotide seequence retrieved from GenBank (deposited as AJ 223185)" (2 pages), Sep. 1998.
"D22" from Opposition—"Translation of nucletide sequence in D21" (5 pages), Jul. 24, 2009.
"D26" from Opposition—"English translation of the Opposed Patent EP 1 036 180 B1"(81 pages), Oct. 29, 2008 Publication date.
Zong-zhao Yang et al.; A Survey on Porcine Circovirus Type 2 Infection and Phylogenetic Analysis of Its ORF2 . . . ; Journal of Zhejiang Unversity Science B ISSN 1673-1581; pp. 148-153; Sep. 2008; Hangzhou City, China.
Does Stress-Free Livestock Mean Safer Food?; http://www.foodnavigator.com; Jun. 4, 2004; Decisionnews Media SAS; 1 page.
Vaccination Guidelines for Swine How to get the maximum benefit when vaccinating your swine heard; VIDO Swine Technical Group-Vaccination Guidelines-Jun. 2004; www.vido.org; pp. 1-25.
Yuna Kim et al.; Characterization of the Recombinant Proteins of Porcine Circovirus TYPE2 Field Isolate Expressed in the Baculovirus System; Journal of Veterinary Science; 200.
European Patent Office (France); Communication; French Search Report; dated Oct. 16, 2008; 10 pages.
Morris et al.; Promoter Influence on Baculovirus-Mediated Gene Expression in Permissive and Nonpermissive Insect Cell Line; J Virol; Dec. 1992, vol. 66, No. 12; pp. 7397-7405.
Morris et al.; Characterization of Productive and Non-Productive ACMNPV Infection in Selected Insect Cell Lines; Virol 197; 1993; pp. 339-348.
Greoener; The Biology of Baculoviruses; vol. 1—Biological Properties and Molecular Biology, Chapter 9; Specificity and Safety of Baculoviruses, 1986, pp. 177-202.
Allan et al., "Experimental infection of colostrum deprived piglets with porcine circovirus 2 (PCV2) and porcine reproductive and respiratory syndrome virus (PRRSV) potentiates PCV2 replication", Arch. Virol., 2000, 145: 2421-2429.
Sorden et al., Development of a polyclonal-antibody-based immunohistochemical method for the detection of type 2 porcine circovirus in formalin-fixed, paraffin-embedded tissue, J Vet Diagn Invest, 1999, 11:528-530.
Inumaru et al., "Expression of biologically active recombinant porcine GM-CSF by baculovirus gene expression system", Immunology and Cell Biology, 1998, vol. 76, pp. 195-201.
Ragona et al., "The transcriptional Factor Egr-1 Is Synthesized by Baculovirus-Infected Insect Cells in an Active, DNA-Binding Form", DNA and Cell Biology, vol. 10, No. 1, Jan. 1991.
Database EMBL, EBI, Hinxton, UK; Wang et al.: XP002557492, Database Accession No. Q9YTB6, May 1, 1999.
GenBank Accession No. AAC61738, Version AAC61738.1, GI:3661517, Sep. 29, 1998.

* cited by examiner

```
 Leu Ala Ser Arg Cys Arg Cys Cys Arg Pro Leu Thr Leu Ser Phe Ala Leu Cys
 Trp Arg Val Glu Ala Ala Ala Ala Gly Arg Cys Arg *** His Phe His Trp Ala
Gly Ala Cys Lys Pro Leu Pro Leu Val Glu Ala Ala Asp Thr Phe Ile Gly Leu
--- --- --- --- --- --- --- --- --- --- --- --- --- --- --- --- --- ---
TGG TCG CGT GAA GCC GTC GCC GTC GTG GAG CCG TCG CAG TCA CTT TTA CGG TTC
      9           18          27          36          45          54
ACC AGC GCA CTT CGG CAG CGG CAG CAC CTC GGC AGC GTC AGT GAA AAT GCC AAG
--- --- --- --- --- --- --- --- --- --- --- --- --- --- --- --- --- ---
Thr Ser Ala Leu Arg Gln Arg Gln His Leu Gly Ser Val Ser Glu Asn Ala Lys
 Pro Ala His Phe Gly Ser Gly Ser Thr Ser Ala Ala Ser Val Lys Met Pro Ser
 Gln Arg Thr Ser Ala Ala Ala Ala Pro Arg Gln Arg Gln *** Lys Cys Gln Ala

 Ser Phe Arg Gly Ala Val Gly Tyr Ser Thr Pro Thr *** Gly *** Tyr Asp Lys
 Leu Phe Ala Ala Arg Leu Gly Met Leu Pro Pro His Glu Gly Lys Ile Ile Arg
Leu Phe Leu Pro Gly Cys Gly Trp Leu Leu His Thr Asn Val Arg Leu Leu Gly
--- --- --- --- --- --- --- --- --- --- --- --- --- --- --- --- --- ---
GTT CTT TTC GCC GGG CGT TGG GGT ATT CTC CAC CCA CAA GTG GGA ATT ATT AGG
     63          72          81          90          99         108
CAA GAA AAG CGG CCC GCA ACC CCA TAA GAG GTG GGT GTT CAC CCT TAA TAA TCC
--- --- --- --- --- --- --- --- --- --- --- --- --- --- --- --- --- ---
Gln Glu Lys Arg Pro Ala Thr Pro *** Glu Val Gly Val His Pro *** *** Ser
 Lys Lys Ser Gly Pro Gln Pro His Lys Arg Trp Val Phe Thr Leu Asn Asn Pro
 Arg Lys Ala Ala Arg Asn Pro Ile Arg Gly Gly Cys Ser Pro Leu Ile Ile Leu

 Arg Pro Pro Ser Phe Cys Phe Val Pro Ala Glu Leu Arg Gly Lys Gln Asn Asn
 Gly Leu Leu Leu Phe Val Phe Tyr Pro Leu Lys Trp Asp Gly Lys Lys Ile Ile
Glu Ser Ser Ser Phe Phe Leu Ile Arg Ser Ser Gly Ile Glu Arg Lys Ser ***
--- --- --- --- --- --- --- --- --- --- --- --- --- --- --- --- --- ---
AAG GCT CCT CCT CTT TTT GTT TTA TGC CCT CGA AGG TTA GAG GGA AAA ACT AAT
    117         126         135         144         153         162
TTC CGA GGA GGA GAA AAA CAA AAT ACG GGA GCT TCC AAT CTC CCT TTT TGA TTA
--- --- --- --- --- --- --- --- --- --- --- --- --- --- --- --- --- ---
Phe Arg Gly Gly Glu Lys Gln Asn Thr Gly Ala Ser Asn Leu Pro Phe *** Leu
 Ser Glu Glu Glu Lys Asn Lys Ile Arg Glu Leu Pro Ile Ser Leu Phe Asp Tyr
 Pro Arg Arg Arg Lys Thr Lys Tyr Gly Ser Phe Gln Ser Pro Phe Leu Ile Ile

 Gln Lys His Arg Pro Leu Asn Pro Leu Pro Tyr Phe Glu Glu Gly Gly Pro Thr
 Lys Asn Thr Ala Leu Phe Thr Gln Phe Leu Thr Ser Ser Arg Val Glu Leu Pro
Lys Thr Gln Pro Ser Ser Pro Lys Ser Ser Pro Leu Val Gly *** Arg Trp Pro
--- --- --- --- --- --- --- --- --- --- --- --- --- --- --- --- --- ---
AAA ACA AAC ACC GCT CCT TCC AAA CCT TCT CCC ATC TTG AGG AGT GGA GGT CCC
    171         180         189         198         207         216
TTT TGT TTG TGG CGA GGA AGG TTT GGA AGA GGG TAG AAC TCC TCA CCT CCA GGG
--- --- --- --- --- --- --- --- --- --- --- --- --- --- --- --- --- ---
Phe Cys Leu Trp Arg Gly Arg Phe Gly Arg Gly *** Asn Ser Ser Pro Pro Gly
 Phe Val Cys Gly Glu Glu Gly Leu Glu Glu Gly Arg Thr Pro His Leu Gln Gly
 Leu Phe Val Ala Arg Lys Val Trp Lys Arg Val Glu Leu Leu Thr Ser Arg Gly

 Gln Ser Asn Gln *** Ser Ala Ser Lys *** Cys Pro Ser Thr Thr Asn Gln His
 Lys Arg Ile Lys Ser Leu Leu Leu Ser Lys Val Leu His Leu Pro Ile Lys Thr
Asn Ala Phe Lys Ala Leu Phe Cys Val Lys Leu Leu Thr Phe His Tyr Lys Pro
--- --- --- --- --- --- --- --- --- --- --- --- --- --- --- --- --- ---
CAA ACG CTT AAA ACG ATT CTT CGT CTG AAA ATT GTT CCA CTT CAC CAT AAA ACC
    225         234         243         252         261         270
GTT TGC GAA TTT TGC TAA GAA GCA GAC TTT TAA CAA GGT GAA GTG CTA TTT TGG
--- --- --- --- --- --- --- --- --- --- --- --- --- --- --- --- --- ---
Val Cys Glu Phe Cys *** Glu Ala Asp Phe *** Gln Gly Glu Val Val Phe Trp
 Phe Ala Asn Phe Ala Lys Lys Gln Thr Phe Asn Lys Val Lys Trp Tyr Phe Gly
 Leu Arg Ile Leu Leu Arg Ser Arg Leu Leu Thr Arg *** Ser Gly Ile Leu Val
```

FIG. 2a

```
 Gly Ser Gly Cys Arg Ser Leu Ser Leu Phe Arg Gly Ala Ser Tyr Leu Ile Ser
 Gly Ala Ala Val Asp Leu Phe Arg Phe Ser Gly Val Leu Leu Ile Phe Phe Val
Ala Arg Gln Trp Met Ser Phe Ala Phe Pro Val Ser Trp Cys Phe Leu Ser Tyr
--- --- --- --- --- --- --- --- --- --- --- --- --- --- --- --- --- ---
ACG GGC GAC GGT GTA GCT CTT TCG CTT TCC TTG GCT GGT CGT CTT ATT TCT TAT
        279         288         297         306         315         324
TGC CCG CTG CCA CAT CGA GAA AGC GAA AGG AAC CGA CCA GCA GAA TAA AGA ATA
--- --- --- --- --- --- --- --- --- --- --- --- --- --- --- --- --- ---
Cys Pro Leu Pro His Arg Glu Ser Glu Arg Asn Arg Pro Ala Glu *** Arg Ile
 Ala Arg Cys His Ile Glu Lys Ala Lys Gly Thr Asp Gln Gln Asn Lys Glu Tyr
  Pro Ala Ala Thr Ser Arg Lys Arg Lys Glu Pro Thr Ser Arg Ile Lys Asn Thr

  Cys Tyr Leu Leu Gly Cys Val *** Arg Thr His Leu Glu Ala Ser Gly Pro Ser
 Ala Thr Phe Phe Ala Val Tyr Lys Asp Leu Thr Ser Ser Arg Pro Val Leu Pro
Gln Leu Leu Ser Pro Trp Met Ser Ile Ser His Pro Ala Gly Arg Phe Trp Pro
--- --- --- --- --- --- --- --- --- --- --- --- --- --- --- --- --- ---
GAC GTC ATT TCT TCC GGT GTA TGA ATA GCT CAC ACC TCG AGG CGC CTT GGT CCC
        333         342         351         360         369         378
CTG CAG TAA AGA AGG CCA CAT ACT TAT CGA GTG TGG AGC TCC GCG GAA CCA GGG
--- --- --- --- --- --- --- --- --- --- --- --- --- --- --- --- --- ---
Leu Gln *** Arg Arg Pro His Thr Tyr Arg Val Trp Ser Ser Ala Glu Pro Gly
 Cys Ser Lys Glu Gly His Ile Leu Ile Glu Cys Gly Ala Pro Arg Asn Gln Gly
  Ala Val Lys Lys Ala Thr Tyr Leu Ser Ser Val Glu Leu Arg Gly Thr Arg Gly

  Ala Cys Arg Gly Thr *** Gln Gln Ser Tyr Gly Lys Pro Ser Pro Thr Lys Pro
 Leu Ala Ala Val Gln Arg Ser Ser His Thr Gly Lys Gln Leu Arg Pro Arg Gln
Phe Arg Leu Ser Arg Asp Val Ala Thr Leu Val Arg Lys Ser Val Pro Asp Lys
--- --- --- --- --- --- --- --- --- --- --- --- --- --- --- --- --- ---
CTT CGC GTC GCT GGA CAG ATG ACG ACA CTC ATG GGA AAA CCT CTG CCC CAG AAA
        387         396         405         414         423         432
GAA GCG CAG CGA CCT GTC TAC TGC TGT GAG TAC CCT TTT GGA GAC GGG GTC TTT
--- --- --- --- --- --- --- --- --- --- --- --- --- --- --- --- --- ---
Glu Ala Gln Arg Pro Val Tyr Cys Cys Glu Tyr Pro Phe Gly Asp Gly Val Phe
 Lys Arg Ser Asp Leu Ser Thr Ala Val Ser Thr Leu Leu Glu Thr Gly Ser Leu
  Ser Ala Ala Thr Cys Leu Leu Leu *** Val Pro Phe Trp Arg Arg Gly Leu Trp

  Ser Gln Leu Arg Ala Thr Glu Gln Leu Thr His Ser Phe Asn Gly Arg Ala Pro
 His Ser Tyr Gly Leu Leu Lys Arg Tyr Arg Ile His Ser Ile Glu Ala Pro Gln
Thr Val Thr Ala Ser Cys Asn Gly Thr Val Tyr Thr Leu Phe Lys Arg Pro Ser
--- --- --- --- --- --- --- --- --- --- --- --- --- --- --- --- --- ---
CCA CTG ACA TCG GCT CGT CAA AGG ACA TTG CAT ACA CTC TTT AAA GGC GCC CGA
        441         450         459         468         477         486
GGT GAC TGT AGC CGA GCA GTT TCC TGT AAC GTA TGT GAG AAA TTT CCG CGG GCT
--- --- --- --- --- --- --- --- --- --- --- --- --- --- --- --- --- ---
Gly Asp Cys Ser Arg Ala Val Ser Cys Asn Val Cys Glu Lys Phe Pro Arg Ala
 Val Thr Val Ala Glu Gln Phe Pro Val Thr Tyr Val Arg Asn Phe Arg Gly Leu
  *** Leu *** Pro Ser Ser Phe Leu *** Arg Met *** Glu Ile Ser Ala Gly Trp

  Gln Val Lys Ser Leu Ser Arg Ser Ser Ala Ala Ala His Asn Ser Ser Leu Gln
 Ser Phe Lys Gln Phe His Ala Pro Leu His Leu Leu Thr Ile Pro Leu Cys Ser
Ala Ser Ser Lys Phe Thr Leu Pro Phe Ile Cys Cys Arg Ser Gln Phe Val Ala
--- --- --- --- --- --- --- --- --- --- --- --- --- --- --- --- --- ---
CCG ACT TGA AAA CTT TCA CTC GCC CTT CTA CGT CGT CGC ACT AAC CTT CTG TCG
        495         504         513         522         531         540
GGC TGA ACT TTT GAA AGT GAG CGG GAA GAT GCA GCA GCG TGA TTG GAA GAC AGC
--- --- --- --- --- --- --- --- --- --- --- --- --- --- --- --- --- ---
Gly *** Thr Phe Glu Ser Glu Arg Glu Asp Ala Ala Ala *** Leu Glu Asp Ser
 Ala Glu Leu Leu Lys Val Ser Gly Lys Met Gln Gln Arg Asp Trp Lys Thr Ala
  Leu Asn Phe *** Lys *** Ala Gly Arg Cys Ser Ser Val Ile Gly Arg Gln Leu
```

FIG. 2b

```
 Val Arg *** Leu Pro Gly Ala Arg Asn His Ser Ser Gly Thr Pro Gly Tyr Asn
  Tyr Val Asp Tyr His Ala Arg Gly Thr Thr Pro Leu Ala Leu Pro Gly Thr Ile
Thr Cys Thr Met Thr Pro Gly Gly Pro Gln Pro Phe Leu Trp His Ala Arg Leu
--- --- --- --- --- --- --- --- --- --- --- --- --- --- --- --- --- ---
ACA TGT GCA GTA TCA CCC GGG CGG GCC AAC ACC CTT CTC GGT CAC CCG GGC ATT
        549         558         567         576         585         594
TGT ACA CGT CAT AGT GGG CCC GCC CGG TTG TGG GAA GAG CCA GTG GGC CCG TAA
--- --- --- --- --- --- --- --- --- --- --- --- --- --- --- --- --- ---
Cys Thr Arg His Ser Gly Pro Ala Arg Leu Trp Glu Glu Pro Val Gly Pro ***
 Val His Val Ile Val Gly Pro Pro Gly Cys Gly Lys Ser Gln Trp Ala Arg Asn
  Tyr Thr Ser *** Trp Ala Arg Pro Val Val Gly Arg Ala Ser Gly Pro Val Ile

  Gln Gln Ala *** Pro Cys Arg Ser Ser Ala *** Tyr Phe Tyr Thr Thr Pro His
 Lys Ser Leu Arg Pro Val Gly Val Pro Leu Arg Thr Ser Ile Leu Pro Pro Ile
Lys Ala Ser Gly Leu Ser Val *** Gln Phe Gly Leu Leu Phe Leu His His Ser
--- --- --- --- --- --- --- --- --- --- --- --- --- --- --- --- --- ---
AAA ACG ACT CGG ATC CCT GTG GAT GAC CTT CGG ATC ATC TTT ATT CAC CAC CCT
        603         612         621         630         639         648
TTT TGC TGA GCC TAG GGA CAC CTA CTG GAA GCC TAG TAG AAA TAA GTG GTG GGA
--- --- --- --- --- --- --- --- --- --- --- --- --- --- --- --- --- ---
Phe Cys *** Ala *** Gly His Leu Leu Glu Ala *** *** Lys *** Val Val Gly
 Phe Ala Glu Pro Arg Asp Thr Tyr Trp Lys Pro Ser Arg Asn Lys Trp Trp Asp
  Leu Leu Ser Leu Gly Thr Pro Thr Gly Ser Leu Val Glu Ile Ser Gly Gly Met

  Ile Asp His Leu Leu Leu Gln Gln Lys Pro His Asn Lys His Ser Thr Val Lys
 Ser Ile Met Ser Phe Phe Asn Asn Asn Gln Ile Ile Lys Ile Ala Pro *** Arg
Pro Tyr *** Pro Ser Ser Thr Thr Thr Lys Ser Ser Lys *** Pro Gln Asn Gly
--- --- --- --- --- --- --- --- --- --- --- --- --- --- --- --- --- ---
ACC TAT AGT ACC TCT TCT TCA ACA ACA AAA CCT ACT AAA AAT ACC GAC CAA TGG
        657         666         675         684         693         702
TGG ATA TCA TGG AGA AGA AGT TGT TGT TTT GGA TGA TTT TTA TGG CTG GTT ACC
--- --- --- --- --- --- --- --- --- --- --- --- --- --- --- --- --- ---
Trp Ile Ser Trp Arg Arg Ser Cys Cys Phe Gly *** Phe Leu Trp Leu Val Thr
 Gly Tyr His Gly Glu Glu Val Val Val Leu Asp Asp Phe Tyr Gly Trp Leu Pro
  Asp Ile Met Glu Lys Lys Leu Leu Phe Trp Met Ile Phe Met Ala Gly Tyr Leu

  Pro His Asp Val Ser Val Thr His Gly Thr Asp Met Ser Gln Leu Ser *** Leu
 Pro Ile Ile *** Gln Ser Gln Thr Val Pro Ile Trp Gln Ser Tyr Leu Ser Phe
Gln Ser Ser Arg Ser Leu Ser His Ser Arg Tyr Gly Asn Val Thr Ser Val Leu
--- --- --- --- --- --- --- --- --- --- --- --- --- --- --- --- --- ---
AAC CCT ACT AGA TGA CTC TGA CAC ACT GGC CAT AGG TAA CTG ACA TCT CTG ATT
        711         720         729         738         747         756
TTG GGA TGA TCT ACT GAG ACT GTG TGA CCG GTA TCC ATT GAC TGT AGA GAC TAA
--- --- --- --- --- --- --- --- --- --- --- --- --- --- --- --- --- ---
Leu Gly *** Ser Thr Glu Thr Val *** Pro Val Ser Ile Asp Cys Arg Asp ***
 Trp Asp Asp Leu Leu Arg Leu Cys Asp Arg Tyr Pro Leu Thr Val Glu Thr Lys
  Gly Met Ile Tyr *** Asp Cys Val Thr Gly Ile His *** Leu *** Arg Leu Lys

  Pro Tyr Gln Glu Lys Lys Pro Gly Cys Tyr Lys Ser *** Trp Cys Asp Pro Gly
 Pro Thr Ser Asn Arg Lys Gln Gly Ala Thr Asn Gln Asn Gly Ala Ile Leu Gly
Pro Pro Val Thr Gly Lys Lys Ala Arg Leu Ile Lys Ile Val Leu Leu *** Ala
--- --- --- --- --- --- --- --- --- --- --- --- --- --- --- --- --- ---
TCC CCC ATG ACA AGG AAA AAA CCG GGC GTC ATA AAA CTA ATG GTC GTT AGT CCG
        765         774         783         792         801         810
AGG GGG TAC TGT TCC TTT TTT GGC CCG CAG TAT TTT GAT TAC CAG CAA TCA GGC
--- --- --- --- --- --- --- --- --- --- --- --- --- --- --- --- --- ---
Arg Gly Tyr Cys Ser Phe Phe Gly Pro Gln Tyr Phe Asp Tyr Gln Gln Ser Gly
 Gly Gly Thr Val Pro Phe Leu Ala Arg Ser Ile Leu Ile Thr Ser Asn Gln Ala
  Gly Val Leu Phe Leu Phe Trp Pro Ala Val Phe *** Leu Pro Ala Ile Arg Pro
```

FIG. 2c

```
 Gly Pro Ile Thr Ser Arg Leu Gln Gln Gly Leu Gln Leu Leu Glu Arg Asp Ser
 Gly Leu Phe Pro Val Gly *** Ser Ser Asp Trp Ser Tyr Phe Ser Glu Ile Pro
Gly Trp Ser His Tyr Glu Glu Val Ala Thr Gly Ala Thr Ser Ala Arg *** Arg
--- --- --- --- --- --- --- --- --- --- --- --- --- --- --- --- --- ---
GGG GGT CCT TAC CAT GAG GAG TTG ACG ACA GGG TCG ACA TCT TCG AGA GAT AGC
        819         828         837         846         855         864
CCC CCA GGA ATG GTA CTC CTC AAC TGC TGT CCC AGC TGT AGA AGC TCT CTA TCG
--- --- --- --- --- --- --- --- --- --- --- --- --- --- --- --- --- ---
Pro Pro Gly Met Val Leu Leu Asn Cys Cys Pro Ser Cys Arg Ser Ser Leu Ser
 Pro Gln Glu Trp Tyr Ser Ser Thr Ala Val Pro Ala Val Glu Ala Leu Tyr Arg
  Pro Arg Asn Gly Thr Pro Gln Leu Leu Ser Gln Leu *** Lys Leu Ser Ile Gly

  Ser *** *** Lys Ala Ile Lys Ser Ser Gln Gln Leu Val Ile Trp Pro Pro Val
 Pro Asn Ser Ser Gln Leu Lys Pro Leu Ser Ser Ser Phe Leu Gly Arg Leu Tyr
Leu Ile Val Val Lys Cys Asn Gln Phe Val Ala Pro Ser Cys Asp Val Ser Thr
--- --- --- --- --- --- --- --- --- --- --- --- --- --- --- --- --- ---
CTC CTA ATG ATG AAA CGT TAA AAC CTT CTG ACG ACC TCT TGT TAG GTG CCT CCA
        873         882         891         900         909         918
GAG GAT TAC TAC TTT GCA ATT TTG GAA GAC TGC TGG AGA ACA ATC CAC GGA GGT
--- --- --- --- --- --- --- --- --- --- --- --- --- --- --- --- --- ---
Glu Asp Tyr Tyr Phe Ala Ile Leu Glu Asp Cys Trp Arg Thr Ile His Gly Gly
 Arg Ile Thr Thr Leu Gln Phe Trp Lys Thr Ala Gly Glu Gln Ser Thr Glu Val
  Gly Leu Leu Leu Cys Asn Phe Gly Arg Leu Leu Glu Asn Asn Pro Arg Arg Tyr

  Arg Leu Gly Ile Gln Leu Leu Pro Gly Val Arg His Gly Lys Gly Met Tyr Phe
 Gly Phe Ala Ser Lys Phe Cys His Val Trp Gly Thr Gly Lys Glu Trp Ile Phe
Gly Ser Pro Arg Asn Ser Ala Thr Ser Gly Gly Gln Ala Arg Lys Gly Tyr Leu
--- --- --- --- --- --- --- --- --- --- --- --- --- --- --- --- --- ---
TGG GCT TCC GGC TAA ACT TCG TCA CCT GGG TGG GAC ACG GGA AAA GGG TAT ATT
        927         936         945         954         963         972
ACC CGA AGG CCG ATT TGA AGC AGT GGA CCC ACC CTG TGC CCT TTT CCC ATA TAA
--- --- --- --- --- --- --- --- --- --- --- --- --- --- --- --- --- ---
Thr Arg Arg Pro Ile *** Ser Ser Gly Pro Thr Leu Cys Pro Phe Pro Ile ***
 Pro Glu Gly Arg Phe Glu Ala Val Asp Pro Pro Cys Ala Leu Phe Pro Tyr Lys
  Pro Lys Ala Asp Leu Lys Gln Trp Thr His Pro Val Pro Phe Ser His Ile Lys

  Leu Asn Ser Leu Arg Lys Gln *** *** Met Thr Ile Thr Lys Ile Lys Ile ***
 Tyr Ile Val Ser Asp Lys Lys Asn Asp Cys Arg Leu Pro Lys *** Lys *** Glu
Ile Phe *** Gln Thr Lys Lys Thr Ile Val Asp Tyr His Asn Lys Asn Lys Asn
--- --- --- --- --- --- --- --- --- --- --- --- --- --- --- --- --- ---
TTA TTT AAT GAC TCA GAA AAA ACA ATA GTG TAG CAT TAC CAA AAA TAA AAA TAA
        981         990         999        1008        1017        1026
AAT AAA TTA CTG AGT CTT TTT TGT TAT CAC ATC GTA ATG GTT TTT ATT TTT ATT
--- --- --- --- --- --- --- --- --- --- --- --- --- --- --- --- --- ---
Asn Lys Leu Leu Ser Leu Phe Cys Tyr His Ile Val Met Val Phe Ile Phe Ile
 Ile Asn Tyr *** Val Phe Phe Val Ile Thr Ser *** Trp Phe Leu Phe Leu Phe
  *** Ile Thr Glu Ser Phe Leu Leu Ser His Arg Asn Gly Phe Tyr Phe Tyr Ser

  Lys Ser Pro Arg Glu Pro Tyr Ile Arg Gln Ile Thr Cys Leu Tyr Asp Val Lys
 Asn Leu Pro Asp Lys Leu Ile Phe Glu Arg Phe Gln Val Tyr Ile Thr Leu Arg
Met *** Leu Thr Lys *** Ser Leu Asn Glu Ser Asn Tyr Met Phe Leu *** Gly
--- --- --- --- --- --- --- --- --- --- --- --- --- --- --- --- --- ---
GTA AAT CTC CCA GAA AGT CCT ATT TAA GAG ACT TAA CAT GTA TTT ATC AGT TGG
       1035        1044        1053        1062        1071        1080
CAT TTA GAG GGT CTT TCA GGA TAA ATT CTC TGA ATT GTA CAT AAA TAG TCA ACC
--- --- --- --- --- --- --- --- --- --- --- --- --- --- --- --- --- ---
His Leu Glu Gly Leu Ser Gly *** Ile Leu *** Ile Val His Lys *** Ser Thr
 Ile *** Arg Val Phe Gln Asp Lys Phe Ser Glu Leu Tyr Ile Asn Ser Gln Pro
  Phe Arg Gly Ser Phe Arg Ile Asn Ser Leu Asn Cys Thr *** Ile Val Asn Leu
```

FIG. 2d

```
 Gly Cys Leu Lys Pro Ser His Asn Cys Lys Pro Ala Cys Leu Gly Pro Arg His
Val Val Tyr Asn Gln Ala Thr Thr Ala Asn Gln Leu Ala Tyr Gly Leu Gly Thr
*** Trp Met Ile Lys Pro Gln Pro Gln Met Lys Ser Arg Met Ala Trp Ala Gln
--- --- --- --- --- --- --- --- --- --- --- --- --- --- --- --- --- ---
AAT GGT GTA TTA AAA CCC GAC ACC AAC GTA AAA CCT CGC GTA TCG GGT CCG GAC
        1089        1098        1107        1116        1125        1134
TTA CCA CAT AAT TTT GGG CTG TGG TTG CAT TTT GGA GCG CAT AGC CCA GGC CTG
--- --- --- --- --- --- --- --- --- --- --- --- --- --- --- --- --- ---
Leu Pro His Asn Phe Gly Leu Trp Leu His Phe Gly Ala His Ser Pro Gly Leu
 Tyr His Ile Ile Leu Gly Cys Gly Cys Ile Leu Glu Arg Ile Ala Gln Ala Cys
  Thr Thr *** Phe Trp Ala Val Val Ala Phe Trp Ser Ala *** Pro Arg Pro Val

 Ala Arg Cys Gln His Pro Tyr Lys Phe Pro Ala Val Ala Pro Lys Lys *** ***
His Glu Val Asn Thr His Thr Asn Leu His Leu Trp Leu Gln Asn Arg Lys Asn
Thr Ser Ser Met Pro Thr Pro Ile *** Ile Ser Gly Cys Ser Thr Glu Lys Ile
--- --- --- --- --- --- --- --- --- --- --- --- --- --- --- --- --- ---
ACA CGA GCT GTA ACC ACA CCC ATA AAT TTA CCT CGG TGT CGA CCA AAG AAA ATA
        1143        1152        1161        1170        1179        1188
TGT GCT CGA CAT TGG TGT GGG TAT TTA AAT GGA GCC ACA GCT GGT TTC TTT TAT
--- --- --- --- --- --- --- --- --- --- --- --- --- --- --- --- --- ---
Cys Ala Arg His Trp Cys Gly Tyr Leu Asn Gly Ala Thr Ala Gly Phe Phe Tyr
 Val Leu Asp Ile Gly Val Gly Ile *** Met Glu Pro Gln Leu Val Ser Phe Ile
  Cys Ser Thr Leu Val Trp Val Phe Lys Trp Ser His Ser Trp Phe Leu Leu Leu

Lys Ala Pro Val Leu *** Asn Asn Pro Arg Ala Arg Thr Gln Pro His Leu Val
 Asn Pro Gln Phe Trp Asp Ile Thr Gln Asp Leu Glu Pro Lys Pro Thr Phe Tyr
  Ile Gln Ser Ser Gly Ile Leu Gln Lys Thr *** Ser Gln Asn Pro Pro Ser Thr
--- --- --- --- --- --- --- --- --- --- --- --- --- --- --- --- --- ---
ATA AAC CGA CCT TGG TTA GTT AAC AAA CCA GAT CGA GAC CAA ACC CCC ACT TCA
        1197        1206        1215        1224        1233        1242
TAT TTG GCT GGA ACC AAT CAA TTG TTT GGT CTA GCT CTG GTT TGG GGG TGA AGT
--- --- --- --- --- --- --- --- --- --- --- --- --- --- --- --- --- ---
Tyr Leu Ala Gly Thr Asn Gln Leu Phe Gly Leu Ala Leu Val Trp Gly *** Ser
 Ile Trp Leu Glu Pro Ile Asn Cys Leu Val *** Leu Trp Phe Gly Gly Gly Val
  Phe Gly Trp Asn Gln Ser Ile Val Trp Ser Ser Ser Gly Leu Gly Val Lys Tyr

  Gln Leu Pro Leu Tyr Leu Ala Ala Lys His His Pro Pro Leu Leu Leu *** Tyr
 Arg Ser His Tyr Thr Phe Pro Gln Arg Ile Thr His Arg Ser Ser Tyr Asn Ile
Gly Pro Thr Thr Pro Leu Pro Ser Gly *** Pro Thr Ala Pro Pro Thr Thr Leu
--- --- --- --- --- --- --- --- --- --- --- --- --- --- --- --- --- ---
TGG ACC TCA CCA TCC ATT TCC CGA CGG AAT ACC ACA CCG CCC TCC TCA TCA ATT
        1251        1260        1269        1278        1287        1296
ACC TGG AGT GGT AGG TAA AGG GCT GCC TTA TGG TGT GGC GGG AGG AGT AGT TAA
--- --- --- --- --- --- --- --- --- --- --- --- --- --- --- --- --- ---
Thr Trp Ser Gly Arg *** Arg Ala Ala Leu Trp Cys Gly Gly Arg Ser Ser ***
 Pro Gly Val Val Gly Lys Gly Leu Pro Tyr Gly Val Ala Gly Gly Val Val Asn
  Leu Glu Trp *** Val Lys Gly Cys Leu Met Val Trp Arg Glu Glu *** Leu Ile

  Leu Pro *** Leu Gly Leu Gln His Leu Pro Asn Cys Leu Gln Cys Gly Leu Tyr
 Tyr Pro Asp Tyr Ala Leu Asn Thr Ser Pro Thr Val Phe Asn Ala Asp Leu Ile
Ile Pro Thr Met Pro Trp Thr Pro Pro Pro Pro *** Leu Thr Pro Met Trp Ser
--- --- --- --- --- --- --- --- --- --- --- --- --- --- --- --- --- ---
ATA TCC CCA GTA TCC GGT TCA ACC ACC TCC CCC AAT GTT TCA ACC GTA GGT TCT
        1305        1314        1323        1332        1341        1350
TAT AGG GGT CAT AGG CCA AGT TGG TGG AGG GGG TTA CAA AGT TGG CAT CCA AGA
--- --- --- --- --- --- --- --- --- --- --- --- --- --- --- --- --- ---
Tyr Arg Gly His Arg Pro Ser Trp Trp Arg Gly Leu Gln Ser Trp His Pro Arg
 Ile Gly Val Ile Gly Gln Val Gly Gly Gly Gly Tyr Lys Val Gly Ile Gln Asp
  *** Gly Ser *** Ala Lys Leu Val Glu Gly Val Thr Lys Leu Ala Ser Lys Ile
```

FIG. 2e

Cys Cys His Val Trp Cys Arg Lys Ser *** Leu His His Pro Arg Gln Pro Leu
Val Val Thr Ser Gly Val Gly Arg Gln Asn Ser Thr Ile Pro Asp Arg Pro Tyr
Leu Leu Leu Pro Gly Leu Val Glu Lys Ile Leu Pro Ser Pro Thr Glu Pro Thr
--- --- --- --- --- --- --- --- --- --- --- --- --- --- --- --- --- ---
ATT GTT GTC ACC TGG GTT GTG GAG AAA CTA ATC TCC ACT ACC CCA GAG ACC CCA
1359 1368 1377 1386 1395 1404
TAA CAA CAG TGG ACC CAA CAC CTC TTT GAT TAG AGG TGA TGG GGT CTC TGG GGT
--- --- --- --- --- --- --- --- --- --- --- --- --- --- --- --- --- ---
Gln Gln Trp Thr Gln His Leu Phe Asp * Arg * Trp Gly Leu Trp Gly
Asn Asn Ser Gly Pro Asn Thr Ser Leu Ile Arg Gly Asp Gly Val Ser Gly Val
Thr Thr Val Asp Pro Thr Pro Leu * Leu Glu Val Met Gly Ser Leu Gly *

Ile * Ile * Gly Lys *** Tyr Pro Leu Ile Pro Phe Thr Pro Thr Pro Pro
Phe Glu Tyr Lys Ala Lys Arg Ile Arg Tyr Tyr Gln Phe Pro Leu Pro Leu Pro
Phe Asn Met Asn Leu Arg Glu Leu Val Thr Thr Asn Ser Leu Tyr Pro Tyr Pro
--- --- --- --- --- --- --- --- --- --- --- --- --- --- --- --- --- ---
TTT TAA GTA TAA ATC GGA AAG ATT ATG CCA TCA TAA CCT TTC CAT CCC CAT CCC
1413 1422 1431 1440 1449 1458
AAA ATT CAT ATT TAG CCT TTC TAA TAC GGT AGT ATT GGA AAG GTA GGG GTA GGG
--- --- --- --- --- --- --- --- --- --- --- --- --- --- --- --- --- ---
Lys Ile His Ile * Pro Phe * Tyr Gly Ser Ile Gly Lys Val Gly Val Gly
Lys Phe Ile Phe Ser Leu Ser Asn Thr Val Val Leu Glu Arg * Gly * Gly
Asn Ser Tyr Leu Ala Phe Leu Ile Arg *** Tyr Trp Lys Gly Arg Gly Arg Gly

Gln His Arg Arg Leu Pro Pro Pro Val Pro Arg His Gln Ile Glu Ala Arg ***
Asn Thr Gly Gly Ser Pro Pro Leu Phe Gln Gly Ile Asn Phe Arg Leu Glu Asn
Thr Pro Ala Ala Gln Pro Pro Ser Ser Ser Ala Ser Thr Ser Asp *** Ser Thr
--- --- --- --- --- --- --- --- --- --- --- --- --- --- --- --- --- ---
CCA ACC ACG GCG GAC TCC CCC CCT CCT TGA CCG GCT ACA ACT TAG AGT CGA GCA
1467 1476 1485 1494 1503 1512
GGT TGG TGC CGC CTG AGG GGG GGA GGA ACT GGC CGA TGT TGA ATC TCA GCT CGT
--- --- --- --- --- --- --- --- --- --- --- --- --- --- --- --- --- ---
Gly Trp Cys Arg Leu Arg Gly Gly Gly Thr Gly Arg Cys *** Ile Ser Ala Arg
Val Gly Ala Ala *** Gly Gly Glu Glu Leu Ala Asp Val Glu Ser Gln Leu Val
Leu Val Pro Pro Glu Gly Gly Arg Asn Trp Pro Met Leu Asn Leu Ser Ser Leu

Cys Glu Leu Ile Ala Ala Leu Thr Arg Arg Lys His His Thr Cys Ile Arg ***
Val Asn Trp Ser Pro Gln Ser His Gly Gly Arg Ile Thr Leu Val Phe Glu Arg
Leu Met Gly Leu His Ser Arg Thr Asp Glu Glu *** Pro Ser Tyr Leu Asn Glu
--- --- --- --- --- --- --- --- --- --- --- --- --- --- --- --- --- ---
ATT GTA AGG TTC TAC CGA CGC TCA CAG GAG GAG AAT ACC ACT CAT GTT TAA GAG
1521 1530 1539 1548 1557 1566
TAA CAT TCC AAG ATG GCT GCG AGT GTC CTC CTC TTA TGG TGA GTA CAA ATT CTC
--- --- --- --- --- --- --- --- --- --- --- --- --- --- --- --- --- ---
* His Ser Lys Met Ala Ala Ser Val Leu Leu Leu Trp * Val Gln Ile Leu
Asn Ile Pro Arg Trp Leu Arg Val Ser Ser Ser Tyr Gly Glu Tyr Lys Phe Ser
Thr Phe Gln Asp Gly Cys Glu Cys Pro Pro Leu Met Val Ser Thr Asn Ser Leu

Phe Pro Pro Phe Gln Leu Tyr Gly Asp Lys Pro Ala Met Gln Leu Pro Lys Gln
Ser Leu Arg Ser Asn Phe Ile Gly Thr Lys Arg Arg Trp Arg Tyr Arg Asn Arg
Leu Phe Ala Pro Ile Ser Ser Val Arg Arg Glu Ala Gly Asp Thr Val Thr Glu
--- --- --- --- --- --- --- --- --- --- --- --- --- --- --- --- --- ---
ATC TTT CCG CCC TTA ACT TCT ATG GGC AGA AAG CCG CGG TAG ACA TTG CCA AAG
1575 1584 1593 1602 1611 1620
TAG AAA GGC GGG AAT TGA AGA TAC CCG TCT TTC GGC GCC ATC TGT AAC GGT TTC
--- --- --- --- --- --- --- --- --- --- --- --- --- --- --- --- --- ---
* Lys Gly Gly Asn * Arg Tyr Pro Ser Phe Gly Ala Ile Cys Asn Gly Phe
Arg Lys Ala Gly Ile Glu Asp Thr Arg Leu Ser Ala Pro Ser Val Thr Val Ser
Glu Arg Arg Glu Leu Lys Ile Pro Val Phe Arg Arg His Leu *** Arg Phe Leu

FIG. 2f

```
 Leu Arg Pro Thr Gly Phe Ile Thr Lys Glu Pro Pro His Lys Trp Ser Pro Gln
Phe Ala Pro His Val Leu Tyr Pro Arg Arg Arg Leu Ile Asn Gly Leu His Ser
Ser Pro Pro Thr Tyr Trp Ile His Asp Glu Gly Ser Ser Thr Glu Leu Ile Ala
--- --- --- --- --- --- --- --- --- --- --- --- --- --- --- --- --- ---
ACT TCC GCC CCA CAT GGT TTA TAC CAG AAG AGG CCT CCT ACA AAG GTT CTA CCG
        1629        1638        1647        1656        1665        1674
TGA AGG CGG GGT GTA CCA AAT ATG GTC TTC TCC GGA GGA TGT TTC CAA GAT GGC
--- --- --- --- --- --- --- --- --- --- --- --- --- --- --- --- --- ---
*** Arg Arg Gly Val Pro Asn Met Val Phe Ser Gly Gly Cys Phe Gln Asp Gly
 Glu Gly Gly Val Tyr Gln Ile Trp Ser Ser Pro Glu Asp Val Ser Lys Met Ala
  Lys Ala Gly Cys Thr Lys Tyr Gly Leu Leu Arg Arg Met Phe Pro Arg Trp Leu

  Pro Pro Pro Asp Thr Lys Gln Pro Leu Ala Glu Lys Ala Val Asp Asp *** Leu
 Arg Pro Arg Thr Arg Arg Arg Arg Tyr Arg Arg Arg Pro Trp Thr Met Arg Tyr
Ala Pro Ala Pro Gly Asp Glu Ala Thr Val Gly Gly Gln Gly Arg *** Gly Ile
--- --- --- --- --- --- --- --- --- --- --- --- --- --- --- --- --- ---
ACG CCC CCG CCC AGG CAG AAG ACG CCA TTG CGG AGG AAC CGG TGC AGT AGG ATA
        1683        1692        1701        1710        1719        1728
TGC GGG GGC GGG TCC GTC TTC TGC GGT AAC GCC TCC TTG GCC ACG TCA TCC TAT
--- --- --- --- --- --- --- --- --- --- --- --- --- --- --- --- --- ---
Cys Gly Gly Gly Ser Val Phe Cys Gly Asn Ala Ser Leu Ala Thr Ser Ser Tyr
 Ala Gly Ala Gly Pro Ser Ser Ala Val Thr Pro Pro Trp Pro Arg His Pro Ile
  Arg Gly Arg Val Arg Leu Leu Arg *** Arg Leu Leu Gly His Val Ile Leu ***

  Leu Ser Leu Leu Ala Ser Ser Tyr Tyr
 Phe His Phe Phe His Ala Ala Thr Thr Asn
Phe Thr Phe Ser Thr Arg Gln Gln Leu Ile
--- --- --- --- --- --- --- --- --- --- -
TTT TCA CTT TCT TCA CGC GAC GAC ATC ATA A 5'
        1737        1746        1755
AAA AGT GAA AGA AGT GCG CTG CTG TAG TAT T 3'
--- --- --- --- --- --- --- --- --- --- -
Lys Ser Glu Arg Ser Ala Leu Leu *** Tyr
 Lys Val Lys Glu Val Arg Cys Cys Ser Ile
  Lys *** Lys Lys Cys Cys Ala Ala Val Val
```

FIG. 2g

```
                             10         20         30         40         50
circopormank    1 ACCAGCGCAC TTCGGCAGCG GCAGCACCTC GGCAGCGTCA GTGAAAATGC  50
circopormeeh    1 ACCAGCGCAC TTCGGCAGCG GCAGCACCTC GGCAGCGTCA GTGAAAATGC  50
circopordfp     1 ACCAGCGCAC TTCGGCAGCG GCAGCACCTC GGCAGCGTCA GTGAAAATGC  50

                             60         70         80         90        100
circopormank   51 CAAGCAAGAA AAGCGGCCCG CAACCCCATA AGAGGTGGGT GTTCACCCTT  100
circopormeeh   51 CAAGCAAGAA AAGCGGCCCG CAACCCCATA AGAGGTGGGT GTTCACCCTT  100
circopordfp    51 CAAGCAAGAA AAGCGGCCCG CAACCCCATA AGAGGTGGGT GTTCACCCTT  100

                            110        120        130        140        150
circopormank  101 AATAATCCTT CCGAGGAGGA GAAAAACAAA ATACGGGAGC TTCCAATCTC  150
circopormeeh  101 AATAATCCTT CCGAGGAGGA GAAAAACAAA ATACGGGAGC TTCCAATCTC  150
circopordfp   101 AATAATCCTT CCGAGGAGGA GAAAAACAAA ATACGGGAGC TTCCAATCTC  150

                            160        170        180        190        200
circopormank  151 CCTTTTTGAT TATTTTGTTT GCGGAGAGGA AGGTTTGGAA GAGGGTAGAA  200
circopormeeh  151 CCTTTTTGAT TATTTTGTTT GCGGAGAGGA AGGTTTGGAA GAGGGTAGAA  200
circopordfp   151 CCTTTTTGAT TATTTTGTTT GTGGCGAGGA AGGTTTGGAA GAGGGTAGAA  200

                            210        220        230        240        250
circopormank  201 CTCCTCACCT CCAGGGGTTT GCTAATTTTG CTAAGAAGCA GACTTTTAAC  250
circopormeeh  201 CTCCTCACCT CCAGGGGTTT GCGAATTTTG CTAAGAAGCA GACTTTTAAC  250
circopordfp   201 CTCCTCACCT CCAGGGGTTT GCGAATTTTG CTAAGAAGCA GACTTTTAAC  250

                            260        270        280        290        300
circopormank  251 AAGGTGAAGT GGTATTTTGG TGCCCGCTGC CACATCGAGA AAGCGAAAGG  300
circopormeeh  251 AAGGTGAAGT GGTATTTTGG TGCCCGCTGC CACATCGAGA AAGCGAAAGG  300
circopordfp   251 AAGGTGAAGT GGTATTTTGG TGCCCGCTGC CACATCGAGA AAGCGAAAGG  300

                            310        320        330        340        350
circopormank  301 AACCGACCAG CAGAATAAAG AATACTGCAG TAAAGAAGGC CACATACTTA  350
circopormeeh  301 AACCGACCAG CAGAATAAAG AATACTGCAG TAAAGAAGGC CACATACTTA  350
circopordfp   301 AACCGACCAG CAGAATAAAG AATACTGCAG TAAAGAAGGC CACATACTTA  350

                            360        370        380        390        400
circopormank  351 TCGAGTGTGG AGCTCCGCGG AACCAGGGGA AGCGCAGCGA CCTGTCTACT  400
circopormeeh  351 TCGAGTGTGG AGCTCCGCGG AACCAGGGGA AGCGCAGCGA CCTGTCTACT  400
circopordfp   351 TCGAGTGTGG AGCTCCGCGG AACCAGGGGA AGCGCAGCGA CCTGTCTACT  400

                            410        420        430        440        450
circopormank  401 GCTGTGAGTA CCCTTTTGGA GACGGGGTCT TTGGTGACTG TAGCCGAGCA  450
circopormeeh  401 GCTGTGAGTA CCCTTTTGGA GACGGGGTCT TTGGTGACTG TAGCCGAGCA  450
circopordfp   401 GCTGTGAGTA CCCTTTTGGA GACGGGGTCT TTGGTGACTG TAGCCGAGCA  450

                            460        470        480        490        500
circopormank  451 GTTCCCTGTA ACGTATGTGA GAAATTTCCG CGGGCTGGCT GAACTTTTGA  500
circopormeeh  451 GTTCCCTGTA ACGTATGTGA GAAATTTCCG CGGGCTGGCT GAACTTTTGA  500
circopordfp   451 GTTTCCTGTA ACGTATGTGA GAAATTTCCG CGGGCTGGCT GAACTTTTGA  500

                            510        520        530        540        550
circopormank  501 AAGTGAGCGG GAAGATGCAG CAGCGTGATT GGAAGACAGC TGTACACGTC  550
circopormeeh  501 AAGTGAGCGG GAAGATGCAG CAGCGTGATT GGAAGACAGC TGTACACGTC  550
circopordfp   501 AAGTGAGCGG GAAGATGCAG CAGCGTGATT GGAAGACAGC TGTACACGTC  550

                            560        570        580        590        600
circopormank  551 ATAGTGGGCC CGCCCGGTTG TGGGAAGAGC CAGTGGCCCC GTAATTTTGC  600
circopormeeh  551 ATAGTGGGCC CGCCCGGTTG TGGGAAGAGC CAGTGGCCCC GTAATTTTGC  600
circopordfp   551 ATAGTGGGCC CGCCCGGTTG TGGGAAGAGC CAGTGGCCCC GTAATTTTGC  600
```

FIG. 3a

```
                        610        620        630        640        650
circopormank   601 TGAGCCTAGC GACACCTACT GGAAGCCTAG TAGAAATAAG TGGTGGGATG 650
circopormeeh   601 TGAGCCTAGG GACACCTACT GGAAGCCTAG TAGAAATAAG TGGTGGGATG 650
circopordfp    601 TGAGCCTAGG GACACCTACT GGAAGCCTAG TAGAAATAAG TGGTGGGATG 650

                        660        670        680        690        700
circopormank   651 GATATCATGG AGAAGAAGTT GTTGTTTTGG ATGATTTTTA TGACTGGTTA 700
circopormeeh   651 GATATCATGG AGAAGAAGTT GTTGTTTTGG ATGATTTTTA TGACTGGTTA 700
circopordfp    651 GATATCATGG AGAAGAAGTT GTTGTTTTGG ATGATTTTTA TGACTGGTTA 700

                        710        720        730        740        750
circopormank   701 CCTTGGGATG ATCTACTGAG ACTGTGTGAC CGGTATCCAT TGACTGTAGA 750
circopormeeh   701 CCTTGGGATG ATCTACTGAG ACTGTGTGAC CGGTATCCAT TGACTGTAGA 750
circopordfp    701 CCTTGGGATG ATCTACTGAG ACTGTGTGAC CGGTATCCAT TGACTGTAGA 750

                        760        770        780        790        800
circopormank   751 GACTAAAGGC GGTACTGTTC CTTTTTTGGC TCGCAGTATT TTGATTACCA 800
circopormeeh   751 GACTAAAGGG GGTACTGTTC CTTTTTTGGC CCGCAGTATT TTGATTACCA 800
circopordfp    751 GACTAAAGGG GGTACTGTTC CTTTTTTGGC CCGCAGTATT TTGATTACCA 800

                        810        820        830        840        850
circopormank   801 GCAATCAGGC CCCCCAGGAA TGGTACTCCT CAACTGCTGT CCCAGCTGTA 850
circopormeeh   801 GCAATCAGGC CCCCCAGGAA TGGTACTCCT CAACTGCTGT CCCAGCTGTA 850
circopordfp    801 GCAATCAGGC CCCCCAGGAA TGGTACTCCT CAACTGCTGT CCCAGCTGTA 850

                        860        870        880        890        900
circopormank   851 GAAGCTCTCT ATCGGAGGAT TACTACTTTG CAATTTTGGA AGACTGCTGG 900
circopormeeh   851 GAAGCTCTCT ATCGGAGGAT TACTACTTTG CAATTTTGGA AGACTGCTGG 900
circopordfp    851 GAAGCTCTCT ATCGGAGGAT TACTACTTTG CAATTTTGGA AGACTGCTGG 900

                        910        920        930        940        950
circopormank   901 AGAACAATCA ACGGAGGTAC CCGAAGGCCG ATTTGAAGCA GTGGACCCAC 950
circopormeeh   901 AGAACAATCC ACGGAGGTAC CCGAAGGCCG ATTTGAAGCA GTGGACCCAC 950
circopordfp    901 AGAACAATCC ACGGAGGTAC CCGAAGGCCG ATTTGAAGCA GTGGACCCAC 950

                        960        970        980        990       1000
circopormank   951 CCTGTGCCCT TTTCCCATAT AAAATAAATT ACTGAGTCTT TTTTGTTATC 1000
circopormeeh   951 CCTGTGCCCT TTTCCCATAT AAAATAAATT ACTGAGTCTT TTTTGTTATC 1000
circopordfp    951 CCTGTGCCCT TTTCCCATAT AAAATAAATT ACTGAGTCTT TTTTGTTATC 1000

                       1010       1020       1030       1040       1050
circopormank  1001 ACATCGTAAT GGTTTTTATT TTTATTTATT TAGAGGGTCT TTTAGGATAA 1050
circopormeeh  1001 ACATCGTAAT GGTTTTTATT TTTATTTATT TAGAGGGTCT TTTAGGATAA 1050
circopordfp   1001 ACATCGTAAT GGTTTTTATT TTTATTCATT TAGAGGGTCT TTCAGGATAA 1050

                       1060       1070       1080       1090       1100
circopormank  1051 ATTCTCTGAA TTGTACATAA ATAGTCAGCC TTACCACATA ATTTTGGGCT 1100
circopormeeh  1051 ATTCTCTGAA TTGTACATAA ATAGTCAGCC TTACCACATA ATTTTGGGCT 1100
circopordfp   1051 ATTCTCTGAA TTGTACATAA ATAGTCAACC TTACCACATA ATTTTGGGCT 1100

                       1110       1120       1130       1140       1150
circopormank  1101 GTGGCTGCAT TTTGGAGCGC ATAGCCGAGG CCTGTGTGCT CGACATTGGT 1150
circopormeeh  1101 GTGGCTGCAT TTTGGAGCGC ATAGCCGAGG CCTGTGTGCT CGACATTGGT 1150
circopordfp   1101 GTGGTTGCAT TTTGGAGCGC ATAGCCCAGG CCTGTGTGCT CGACATTGGT 1150

                       1160       1170       1180       1190       1200
circopormank  1151 GTGGGTATTT AAATGGAGCC ACAGCTGGTT TCTTTTATTA TTTGGGTGGA 1200
circopormeeh  1151 GTGGGTATTT AAATGGAGCC ACAGCTGGTT TCTTTTATTA TTTGGGTGGA 1200
circopordfp   1151 GTGGGTATTT AAATGGAGCC ACAGCTGGTT TCTTTTATTA TTTGGCTGGA 1200
```

FIG. 3b

```
                          1210       1220       1230       1240       1250
circopormank   1201 ACCATTCAAT TGTTTGGTCC AGCTCAGGTT TGGGGGTGAA GTACCTGGAG  1250
circopormeeh   1201 ACCAATCAAT TGTTTGGTCC AGCTCAGGTT TGGGGGTGAA GTACCTGGAG  1250
circopordfp    1201 ACCAATCAAT TGTTTGGTCT AGCTCTGGTT TGGGGGTGAA GTACCTGGAG  1250

                          1260       1270       1280       1290       1300
circopormank   1251 TGGTAGGTAA AGGGCTGCCT TATGGTGTGG CGGGAGGAGT AGTTAATATA  1300
circopormeeh   1251 TGGTAGGTAA AGGGCTGCCT TATGGTGTGG CGGGAGGAGT AGTTAATATA  1300
circopordfp    1251 TGGTAGGTAA AGGGCTGCCT TATGGTGTGG CGGGAGGAGT AGTTAATATA  1300

                          1310       1320       1330       1340       1350
circopormank   1301 GGGGTCATAG GCCAAGTTGG TGGAGGGGGT TACAAAGTTG GCATCCAAGA  1350
circopormeeh   1301 GGGGTCATAG GCCAAGTTGG TGGAGGGGGT TACAAAGTTG GCATCCAAGA  1350
circopordfp    1301 GGGGTCATAG GCCAAGTTGG TGGAGGGGGT TACAAAGTTG GCATCCAAGA  1350

                          1360       1370       1380       1390       1400
circopormank   1351 TAACAACAGT GGACCCAACA CCTCTTTCAT TAGAGGTGAT GGGGTCTCTG  1400
circopormeeh   1351 TAACAACAGT GGACCCAACA CCTCTTTGAT TAGAGGTGAT GGGGTCTCTG  1400
circopordfp    1351 TAACAACAGT GGACCCAACA CCTCTTTGAT TAGAGGTGAT GGGGTCTCTG  1400

                          1410       1420       1430       1440       1450
circopormank   1401 GGCTAAAATT CATATTTAGC CTTTCTAATA CGGTAGTATT GGAAAGGTAG  1450
circopormeeh   1401 GGCTAAAATT CATATTTAGC CTTTCTAATA CGGTAGTATT GGAAAGGTAG  1450
circopordfp    1401 GGCTAAAATT CATATTTAGC CTTTCTAATA CGGTAGTATT GGAAAGGTAG  1450

                          1460       1470       1480       1490       1500
circopormank   1451 GGGTAGGGGG TTGGTGCCGC CTGAGGGGGG GAGGAACTGG CCGATGTTGA  1500
circopormeeh   1451 GGGTAGGGGG TTGGTGCCGC CTGAGGGGGG GAGGAACTGG CCGATGTTGA  1500
circopordfp    1451 GGGTAGGGGG TTGGTGCCGC CTGAGGGGGG GAGGAACTGG CCGATGTTGA  1500

                          1510       1520       1530       1540       1550
circopormank   1501 ATCTGAGGTG GTTAACATGC CAAGATGGCT GCGAGTATCC TCCTTTTATG  1550
circopormeeh   1501 ATTTGAGGTA GTTAACATTC CAAGATGGCT GCGAGTATCC TCCTTTTATG  1550
circopordfp    1501 ATCTCAGCTC GTTAACATTC CAAGATGGCT GCGAGTGTCC TCCTCTTATG  1550

                          1560       1570       1580       1590       1600
circopormank   1551 GTGATTACAA ATTCTTTAGA AAGGCGGCAA TTGAAGATAC CCGTCTTTCG  1600
circopormeeh   1551 GTGAGTACAA ATTCTGTAGA AAGGCGGGAA TTGAAGATAC CCGTCTTTCG  1600
circopordfp    1551 GTGAGTACAA ATTCTCTAGA AAGGCGGGAA TTGAAGATAC CCGTCTTTCG  1600

                          1610       1620       1630       1640       1650
circopormank   1601 GCGCCATCTG TAACGGTTTC TGAAGGCGGG GTGTGCCAAA TATGGTCTTC  1650
circopormeeh   1601 GCGCCATCTG TAACGGTTTC TGAAGGCGGG GTGTGCCAAA TATGGTCTTC  1650
circopordfp    1601 GCGCCATCTG TAACGGTTTC TGAAGGCGGG GTGTACCAAA TATGGTCTTC  1650

                          1660       1670       1680       1690       1700
circopormank   1651 TCCGGAGGAT GTTTCCAAGA TGGCTGCGGG GGCGGGTCCT TCTTCTGCGG  1700
circopormeeh   1651 TCCGGAGGAT GTTTCCAAGA TGGCTGCGGG GGCGGGTCCT TCTTCTGCGG  1700
circopordfp    1651 TCCGGAGGAT GTTTCCAAGA TGGCTGCGGG GGCGGGTCCG TCTTCTGCGG  1700

                          1710       1720       1730       1740       1750
circopormank   1701 TAACGCCTCC TTGGCCACGT CATCCTATAA AAGTGAAAGA AGTGCGCTGC  1750
circopormeeh   1701 TAACGCCTCC TTGGCCACGT CATCCTATAA AAGTGAAAGA AGTGCGCTGC  1750
circopordfp    1701 TAACGCCTCC TTGGCCACGT CATCCTATAA AAGTGAAAGA AGTGCGCTGC  1750

                          1760       1770       1780       1790       1800
circopormank   1751 TGTAGTATT. .......... .......... .......... ..........  1800
circopormeeh   1751 TGTAGTATT. .......... .......... .......... ..........  1800
circopordfp    1751 TGTAGTATT. .......... .......... .......... ..........  1800
```

FIG. 3c

```
                        10         20         30         40         50
circopormank    1 NPSKKSGPQP HKRWVFTLNN PSEEEKNKIR ELPISLFDYF VCGEEGLEEG  50
circopormeeh    1 NPSKKSGPQP HKRWVFTLNN PSEEEKNKIR ELPISLFDYF VCGEEGLEEG  50
circopordfp[    1 NPSKKSGPQP HKRWVFTLNN PSEEEKNKIR ELPISLFDYF VCGEEGLEEG  50

                        60         70         80         90        100
circopormank   51 RTAHLQGFAN FAKKQTFNKV KWYFGARCHI EKAKGTDQQN KEYCSKEGHI 100
circopormeeh   51 RTPHLQGFAN FAKKQTFNKV KWYFGARCHI EKAKGTDQQN KEYCSKEGHI 100
circopordfp[   51 RTPHLQGFAN FAKKQTFNKV KWYFGARCHI EKAKGTDQQN KEYCSKEGHI 100

                       110        120        130        140        150
circopormank  101 LIECGAPRNQ GKRSDLSTAV STLLETGSLV TVAEQFPVTY VRNFRGLAEL 150
circopormeeh  101 LIECGAPRNQ GKRSDLSTAV STLLETGSLV TVAEQFPVTY VRNFRGLAEL 150
circopordfp[  101 LIECGAPRNQ GKRSDLSTAV STLLETGSLV TVAEQFPVTY VRNFRGLAEL 150

                       160        170        180        190        200
circopormank  151 LKVSGKMQQR DWKTAVHVIV GPPGCGKSQW ARNFAEPSQT YWKPSRNKWH 200
circopormeeh  151 LKVSGKMQQR DWKTAVHVIV GPPGCGKSQW ARNFAEPRQT YWKPSRNKWH 200
circopordfp[  151 LKVSGKMQQR DWKTAVHVIV GPPGCGKSQW ARNFAEPRQT YWKPSRNKWH 200

                       210        220        230        240        250
circopormank  201 DGYHGEEVVV LDDFYGWLPW DDLLRLCDRY PLTVETKGGT VPFLARSILI 250
circopormeeh  201 DGYHGEEVVV LDDFYGWLPW DDLLRLCDRY PLTVETKGGT VPFLARSILI 250
circopordfp[  201 DGYHGEEVVV LDDFYGWLPW DDLLRLCDRY PLTVETKGGT VPFLARSILI 250

                       260        270        280        290        300
circopormank  251 TSNQAPQEWY SSTAVPAVEA LYRRITTLQF WKTAGEQSTE VPEGRFEAVD 300
circopormeeh  251 TSNQAPQEWY SSTAVPAVEA LYRRITTLQF WKTAGEQSTE VPEGRFEAVD 300
circopordfp[  251 TSNQAPQEWY SSTAVPAVEA LYRRITTLQF WKTAGEQSTE VPEGRFEAVD 300

                       310        320        330        340        350
circopormank  301 PPCALFPYKI NY........ .......... .......... .......... 350
circopormeeh  301 PPCALFPYKI NY........ .......... .......... .......... 350
circopordfp[  301 PPCALFPYKI NY........ .......... .......... .......... 350
```

FIG. 4

```
                         10         20         30         40         50
circopormank   1 MTWPRRRYRR RRTRPRSHLG NILRRRPYLA HPAFRNRYRW RRKTGIFNQR   50
circopormeeh   1 MTWPRRRYRR RRTRPRSHLG NILRRRPYLA HPAFRNRYRW RRKTGIFNSR   50
circopordfp[   1 MTWPRRRYRR RRTRPRSHLG NILRRRPYLV HPAFRNRYRW RRKTGIFNSR   50

                         60         70         80         90        100
circopormank  51 LSKEFVITIK GGYSQPSWIV NILRFNIGQF LPPSGGTNPL PLPFQYYRIR  100
circopormeeh  51 LSTEFVLTIK GGYSQPSWNV NYLKFNIGQF LPPSGGTNPL PLPFQYYRIR  100
circopordfp[  51 LSREFVLTIR GGISQPSWNV NFLRFNIGQF LPPSGGTNPL PLPFQYYRIR  100

                        110        120        130        140        150
circopormank 101 KAKYEFYPRD PITSNERGVG STVVILDANF VTPSTNLAYD PYINYSSRHT  150
circopormeeh 101 KAKYEFYPRD PITSNQRGVG STVVILDANF VTPSTNLAYD PYINYSSRHT  150
circopordfp[ 101 KAKYEFYPRD PITSNQRGVG STVVILDANF VTPSTNLAYD PYINYSSRHT  150

                        160        170        180        190        200
circopormank 151 IRQPFTYHSR YFTPKPELDQ TIEWFHPNNK RNQLWLHLNT HTNVEHTGLG  200
circopormeeh 151 IRQPFTYHSR YFTPKPELDQ TIDWFHPNNK RNQLWLHLNT HTNVEHTGLG  200
circopordfp[ 151 IRQPFTYHSR YFTPKPELDQ TIDWFQPNNK RNQLWLHLNT HTNVEHTGLG  200

                        210        220        230        240        250
circopormank 201 YALQNAATAQ NYVVRLTIYV QFREFILKDP LNK*...... ..........  250
circopormeeh 201 YALQNAATAQ NYVVRLTIYV QFREFILKDP LNK*...... ..........  250
circopordfp[ 201 YALQNATTAQ NYVVRLTIYV QFREFILKDP LNE*...... ..........  250
```

FIG. 5

```
                         10         20         30         40         50
circopormank   1 MISIPPLIST RLPVGVARLS KITGPLALPT TGRAHYDVYS CLPITLLHLP   50
circopormeeh   1 MISIPPLIST RLPVGVPRLS KITGPLALPT TGRAHYDVYS CLPITLLHLP   50
circopordfp[   1 MISIPPLIST RLPVGVPRLS KITGPLALPT TGRAHYDVYS CLPITLLHLP   50

                         60         70         80         90        100
circopormank  51 AHFQKFSQPA EISHIRYREL LGYSHQRPRL QKGTHSSRQV AALPLVPRSS  100
circopormeeh  51 AHFQKFSQPA EISHIRYREL LGYSHQRPRL QKGTHSSRQV AALPLVPRSS  100
circopordfp[  51 AHFQKFSQPA EISHIRYRKL LGYSHQRPRL QKGTHSSRQV AALPLVPRSS  100

                        110        120        130        140        150
circopormank 101 TLDKYVAFFT AVFFILLVGS FRFLDVAAGT KIPLHLVKSL LLSKISKPLE  150
circopormeeh 101 TLDKYVAFFT AVFFILLVGS FRFLDVAAGT KIPLHLVKSL LLSKIRKPLE  150
circopordfp[ 101 TLDKYVAFFT AVFFILLVGS FRFLDVAAGT KIPLHLVKSL LLSKIRKPLE  150

                        160        170        180        190        200
circopormank 151 VSSSTLFQTF LSANKIIKKG DWKLPYFVFL LLGRIIKGEH PPLMGLRAAF  200
circopormeeh 151 VRSSTLFQTF LSANKIIKKG DWKLPYFVFL LLGRIIKGEH PPLMGLRAAF  200
circopordfp[ 151 VRSSTLFQTF LATNKIIKKG DWKLPYFVFL LLGRIIKGEH PPLMGLRAAF  200

                        210        220        230        240        250
circopormank 201 LAWHFH*... .......... .......... .......... ..........  250
circopormeeh 201 LAWHFEH... .......... .......... .......... ..........  250
circopordfp[ 201 LAWHFH-... .......... .......... .......... ..........  250
```

FIG. 6

```
     Leu Ala Ser Arg Cys Arg Cys Cys Arg Pro Leu Val Glu Ala Ala Val His Gly
    Trp Arg Val Glu Ala Ala Ala Ala Gly Arg Cys Cys Arg Leu Leu Leu Met Gly
   Gly Ala Cys Lys Pro Leu Pro Leu Val Glu Ala Ala Gly *** Cys Cys Cys Ala
   --- --- --- --- --- --- --- --- --- --- --- --- --- --- --- --- --- ---
3' TGG TCG CGT GAA GCC GTC GCC GTC GTG GAG CCG TCG TGG AGT CGT CGT TGT ACG
            9          18          27          36          45          54
5' ACC AGC GCA CTT CGG CAG CGG CAG CAC CTC GGC AGC ACC TCA GCA GCA ACA TGC
   --- --- --- --- --- --- --- --- --- --- --- --- --- --- --- --- --- ---
   Thr Ser Ala Leu Arg Gln Arg Gln His Leu Gly Ser Thr Ser Ala Ala Thr Cys
    Pro Ala His Phe Gly Ser Gly Ser Thr Ser Ala Ala Pro Gln Gln Gln His Ala
     Gln Arg Thr Ser Ala Ala Ala Ala Pro Arg Gln His Leu Ser Ser Asn Met Pro

     Ala Leu Leu Ile Ser Ser Ala Ser Gly Leu Gly Met Phe Pro Pro His Glu Ser
    Leu Leu Phe Phe Pro Leu Leu Pro Gly Trp Gly Trp Leu Leu His Thr Asn Val
   Trp Cys Ser Ser His Phe Phe Arg Val Gly Val Gly Tyr Phe Thr Pro Thr ***
   --- --- --- --- --- --- --- --- --- --- --- --- --- --- --- --- --- ---
   GGT CGT TCT TCT TAC CTT CTT CGC CTG GGG TTG GGG TAT TTT CCA CCC ACA AGT
            63          72          81          90          99         108
   CCA GCA AGA AGA ATG GAA GAA GCG GAC CCC AAC CCC ATA AAA GGT GGG TGT TCA
   --- --- --- --- --- --- --- --- --- --- --- --- --- --- --- --- --- ---
   Pro Ala Arg Arg Met Glu Glu Ala Asp Pro Asn Pro Ile Lys Gly Gly Cys Ser
    Gln Gln Glu Glu Trp Lys Lys Arg Thr Pro Thr Pro *** Lys Val Gly Val His
     Ser Lys Lys Asn Gly Arg Ser Gly Pro Gln Pro His Lys Arg Trp Val Phe Thr

     Gln Ile Ile Arg Gly Phe Val Leu Ala Leu Phe Tyr Pro Ile Lys Trp Tyr Gly
    Arg Phe Leu Gly Glu Ser Ser Ser Arg Leu Phe Ile Arg Ser Arg Gly Ile Asp
   Glu Ser Tyr Asp Lys Arg Leu Arg Ala Cys Ser Phe Val Pro Asp Glu Leu Ile
   --- --- --- --- --- --- --- --- --- --- --- --- --- --- --- --- --- ---
   GAG ACT TAT TAG GAA GGC TTC TGC TCG CGT TCT TTT ATG CCC TAG AAG GTT ATA
           117         126         135         144         153         162
   CTC TGA ATA ATC CTT CCG AAG ACG AGC GCA AGA AAA TAC GGG ATC TTC CAA TAT
   --- --- --- --- --- --- --- --- --- --- --- --- --- --- --- --- --- ---
   Leu *** Ile Ile Leu Pro Lys Thr Ser Ala Arg Lys Tyr Gly Ile Phe Gln Tyr
    Ser Glu *** Ser Phe Arg Arg Arg Ala Gln Glu Asn Thr Gly Ser Ser Asn Ile
     Leu Asn Asn Pro Ser Glu Asp Glu Arg Lys Lys Ile Arg Asp Leu Pro Ile Ser

     *** Lys Ile Ile Lys Asn Asn Ala Leu Leu Thr Ile Leu Phe Ser Ser Cys Arg
    Arg Asn Ser *** Lys Ile Thr Pro Ser Ser Pro Leu Ser Ser Pro Arg Val Gly
   Gly Ile Gln Asn Asn *** Gln Gln Arg Pro Pro Tyr His Pro Leu Val Phe Val
   --- --- --- --- --- --- --- --- --- --- --- --- --- --- --- --- --- ---
   GGG ATA AAC TAA TAA AAT AAC AAC CGC TCC TCC CAT TAC TCC TTC CTG CTT GTG
           171         180         189         198         207         216
   CCC TAT TTG ATT ATT TTA TTG TTG GCG AGG AGG GTA ATG AGG AAG GAC GAA CAC
   --- --- --- --- --- --- --- --- --- --- --- --- --- --- --- --- --- ---
   Pro Tyr Leu Ile Ile Leu Leu Leu Ala Arg Arg Val Met Arg Lys Asp Glu His
    Pro Ile *** Leu Phe Tyr Cys Trp Arg Gly Gly *** *** Gly Arg Thr Asn Thr
     Leu Phe Asp Tyr Phe Ile Val Gly Glu Glu Gly Asn Glu Glu Gly Arg Thr Pro

     Val Glu Leu Pro Glu Ser Ile Lys His Leu Leu Leu Ser Lys Ile Phe His Leu
    *** Arg Trp Pro Asn Ala Leu Lys Thr Phe Phe Cys Val Lys Leu Leu Thr Phe
   Glu Gly Gly Pro Thr Arg *** Asn Gln Ser Ser Ala Ser Lys *** Tyr Leu Ser
   --- --- --- --- --- --- --- --- --- --- --- --- --- --- --- --- --- ---
   GAG TGG AGG TCC CCA AGC GAT TAA AAC ACT TCT TCG TCT GAA AAT TAT TTC ACT
           225         234         243         252         261         270
   CTC ACC TCC AGG GGT TCG CTA ATT TTG TGA AGA AGC AGA CTT TTA ATA AAG TGA
   --- --- --- --- --- --- --- --- --- --- --- --- --- --- --- --- --- ---
   Leu Thr Ser Arg Gly Ser Leu Ile Leu *** Arg Ser Arg Leu Leu Ile Lys ***
    Ser Pro Pro Gly Val Arg *** Phe Cys Glu Glu Ala Asp Phe *** *** Ser Glu
     His Leu Gln Gly Phe Ala Asn Phe Val Lys Lys Gln Thr Phe Asn Lys Val Lys
```

FIG. 8a

```
Pro Ile Gln Thr Gly Ala Ala Val Asp Leu Phe Arg Phe Ser Cys Ile Leu Leu
His Tyr Lys Pro Ala Arg Gln Trp Met Ser Phe Ala Phe Pro Val Ser *** Cys
Thr Thr Asn Pro His Gly Ser Gly Cys Arg Ser Leu Ser Leu Phe Leu Asp Ala
--- --- --- --- --- --- --- --- --- --- --- --- --- --- --- --- --- ---
TCA CCA TAA ACC CAC GGG CGA CGG TGT AGC TCT TTC GCT TTC CTT GTC TAG TCG
        279         288         297         306         315         324
AGT GGT ATT TGG GTG CCC GCT GCC ACA TCG AGA AAG CGA AAG GAA CAG ATC AGC
--- --- --- --- --- --- --- --- --- --- --- --- --- --- --- --- --- ---
Ser Gly Ile Trp Val Pro Ala Ala Thr Ser Arg Lys Arg Lys Glu Gln Ile Ser
Val Val Phe Gly Cys Pro Leu Pro His Arg Glu Ser Glu Arg Asn Arg Ser Ala
Trp Tyr Leu Gly Ala Arg Cys His Ile Glu Lys Ala Lys Gly Thr Asp Gln Gln
```

```
Ile Phe Phe Val Ala Thr Phe Phe Ala Val *** Gln His Leu Thr Ser Ser Arg
Phe Leu Ser Tyr Gln Leu Leu Ser Pro Leu Lys Ser His Ser His Pro Ala Gly
Ser Tyr Leu Ile Ser Cys Tyr Leu Leu Cys Ser Val Ser Pro Thr His Leu Glu
--- --- --- --- --- --- --- --- --- --- --- --- --- --- --- --- --- ---
TCT TAT TTC TTA TGA CGT CAT TTC TTC CGT TGA ATG ACT ACC TCA CAC CTC GAG
        333         342         351         360         369         378
AGA ATA AAG AAT ACT GCA GTA AAG AAG GCA ACT TAC TGA TGG AGT GTG GAG CTC
--- --- --- --- --- --- --- --- --- --- --- --- --- --- --- --- --- ---
Arg Ile Lys Asn Thr Ala Val Lys Lys Ala Thr Tyr *** Trp Ser Val Glu Leu
Glu *** Arg Ile Leu Gln *** Arg Arg Gln Leu Thr Asp Gly Val Trp Ser Ser
Asn Lys Glu Tyr Cys Ser Lys Glu Gly Asn Leu Leu Met Glu Cys Gly Ala Pro
```

```
Ser Arg Leu Ser Leu Pro Thr Val Gln Arg Ser Ser His Thr Gly Gln Gln Leu
Leu Asp *** Pro Cys Arg Leu Ser Arg Asp Val Ala Thr Leu Val Lys Asn Ser
*** Ile Glu Pro Val Val Ser His Gly Thr *** Gln Gln Ser Tyr Arg Thr Pro
--- --- --- --- --- --- --- --- --- --- --- --- --- --- --- --- --- ---
GAT CTA GAG TCC CTG TTG CCT CAC TGG ACA GAT GAC GAC ACT CAT GGA ACA ACC
        387         396         405         414         423         432
CTA GAT CTC AGG GAC AAC GGA GTG ACC TGT CTA CTG CTG TGA GTA CCT TGT TGG
--- --- --- --- --- --- --- --- --- --- --- --- --- --- --- --- --- ---
Leu Asp Leu Arg Asp Asn Gly Val Thr Cys Leu Leu Leu *** Val Pro Cys Trp
*** Ile Ser Gly Thr Thr Glu *** Pro Val Tyr Cys Cys Glu Tyr Leu Val Gly
Arg Ser Gln Gly Gln Arg Ser Asp Leu Ser Thr Ala Val Ser Thr Leu Leu Glu
```

```
Ala Pro Thr Gln His Gly Asn Cys Leu Leu Val Arg Tyr Arg Lys Asp Ser Ile
Leu Pro Leu Arg Thr Val Thr Ala Ser Cys Cys Gly Thr Val Asn Thr Leu Phe
Ser Arg Ser Asp Pro Ser Arg Gln Leu Ala Ala Gly Gln Leu Thr Gln *** Phe
--- --- --- --- --- --- --- --- --- --- --- --- --- --- --- --- --- ---
TCT CGC CCT CAG ACC ACT GGC AAC GTC TCG TCG TGG GAC ATT GCA AAC AGT CTT
        441         450         459         468         477         486
AGA GCG GGA GTC TGG TGA CCG TTG CAG AGC AGC ACC CTG TAA CGT TTG TCA GAA
--- --- --- --- --- --- --- --- --- --- --- --- --- --- --- --- --- ---
Arg Ala Gly Val Trp *** Pro Leu Gln Ser Ser Thr Leu *** Arg Leu Ser Glu
Glu Arg Glu Ser Gly Asp Arg Cys Arg Ala Ala Pro Cys Asn Val Cys Gln Lys
Ser Gly Ser Leu Val Thr Val Ala Glu Gln His Pro Val Thr Phe Val Arg Asn
```

```
Glu Ala Pro Gln Ser Phe Lys Gln Phe His Ala Pro Phe His Leu Leu Thr Ile
Lys Arg Pro Ser Ala Ser Ser Lys Phe Thr Leu Pro Phe Ile Cys Phe Arg Ser
Asn Gly Arg Ala Pro Gln Val Lys Ser Leu Ser Arg Ser Phe Ala Ser Ala His
--- --- --- --- --- --- --- --- --- --- --- --- --- --- --- --- --- ---
TAA AGG CGC CCG ACC GAC TTG AAA ACT TTC ACT CGC CCT TTT ACG TCT TCG CAC
        495         504         513         522         531         540
ATT TCC GCG GGC TGG CTG AAC TTT TGA AAG TGA GCG GGA AAA TGC AGA AGC GTG
--- --- --- --- --- --- --- --- --- --- --- --- --- --- --- --- --- ---
Ile Ser Ala Gly Trp Leu Asn Phe *** Lys *** Ala Gly Lys Cys Arg Ser Val
Phe Pro Arg Ala Gly *** Thr Phe Glu Ser Glu Arg Glu Asn Ala Glu Ala ***
Phe Arg Gly Leu Ala Glu Leu Leu Lys Val Ser Gly Lys Met Gln Lys Arg Asp
```

FIG. 8b

```
 Pro Leu Ser Ile Tyr Val Asp Asn His Pro Trp Arg Pro Thr Thr Phe Ala Phe
Gln Phe Val Leu Thr Cys Thr Met Thr Pro Gly Gly Pro His Pro Leu Leu Leu
Asn Ser Ser *** His Val Arg *** Gln Pro Ala Val Gln Thr His Tyr Phe Cys
--- --- --- --- --- --- --- --- --- --- --- --- --- --- --- --- --- ---
TAA CCT TCT GAT TAC ATG TGC AGT AAC ACC CCG GTG GAC CCA CAC CAT TTT CGT
        549         558         567         576         585         594
ATT GGA AGA CTA ATG TAC ACG TCA TTG TGG GGC CAC CTG GGT GTG GTA AAA GCA
--- --- --- --- --- --- --- --- --- --- --- --- --- --- --- --- --- ---
Ile Gly Arg Leu Met Tyr Thr Ser Leu Trp Gly His Leu Gly Val Val Lys Ala
 Leu Glu Asp *** Cys Thr Arg His Cys Gly Ala Thr Trp Val Trp *** Lys Gln
  Trp Lys Thr Asn Val His Val Ile Val Gly Pro Pro Gly Cys Gly Lys Ser Lys

 Pro Ser Ser Ile Lys Cys Val Arg Phe Gly Cys Val Pro Phe Trp Arg Ser Val
His Ala Ala Leu Lys Ala Ser Gly Ser Val Val Tyr Gln Phe Gly Gly Leu Phe
Ile Pro Gln *** Asn Gln Leu Gly Pro Phe Trp Met Ser Ser Val Val *** Phe
--- --- --- --- --- --- --- --- --- --- --- --- --- --- --- --- --- ---
TTA CCC GAC GAT TAA AAC GTC TGG GCC TTT GGT GTA TGA CCT TTG GTG GAT CTT
        603         612         621         630         639         648
AAT GGG CTG CTA ATT TTG CAG ACC CGG AAA CCA CAT ACT GGA AAC CAC CTA GAA
--- --- --- --- --- --- --- --- --- --- --- --- --- --- --- --- --- ---
Asn Gly Leu Leu Ile Leu Gln Thr Arg Lys Pro His Thr Gly Asn His Leu Glu
 Met Gly Cys *** Phe Cys Arg Pro Gly Asn His Ile Leu Glu Thr Thr *** Lys
  Trp Ala Ala Asn Phe Ala Asp Pro Glu Thr Thr Tyr Trp Lys Pro Pro Arg Asn

 Leu Pro Pro Ile Thr Val Met Thr Phe Phe His Asn Asn Asn Ile Val Lys Ile
Leu His His Ser Pro *** Trp Pro Ser Ser Thr Thr Thr Ile Ser Ser Lys ***
Cys Thr Thr Pro His Asn Gly His His Leu Leu Pro Gln *** Gln His Ser Lys
--- --- --- --- --- --- --- --- --- --- --- --- --- --- --- --- --- ---
TGT TCA CCA CCC TAC CAA TGG TAC CAC TTC TTC ACC AAC AAT AAC TAC TGA AAA
        657         666         675         684         693         702
ACA AGT GGT GGG ATG GTT ACC ATG GTG AAG AAG TGG TTG TTA TTG ATG ACT TTT
--- --- --- --- --- --- --- --- --- --- --- --- --- --- --- --- --- ---
Thr Ser Gly Gly Met Val Thr Met Val Lys Lys Trp Leu Leu Leu Met Thr Phe
 Gln Val Val Gly Trp Leu Pro Trp *** Arg Ser Gly Cys Tyr *** *** Leu Leu
  Lys Trp Trp Asp Gly Tyr His Gly Glu Glu Val Val Val Ile Asp Asp Phe Tyr

 Ala Pro Gln Gly Pro Ile Ile *** Gln Ser Gln Thr Ile Ser Ile Trp Gln Ser
Pro Gln Ser Gly Gln Ser Ser Arg Ser Leu Ser His Ser Arg Tyr Gly Asn Val
His Ser Ala Ala Arg Pro His Asp Val Ser Val Thr His Asp Ile Asp Met Ser
--- --- --- --- --- --- --- --- --- --- --- --- --- --- --- --- --- ---
TAC CGA CCG ACG GGA CCC TAC TAG ATG ACT CTG ACA CAC TAG CTA TAG GTA ACT
        711         720         729         738         747         756
ATG GCT GGC TGC CCT GGG ATG ATC TAC TGA GAC TGT GTG ATC GAT ATC CAT TGA
--- --- --- --- --- --- --- --- --- --- --- --- --- --- --- --- --- ---
Met Ala Gly Cys Pro Gly Met Ile Tyr *** Asp Cys Val Ile Asp Ile His ***
 Trp Leu Ala Ala Leu Gly *** Ser Thr Glu Thr Val *** Ser Ile Ser Ile Asp
  Gly Trp Leu Pro Trp Asp Asp Leu Leu Arg Leu Cys Asp Arg Tyr Pro Leu Thr

 Tyr Leu Ser Phe Thr Ser Ser Tyr Arg Lys Gln Gly Ala Thr Asn Gln Asn Gly
Thr Ser Val Leu Pro Pro Val Thr Gly Lys Lys Ala Arg Leu Ile Arg Ile Val
Gln Leu Ser *** Leu His Phe Gln Val Lys Lys Pro Gly Cys Tyr Glu Ser ***
--- --- --- --- --- --- --- --- --- --- --- --- --- --- --- --- --- ---
GAC ATC TCT GAT TTC CAC CTT GAC ATG GAA AAA ACC GGG CGT CAT AAG ACT AAT
        765         774         783         792         801         810
CTG TAG AGA CTA AAG GTG GAA CTG TAC CTT TTT TGG CCC GCA GTA TTC TGA TTA
--- --- --- --- --- --- --- --- --- --- --- --- --- --- --- --- --- ---
Leu *** Arg Leu Lys Val Glu Leu Tyr Leu Phe Trp Pro Ala Val Phe *** Leu
 Cys Arg Asp *** Arg Trp Asn Cys Thr Phe Phe Gly Pro Gln Tyr Ser Asp Tyr
  Val Glu Thr Lys Gly Gly Thr Val Pro Phe Leu Ala Arg Ser Ile Leu Ile Thr
```

FIG. 8c

Ala Ile Leu Gly Arg Gln Phe Pro Val Gly *** Ser Ser Asp Trp Ser Tyr Phe
Leu Leu *** Val Gly Asn Ser His Tyr Glu Glu Val Ala Thr Gly Ala Thr Ser
Trp Cys Asp Ser Gly Thr Pro Ile Thr Ser Arg Leu Gln Gln Gly Leu Gln Leu
--- --- --- --- --- --- --- --- --- --- --- --- --- --- --- --- --- ---
GGT CGT TAG TCT GGG GCA ACC TTA CCA TGA GGA GTT GAC GAC AGG GTC GAC ATC
819 828 837 846 855 864
CCA GCA ATC AGA CCC CGT TGG AAT GGT ACT CCT CAA CTG CTG TCC CAG CTG TAG
--- --- --- --- --- --- --- --- --- --- --- --- --- --- --- --- --- ---
Pro Ala Ile Arg Pro Arg Trp Asn Gly Thr Pro Gln Leu Leu Ser Gln Leu ***
Gln Gln Ser Asp Pro Val Gly Met Val Leu Leu Asn Cys Cys Pro Ser Cys Arg
Ser Asn Gln Thr Pro Leu Glu Trp Tyr Ser Ser Thr Ala Val Pro Ala Val Glu

Ser Lys Ile Pro Pro Asn Ser Gly Gln Tyr Lys Pro Leu Ile Ser Cys Phe Leu
Ala Arg *** Arg Leu Ile Val Glu Lys Thr Asn Gln Phe Phe Ala Val Ser Cys
Leu Glu Lys Asp Ser Ser * Lys Arg Pro Ile Lys Ser Ser His * Leu Val
--- --- --- --- --- --- --- --- --- --- --- --- --- --- --- --- --- ---
TTC GAG AAA TAG CCT CCT AAT GAA GGA ACC ATA AAA CCT TCT TAC GAT GTC TTG
873 882 891 900 909 918
AAG CTC TTT ATC GGA GGA TTA CTT CCT TGG TAT TTT GGA AGA ATG CTA CAG AAC
--- --- --- --- --- --- --- --- --- --- --- --- --- --- --- --- --- ---
Lys Leu Phe Ile Gly Gly Leu Leu Pro Trp Tyr Phe Gly Arg Met Leu Gln Asn
Ser Ser Leu Ser Glu Asp Tyr Phe Leu Gly Ile Leu Glu Glu Cys Tyr Arg Thr
Ala Leu Tyr Arg Arg Ile Thr Ser Leu Val Phe Trp Lys Asn Ala Thr Glu Gln

Gly Arg Leu Phe Pro Ala Leu Glu Asp Gly Lys Gly Gly Trp Ala Arg Phe Lys
Asp Val Ser Ser Pro Pro Trp Asn Thr Val Arg Glu Gly Gly His Gly Ser Asn
Ile Trp Pro Pro Leu Pro Gly Thr Arg *** Gly Lys Gly Gly Met Gly Gln Ile
--- --- --- --- --- --- --- --- --- --- --- --- --- --- --- --- --- ---
TTA GGT GCC TCC TTC CCC CGG TCA AGC AGT GGG AAA GGG GGG GTA CGG GAC TTA
927 936 945 954 963 972
AAT CCA CGG AGG AAG GGG GCC AGT TCG TCA CCC TTT CCC CCC CAT GCC CTG AAT
--- --- --- --- --- --- --- --- --- --- --- --- --- --- --- --- --- ---
Asn Pro Arg Arg Lys Gly Ala Ser Ser Ser Pro Phe Pro Pro His Ala Leu Asn
Ile His Gly Gly Arg Gly Pro Val Arg His Pro Phe Pro Pro Met Pro *** Ile
Ser Thr Glu Glu Gly Gly Gln Phe Val Thr Leu Ser Pro Pro Cys Pro Glu Phe

Trp Ile Phe Tyr Ile Val Ser Asp Lys Lys Asp Ser Arg Leu Pro Lys * *
Gly Tyr Ser Ile Phe *** Gln Thr Lys Lys Ile Val Glu Tyr His Asn Lys Asn
Glu Met His Phe Leu Asn Ser Leu Arg Lys * * Lys Thr Ile Thr Lys Ile
--- --- --- --- --- --- --- --- --- --- --- --- --- --- --- --- --- ---
AAG GTA TAC TTT ATT TAA TGA CTC AGA AAA AAT AGT GAA GCA TTA CCA AAA ATA
981 990 999 1008 1017 1026
TTC CAT ATG AAA TAA ATT ACT GAG TCT TTT TTA TCA CTT CGT AAT GGT TTT TAT
--- --- --- --- --- --- --- --- --- --- --- --- --- --- --- --- --- ---
Phe His Met Lys *** Ile Thr Glu Ser Phe Leu Ser Leu Arg Asn Gly Phe Tyr
Ser Ile *** Asn Lys Leu Leu Ser Leu Phe Tyr His Phe Val Met Val Phe Ile
Pro Tyr Glu Ile Asn Tyr * Val Phe Phe Ile Thr Ser * Trp Phe Leu Leu

Glu Asn Leu Thr Leu His Pro Thr Lys Leu Ile Leu Asn Glu Ser Asn Tyr Met
Asn Met Leu Pro * Thr Pro Pro Arg * Phe *** Ile Arg Gln Ile Thr Cys
Ile * * Pro Asn Leu Pro Pro Asp Lys Phe Asn Phe Glu Arg Phe Gln Val
--- --- --- --- --- --- --- --- --- --- --- --- --- --- --- --- --- ---
ATA AGT AAT TCC CAA TTC ACC CCC CAG AAA TTT TAA TTT AAG AGA CTT AAC ATG
1035 1044 1053 1062 1071 1080
TAT TCA TTA AGG GTT AAG TGG GGG GTC TTT AAA ATT AAA TTC TCT GAA TTG TAC
--- --- --- --- --- --- --- --- --- --- --- --- --- --- --- --- --- ---
Tyr Ser Leu Arg Val Lys Trp Gly Val Phe Lys Ile Lys Phe Ser Glu Leu Tyr
Ile His *** Gly Leu Ser Gly Gly Ser Leu Lys Leu Asn Ser Leu Asn Cys Thr
Phe Ile Lys Gly * Val Gly Gly Leu * Asn * Ile Leu * Ile Val His

FIG. 8d

```
 Cys Pro *** Val Ser Ile Thr Asn Arg Thr Thr Tyr Val Thr Lys Ser Arg Leu
 Val His Asn Cys Pro Tyr Gln Ile Gly Pro Arg Ile Tyr Gln Lys Arg Val Cys
Tyr Met Thr Val Arg Ile Asn Tyr Glu Gln Asp Tyr Ile Ser Asn Glu Phe Ala
--- --- --- --- --- --- --- --- --- --- --- --- --- --- --- --- --- ---
TAT GTA CCA ATG TGC CTA TAA CAT AAG GAC CAG CAT ATA TGA CAA AAG CTT GCG
        1089        1098        1107        1116        1125        1134
ATA CAT GGT TAC ACG GAT ATT GTA TTC CTG GTC GTA TAT ACT GTT TTC GAA CGC
--- --- --- --- --- --- --- --- --- --- --- --- --- --- --- --- --- ---
Ile His Gly Tyr Thr Asp Ile Val Phe Leu Val Val Tyr Thr Val Phe Glu Arg
 Tyr Met Val Thr Arg Ile Leu Tyr Ser Trp Ser Tyr Ile Leu Phe Ser Asn Ala
  Thr Trp Leu His Gly Tyr Cys Ile Pro Gly Arg Ile Tyr Cys Phe Arg Thr Gln

 Ala Ser Ala *** Thr Thr *** Met Glu Leu Leu Lys Tyr Asp *** Gly Cys Ser
 His Arg Pro Arg Arg Pro Arg Cys Lys Trp Cys Asn Thr Thr Glu Ala Val Ala
Thr Gly Leu Gly Val His Asp Val Asn Gly Ala Thr Gln Leu Arg Leu Trp Leu
--- --- --- --- --- --- --- --- --- --- --- --- --- --- --- --- --- ---
TCA CGG CTC CGG ATG CAC CAG ATG TAA AGG TCG TCA AAC ATC AGA GTC GGT GTC
        1143        1152        1161        1170        1179        1188
AGT GCC GAG GCC TAC GTG GTC TAC ATT TCC AGC AGT TTG TAG TCT CAG CCA CAG
--- --- --- --- --- --- --- --- --- --- --- --- --- --- --- --- --- ---
Ser Ala Glu Ala Tyr Val Val Tyr Ile Ser Ser Ser Leu *** Ser Gln Pro Gln
 Val Pro Arg Pro Thr Trp Ser Thr Phe Pro Ala Val Cys Ser Leu Ser His Ser
  Cys Arg Gly Leu Arg Gly Leu His Phe Gln Gln Phe Val Val Ser Ala Thr Ala

 Thr Glu Lys Thr Thr Gln Asn Ser Thr Ile Leu Leu Ser Ile *** Ser Leu Asn
 Pro Lys Lys Gln Gln Lys Thr Pro Leu Leu *** Tyr His Phe Arg Pro Cys Thr
Gln Asn Arg Lys Asn Asn Pro Gln Phe Tyr Asp Ile Thr Phe Asp Leu Val Pro
--- --- --- --- --- --- --- --- --- --- --- --- --- --- --- --- --- ---
GAC CAA AGA AAA CAA CAA ACC AAC CTT CAT TAG TTA TCA CTT TAG ATC CTG TCC
        1197        1206        1215        1224        1233        1242
CTG GTT TCT TTT GTT GTT TGG TTG GAA GTA ATC AAT AGT GAA ATC TAG GAC AGG
--- --- --- --- --- --- --- --- --- --- --- --- --- --- --- --- --- ---
Leu Val Ser Phe Val Val Trp Leu Glu Val Ile Asn Ser Glu Ile *** Asp Arg
 Trp Phe Leu Leu Leu Phe Gly Trp Lys *** Ser Ile Val Lys Ser Arg Thr Gly
  Gly Phe Phe Cys Cys Leu Val Gly Ser Asn Gln *** *** Asn Leu Gly Gln Val

 Pro Pro Leu Thr Gly Pro Thr Thr Pro Ser Pro Ser Pro *** Pro Ile Ala Pro
 Gln Pro Tyr Leu Val Pro Leu Pro Leu Leu Leu Ala Pro Asn His Tyr Pro Pro
Lys Pro Thr Phe Tyr Arg Ser His Tyr Ser Phe Pro Gln Thr Ile Thr His Arg
--- --- --- --- --- --- --- --- --- --- --- --- --- --- --- --- --- ---
AAA CCC CCA TTT CAT GGC CCT CAC CAT CCT CTT CCC GAC CCA ATA CCA TAC CGC
        1251        1260        1269        1278        1287        1296
TTT GGG GGT AAA GTA CCG GGA GTG GTA GGA GAA GGG CTG GGT TAT GGT ATG GCG
--- --- --- --- --- --- --- --- --- --- --- --- --- --- --- --- --- ---
Phe Gly Gly Lys Val Pro Gly Val Val Gly Glu Gly Leu Gly Tyr Gly Met Ala
 Leu Gly Val Lys Tyr Arg Glu Trp *** Glu Lys Gly Trp Val Met Val Trp Arg
  Trp Gly *** Ser Thr Gly Ser Gly Arg Arg Arg Ala Gly Leu Trp Tyr Gly Gly

 Pro Thr Thr *** Met Pro Thr Met Pro Ser Pro Gln Pro Arg Gln *** Leu Thr
 Leu Leu Leu Lys Cys Leu Pro *** Leu His Pro Ser His Gly Lys Asn Cys Leu
Ser Ser Tyr Asn Val Tyr Pro Asp Tyr Thr Leu Ala Thr Ala Lys Thr Val Phe
--- --- --- --- --- --- --- --- --- --- --- --- --- --- --- --- --- ---
CCT CCT CAT CAA ATG TAT CCC CAG TAT CCA CTC CCG ACA CCG GAA ACA ATG TTT
        1305        1314        1323        1332        1341        1350
GGA GGA GTA GTT TAC ATA GGG GTC ATA GGT GAG GGC TGT GGC CTT TGT TAC AAA
--- --- --- --- --- --- --- --- --- --- --- --- --- --- --- --- --- ---
Gly Gly Val Val Tyr Ile Gly Val Ile Gly Glu Gly Cys Gly Leu Cys Tyr Lys
 Glu Glu *** Phe Thr *** Gly Ser *** Val Arg Ala Val Ala Phe Val Thr Lys
  Arg Ser Ser Leu His Arg Gly His Arg *** Gly Leu Trp Pro Leu Leu Gln Ser
```

FIG. 8e

```
 Ile Met *** Phe Leu Leu Val Pro Ala Trp Glu Gly Thr Val Arg Pro Ser Arg
*** *** Arg Phe Tyr Cys Cys Gln Leu Gly Ser Gly Gln *** Gly Pro His Asp
Asn Asp Asp Leu Ile Val Ala Ser Ser Gly Val Gly Arg Asp Gly Gln Thr Ile
--- --- --- --- --- --- --- --- --- --- --- --- --- --- --- --- --- ---
CAA TAG TAG ATT TTA TTG TCG TGA CCT CGG GTG AGG GGA CAG TGG GAC CCA CTA
        1359        1368        1377        1386        1395        1404
GTT ATC ATC TAA AAT AAC AGC ACT GGA GCC CAC TCC CCT GTC ACC CTG GGT GAT
--- --- --- --- --- --- --- --- --- --- --- --- --- --- --- --- --- ---
Val Ile Ile *** Asn Asn Ser Thr Gly Ala His Ser Pro Val Thr Leu Gly Asp
 Leu Ser Ser Lys Ile Thr Ala Leu Glu Pro Thr Pro Leu Ser Pro Trp Val Ile
  Tyr His Leu Lys *** Gln His Trp Ser Pro Leu Pro Cys His Pro Gly *** Ser

  Pro Ala Pro Gly Ser Asn Leu Arg Leu Arg Glu *** Glu Thr Thr Asn Leu Pro
 Pro Leu Leu Ala Leu Ile *** Gly *** Gly Lys Lys Asn Gln Leu Ile *** Leu
Pro Ser Cys Pro Trp Phe Glu Val Lys Val Lys Arg Ile Arg Tyr Tyr Glu Phe
--- --- --- --- --- --- --- --- --- --- --- --- --- --- --- --- --- ---
GCC CCT CGT CCC GGT CTT AAG TTG GAA TTG GAA AGA ATA AGA CAT CAT AAG TTT
        1413        1422        1431        1440        1449        1458
CGG GGA GCA GGG CCA GAA TTC AAC CTT AAC CTT TCT TAT TCT GTA GTA TTC AAA
--- --- --- --- --- --- --- --- --- --- --- --- --- --- --- --- --- ---
Arg Gly Ala Gly Pro Glu Phe Asn Leu Asn Leu Ser Tyr Ser Val Val Phe Lys
 Gly Glu Gln Gly Gln Asn Ser Thr Leu Thr Phe Leu Ile Leu *** Tyr Ser Lys
  Gly Ser Arg Ala Arg Ile Gln Pro *** Pro Phe Leu Phe Cys Ser Ile Gln Arg

  Cys Leu Ala Pro Thr Gln Gly Gly Glu Gln Pro Phe Phe Thr Met Leu Ile Ser
 Ala Cys Leu Pro Pro Lys Val Gly Arg Arg Pro Ser Ser Leu *** *** Tyr Gln
Pro Val Ser Arg Pro Asn Ser Gly Gly Gly Pro Pro Leu Phe Asp Asn Ile Asn
--- --- --- --- --- --- --- --- --- --- --- --- --- --- --- --- --- ---
CCC GTG TCT CGC CCC CAA ACT GGG GGG AGG ACC CCC TTC TTT CAG TAA TTA TAA
        1467        1476        1485        1494        1503        1512
GGG CAC ACA GCG GGG GTT TGA CCC CCC TCC TGG GGG AGG AAA GTC ATT AAT ATT
--- --- --- --- --- --- --- --- --- --- --- --- --- --- --- --- --- ---
Gly His Arg Ala Gly Val *** Pro Pro Ser Trp Gly Lys Lys Val Ile Asn Ile
 Gly Thr Glu Arg Gly Phe Asp Pro Pro Pro Gly Gly Arg Lys Ser Leu Ile Leu
  Ala Gln Ser Gly Gly Leu Thr Pro Leu Leu Gly Glu Glu Ser His *** Tyr ***

  Asp *** *** Thr Trp Arg Gly Pro Pro Arg Glu Ser Gln Pro Glu Ser Ser Leu
 Ile Glu Asp His Gly Gly Gly Leu Leu Ala Asn Gln Ser His Asn Ala Gln Cys
Phe Arg Met Met Asp Val Ala Trp Ser Pro Thr Arg Val Thr Thr Arg Lys Val
--- --- --- --- --- --- --- --- --- --- --- --- --- --- --- --- --- ---
CCT AGA GTA GTA CAG GTG GCG GGT CCT CCC GCA AGA CTG ACA CCA AGC GAA CTG
        1521        1530        1539        1548        1557        1566
GAA TCT CAT CAT GTC CAC CGC CCA GGA GGG CGT TCT GAC TGT GGT TCG CTT GAC
--- --- --- --- --- --- --- --- --- --- --- --- --- --- --- --- --- ---
Glu Ser His His Val His Arg Pro Gly Gly Arg Ser Asp Cys Gly Ser Leu Asp
 Asn Leu Ile Met Ser Thr Ala Gln Glu Gly Val Leu Thr Val Val Arg Leu Thr
  Ile Ser Ser Cys Pro Pro Pro Arg Arg Ala Phe *** Leu Trp Phe Ala *** Gln

  Ile Asp Ser Pro Ala Pro Ser Ala Pro Thr Ser Ser Ala Met Lys Gly Glu Gly
 Tyr Ile Arg Leu His Pro Leu Pro Pro His Gln Leu His Trp Lys Glu Lys Glu
Thr Tyr Gly Phe Thr Arg Ser Leu Arg Thr Asn Phe Ile Gly Asn Lys Arg Arg
--- --- --- --- --- --- --- --- --- --- --- --- --- --- --- --- --- ---
TCA TAT AGG CTT CCA CGC CCT CTC CGC CCA CAA CTT CTA CGG TAA AAA GGA AGA
        1575        1584        1593        1602        1611        1620
AGT ATA TCC GAA GGT GCG GGA GAG GCG GGT GTT GAA GAT GCC ATT TTT CTT TCT
--- --- --- --- --- --- --- --- --- --- --- --- --- --- --- --- --- ---
Ser Ile Ser Glu Gly Ala Gly Glu Ala Gly Val Glu Asp Ala Ile Phe Pro Ser
 Val Tyr Pro Lys Val Arg Glu Arg Arg Val Leu Lys Met Pro Phe Phe Leu Leu
  Tyr Ile Arg Arg Cys Gly Arg Gly Gly Cys *** Arg Cys His Phe Ser Phe Ser
```

FIG. 8f

```
  Ala Thr Val Thr Ala Pro Thr Ser Ser Gly Pro Ala Ala Ala Ser Ser Arg Ala
 Leu Pro Leu Pro Pro Pro Pro Pro Arg Ala Leu Pro Pro Pro Pro Pro Asp Pro
Trp Arg Tyr Arg His Arg Pro His Val Leu Trp Pro Arg Arg Arg Leu Ile Gln
--- --- --- --- --- --- --- --- --- --- --- --- --- --- --- --- --- ---
GGT CGC CAT TGC CAC CGC CCC CAC CTG CTC GGT CCC CGC CGC CGC CTC CTA GAC
        1629        1638        1647        1656        1665        1674
CCA GCG GTA ACG GTG GCG GGG GTG GAC GAG CCA GGG GCG GCG GCG GAG GAT CTG
--- --- --- --- --- --- --- --- --- --- --- --- --- --- --- --- --- ---
Pro Ala Val Thr Val Ala Gly Val Asp Glu Pro Gly Ala Ala Ala Glu Asp Leu
 Gln Arg *** Arg Trp Arg Gly Trp Thr Ser Gln Gly Arg Arg Arg Arg Ile Trp
  Ser Gly Asn Gly Gly Gly Gly Gly Arg Ala Arg Gly Gly Gly Gly Gly Ser Gly

  Leu Ile Ala Ala Pro Ala Thr Asp Glu Glu Glu Thr Val Gly Gly Gln Ile Arg
 Trp Ser Pro Gln Pro Pro Pro Thr Lys Lys Lys Pro Leu Ala Glu Lys Ser Val
Gly Leu His Ser Arg Pro Arg His Arg Arg Arg Arg Tyr Arg Arg Arg Pro Tyr
--- --- --- --- --- --- --- --- --- --- --- --- --- --- --- --- --- ---
CGG TTC TAC CGA CGC CCC CGC CAC AGA AGA AGA AGC CAT TGC GGA GGA ACC TAT
        1683        1692        1701        1710        1719        1728
GCC AAG ATG GCT GCG GGG GCG GTG TCT TCT TCT TCG GTA ACG CCT CCT TGG ATA
--- --- --- --- --- --- --- --- --- --- --- --- --- --- --- --- --- ---
Ala Lys Met Ala Ala Gly Ala Val Ser Ser Ser Ser Val Thr Pro Pro Thr Ile
 Pro Arg Trp Leu Arg Gly Arg Cys Leu Leu Leu Arg *** Arg Leu Leu Gly Tyr
  Gln Asp Gly Cys Gly Gly Gly Val Phe Phe Phe Gly Asn Ala Ser Leu Asp Thr

  *** Ile Gln Phe Arg Phe Phe His Ala Thr Leu Ile
 Asp Tyr Arg Phe Val Phe Ser Thr Arg Gln Leu Tyr
Thr Met Asp Ser Phe Ser Leu Leu Ala Ser Tyr Thr Asn
--- --- --- --- --- --- --- --- --- --- --- --- ---
GCA GTA TAG ACT TTT GCT TTC TTC ACG CGA CAT TCA TAA 5'
        1737        1746        1755        1764
CGT CAT ATC TGA AAA CGA AAG AAG TGC GCT GTA AGT ATT 3'
--- --- --- --- --- --- --- --- --- --- --- --- ---
Arg His Ile *** Lys Arg Lys Lys Cys Ala Val Ser Ile
 Val Ile Ser Glu Asn Glu Arg Ser Ala Leu *** Val
  Ser Tyr Leu Lys Thr Lys Glu Val Arg Cys Lys Tyr
```

FIG. 8g

TYPE B
SPOT NO. 104 TO 159

TYPE A
SPOT NO. 160 TO 215

```
        1                                                      50 51
pcvA  MTWPRRRYRR RRTRPRSHLG NILRRRPYLV HPAFRNYRW RRKTGIFNSR LSREFVLTI. RGGHSQPSWN
pcvB  MTYPRRRYRR RRHRPRSHLG QILRRRPWLV HP..RHYRW RRKNGIFNTR LSRTFGYTVK RTTVRTPSWA

      peptide 177                 100 101              peptides 188 to 189
pcvA VNELRFNIGQ FLPPSGGTNP LPLPFQYYRI RKAKYEFYPR DPITSNQRGV GSTVVILDAN FVTPSTNLAY
pcvB VDMMRFNIND FLPPGGGSNP RSVPFEYYRI RKVKVEFWPC SPITQGDRGV GSSAVILDDN FVTKATALTY
      peptide 121                                  peptides 132 to 133

           150 151                                                  peptide 208
pcvA DPYINYSSRH TIRQPFTYHS RYFTPKPELD QTIDWFQPNN KRNQLWLHLN THTNVEHTGL GYALQNATTA
pcvB DPYVNYSSRH TITQPFSYHS RYFTPKPVLD FTIDYFQPNN KRNQLWLRLQ TAGNVDHVGL GTAFENSIYD
                                                                     peptide 152

                            235
pcvA QNYVVRLTIY VQFREFILKD P.LNE
pcvB QEYNIRVTMY VQFREFNFKD PPLNP
```

FIG. 13

SEQUENCE LISTING

```
<160> NUMBER OF SEQ ID NOS: 177

<210> SEQ ID NO 1
<211> LENGTH: 1759
<212> TYPE: DNA
<213> ORGANISM: Type A PWD circovirus
<220> FEATURE:
<221> NAME/KEY: CDS
<222> LOCATION: (1)..(78)
<220> FEATURE:
<221> NAME/KEY: CDS
<222> LOCATION: (82)..(99)
<220> FEATURE:
<221> NAME/KEY: CDS
<222> LOCATION: (106)..(156)
<220> FEATURE:
<221> NAME/KEY: CDS
<222> LOCATION: (160)..(195)
<220> FEATURE:
<221> NAME/KEY: CDS
<222> LOCATION: (199)..(231)
<220> FEATURE:
<221> NAME/KEY: CDS
<222> LOCATION: (235)..(246)
<220> FEATURE:
<221> NAME/KEY: CDS
<222> LOCATION: (250)..(315)
<220> FEATURE:
<221> NAME/KEY: CDS
<222> LOCATION: (319)..(330)
<220> FEATURE:
<221> NAME/KEY: CDS
<222> LOCATION: (334)..(489)
<220> FEATURE:
<221> NAME/KEY: CDS
<222> LOCATION: (493)..(525)
<220> FEATURE:
<221> NAME/KEY: CDS
<222> LOCATION: (529)..(591)
<220> FEATURE:
<221> NAME/KEY: CDS
<222> LOCATION: (595)..(600)
<220> FEATURE:
<221> NAME/KEY: CDS
<222> LOCATION: (604)..(606)
<220> FEATURE:
<221> NAME/KEY: CDS
<222> LOCATION: (610)..(627)
<220> FEATURE:
<221> NAME/KEY: CDS
<222> LOCATION: (634)..(636)
<220> FEATURE:
<221> NAME/KEY: CDS
<222> LOCATION: (640)..(681)
<220> FEATURE:
<221> NAME/KEY: CDS
<222> LOCATION: (685)..(708)
<220> FEATURE:
<221> NAME/KEY: CDS
<222> LOCATION: (712)..(726)
<220> FEATURE:
<221> NAME/KEY: CDS
```

-continued

```
<222> LOCATION: (730)..(753)
<220> FEATURE:
<221> NAME/KEY: CDS
<222> LOCATION: (757)..(933)
<220> FEATURE:
<221> NAME/KEY: CDS
<222> LOCATION: (937)..(969)
<220> FEATURE:
<221> NAME/KEY: CDS
<222> LOCATION: (973)..(1047)
<220> FEATURE:
<221> NAME/KEY: CDS
<222> LOCATION: (1051)..(1056)
<220> FEATURE:
<221> NAME/KEY: CDS
<222> LOCATION: (1060)..(1071)
<220> FEATURE:
<221> NAME/KEY: CDS
<222> LOCATION: (1075)..(1236)
<220> FEATURE:
<221> NAME/KEY: CDS
<222> LOCATION: (1240)..(1257)
<220> FEATURE:
<221> NAME/KEY: CDS
<222> LOCATION: (1261)..(1293)
<220> FEATURE:
<221> NAME/KEY: CDS
<222> LOCATION: (1297)..(1350)
<220> FEATURE:
<221> NAME/KEY: CDS
<222> LOCATION: (1354)..(1380)
<220> FEATURE:
<221> NAME/KEY: CDS
<222> LOCATION: (1384)..(1386)
<220> FEATURE:
<221> NAME/KEY: CDS
<222> LOCATION: (1390)..(1416)
<220> FEATURE:
<221> NAME/KEY: CDS
<222> LOCATION: (1420)..(1425)
<220> FEATURE:
<221> NAME/KEY: CDS
<222> LOCATION: (1429)..(1497)
<220> FEATURE:
<221> NAME/KEY: CDS
<222> LOCATION: (1501)..(1512)
<220> FEATURE:
<221> NAME/KEY: CDS
<222> LOCATION: (1516)..(1551)
<220> FEATURE:
<221> NAME/KEY: CDS
<222> LOCATION: (1555)..(1566)
<220> FEATURE:
<221> NAME/KEY: CDS
<222> LOCATION: (1570)..(1581)
<220> FEATURE:
<221> NAME/KEY: CDS
<222> LOCATION: (1585)..(1620)
<220> FEATURE:
<221> NAME/KEY: CDS
<222> LOCATION: (1624)..(1752)
<220> FEATURE:
<221> NAME/KEY: CDS
<222> LOCATION: (1756)..(1758)

<400> SEQUENCE: 1

acc agc gca ctt cgg cag cgg cag cac ctc ggc agc gtc agt gaa aat       48
Thr Ser Ala Leu Arg Gln Arg Gln His Leu Gly Ser Val Ser Glu Asn
1               5                   10                  15

gcc aag caa gaa aag cgg ccc gca acc cca taa gag gtg ggt gtt cac       96
Ala Lys Gln Glu Lys Arg Pro Ala Thr Pro     Glu Val Gly Val His
            20                  25                  30

cct taataa tcc ttc cga gga gga gaa aaa caa aat acg gga gct tcc       144
Pro        Ser Phe Arg Gly Gly Glu Lys Gln Asn Thr Gly Ala Ser
                   35                  40                  45
```

-continued

```
aat ctc cct ttt tga tta ttt tgt ttg tgg cga gga agg ttt gga aga      192
Asn Leu Pro Phe     Leu Phe Cys Leu Trp Arg Gly Arg Phe Gly Arg
                    50                  55                  60

ggg tag aac tcc tca cct cca ggg gtt tgc gaa ttt tgc taa gaa gca      240
Gly     Asn Ser Ser Pro Pro Gly Val Cys Glu Phe Cys     Glu Ala
                    65                  70

gac ttt taa caa ggt gaa gtg gta ttt tgg tgc ccg ctg cca cat cga      288
Asp Phe     Gln Gly Glu Val Val Phe Trp Cys Pro Leu Pro His Arg
75                      80                  85

gaa agc gaa agg aac cga cca gca gaa taa aga ata ctg cag taa aga      336
Glu Ser Glu Arg Asn Arg Pro Ala Glu     Arg Ile Leu Gln     Arg
90                  95                      100

agg cca cat act tat cga gtg tgg agc tcc gcg gaa cca ggg gaa gcg      384
Arg Pro His Thr Tyr Arg Val Trp Ser Ser Ala Glu Pro Gly Glu Ala
    105                 110                 115

cag cga cct gtc tac tgc tgt gag tac cct ttt gga gac ggg gtc ttt      432
Gln Arg Pro Val Tyr Cys Cys Glu Tyr Pro Phe Gly Asp Gly Val Phe
120                 125                 130                 135

ggt gac tgt agc cga gca gtt tcc tgt aac gta tgt gag aaa ttt ccg      480
Gly Asp Cys Ser Arg Ala Val Ser Cys Asn Val Cys Glu Lys Phe Pro
                140                 145                 150

cgg gct ggc tga act ttt gaa agt gag cgg gaa gat gca gaa gcg tga      528
Arg Ala Gly     Thr Phe Glu Ser Glu Arg Glu Asp Ala Glu Ala
                155                 160                 165

ttg gaa gac agc tgt aca cgt cat agt ggg ccc gcc cgg ttg tgg gaa      576
Leu Glu Asp Ser Cys Thr Arg His Ser Gly Pro Ala Arg Leu Trp Glu
                170                 175                 180

gag cca gtg ggc ccg taa ttt tgc tga gcc tag gga cac cta ctg gaa      624
Glu Pro Val Gly Pro     Phe Cys     Ala     Gly His Leu Leu Glu
            185                         190

gcc tagtag aaa taa gtg gtg gga tgg ata tca tgg aga aga agt tgt       672
Ala        Lys     Val Val Gly Trp Ile Ser Trp Arg Arg Ser Cys
195                            200                 205

tgt ttt gga tga ttt tta tgg ctg gtt acc ttg gga tga tct act gag      720
Cys Phe Gly     Phe Leu Trp Leu Val Thr Leu Gly     Ser Thr Glu
    210                     215                     220

act gtg tga ccg gta tcc att gac tgt aga gac taa agg ggg tac tgt      768
Thr Val     Pro Val Ser Ile Asp Cys Arg Asp     Arg Gly Tyr Cys
                225                 230                     235

tcc ttt ttt ggc ccg cag tat ttt gat tac cag caa tca ggc ccc cca      816
Ser Phe Phe Gly Pro Gln Tyr Phe Asp Tyr Gln Gln Ser Gly Pro Pro
                240                 245                 250

gga atg gta ctc ctc aac tgc tgt ccc agc tgt aga agc tct cta tcg      864
Gly Met Val Leu Leu Asn Cys Cys Pro Ser Cys Arg Ser Ser Leu Ser
            255                 260                 265

gag gat tac tac ttt gca att ttg gaa gac tgc tgg aga aca atc cac      912
Glu Asp Tyr Tyr Phe Ala Ile Leu Glu Asp Cys Trp Arg Thr Ile His
        270                 275                 280

gga ggt acc cga agg ccg att tga agc agt gga ccc acc ctg tgc cct      960
Gly Gly Thr Arg Arg Pro Ile     Ser Ser Gly Pro Thr Leu Cys Pro
    285                 290                 295

ttt ccc ata taa aat aaa tta ctg agt ctt ttt tgt tat cac atc gta     1008
Phe Pro Ile     Asn Lys Leu Leu Ser Leu Phe Cys Tyr His Ile Val
    300                     305                 310

atg gtt ttt att ttt att cat tta gag ggt ctt tca gga taa att ctc     1056
Met Val Phe Ile Phe Ile His Leu Glu Gly Leu Ser Gly     Ile Leu
    315                 320                 325

tga att gta cat aaa tag tca acc tta cca cat aat ttt ggg ctg tgg     1104
    Ile Val His Lys     Ser Thr Leu Pro His Asn Phe Gly Leu Trp
        330                     335                 340
```

-continued

```
ttg cat ttt gga gcg cat agc cca ggc ctg tgt gct cga cat tgg tgt      1152
Leu His Phe Gly Ala His Ser Pro Gly Leu Cys Ala Arg His Trp Cys
        345                 350                 355

ggg tat tta aat gga gcc aca gct ggt ttc ttt tat tat ttg gct gga      1200
Gly Tyr Leu Asn Gly Ala Thr Ala Gly Phe Phe Tyr Tyr Leu Ala Gly
    360                 365                 370

acc aat caa ttg ttt ggt cta gct ctg gtt tgg ggg tga agt acc tgg      1248
Thr Asn Gln Leu Phe Gly Leu Ala Leu Val Trp Gly     Ser Thr Trp
375                 380                 385

agt ggt agg taa agg gct gcc tta tgg tgt ggc ggg agg agt agt taa      1296
Ser Gly Arg     Arg Ala Ala Leu Trp Cys Gly Gly Arg Ser Ser
390                 395                 400

tat agg ggt cat agg cca agt tgg tgg agg ggg tta caa agt tgg cat      1344
Tyr Arg Gly His Arg Pro Ser Trp Trp Arg Gly Leu Gln Ser Trp His
    405                 410                 415

cca aga taa caa cag tgg acc caa cac ctc ttt gat tag agg tga tgg      1392
Pro Arg     Gln Gln Trp Thr Gln His Leu Phe Asp     Arg     Trp
420                 425                 430

ggt ctc tgg ggt aaa att cat att tag cct ttc taa tac ggt agt att      1440
Gly Leu Trp Gly Lys Ile His Ile     Pro Phe     Tyr Gly Ser Ile
        435                 440                 445

gga aag gta ggg gta ggg ggt tgg tgc cgc ctg agg ggg gga gga act      1488
Gly Lys Val Gly Val Gly Gly Trp Cys Arg Leu Arg Gly Gly Gly Thr
            450                 455                 460

ggc cga tgt tga atc tca gct cgt taa cat tcc aag atg gct gcg agt      1536
Gly Arg Cys     Ile Ser Ala Arg     His Ser Lys Met Ala Ala Ser
        465                 470                 475

gtc ctc ctc tta tgg tga gta caa att ctc tag aaa ggc ggg aat tga      1584
Val Leu Leu Leu Trp     Val Gln Ile Leu     Lys Gly Gly Asn
            480                 485

aga tac ccg tct ttc ggc gcc atc tgt aac ggt ttc tga agg cgg ggt      1632
Arg Tyr Pro Ser Phe Gly Ala Ile Cys Asn Gly Phe     Arg Arg Gly
490                 495                 500

gta cca aat atg gtc ttc tcc gga gga tgt ttc caa gat ggc tgc ggg      1680
Val Pro Asn Met Val Phe Ser Gly Gly Cys Phe Gln Asp Gly Cys Gly
505                 510                 515                 520

ggc ggg tcc gtc ttc tgc ggt aac gcc tcc ttg gcc acg tca tcc tat      1728
Gly Gly Ser Val Phe Cys Gly Asn Ala Ser Leu Ala Thr Ser Ser Tyr
                525                 530                 535

aaa agt gaa aga agt gcg ctg ctg tag tat t                            1759
Lys Ser Glu Arg Ser Ala Leu Leu     Tyr
            540                 545


<210> SEQ ID NO 2
<211> LENGTH: 545
<212> TYPE: PRT
<213> ORGANISM: Type A PWD circovirus

<400> SEQUENCE: 2

Thr Ser Ala Leu Arg Gln Arg Gln His Leu Gly Ser Val Ser Glu Asn
1               5                   10                  15

Ala Lys Gln Glu Lys Arg Pro Ala Thr Pro Glu Val Gly Val His Pro
            20                  25                  30

Ser Phe Arg Gly Gly Glu Lys Gln Asn Thr Gly Ala Ser Asn Leu Pro
        35                  40                  45

Phe Leu Phe Cys Leu Trp Arg Gly Arg Phe Gly Arg Gly Asn Ser Ser
    50                  55                  60

Pro Pro Gly Val Cys Glu Phe Cys Glu Ala Asp Phe Gln Gly Glu Val
65                  70                  75                  80
```

-continued

```
Val Phe Trp Cys Pro Leu Pro His Arg Glu Ser Glu Arg Asn Arg Pro
                85                  90                  95

Ala Glu Arg Ile Leu Gln Arg Arg Pro His Thr Tyr Arg Val Trp Ser
            100                 105                 110

Ser Ala Glu Pro Gly Glu Ala Gln Arg Pro Val Tyr Cys Cys Glu Tyr
        115                 120                 125

Pro Phe Gly Asp Gly Val Phe Gly Asp Cys Ser Arg Ala Val Ser Cys
    130                 135                 140

Asn Val Cys Glu Lys Phe Pro Arg Ala Gly Thr Phe Glu Ser Glu Arg
145                 150                 155                 160

Glu Asp Ala Glu Ala Leu Glu Asp Ser Cys Thr Arg His Ser Gly Pro
                165                 170                 175

Ala Arg Leu Trp Glu Glu Pro Val Gly Pro Phe Cys Ala Gly His Leu
            180                 185                 190

Leu Glu Ala Lys Val Val Gly Trp Ile Ser Trp Arg Arg Ser Cys Cys
        195                 200                 205

Phe Gly Phe Leu Trp Leu Val Thr Leu Gly Ser Thr Glu Thr Val Pro
    210                 215                 220

Val Ser Ile Asp Cys Arg Asp Arg Gly Tyr Cys Ser Phe Phe Gly Pro
225                 230                 235                 240

Gln Tyr Phe Asp Tyr Gln Gln Ser Gly Pro Pro Gly Met Val Leu Leu
                245                 250                 255

Asn Cys Cys Pro Ser Cys Arg Ser Ser Leu Ser Glu Asp Tyr Tyr Phe
            260                 265                 270

Ala Ile Leu Glu Asp Cys Trp Arg Thr Ile His Gly Gly Thr Arg Arg
        275                 280                 285

Pro Ile Ser Ser Gly Pro Thr Leu Cys Pro Phe Pro Ile Asn Lys Leu
    290                 295                 300

Leu Ser Leu Phe Cys Tyr His Ile Val Met Val Phe Ile Phe Ile His
305                 310                 315                 320

Leu Glu Gly Leu Ser Gly Ile Leu Ile Val His Lys Ser Thr Leu Pro
                325                 330                 335

His Asn Phe Gly Leu Trp Leu His Phe Gly Ala His Ser Pro Gly Leu
            340                 345                 350

Cys Ala Arg His Trp Cys Gly Tyr Leu Asn Gly Ala Thr Ala Gly Phe
        355                 360                 365

Phe Tyr Tyr Leu Ala Gly Thr Asn Gln Leu Phe Gly Leu Ala Leu Val
    370                 375                 380

Trp Gly Ser Thr Trp Ser Gly Arg Arg Ala Ala Leu Trp Cys Gly Gly
385                 390                 395                 400

Arg Ser Ser Tyr Arg Gly His Arg Pro Ser Trp Trp Arg Gly Leu Gln
                405                 410                 415

Ser Trp His Pro Arg Gln Gln Trp Thr Gln His Leu Phe Asp Arg Trp
            420                 425                 430

Gly Leu Trp Gly Lys Ile His Ile Pro Phe Tyr Gly Ser Ile Gly Lys
        435                 440                 445

Val Gly Val Gly Gly Trp Cys Arg Leu Arg Gly Gly Gly Thr Gly Arg
    450                 455                 460

Cys Ile Ser Ala Arg His Ser Lys Met Ala Ala Ser Val Leu Leu Leu
465                 470                 475                 480

Trp Val Gln Ile Leu Lys Gly Gly Asn Arg Tyr Pro Ser Phe Gly Ala
                485                 490                 495
```

-continued

```
Ile Cys Asn Gly Phe Arg Arg Gly Val Pro Asn Met Val Phe Ser Gly
            500                 505                 510

Gly Cys Phe Gln Asp Gly Cys Gly Gly Gly Ser Val Phe Cys Gly Asn
        515                 520                 525

Ala Ser Leu Ala Thr Ser Ser Tyr Lys Ser Glu Arg Ser Ala Leu Leu
    530                 535                 540

Tyr
545


<210> SEQ ID NO 3
<211> LENGTH: 577
<212> TYPE: PRT
<213> ORGANISM: Type A PWD circovirus

<400> SEQUENCE: 3

Pro Ala His Phe Gly Ser Gly Ser Thr Ser Ala Ala Ser Val Lys Met
1               5                   10                  15

Pro Ser Lys Lys Ser Gly Pro Gln Pro His Lys Arg Trp Val Phe Thr
            20                  25                  30

Leu Asn Asn Pro Ser Glu Glu Glu Lys Asn Lys Ile Arg Glu Leu Pro
        35                  40                  45

Ile Ser Leu Phe Asp Tyr Phe Val Cys Gly Glu Glu Gly Leu Glu Glu
    50                  55                  60

Gly Arg Thr Pro His Leu Gln Gly Phe Ala Asn Phe Ala Lys Lys Gln
65                  70                  75                  80

Thr Phe Asn Lys Val Lys Trp Tyr Phe Gly Ala Arg Cys His Ile Glu
                85                  90                  95

Lys Ala Lys Gly Thr Asp Gln Gln Asn Lys Glu Tyr Cys Ser Lys Glu
            100                 105                 110

Gly His Ile Leu Ile Glu Cys Gly Ala Pro Arg Asn Gln Gly Lys Arg
        115                 120                 125

Ser Asp Leu Ser Thr Ala Val Ser Thr Leu Leu Glu Thr Gly Ser Leu
    130                 135                 140

Val Thr Val Ala Glu Gln Phe Pro Val Thr Tyr Val Arg Asn Phe Arg
145                 150                 155                 160

Gly Leu Ala Glu Leu Leu Lys Val Ser Gly Lys Met Gln Lys Arg Asp
                165                 170                 175

Trp Lys Thr Ala Val His Val Ile Val Gly Pro Pro Gly Cys Gly Lys
            180                 185                 190

Ser Gln Trp Ala Arg Asn Phe Ala Glu Pro Arg Asp Thr Tyr Trp Lys
        195                 200                 205

Pro Ser Arg Asn Lys Trp Trp Asp Gly Tyr His Gly Glu Glu Val Val
    210                 215                 220

Val Leu Asp Asp Phe Tyr Gly Trp Leu Pro Trp Asp Asp Leu Leu Arg
225                 230                 235                 240

Leu Cys Asp Arg Tyr Pro Leu Thr Val Glu Thr Lys Gly Gly Thr Val
                245                 250                 255

Pro Phe Leu Ala Arg Ser Ile Leu Ile Thr Ser Asn Gln Ala Pro Gln
            260                 265                 270

Glu Trp Tyr Ser Ser Thr Ala Val Pro Ala Val Glu Ala Leu Tyr Arg
        275                 280                 285

Arg Ile Thr Thr Leu Gln Phe Trp Lys Thr Ala Gly Glu Gln Ser Thr
    290                 295                 300

Glu Val Pro Glu Gly Arg Phe Glu Ala Val Asp Pro Pro Cys Ala Leu
305                 310                 315                 320
```

-continued

```
Phe Pro Tyr Lys Ile Asn Tyr Val Phe Phe Val Ile Thr Ser Trp Phe
                325                 330                 335

Leu Phe Leu Phe Ile Arg Val Phe Gln Asp Lys Phe Ser Glu Leu Tyr
            340                 345                 350

Ile Asn Ser Gln Pro Tyr His Ile Ile Leu Gly Cys Gly Cys Ile Leu
        355                 360                 365

Glu Arg Ile Ala Gln Ala Cys Val Leu Asp Ile Gly Val Gly Ile Met
    370                 375                 380

Glu Pro Gln Leu Val Ser Phe Ile Ile Trp Leu Glu Pro Ile Asn Cys
385                 390                 395                 400

Leu Val Leu Trp Phe Gly Gly Glu Val Pro Gly Val Val Gly Lys Gly
                405                 410                 415

Leu Pro Tyr Gly Val Ala Gly Gly Val Val Asn Ile Gly Val Ile Gly
            420                 425                 430

Gln Val Gly Gly Gly Gly Tyr Lys Val Gly Ile Gln Asp Asn Asn Ser
        435                 440                 445

Gly Pro Asn Thr Ser Leu Ile Arg Gly Asp Gly Val Ser Gly Val Lys
    450                 455                 460

Phe Ile Phe Ser Leu Ser Asn Thr Val Val Leu Glu Arg Gly Val Gly
465                 470                 475                 480

Ala Ala Gly Gly Glu Glu Leu Ala Asp Val Glu Ser Gln Leu Val Asn
                485                 490                 495

Ile Pro Arg Trp Leu Arg Val Ser Ser Ser Tyr Gly Glu Tyr Lys Phe
            500                 505                 510

Ser Arg Lys Ala Gly Ile Glu Asp Thr Arg Leu Ser Ala Pro Ser Val
        515                 520                 525

Thr Val Ser Glu Gly Gly Val Tyr Gln Ile Trp Ser Ser Pro Glu Asp
    530                 535                 540

Val Ser Lys Met Ala Ala Gly Ala Gly Pro Ser Ser Ala Val Thr Pro
545                 550                 555                 560

Pro Trp Pro Arg His Pro Ile Lys Val Lys Glu Val Arg Cys Cys Ser
                565                 570                 575

Ile


<210> SEQ ID NO 4
<211> LENGTH: 553
<212> TYPE: PRT
<213> ORGANISM: Type A PWD circovirus

<400> SEQUENCE: 4

Gln Arg Thr Ser Ala Ala Ala Ala Pro Arg Gln Arg Gln Lys Cys Gln
1               5                   10                  15

Ala Arg Lys Ala Ala Arg Asn Pro Ile Arg Gly Gly Cys Ser Pro Leu
            20                  25                  30

Leu Pro Arg Arg Arg Lys Thr Lys Tyr Gly Ser Phe Gln Ser Pro Phe
        35                  40                  45

Leu Ile Ile Leu Phe Val Ala Arg Lys Val Trp Lys Arg Val Glu Leu
    50                  55                  60

Leu Thr Ser Arg Gly Leu Arg Ile Leu Leu Arg Ser Arg Leu Leu Thr
65                  70                  75                  80

Arg Ser Gly Ile Leu Val Pro Ala Ala Thr Ser Arg Lys Arg Lys Glu
                85                  90                  95

Pro Thr Ser Arg Ile Lys Asn Thr Ala Val Lys Lys Ala Thr Tyr Leu
            100                 105                 110
```

-continued

```
Ser Ser Val Glu Leu Arg Gly Thr Arg Gly Ser Ala Ala Thr Cys Leu
        115                 120                 125

Leu Leu Val Pro Phe Trp Arg Arg Gly Leu Trp Leu Pro Ser Ser Phe
    130                 135                 140

Leu Arg Met Glu Ile Ser Ala Gly Trp Leu Asn Phe Lys Ala Gly Arg
145                 150                 155                 160

Cys Arg Ser Val Ile Gly Arg Gln Leu Tyr Thr Ser Trp Ala Arg Pro
                165                 170                 175

Val Val Gly Arg Ala Ser Gly Pro Val Ile Leu Leu Ser Leu Gly Thr
            180                 185                 190

Pro Thr Gly Ser Leu Val Glu Ile Ser Gly Gly Met Asp Ile Met Glu
        195                 200                 205

Lys Lys Leu Leu Phe Trp Met Ile Phe Met Ala Gly Tyr Leu Gly Met
    210                 215                 220

Ile Tyr Asp Cys Val Thr Gly Ile His Leu Arg Leu Lys Gly Val Leu
225                 230                 235                 240

Phe Leu Phe Trp Pro Ala Val Phe Leu Pro Ala Ile Arg Pro Pro Arg
                245                 250                 255

Asn Gly Thr Pro Gln Leu Leu Ser Gln Leu Lys Leu Ser Ile Gly Gly
            260                 265                 270

Leu Leu Leu Cys Asn Phe Gly Arg Leu Leu Glu Asn Asn Pro Arg Arg
        275                 280                 285

Tyr Pro Lys Ala Asp Leu Lys Gln Trp Thr His Pro Val Pro Phe Ser
    290                 295                 300

His Ile Lys Ile Thr Glu Ser Phe Leu Leu Ser His Arg Asn Gly Phe
305                 310                 315                 320

Tyr Phe Tyr Ser Phe Arg Gly Ser Phe Arg Ile Asn Ser Leu Asn Cys
                325                 330                 335

Thr Ile Val Asn Leu Thr Thr Phe Trp Ala Val Val Ala Phe Trp Ser
            340                 345                 350

Ala Pro Arg Pro Val Cys Ser Thr Leu Val Trp Val Phe Lys Trp Ser
        355                 360                 365

His Ser Trp Phe Leu Leu Leu Phe Gly Trp Asn Gln Ser Ile Val Trp
    370                 375                 380

Ser Ser Ser Gly Leu Gly Val Lys Tyr Leu Glu Trp Val Lys Gly Cys
385                 390                 395                 400

Leu Met Val Trp Arg Glu Glu Leu Ile Gly Ser Ala Lys Leu Val Glu
                405                 410                 415

Gly Val Thr Lys Leu Ala Ser Lys Ile Thr Thr Val Asp Pro Thr Pro
            420                 425                 430

Leu Leu Glu Val Met Gly Ser Leu Gly Asn Ser Tyr Leu Ala Phe Leu
        435                 440                 445

Ile Arg Tyr Trp Lys Gly Arg Gly Arg Gly Leu Val Pro Pro Glu Gly
    450                 455                 460

Gly Arg Asn Trp Pro Met Leu Asn Leu Ser Ser Leu Thr Phe Gln Asp
465                 470                 475                 480

Gly Cys Glu Cys Pro Pro Leu Met Val Ser Thr Asn Ser Leu Glu Arg
                485                 490                 495

Arg Glu Leu Lys Ile Pro Val Phe Arg Arg His Leu Arg Phe Leu Lys
            500                 505                 510

Ala Gly Cys Thr Lys Tyr Gly Leu Leu Arg Arg Met Phe Pro Arg Trp
        515                 520                 525
```

-continued

Leu Arg Gly Arg Val Arg Leu Leu Arg Arg Leu Leu Gly His Val Ile
530 535 540

Leu Lys Lys Lys Cys Ala Ala Val Val
545 550

<210> SEQ ID NO 5
<211> LENGTH: 1759
<212> TYPE: DNA
<213> ORGANISM: Type A PWD circovirus

<400> SEQUENCE: 5
aatactacag cagcgcactt ctttcacttt tataggatga cgtggccaag gaggcgttac 60
cgcagaagac ggacccgccc ccgcagccat cttggaaacg tcctccggag aagaccatat 120
ttggtacacc ccgccttcag aaaccgttac agatggcgcc gaaagacggg tatcttcaat 180
tcccgccttt ctagagaatt tgtactcacc ataagaggag gacactcgca gccatcttgg 240
aatgttaacg agctgagatt caacatcggc cagttcctcc cccctcagg cggcaccaac 300 cccctacccc tacctttcca atactaccgt attagaaagg ctaaatatga attttacccc 360
agagacccca tcacctctaa tcaaagaggt gttgggtcca ctgttgttat cttggatgcc 420
aactttgtaa ccccctccac caacttggcc tatgacccct atattaacta ctcctcccgc 480
cacaccataa ggcagccctt tacctaccac tccaggtact tcaccccaa accagagcta 540 gaccaaacaa ttgattggtt ccagccaaat aataaaagaa accagctgtg gctccattta 600
aatacccaca ccaatgtcga gcacacaggc ctgggctatg cgctccaaaa tgcaaccaca 660
gcccaaaatt atgtggtaag gttgactatt tatgtacaat tcagagaatt tatcctgaaa 720
gaccctctaa atgaataaaa ataaaaacca ttacgatgtg ataacaaaaa agactcagta 780
atttatttta tatgggaaaa gggcacaggg tgggtccact gcttcaaatc ggccttcggg 840
tacctccgtg gattgttctc cagcagtctt ccaaaattgc aaagtagtaa tcctccgata 900
gagagcttct acagctggga cagcagttga ggagtaccat tcctgggggg cctgattgct 960
ggtaatcaaa atactgcggg ccaaaaaagg aacagtaccc cctttagtct ctacagtcaa 1020
tggataccgg tcacacagtc tcagtagatc atcccaaggt aaccagccat aaaaatcatc 1080
caaaacaaca acttcttctc catgatatcc atcccaccac ttatttctac taggcttcca 1140
gtaggtgtcc ctaggctcag caaaattacg ggcccactgg ctcttcccac aaccgggcgg 1200
gcccactatg acgtgtacag ctgtcttcca atcacgctgc tgcatcttcc cgctcacttt 1260
caaaagttca gccagcccgc ggaaatttct cacatacgtt acaggaaact gctcggctac 1320
agtcaccaaa gaccccgtct ccaaaagggt actcacagca gtagacaggt cgctgcgctt 1380
cccctggttc cgcggagctc cacactcgat aagtatgtgg ccttctttac tgcagtattc 1440
tttattctgc tggtcggttc ctttcgcttt ctcgatgtgg cagcgggcac caaaatacca 1500
cttcaccttg ttaaaagtct gcttcttagc aaaattcgca aacccctgga ggtgaggagt 1560
tctaccctct tccaaacctt cctcgccaca aacaaaataa tcaaaaaggg agattggaag 1620
ctcccgtatt ttgtttttct cctcctcgga aggattatta agggtgaaca cccacctctt 1680
atggggttgc gggccgcttt tcttgcttgg cattttcact gacgctgccg aggtgctgcc 1740
gctgccgaag tgcgctggt 1759

<210> SEQ ID NO 6
<211> LENGTH: 567
<212> TYPE: PRT
<213> ORGANISM: Type A PWD circovirus -continued

<400> SEQUENCE: 6

```
Gly Ala Cys Lys Pro Leu Pro Leu Val Glu Ala Ala Asp Thr Phe Ile
1               5                   10                  15

Gly Leu Leu Phe Leu Pro Gly Cys Gly Trp Leu Leu His Thr Asn Val
            20                  25                  30

Arg Leu Leu Gly Glu Ser Ser Ser Phe Phe Leu Ile Arg Ser Ser Gly
        35                  40                  45

Ile Glu Arg Lys Ser Lys Thr Gln Pro Ser Ser Pro Lys Ser Ser Pro
    50                  55                  60

Leu Val Gly Arg Trp Pro Asn Ala Phe Lys Ala Leu Phe Cys Val Lys
65                  70                  75                  80

Leu Leu Thr Phe His Tyr Lys Pro Ala Arg Gln Trp Met Ser Phe Ala
                85                  90                  95

Phe Pro Val Ser Trp Cys Phe Leu Ser Tyr Gln Leu Leu Ser Pro Trp
            100                 105                 110

Met Ser Ile Ser His Pro Ala Gly Arg Phe Trp Pro Phe Arg Leu Ser
        115                 120                 125

Arg Asp Val Ala Thr Leu Val Arg Lys Ser Val Pro Asp Lys Thr Val
    130                 135                 140

Thr Ala Ser Cys Asn Gly Thr Val Tyr Thr Leu Phe Lys Arg Pro Ser
145                 150                 155                 160

Ala Ser Ser Lys Phe Thr Leu Pro Phe Ile Cys Cys Arg Ser Gln Phe
                165                 170                 175

Val Ala Thr Cys Thr Met Thr Pro Gly Gly Pro Gln Pro Phe Leu Trp
            180                 185                 190

His Ala Arg Leu Lys Ala Ser Gly Leu Ser Val Gln Phe Gly Leu Leu
        195                 200                 205

Phe Leu His His Ser Pro Tyr Pro Ser Ser Thr Thr Thr Lys Ser Ser
    210                 215                 220

Lys Pro Gln Asn Gly Gln Ser Ser Arg Ser Leu Ser His Ser Arg Tyr
225                 230                 235                 240

Gly Asn Val Thr Ser Val Leu Pro Pro Val Thr Gly Lys Lys Ala Arg
                245                 250                 255

Leu Ile Lys Ile Val Leu Leu Ala Gly Trp Ser His Tyr Glu Glu Val
            260                 265                 270

Ala Thr Gly Ala Thr Ser Ala Arg Arg Leu Ile Val Val Lys Cys Asn
        275                 280                 285

Gln Phe Val Ala Pro Ser Cys Asp Val Ser Thr Gly Ser Pro Arg Asn
    290                 295                 300

Ser Ala Thr Ser Gly Gly Gln Ala Arg Lys Gly Tyr Leu Ile Phe Gln
305                 310                 315                 320

Thr Lys Lys Thr Ile Val Asp Tyr His Asn Lys Asn Lys Asn Met Leu
                325                 330                 335

Thr Lys Ser Leu Asn Glu Ser Asn Tyr Met Phe Leu Gly Trp Met Ile
            340                 345                 350

Lys Pro Gln Pro Gln Met Lys Ser Arg Met Ala Trp Ala Gln Thr Ser
        355                 360                 365

Ser Met Pro Thr Pro Ile Ile Ser Gly Cys Ser Thr Glu Lys Ile Ile
    370                 375                 380

Gln Ser Ser Gly Ile Leu Gln Lys Thr Ser Gln Asn Pro Pro Ser Thr
385                 390                 395                 400

Gly Pro Thr Thr Pro Leu Pro Ser Gly Pro Thr Ala Pro Pro Thr Thr
```

-continued

```
                405                 410                 415

Leu Ile Pro Thr Met Pro Trp Thr Pro Pro Pro Pro Leu Thr Pro Met
            420                 425                 430

Trp Ser Leu Leu Leu Pro Gly Leu Val Glu Lys Ile Leu Pro Ser Pro
        435                 440                 445

Thr Glu Pro Thr Phe Asn Met Asn Leu Arg Glu Leu Val Thr Thr Asn
    450                 455                 460

Ser Leu Tyr Pro Tyr Pro Thr Pro Ala Ala Gln Pro Pro Ser Ser Ser
465                 470                 475                 480

Ala Ser Thr Ser Asp Ser Thr Leu Met Gly Leu His Ser Arg Thr Asp
                485                 490                 495

Glu Glu Pro Ser Tyr Leu Asn Glu Leu Phe Ala Pro Ile Ser Ser Val
            500                 505                 510

Arg Arg Glu Ala Gly Asp Thr Val Thr Glu Ser Pro Pro Thr Tyr Trp
        515                 520                 525

Ile His Asp Glu Gly Ser Ser Thr Glu Leu Ile Ala Ala Pro Ala Pro
    530                 535                 540

Gly Asp Glu Ala Thr Val Gly Gly Gln Gly Arg Gly Ile Phe Thr Phe
545                 550                 555                 560

Ser Thr Arg Gln Gln Leu Ile
                565


<210> SEQ ID NO 7
<211> LENGTH: 580
<212> TYPE: PRT
<213> ORGANISM: Type A PWD circovirus

<400> SEQUENCE: 7

Trp Arg Val Glu Ala Ala Ala Ala Gly Arg Cys Arg His Phe His Trp
1               5                   10                  15

Ala Leu Phe Ala Ala Arg Leu Gly Met Leu Pro Pro His Glu Gly Lys
            20                  25                  30

Ile Ile Arg Gly Leu Leu Leu Phe Val Phe Tyr Pro Leu Lys Trp Asp
        35                  40                  45

Gly Lys Lys Ile Ile Lys Asn Thr Ala Leu Phe Thr Gln Phe Leu Thr
    50                  55                  60

Ser Ser Arg Val Glu Leu Pro Lys Arg Ile Lys Ser Leu Leu Leu Ser
65                  70                  75                  80

Lys Val Leu His Leu Pro Ile Lys Thr Gly Ala Ala Val Asp Leu Phe
                85                  90                  95

Arg Phe Ser Gly Val Leu Leu Ile Phe Phe Val Ala Thr Phe Phe Ala
            100                 105                 110

Val Tyr Lys Asp Leu Thr Ser Ser Arg Pro Val Leu Pro Leu Ala Ala
        115                 120                 125

Val Gln Arg Ser Ser His Thr Gly Lys Gln Leu Arg Pro Arg Gln His
    130                 135                 140

Ser Tyr Gly Leu Leu Lys Arg Tyr Arg Ile His Ser Ile Glu Ala Pro
145                 150                 155                 160

Gln Ser Phe Lys Gln Phe His Ala Pro Leu His Leu Leu Thr Ile Pro
                165                 170                 175

Leu Cys Ser Tyr Val Asp Tyr His Ala Arg Gly Thr Thr Pro Leu Ala
            180                 185                 190

Leu Pro Gly Thr Ile Lys Ser Leu Arg Pro Val Gly Val Pro Leu Arg
        195                 200                 205
```

-continued

```
Thr Ser Ile Leu Pro Pro Ile Ser Ile Met Ser Phe Phe Asn Asn Asn
    210                 215                 220

Gln Ile Ile Lys Ile Ala Pro Arg Pro Ile Ile Gln Ser Gln Thr Val
225                 230                 235                 240

Pro Ile Trp Gln Ser Tyr Leu Ser Phe Pro Thr Ser Asn Arg Lys Gln
                245                 250                 255

Gly Ala Thr Asn Gln Asn Gly Ala Ile Leu Gly Gly Leu Phe Pro Val
            260                 265                 270

Gly Ser Ser Asp Trp Ser Tyr Phe Ser Glu Ile Pro Pro Asn Ser Ser
        275                 280                 285

Gln Leu Lys Pro Leu Ser Ser Ser Phe Leu Gly Arg Leu Tyr Gly Phe
    290                 295                 300

Ala Ser Lys Phe Cys His Val Trp Gly Thr Gly Lys Glu Trp Ile Phe
305                 310                 315                 320

Tyr Ile Val Ser Asp Lys Lys Asn Asp Cys Arg Leu Pro Lys Lys Glu
                325                 330                 335

Asn Leu Pro Asp Lys Leu Ile Phe Glu Arg Phe Gln Val Tyr Ile Thr
            340                 345                 350

Leu Arg Val Val Tyr Asn Gln Ala Thr Thr Ala Asn Gln Leu Ala Tyr
        355                 360                 365

Gly Leu Gly Thr His Glu Val Asn Thr His Thr Asn Leu His Leu Trp
    370                 375                 380

Leu Gln Asn Arg Lys Asn Asn Pro Gln Phe Trp Asp Ile Thr Gln Asp
385                 390                 395                 400

Leu Glu Pro Lys Pro Thr Phe Tyr Arg Ser His Tyr Thr Phe Pro Gln
                405                 410                 415

Arg Ile Thr His Arg Ser Ser Tyr Asn Ile His Pro Asp Tyr Ala Leu
            420                 425                 430

Asn Thr Ser Pro Thr Val Phe Asn Ala Asp Leu Ile Val Val Thr Ser
        435                 440                 445

Gly Val Gly Arg Gln Asn Ser Thr Ile Pro Asp Arg Pro Tyr Phe Glu
    450                 455                 460

Tyr Lys Ala Lys Arg Ile Arg Tyr Tyr Gln Phe Pro Leu Pro Leu Pro
465                 470                 475                 480

Asn Thr Gly Gly Ser Pro Pro Leu Phe Gln Gly Ile Asn Phe Arg Leu
                485                 490                 495

Glu Asn Val Asn Trp Ser Pro Gln Ser His Gly Gly Arg Ile Thr Leu
            500                 505                 510

Val Phe Glu Arg Ser Leu Arg Ser Asn Phe Ile Gly Thr Lys Arg Arg
        515                 520                 525

Trp Arg Tyr Arg Asn Arg Phe Ala Pro His Val Leu Tyr Pro Arg Arg
    530                 535                 540

Arg Leu Ile Asn Gly Leu His Ser Arg Pro Arg Thr Arg Arg Arg Arg
545                 550                 555                 560

Tyr Arg Arg Arg Pro Trp Thr Met Arg Tyr Phe His Phe Phe His Ala
                565                 570                 575

Ala Thr Thr Asn
            580
```

<210> SEQ ID NO 8
<211> LENGTH: 557
<212> TYPE: PRT
<213> ORGANISM: Type A PWD circovirus

<400> SEQUENCE: 8

-continued

```
Leu Ala Ser Arg Cys Arg Cys Cys Arg Pro Leu Thr Leu Ser Phe Ala
1               5                   10                  15

Leu Cys Ser Phe Arg Gly Ala Val Gly Tyr Ser Thr Pro Thr Gly Tyr
            20                  25                  30

Asp Lys Arg Pro Pro Ser Phe Cys Phe Val Pro Ala Glu Leu Arg Gly
        35                  40                  45

Lys Gln Asn Asn Gln Lys His Arg Pro Leu Asn Pro Leu Pro Tyr Phe
    50                  55                  60

Glu Glu Gly Gly Pro Thr Gln Ser Asn Gln Ser Ala Ser Lys Cys Pro
65                  70                  75                  80

Ser Thr Thr Asn Gly His Gly Ser Gly Cys Arg Ser Leu Ser Leu Phe
                85                  90                  95

Arg Gly Ala Ser Tyr Leu Ile Ser Cys Tyr Leu Leu Gly Cys Val Arg
            100                 105                 110

Thr His Leu Glu Ala Ser Gly Pro Ser Ala Cys Arg Gly Thr Gln Gln
        115                 120                 125

Ser Tyr Gly Lys Pro Ser Pro Thr Lys Pro Ser Gln Leu Arg Ala Thr
    130                 135                 140

Glu Gln Leu Thr His Ser Phe Asn Gly Arg Ala Pro Gln Val Lys Ser
145                 150                 155                 160

Leu Ser Arg Ser Ser Ala Ala Ala His Asn Ser Ser Leu Gln Val Arg
                165                 170                 175

Leu Pro Gly Ala Arg Asn His Ser Ser Gly Thr Pro Gly Tyr Asn Gln
            180                 185                 190

Gln Ala Pro Cys Arg Ser Ser Ala Tyr Phe Tyr Thr Thr Pro His Ile
        195                 200                 205

Asp His Leu Leu Leu Gln Gln Lys Pro His Asn Lys His Ser Thr Val
    210                 215                 220

Lys Pro His Asp Val Ser Val Thr His Gly Thr Asp Met Ser Gln Leu
225                 230                 235                 240

Ser Leu Pro Tyr Gln Glu Lys Lys Pro Gly Cys Tyr Lys Ser Trp Cys
                245                 250                 255

Asp Pro Gly Gly Pro Ile Thr Ser Arg Leu Gln Gln Gly Leu Gln Leu
            260                 265                 270

Leu Glu Arg Asp Ser Ser Lys Ala Ile Lys Ser Ser Gln Gln Leu Val
        275                 280                 285

Ile Trp Pro Pro Val Arg Leu Gly Ile Gln Leu Leu Pro Gly Val Arg
    290                 295                 300

His Gly Lys Gly Met Tyr Phe Leu Asn Ser Leu Arg Lys Gln Met Thr
305                 310                 315                 320

Ile Thr Lys Ile Lys Ile Lys Ser Pro Arg Glu Pro Tyr Ile Arg Gln
                325                 330                 335

Ile Thr Cys Leu Tyr Asp Val Lys Gly Cys Leu Lys Pro Ser His Asn
            340                 345                 350

Cys Lys Pro Ala Cys Leu Gly Pro Arg His Ala Arg Cys Gln His Pro
        355                 360                 365

Tyr Lys Phe Pro Ala Val Val Pro Lys Lys Lys Ala Pro Val Leu Asn
    370                 375                 380

Asn Pro Arg Ala Arg Thr Gln Pro His Leu Val Gln Leu Pro Leu Tyr
385                 390                 395                 400

Leu Ala Ala Lys His His Pro Pro Leu Leu Leu Tyr Leu Pro Leu Gly
                405                 410                 415
```

-continued

```
Leu Gln His Leu Pro Asn Cys Leu Gln Cys Gly Leu Tyr Cys Cys His
            420                 425                 430

Val Trp Cys Arg Lys Ser Leu His His Pro Arg Gln Pro Leu Ile Ile
        435                 440                 445

Gly Lys Tyr Pro Leu Ile Pro Phe Thr Pro Thr Pro Pro Gln His Arg
    450                 455                 460

Arg Leu Pro Pro Pro Val Pro Arg His Gln Ile Glu Ala Arg Cys Glu
465                 470                 475                 480

Leu Ile Ala Ala Leu Thr Arg Arg Lys His His Thr Cys Ile Arg Phe
                485                 490                 495

Pro Pro Phe Gln Leu Tyr Gly Asp Lys Pro Ala Met Gln Leu Pro Lys
            500                 505                 510

Gln Leu Arg Pro Thr Gly Phe Ile Thr Lys Glu Pro Pro His Lys Trp
        515                 520                 525

Ser Pro Gln Pro Pro Pro Asp Thr Lys Gln Pro Leu Ala Glu Lys Ala
    530                 535                 540

Val Asp Asp Leu Leu Ser Leu Leu Ala Ser Ser Tyr Tyr
545                 550                 555


<210> SEQ ID NO 9
<211> LENGTH: 939
<212> TYPE: DNA
<213> ORGANISM: Type A PWD circovirus
<220> FEATURE:
<221> NAME/KEY: CDS
<222> LOCATION: (1)..(936)

<400> SEQUENCE: 9

atg cca agc aag aaa agc ggc ccg caa ccc cat aag agg tgg gtg ttc       48
Met Pro Ser Lys Lys Ser Gly Pro Gln Pro His Lys Arg Trp Val Phe
1               5                   10                  15

acc ctt aat aat cct tcc gag gag gag aaa aac aaa ata cgg gag ctt       96
Thr Leu Asn Asn Pro Ser Glu Glu Glu Lys Asn Lys Ile Arg Glu Leu
            20                  25                  30

cca atc tcc ctt ttt gat tat ttt gtt tgt ggc gag gaa ggt ttg gaa      144
Pro Ile Ser Leu Phe Asp Tyr Phe Val Cys Gly Glu Glu Gly Leu Glu
        35                  40                  45

gag ggt aga act cct cac ctc cag ggg ttt gcg aat ttt gct aag aag      192
Glu Gly Arg Thr Pro His Leu Gln Gly Phe Ala Asn Phe Ala Lys Lys
    50                  55                  60

cag act ttt aac aag gtg aag tgg tat ttt ggt gcc cgc tgc cac atc      240
Gln Thr Phe Asn Lys Val Lys Trp Tyr Phe Gly Ala Arg Cys His Ile
65                  70                  75                  80

gag aaa gcg aaa gga acc gac cag cag aat aaa gaa tac tgc agt aaa      288
Glu Lys Ala Lys Gly Thr Asp Gln Gln Asn Lys Glu Tyr Cys Ser Lys
                85                  90                  95

gaa ggc cac ata ctt atc gag tgt gga gct ccg cgg aac cag ggg aag      336
Glu Gly His Ile Leu Ile Glu Cys Gly Ala Pro Arg Asn Gln Gly Lys
            100                 105                 110

cgc agc gac ctg tct act gct gtg agt acc ctt ttg gag acg ggg tct      384
Arg Ser Asp Leu Ser Thr Ala Val Ser Thr Leu Leu Glu Thr Gly Ser
        115                 120                 125

ttg gtg act gta gcc gag cag ttt cct gta acg tat gtg aga aat ttc      432
Leu Val Thr Val Ala Glu Gln Phe Pro Val Thr Tyr Val Arg Asn Phe
    130                 135                 140

cgc ggg ctg gct gaa ctt ttg aaa gtg agc ggg aag atg cag cag cgt      480
Arg Gly Leu Ala Glu Leu Leu Lys Val Ser Gly Lys Met Gln Gln Arg
145                 150                 155                 160

gat tgg aag aca gct gta cac gtc ata gtg ggc ccg ccc ggt tgt ggg      528
```

-continued

```
Asp Trp Lys Thr Ala Val His Val Ile Val Gly Pro Pro Gly Cys Gly
                165                 170                 175

aag agc cag tgg gcc cgt aat ttt gct gag cct agg gac acc tac tgg      576
Lys Ser Gln Trp Ala Arg Asn Phe Ala Glu Pro Arg Asp Thr Tyr Trp
            180                 185                 190

aag cct agt aga aat aag tgg tgg gat gga tat cat gga gaa gaa gtt      624
Lys Pro Ser Arg Asn Lys Trp Trp Asp Gly Tyr His Gly Glu Glu Val
        195                 200                 205

gtt gtt ttg gat gat ttt tat ggc tgg tta cct tgg gat gat cta ctg      672
Val Val Leu Asp Asp Phe Tyr Gly Trp Leu Pro Trp Asp Asp Leu Leu
    210                 215                 220

aga ctg tgt gac cgg tat cca ttg act gta gag act aaa ggg ggt act      720
Arg Leu Cys Asp Arg Tyr Pro Leu Thr Val Glu Thr Lys Gly Gly Thr
225                 230                 235                 240

gtt cct ttt ttg gcc cgc agt att ttg att acc agc aat cag gcc ccc      768
Val Pro Phe Leu Ala Arg Ser Ile Leu Ile Thr Ser Asn Gln Ala Pro
                245                 250                 255

cag gaa tgg tac tcc tca act gct gtc cca gct gta gaa gct ctc tat      816
Gln Glu Trp Tyr Ser Ser Thr Ala Val Pro Ala Val Glu Ala Leu Tyr
            260                 265                 270

cgg agg att act act ttg caa ttt tgg aag act gct gga gaa caa tcc      864
Arg Arg Ile Thr Thr Leu Gln Phe Trp Lys Thr Ala Gly Glu Gln Ser
        275                 280                 285

acg gag gta ccc gaa ggc cga ttt gaa gca gtg gac cca ccc tgt gcc      912
Thr Glu Val Pro Glu Gly Arg Phe Glu Ala Val Asp Pro Pro Cys Ala
    290                 295                 300

ctt ttc cca tat aaa ata aat tac tga                                  939
Leu Phe Pro Tyr Lys Ile Asn Tyr
305                 310


<210> SEQ ID NO 10
<211> LENGTH: 312
<212> TYPE: PRT
<213> ORGANISM: Type A PWD circovirus

<400> SEQUENCE: 10

Met Pro Ser Lys Lys Ser Gly Pro Gln Pro His Lys Arg Trp Val Phe
1               5                   10                  15

Thr Leu Asn Asn Pro Ser Glu Glu Glu Lys Asn Lys Ile Arg Glu Leu
            20                  25                  30

Pro Ile Ser Leu Phe Asp Tyr Phe Val Cys Gly Glu Glu Gly Leu Glu
        35                  40                  45

Glu Gly Arg Thr Pro His Leu Gln Gly Phe Ala Asn Phe Ala Lys Lys
    50                  55                  60

Gln Thr Phe Asn Lys Val Lys Trp Tyr Phe Gly Ala Arg Cys His Ile
65                  70                  75                  80

Glu Lys Ala Lys Gly Thr Asp Gln Gln Asn Lys Glu Tyr Cys Ser Lys
                85                  90                  95

Glu Gly His Ile Leu Ile Glu Cys Gly Ala Pro Arg Asn Gln Gly Lys
            100                 105                 110

Arg Ser Asp Leu Ser Thr Ala Val Ser Thr Leu Leu Glu Thr Gly Ser
        115                 120                 125

Leu Val Thr Val Ala Glu Gln Phe Pro Val Thr Tyr Val Arg Asn Phe
    130                 135                 140

Arg Gly Leu Ala Glu Leu Leu Lys Val Ser Gly Lys Met Gln Gln Arg
145                 150                 155                 160

Asp Trp Lys Thr Ala Val His Val Ile Val Gly Pro Pro Gly Cys Gly
                165                 170                 175
```

-continued

```
Lys Ser Gln Trp Ala Arg Asn Phe Ala Glu Pro Arg Asp Thr Tyr Trp
            180                 185                 190

Lys Pro Ser Arg Asn Lys Trp Trp Asp Gly Tyr His Gly Glu Glu Val
        195                 200                 205

Val Val Leu Asp Asp Phe Tyr Gly Trp Leu Pro Trp Asp Asp Leu Leu
    210                 215                 220

Arg Leu Cys Asp Arg Tyr Pro Leu Thr Val Glu Thr Lys Gly Gly Thr
225                 230                 235                 240

Val Pro Phe Leu Ala Arg Ser Ile Leu Ile Thr Ser Asn Gln Ala Pro
                245                 250                 255

Gln Glu Trp Tyr Ser Ser Thr Ala Val Pro Ala Val Glu Ala Leu Tyr
            260                 265                 270

Arg Arg Ile Thr Thr Leu Gln Phe Trp Lys Thr Ala Gly Glu Gln Ser
        275                 280                 285

Thr Glu Val Pro Glu Gly Arg Phe Glu Ala Val Asp Pro Pro Cys Ala
    290                 295                 300

Leu Phe Pro Tyr Lys Ile Asn Tyr
305                 310


<210> SEQ ID NO 11
<211> LENGTH: 702
<212> TYPE: DNA
<213> ORGANISM: Type A PWD circovirus
<220> FEATURE:
<221> NAME/KEY: CDS
<222> LOCATION: (1)..(699)

<400> SEQUENCE: 11

atg acg tgg cca agg agg cgt tac cgc aga aga cgg acc cgc ccc cgc       48
Met Thr Trp Pro Arg Arg Arg Tyr Arg Arg Arg Arg Thr Arg Pro Arg
1               5                   10                  15

agc cat ctt gga aac atc ctc cgg aga aga cca tat ttg gta cac ccc       96
Ser His Leu Gly Asn Ile Leu Arg Arg Arg Pro Tyr Leu Val His Pro
            20                  25                  30

gcc ttc aga aac cgt tac aga tgg cgc cga aag acg ggt atc ttc aat      144
Ala Phe Arg Asn Arg Tyr Arg Trp Arg Arg Lys Thr Gly Ile Phe Asn
        35                  40                  45

tcc cgc ctt tct aga gaa ttt gta ctc acc ata aga gga gga cac tcg      192
Ser Arg Leu Ser Arg Glu Phe Val Leu Thr Ile Arg Gly Gly His Ser
    50                  55                  60

cag cca tct tgg aat gtt aac gag ctg aga ttc aac atc ggc cag ttc      240
Gln Pro Ser Trp Asn Val Asn Glu Leu Arg Phe Asn Ile Gly Gln Phe
65                  70                  75                  80

ctc ccc ccc tca ggc ggc acc aac ccc cta ccc cta cct ttc caa tac      288
Leu Pro Pro Ser Gly Gly Thr Asn Pro Leu Pro Leu Pro Phe Gln Tyr
                85                  90                  95

tac cgt att aga aag gct aaa tat gaa ttt tac ccc aga gac ccc atc      336
Tyr Arg Ile Arg Lys Ala Lys Tyr Glu Phe Tyr Pro Arg Asp Pro Ile
            100                 105                 110

acc tct aat caa aga ggt gtt ggg tcc act gtt gtt atc ttg gat gcc      384
Thr Ser Asn Gln Arg Gly Val Gly Ser Thr Val Val Ile Leu Asp Ala
        115                 120                 125

aac ttt gta acc ccc tcc acc aac ttg gcc tat gac ccc tat att aac      432
Asn Phe Val Thr Pro Ser Thr Asn Leu Ala Tyr Asp Pro Tyr Ile Asn
    130                 135                 140

tac tcc tcc cgc cac acc ata agg cag ccc ttt acc tac cac tcc agg      480
Tyr Ser Ser Arg His Thr Ile Arg Gln Pro Phe Thr Tyr His Ser Arg
145                 150                 155                 160
```

-continued

```
tac ttc acc ccc aaa cca gag cta gac caa aca att gat tgg ttc cag      528
Tyr Phe Thr Pro Lys Pro Glu Leu Asp Gln Thr Ile Asp Trp Phe Gln
                165                 170                 175

cca aat aat aaa aga aac cag ctg tgg ctc cat tta aat acc cac acc      576
Pro Asn Asn Lys Arg Asn Gln Leu Trp Leu His Leu Asn Thr His Thr
            180                 185                 190

aat gtc gag cac aca ggc ctg ggc tat gcg ctc caa aat gca acc aca      624
Asn Val Glu His Thr Gly Leu Gly Tyr Ala Leu Gln Asn Ala Thr Thr
        195                 200                 205

gcc caa aat tat gtg gta agg ttg act att tat gta caa ttc aga gaa      672
Ala Gln Asn Tyr Val Val Arg Leu Thr Ile Tyr Val Gln Phe Arg Glu
    210                 215                 220

ttt atc ctg aaa gac cct cta aat gaa taa                              702
Phe Ile Leu Lys Asp Pro Leu Asn Glu
225                 230


<210> SEQ ID NO 12
<211> LENGTH: 233
<212> TYPE: PRT
<213> ORGANISM: Type A PWD circovirus

<400> SEQUENCE: 12

Met Thr Trp Pro Arg Arg Arg Tyr Arg Arg Arg Arg Thr Arg Pro Arg
1               5                   10                  15

Ser His Leu Gly Asn Ile Leu Arg Arg Arg Pro Tyr Leu Val His Pro
            20                  25                  30

Ala Phe Arg Asn Arg Tyr Arg Trp Arg Arg Lys Thr Gly Ile Phe Asn
        35                  40                  45

Ser Arg Leu Ser Arg Glu Phe Val Leu Thr Ile Arg Gly Gly His Ser
    50                  55                  60

Gln Pro Ser Trp Asn Val Asn Glu Leu Arg Phe Asn Ile Gly Gln Phe
65                  70                  75                  80

Leu Pro Pro Ser Gly Gly Thr Asn Pro Leu Pro Leu Pro Phe Gln Tyr
                85                  90                  95

Tyr Arg Ile Arg Lys Ala Lys Tyr Glu Phe Tyr Pro Arg Asp Pro Ile
            100                 105                 110

Thr Ser Asn Gln Arg Gly Val Gly Ser Thr Val Val Ile Leu Asp Ala
        115                 120                 125

Asn Phe Val Thr Pro Ser Thr Asn Leu Ala Tyr Asp Pro Tyr Ile Asn
    130                 135                 140

Tyr Ser Ser Arg His Thr Ile Arg Gln Pro Phe Thr Tyr His Ser Arg
145                 150                 155                 160

Tyr Phe Thr Pro Lys Pro Glu Leu Asp Gln Thr Ile Asp Trp Phe Gln
                165                 170                 175

Pro Asn Asn Lys Arg Asn Gln Leu Trp Leu His Leu Asn Thr His Thr
            180                 185                 190

Asn Val Glu His Thr Gly Leu Gly Tyr Ala Leu Gln Asn Ala Thr Thr
        195                 200                 205

Ala Gln Asn Tyr Val Val Arg Leu Thr Ile Tyr Val Gln Phe Arg Glu
    210                 215                 220

Phe Ile Leu Lys Asp Pro Leu Asn Glu
225                 230


<210> SEQ ID NO 13
<211> LENGTH: 621
<212> TYPE: DNA
<213> ORGANISM: Type A PWD circovirus
<220> FEATURE:
```

-continued

```
<221> NAME/KEY: CDS
<222> LOCATION: (1)..(618)

<400> SEQUENCE: 13

atg ata tcc atc cca cca ctt att tct act agg ctt cca gta ggt gtc       48
Met Ile Ser Ile Pro Pro Leu Ile Ser Thr Arg Leu Pro Val Gly Val
1               5                   10                  15

cct agg ctc agc aaa att acg ggc cca ctg gct ctt ccc aca acc ggg       96
Pro Arg Leu Ser Lys Ile Thr Gly Pro Leu Ala Leu Pro Thr Thr Gly
            20                  25                  30

cgg gcc cac tat gac gtg tac agc tgt ctt cca atc acg ctg ctg cat      144
Arg Ala His Tyr Asp Val Tyr Ser Cys Leu Pro Ile Thr Leu Leu His
        35                  40                  45

ctt ccc gct cac ttt caa aag ttc agc cag ccc gcg gaa att tct cac      192
Leu Pro Ala His Phe Gln Lys Phe Ser Gln Pro Ala Glu Ile Ser His
    50                  55                  60

ata cgt tac agg aaa ctg ctc ggc tac agt cac caa aga ccc cgt ctc      240
Ile Arg Tyr Arg Lys Leu Leu Gly Tyr Ser His Gln Arg Pro Arg Leu
65                  70                  75                  80

caa aag ggt act cac agc agt aga cag gtc gct gcg ctt ccc ctg gtt      288
Gln Lys Gly Thr His Ser Ser Arg Gln Val Ala Ala Leu Pro Leu Val
                85                  90                  95

ccg cgg agc tcc aca ctc gat aag tat gtg gcc ttc ttt act gca gta      336
Pro Arg Ser Ser Thr Leu Asp Lys Tyr Val Ala Phe Phe Thr Ala Val
            100                 105                 110

ttc ttt att ctg ctg gtc ggt tcc ttt cgc ttt ctc gat gtg gca gcg      384
Phe Phe Ile Leu Leu Val Gly Ser Phe Arg Phe Leu Asp Val Ala Ala
        115                 120                 125

ggc acc aaa ata cca ctt cac ctt gtt aaa agt ctg ctt ctt agc aaa      432
Gly Thr Lys Ile Pro Leu His Leu Val Lys Ser Leu Leu Leu Ser Lys
    130                 135                 140

att cgc aaa ccc ctg gag gtg agg agt tct acc ctc ttc caa acc ttc      480
Ile Arg Lys Pro Leu Glu Val Arg Ser Ser Thr Leu Phe Gln Thr Phe
145                 150                 155                 160

ctc gcc aca aac aaa ata atc aaa aag gga gat tgg aag ctc ccg tat      528
Leu Ala Thr Asn Lys Ile Ile Lys Lys Gly Asp Trp Lys Leu Pro Tyr
                165                 170                 175

ttt gtt ttt ctc ctc ctc gga agg att att aag ggt gaa cac cca cct      576
Phe Val Phe Leu Leu Leu Gly Arg Ile Ile Lys Gly Glu His Pro Pro
            180                 185                 190

ctt atg ggg ttg cgg gcc gct ttt ctt gct tgg cat ttt cac tga          621
Leu Met Gly Leu Arg Ala Ala Phe Leu Ala Trp His Phe His
        195                 200                 205


<210> SEQ ID NO 14
<211> LENGTH: 206
<212> TYPE: PRT
<213> ORGANISM: Type A PWD circovirus

<400> SEQUENCE: 14

Met Ile Ser Ile Pro Pro Leu Ile Ser Thr Arg Leu Pro Val Gly Val
1               5                   10                  15

Pro Arg Leu Ser Lys Ile Thr Gly Pro Leu Ala Leu Pro Thr Thr Gly
            20                  25                  30

Arg Ala His Tyr Asp Val Tyr Ser Cys Leu Pro Ile Thr Leu Leu His
        35                  40                  45

Leu Pro Ala His Phe Gln Lys Phe Ser Gln Pro Ala Glu Ile Ser His
    50                  55                  60

Ile Arg Tyr Arg Lys Leu Leu Gly Tyr Ser His Gln Arg Pro Arg Leu
65                  70                  75                  80
```

-continued

```
Gln Lys Gly Thr His Ser Ser Arg Gln Val Ala Ala Leu Pro Leu Val
                85                  90                  95

Pro Arg Ser Ser Thr Leu Asp Lys Tyr Val Ala Phe Phe Thr Ala Val
            100                 105                 110

Phe Phe Ile Leu Leu Val Gly Ser Phe Arg Phe Leu Asp Val Ala Ala
        115                 120                 125

Gly Thr Lys Ile Pro Leu His Leu Val Lys Ser Leu Leu Leu Ser Lys
    130                 135                 140

Ile Arg Lys Pro Leu Glu Val Arg Ser Ser Thr Leu Phe Gln Thr Phe
145                 150                 155                 160

Leu Ala Thr Asn Lys Ile Ile Lys Lys Gly Asp Trp Lys Leu Pro Tyr
                165                 170                 175

Phe Val Phe Leu Leu Leu Gly Arg Ile Ile Lys Gly Glu His Pro Pro
            180                 185                 190

Leu Met Gly Leu Arg Ala Ala Phe Leu Ala Trp His Phe His
        195                 200                 205
```

```
<210> SEQ ID NO 15
<211> LENGTH: 1767
<212> TYPE: DNA
<213> ORGANISM: Type B PWD circovirus
<220> FEATURE:
<221> NAME/KEY: CDS
<222> LOCATION: (1)..(111)
<220> FEATURE:
<221> NAME/KEY: CDS
<222> LOCATION: (115)..(243)
<220> FEATURE:
<221> NAME/KEY: CDS
<222> LOCATION: (247)..(267)
<220> FEATURE:
<221> NAME/KEY: CDS
<222> LOCATION: (271)..(360)
<220> FEATURE:
<221> NAME/KEY: CDS
<222> LOCATION: (364)..(417)
<220> FEATURE:
<221> NAME/KEY: CDS
<222> LOCATION: (421)..(447)
<220> FEATURE:
<221> NAME/KEY: CDS
<222> LOCATION: (451)..(471)
<220> FEATURE:
<221> NAME/KEY: CDS
<222> LOCATION: (475)..(510)
<220> FEATURE:
<221> NAME/KEY: CDS
<222> LOCATION: (514)..(516)
<220> FEATURE:
<221> NAME/KEY: CDS
<222> LOCATION: (520)..(729)
<220> FEATURE:
<221> NAME/KEY: CDS
<222> LOCATION: (733)..(753)
<220> FEATURE:
<221> NAME/KEY: CDS
<222> LOCATION: (757)..(759)
<220> FEATURE:
<221> NAME/KEY: CDS
<222> LOCATION: (763)..(804)
<220> FEATURE:
<221> NAME/KEY: CDS
<222> LOCATION: (808)..(861)
<220> FEATURE:
<221> NAME/KEY: CDS
<222> LOCATION: (865)..(984)
<220> FEATURE:
<221> NAME/KEY: CDS
<222> LOCATION: (988)..(1173)
<220> FEATURE:
```

-continued

```
<221> NAME/KEY: CDS
<222> LOCATION: (1177)..(1233)
<220> FEATURE:
<221> NAME/KEY: CDS
<222> LOCATION: (1237)..(1359)
<220> FEATURE:
<221> NAME/KEY: CDS
<222> LOCATION: (1363)..(1476)
<220> FEATURE:
<221> NAME/KEY: CDS
<222> LOCATION: (1480)..(1737)
<220> FEATURE:
<221> NAME/KEY: CDS
<222> LOCATION: (1741)..(1767)

<400> SEQUENCE: 15

acc agc gca ctt cgg cag cgg cag cac ctc ggc agc acc tca gca gca       48
Thr Ser Ala Leu Arg Gln Arg Gln His Leu Gly Ser Thr Ser Ala Ala
1               5                   10                  15

aca tgc cca gca aga aga atg gaa gaa gcg gac ccc aac ccc ata aaa       96
Thr Cys Pro Ala Arg Arg Met Glu Glu Ala Asp Pro Asn Pro Ile Lys
            20                  25                  30

ggt ggg tgt tca ctc tga ata atc ctt ccg aag acg agc gca aga aaa      144
Gly Gly Cys Ser Leu     Ile Ile Leu Pro Lys Thr Ser Ala Arg Lys
        35                  40                      45

tac ggg atc ttc caa tat ccc tat ttg att att tta ttg ttg gcg agg      192
Tyr Gly Ile Phe Gln Tyr Pro Tyr Leu Ile Ile Leu Leu Leu Ala Arg
        50                  55                  60

agg gta atg agg aag gac gaa cac ctc acc tcc agg ggt tcg cta att      240
Arg Val Met Arg Lys Asp Glu His Leu Thr Ser Arg Gly Ser Leu Ile
    65                  70                  75

ttg tga aga agc aga ctt tta ata aag tga agt ggt att tgg gtg ccc      288
Leu     Arg Ser Arg Leu Leu Ile Lys     Ser Gly Ile Trp Val Pro
80                      85                      90

gct gcc aca tcg aga aag cga aag gaa cag atc agc aga ata aag aat      336
Ala Ala Thr Ser Arg Lys Arg Lys Glu Gln Ile Ser Arg Ile Lys Asn
    95                  100                 105

act gca gta aag aag gca act tac tga tgg agt gtg gag ctc cta gat      384
Thr Ala Val Lys Lys Ala Thr Tyr     Trp Ser Val Glu Leu Leu Asp
110                 115                 120

ctc agg gac aac gga gtg acc tgt cta ctg ctg tga gta cct tgt tgg      432
Leu Arg Asp Asn Gly Val Thr Cys Leu Leu Leu     Val Pro Cys Trp
125                 130                 135

aga gcg gga gtc tgg tga ccg ttg cag agc agc acc ctg taa cgt ttg      480
Arg Ala Gly Val Trp     Pro Leu Gln Ser Ser Thr Leu     Arg Leu
140                     145                 150

tca gaa att tcc gcg ggc tgg ctg aac ttt tga aag tga gcg gga aaa      528
Ser Glu Ile Ser Ala Gly Trp Leu Asn Phe     Lys     Ala Gly Lys
    155                 160                         165

tgc aga agc gtg att gga aga cta atg tac acg tca ttg tgg ggc cac      576
Cys Arg Ser Val Ile Gly Arg Leu Met Tyr Thr Ser Leu Trp Gly His
        170                 175                 180

ctg ggt gtg gta aaa gca aat ggg ctg cta att ttg cag acc cgg aaa      624
Leu Gly Val Val Lys Ala Asn Gly Leu Leu Ile Leu Gln Thr Arg Lys
    185                 190                 195

cca cat act gga aac cac cta gaa aca agt ggt ggg atg gtt acc atg      672
Pro His Thr Gly Asn His Leu Glu Thr Ser Gly Gly Met Val Thr Met
200                 205                 210                 215

gtg aag aag tgg ttg tta ttg atg act ttt atg gct ggc tgc cct ggg      720
Val Lys Lys Trp Leu Leu Leu Met Thr Phe Met Ala Gly Cys Pro Gly
                220                 225                 230

atg atc tac tga gac tgt gtg atc gat atc cat tga ctg tag aga cta      768
Met Ile Tyr     Asp Cys Val Ile Asp Ile His     Leu     Arg Leu
```

-continued

```
                235                 240

aag gtg gaa ctg tac ctt ttt tgg ccc gca gta ttc tga tta cca gca      816
Lys Val Glu Leu Tyr Leu Phe Trp Pro Ala Val Phe     Leu Pro Ala
245                 250                 255

atc aga ccc cgt tgg aat ggt act cct caa ctg ctg tcc cag ctg tag      864
Ile Arg Pro Arg Trp Asn Gly Thr Pro Gln Leu Leu Ser Gln Leu
260                 265                 270

aag ctc ttt atc gga gga tta ctt cct tgg tat ttt gga aga atg cta      912
Lys Leu Phe Ile Gly Gly Leu Leu Pro Trp Tyr Phe Gly Arg Met Leu
275                 280                 285                 290

cag aac aat cca cgg agg aag ggg gcc agt tcg tca ccc ttt ccc ccc      960
Gln Asn Asn Pro Arg Arg Lys Gly Ala Ser Ser Ser Pro Phe Pro Pro
                295                 300                 305

cat gcc ctg aat ttc cat atg aaa taa att act gag tct ttt tta tca     1008
His Ala Leu Asn Phe His Met Lys     Ile Thr Glu Ser Phe Leu Ser
            310                 315                 320

ctt cgt aat ggt ttt tat tat tca tta agg gtt aag tgg ggg gtc ttt     1056
Leu Arg Asn Gly Phe Tyr Tyr Ser Leu Arg Val Lys Trp Gly Val Phe
            325                 330                 335

aaa att aaa ttc tct gaa ttg tac ata cat ggt tac acg gat att gta     1104
Lys Ile Lys Phe Ser Glu Leu Tyr Ile His Gly Tyr Thr Asp Ile Val
        340                 345                 350

ttc ctg gtc gta tat act gtt ttc gaa cgc agt gcc gag gcc tac gtg     1152
Phe Leu Val Val Tyr Thr Val Phe Glu Arg Ser Ala Glu Ala Tyr Val
    355                 360                 365

gtc tac att tcc agc agt ttg tag tct cag cca cag ctg gtt tct ttt     1200
Val Tyr Ile Ser Ser Ser Leu     Ser Gln Pro Gln Leu Val Ser Phe
370                 375                 380

gtt gtt tgg ttg gaa gta atc aat agt gaa atc tag gac agg ttt ggg     1248
Val Val Trp Leu Glu Val Ile Asn Ser Glu Ile     Asp Arg Phe Gly
385                 390                 395

ggt aaa gta ccg gga gtg gta gga gaa ggg ctg ggt tat ggt atg gcg     1296
Gly Lys Val Pro Gly Val Val Gly Glu Gly Leu Gly Tyr Gly Met Ala
400                 405                 410                 415

gga gga gta gtt tac ata ggg gtc ata ggt gag ggc tgt ggc ctt tgt     1344
Gly Gly Val Val Tyr Ile Gly Val Ile Gly Glu Gly Cys Gly Leu Cys
                420                 425                 430

tac aaa gtt atc atc taa aat aac agc act gga gcc cac tcc cct gtc     1392
Tyr Lys Val Ile Ile     Asn Asn Ser Thr Gly Ala His Ser Pro Val
            435                 440                 445

acc ctg ggt gat cgg gga gca ggg cca gaa ttc aac ctt aac ctt tct     1440
Thr Leu Gly Asp Arg Gly Ala Gly Pro Glu Phe Asn Leu Asn Leu Ser
            450                 455                 460

tat tct gta gta ttc aaa ggg cac aga gcg ggg gtt tga ccc ccc tcc     1488
Tyr Ser Val Val Phe Lys Gly His Arg Ala Gly Val     Pro Pro Ser
        465                 470                 475

tgg ggg aag aaa gtc att aat att gaa tct cat cat gtc cac cgc cca     1536
Trp Gly Lys Lys Val Ile Asn Ile Glu Ser His His Val His Arg Pro
        480                 485                 490

gga ggg cgt tct gac tgt ggt tcg ctt gac agt ata tcc gaa ggt gcg     1584
Gly Gly Arg Ser Asp Cys Gly Ser Leu Asp Ser Ile Ser Glu Gly Ala
    495                 500                 505

gga gag gcg ggt gtt gaa gat gcc att ttt cct tct cca gcg gta acg     1632
Gly Glu Ala Gly Val Glu Asp Ala Ile Phe Pro Ser Pro Ala Val Thr
510                 515                 520                 525

gtg gcg ggg gtg gac gag cca ggg gcg gcg gcg gag gat ctg gcc aag     1680
Val Ala Gly Val Asp Glu Pro Gly Ala Ala Ala Glu Asp Leu Ala Lys
                530                 535                 540

atg gct gcg ggg gcg gtg tct tct tct tcg gta acg cct cct tgg ata     1728
```

-continued

```
Met Ala Ala Gly Ala Val Ser Ser Ser Ser Val Thr Pro Pro Trp Ile
            545                 550                 555

cgt cat atc tga aaa cga aag aag tgc gct gta agt att                1767
Arg His Ile     Lys Arg Lys Lys Cys Ala Val Ser Ile
        560                 565


<210> SEQ ID NO 16
<211> LENGTH: 569
<212> TYPE: PRT
<213> ORGANISM: Type B PWD circovirus

<400> SEQUENCE: 16

Thr Ser Ala Leu Arg Gln Arg Gln His Leu Gly Ser Thr Ser Ala Ala
1               5                   10                  15

Thr Cys Pro Ala Arg Arg Met Glu Glu Ala Asp Pro Asn Pro Ile Lys
            20                  25                  30

Gly Gly Cys Ser Leu Ile Ile Leu Pro Lys Thr Ser Ala Arg Lys Tyr
        35                  40                  45

Gly Ile Phe Gln Tyr Pro Tyr Leu Ile Ile Leu Leu Ala Arg Arg
    50                  55                  60

Val Met Arg Lys Asp Glu His Leu Thr Ser Arg Gly Ser Leu Ile Leu
65                  70                  75                  80

Arg Ser Arg Leu Leu Ile Lys Ser Gly Ile Trp Val Pro Ala Ala Thr
                85                  90                  95

Ser Arg Lys Arg Lys Glu Gln Ile Ser Arg Ile Lys Asn Thr Ala Val
            100                 105                 110

Lys Lys Ala Thr Tyr Trp Ser Val Glu Leu Leu Asp Leu Arg Asp Asn
        115                 120                 125

Gly Val Thr Cys Leu Leu Leu Val Pro Cys Trp Arg Ala Gly Val Trp
    130                 135                 140

Pro Leu Gln Ser Ser Thr Leu Arg Leu Ser Glu Ile Ser Ala Gly Trp
145                 150                 155                 160

Leu Asn Phe Lys Ala Gly Lys Cys Arg Ser Val Ile Gly Arg Leu Met
                165                 170                 175

Tyr Thr Ser Leu Trp Gly His Leu Gly Val Val Lys Ala Asn Gly Leu
            180                 185                 190

Leu Ile Leu Gln Thr Arg Lys Pro His Thr Gly Asn His Leu Glu Thr
        195                 200                 205

Ser Gly Gly Met Val Thr Met Val Lys Lys Trp Leu Leu Leu Met Thr
    210                 215                 220

Phe Met Ala Gly Cys Pro Gly Met Ile Tyr Asp Cys Val Ile Asp Ile
225                 230                 235                 240

His Leu Arg Leu Lys Val Glu Leu Tyr Leu Phe Trp Pro Ala Val Phe
                245                 250                 255

Leu Pro Ala Ile Arg Pro Arg Trp Asn Gly Thr Pro Gln Leu Leu Ser
            260                 265                 270

Gln Leu Lys Leu Phe Ile Gly Gly Leu Leu Pro Trp Tyr Phe Gly Arg
        275                 280                 285

Met Leu Gln Asn Asn Pro Arg Arg Lys Gly Ala Ser Ser Ser Pro Phe
    290                 295                 300

Pro Pro His Ala Leu Asn Phe His Met Lys Ile Thr Glu Ser Phe Leu
305                 310                 315                 320

Ser Leu Arg Asn Gly Phe Tyr Tyr Ser Leu Arg Val Lys Trp Gly Val
                325                 330                 335

Phe Lys Ile Lys Phe Ser Glu Leu Tyr Ile His Gly Tyr Thr Asp Ile
```

-continued

```
            340                 345                 350

Val Phe Leu Val Val Tyr Thr Val Phe Glu Arg Ser Ala Glu Ala Tyr
        355                 360                 365

Val Val Tyr Ile Ser Ser Ser Leu Ser Gln Pro Gln Leu Val Ser Phe
    370                 375                 380

Val Val Trp Leu Glu Val Ile Asn Ser Glu Ile Asp Arg Phe Gly Gly
385                 390                 395                 400

Lys Val Pro Gly Val Val Gly Glu Gly Leu Gly Tyr Gly Met Ala Gly
                405                 410                 415

Gly Val Val Tyr Ile Gly Val Ile Gly Glu Gly Cys Gly Leu Cys Tyr
            420                 425                 430

Lys Val Ile Ile Asn Asn Ser Thr Gly Ala His Ser Pro Val Thr Leu
        435                 440                 445

Gly Asp Arg Gly Ala Gly Pro Glu Phe Asn Leu Asn Leu Ser Tyr Ser
    450                 455                 460

Val Val Phe Lys Gly His Arg Ala Gly Val Pro Pro Ser Trp Gly Lys
465                 470                 475                 480

Lys Val Ile Asn Ile Glu Ser His His Val His Arg Pro Gly Gly Arg
                485                 490                 495

Ser Asp Cys Gly Ser Leu Asp Ser Ile Ser Glu Gly Ala Gly Glu Ala
            500                 505                 510

Gly Val Glu Asp Ala Ile Phe Pro Ser Pro Ala Val Thr Val Ala Gly
        515                 520                 525

Val Asp Glu Pro Gly Ala Ala Ala Glu Asp Leu Ala Lys Met Ala Ala
    530                 535                 540

Gly Ala Val Ser Ser Ser Ser Val Thr Pro Pro Trp Ile Arg His Ile
545                 550                 555                 560

Lys Arg Lys Lys Cys Ala Val Ser Ile
                565


<210> SEQ ID NO 17
<211> LENGTH: 542
<212> TYPE: PRT
<213> ORGANISM: Type B PWD circovirus

<400> SEQUENCE: 17

Pro Ala His Phe Gly Ser Gly Ser Thr Ser Ala Ala Pro Gln Gln Gln
1               5                   10                  15

His Ala Gln Gln Glu Glu Trp Lys Lys Arg Thr Pro Thr Pro Lys Val
            20                  25                  30

Gly Val His Ser Glu Ser Phe Arg Arg Arg Ala Gln Glu Asn Thr Gly
        35                  40                  45

Ser Ser Asn Ile Pro Ile Leu Phe Tyr Cys Trp Arg Gly Gly Gly Arg
    50                  55                  60

Thr Asn Thr Ser Pro Pro Gly Val Arg Phe Cys Glu Glu Ala Asp Phe
65                  70                  75                  80

Ser Glu Val Val Phe Gly Cys Pro Leu Pro His Arg Glu Ser Glu Arg
                85                  90                  95

Asn Arg Ser Ala Glu Arg Ile Leu Gln Arg Arg Gln Leu Thr Asp Gly
            100                 105                 110

Val Trp Ser Ser Ile Ser Gly Thr Thr Glu Pro Val Tyr Cys Cys Glu
        115                 120                 125

Tyr Leu Val Gly Glu Arg Glu Ser Gly Asp Arg Cys Arg Ala Ala Pro
    130                 135                 140
```

-continued

```
Cys Asn Val Cys Gln Lys Phe Pro Arg Ala Gly Thr Phe Glu Ser Glu
145                 150                 155                 160

Arg Glu Asn Ala Glu Ala Cys Thr Arg His Cys Gly Ala Thr Trp Val
                165                 170                 175

Trp Lys Gln Met Gly Cys Phe Cys Arg Pro Gly Asn His Ile Leu Glu
            180                 185                 190

Thr Thr Lys Gln Val Val Gly Trp Leu Pro Trp Arg Ser Gly Cys Tyr
        195                 200                 205

Leu Leu Trp Leu Ala Ala Leu Gly Ser Thr Glu Thr Val Ser Ile Ser
    210                 215                 220

Ile Asp Cys Arg Asp Arg Trp Asn Cys Thr Phe Phe Gly Pro Gln Tyr
225                 230                 235                 240

Ser Asp Tyr Gln Gln Ser Asp Pro Val Gly Met Val Leu Leu Asn Cys
                245                 250                 255

Cys Pro Ser Cys Arg Ser Ser Leu Ser Glu Asp Tyr Phe Leu Gly Ile
            260                 265                 270

Leu Glu Glu Cys Tyr Arg Thr Ile His Gly Gly Arg Gly Pro Val Arg
        275                 280                 285

His Pro Phe Pro Pro Met Pro Asn Lys Leu Leu Ser Leu Phe Tyr His
    290                 295                 300

Phe Val Met Val Phe Ile Ile His Gly Leu Ser Gly Gly Ser Leu Lys
305                 310                 315                 320

Leu Asn Ser Leu Asn Cys Thr Tyr Met Val Thr Arg Ile Leu Tyr Ser
                325                 330                 335

Trp Ser Tyr Ile Leu Phe Ser Asn Ala Val Pro Arg Pro Thr Trp Ser
            340                 345                 350

Thr Phe Pro Ala Val Cys Ser Leu Ser His Ser Trp Phe Leu Leu Leu
        355                 360                 365

Phe Gly Trp Lys Ser Ile Val Lys Ser Arg Thr Gly Leu Gly Val Lys
    370                 375                 380

Tyr Arg Glu Trp Glu Lys Gly Trp Val Met Val Trp Arg Glu Glu Val
385                 390                 395                 400

Arg Ala Val Ala Phe Val Thr Lys Leu Ser Ser Lys Ile Thr Ala Leu
                405                 410                 415

Glu Pro Thr Pro Leu Ser Pro Trp Val Ile Gly Glu Gln Gly Gln Asn
            420                 425                 430

Ser Thr Leu Thr Phe Leu Ile Leu Tyr Ser Lys Gly Thr Glu Arg Gly
        435                 440                 445

Phe Asp Pro Pro Pro Gly Gly Arg Lys Ser Leu Ile Leu Asn Leu Ile
    450                 455                 460

Met Ser Thr Ala Gln Glu Gly Val Leu Thr Val Val Arg Leu Thr Val
465                 470                 475                 480

Tyr Pro Lys Val Arg Glu Arg Arg Val Leu Lys Met Pro Phe Phe Leu
                485                 490                 495

Leu Gln Arg Arg Trp Arg Gly Trp Thr Ser Gln Gly Arg Arg Arg Arg
            500                 505                 510

Ile Trp Pro Arg Trp Leu Arg Gly Arg Cys Leu Leu Leu Arg Arg Leu
        515                 520                 525

Leu Gly Tyr Val Ile Ser Glu Asn Glu Arg Ser Ala Leu Val
    530                 535                 540
```

<210> SEQ ID NO 18
<211> LENGTH: 566
<212> TYPE: PRT

-continued

<213> ORGANISM: Type B PWD circovirus

<400> SEQUENCE: 18

```
Gln Arg Thr Ser Ala Ala Ala Ala Pro Arg Gln His Leu Ser Ser Asn
1               5                   10                  15

Met Pro Ser Lys Lys Asn Gly Arg Ser Gly Pro Gln Pro His Lys Arg
            20                  25                  30

Trp Val Phe Thr Leu Asn Asn Pro Ser Glu Asp Glu Arg Lys Lys Ile
        35                  40                  45

Arg Asp Leu Pro Ile Ser Leu Phe Asp Tyr Phe Ile Val Gly Glu Glu
    50                  55                  60

Gly Asn Glu Glu Gly Arg Thr Pro His Leu Gln Gly Phe Ala Asn Phe
65                  70                  75                  80

Val Lys Lys Gln Thr Phe Asn Lys Val Lys Trp Tyr Leu Gly Ala Arg
                85                  90                  95

Cys His Ile Glu Lys Ala Lys Gly Thr Asp Gln Gln Asn Lys Glu Tyr
            100                 105                 110

Cys Ser Lys Glu Gly Asn Leu Leu Met Glu Cys Gly Ala Pro Arg Ser
        115                 120                 125

Gln Gly Gln Arg Ser Asp Leu Ser Thr Ala Val Ser Thr Leu Leu Glu
    130                 135                 140

Ser Gly Ser Leu Val Thr Val Ala Glu Gln His Pro Val Thr Phe Val
145                 150                 155                 160

Arg Asn Phe Arg Gly Leu Ala Glu Leu Leu Lys Val Ser Gly Lys Met
                165                 170                 175

Gln Lys Arg Asp Trp Lys Thr Asn Val His Val Ile Val Gly Pro Pro
            180                 185                 190

Gly Cys Gly Lys Ser Lys Trp Ala Ala Asn Phe Ala Asp Pro Glu Thr
        195                 200                 205

Thr Tyr Trp Lys Pro Pro Arg Asn Lys Trp Trp Asp Gly Tyr His Gly
    210                 215                 220

Glu Glu Val Val Val Ile Asp Asp Phe Tyr Gly Trp Leu Pro Trp Asp
225                 230                 235                 240

Asp Leu Leu Arg Leu Cys Asp Arg Tyr Pro Leu Thr Val Glu Thr Lys
                245                 250                 255

Gly Gly Thr Val Pro Phe Leu Ala Arg Ser Ile Leu Ile Thr Ser Asn
            260                 265                 270

Gln Thr Pro Leu Glu Trp Tyr Ser Ser Thr Ala Val Pro Ala Val Glu
        275                 280                 285

Ala Leu Tyr Arg Arg Ile Thr Ser Leu Val Phe Trp Lys Asn Ala Thr
    290                 295                 300

Glu Gln Ser Thr Glu Glu Gly Gly Gln Phe Val Thr Leu Ser Pro Pro
305                 310                 315                 320

Cys Pro Glu Phe Pro Tyr Glu Ile Asn Tyr Val Phe Phe Ile Thr Ser
                325                 330                 335

Trp Phe Leu Leu Phe Ile Lys Gly Val Gly Gly Leu Ile Val His Thr
            340                 345                 350

Trp Leu His Gly Tyr Cys Ile Pro Gly Arg Ile Tyr Cys Phe Arg Thr
        355                 360                 365

Gln Cys Arg Gly Leu Arg Gly Leu His Phe Gln Gln Phe Val Val Ser
    370                 375                 380

Ala Thr Ala Gly Phe Phe Cys Cys Leu Val Gly Ser Asn Gln Asn Leu
385                 390                 395                 400
```

-continued

```
Gly Gln Val Trp Gly Ser Thr Gly Ser Gly Arg Arg Arg Ala Gly Leu
                405                 410                 415

Trp Tyr Gly Gly Arg Ser Ser Leu His Arg Gly His Arg Gly Leu Trp
            420                 425                 430

Pro Leu Leu Gln Ser Tyr His Leu Lys Gln His Trp Ser Pro Leu Pro
        435                 440                 445

Cys His Pro Gly Ser Gly Ser Arg Ala Arg Ile Gln Pro Pro Phe Leu
    450                 455                 460

Phe Cys Ser Ile Gln Arg Ala Gln Ser Gly Gly Leu Thr Pro Leu Leu
465                 470                 475                 480

Gly Glu Glu Ser His Ile Ser Ser Cys Pro Pro Pro Arg Arg Ala Phe
                485                 490                 495

Leu Trp Phe Ala Gln Tyr Ile Arg Arg Cys Gly Arg Gly Gly Cys Arg
            500                 505                 510

Cys His Phe Ser Phe Ser Ser Gly Asn Gly Gly Gly Gly Gly Arg Ala
        515                 520                 525

Arg Gly Gly Gly Gly Gly Ser Gly Gln Asp Gly Cys Gly Gly Gly Val
    530                 535                 540

Phe Phe Phe Gly Asn Ala Ser Leu Asp Thr Ser Tyr Leu Lys Thr Lys
545                 550                 555                 560

Glu Val Arg Cys Lys Tyr
                565


<210> SEQ ID NO 19
<211> LENGTH: 1767
<212> TYPE: DNA
<213> ORGANISM: Type B PWD circovirus

<400> SEQUENCE: 19

aatacttaca gcgcacttct ttcgttttca gatatgacgt atccaaggag gcgttaccga     60

agaagaagac accgcccccg cagccatctt ggccagatcc tccgccgccg cccctggctc    120

gtccaccccc gccaccgtta ccgctggaga aggaaaaatg gcatcttcaa cacccgcctc    180

tcccgcacct tcggatatac tgtcaagcga accacagtca gaacgccctc ctgggcggtg    240

gacatgatga gattcaatat taatgacttt cttcccccag gagggggggtc aaacccccgc    300

tctgtgccct ttgaatacta cagaataaga aaggttaagg ttgaattctg gccctgctcc    360

ccgatcaccc agggtgacag gggagtgggc tccagtgctg ttattttaga tgataacttt    420

gtaacaaagg ccacagccct cacctatgac ccctatgtaa actactcctc ccgccatacc    480

ataacccagc ccttctccta ccactcccgg tactttaccc ccaaacctgt cctagatttc    540

actattgatt acttccaacc aaacaacaaa agaaaccagc tgtggctgag actacaaact    600

gctggaaatg tagaccacgt aggcctcggc actgcgttcg aaaacagtat atacgaccag    660

gaatacaata tccgtgtaac catgtatgta caattcagag aatttaattt taaagacccc    720

ccacttaacc cttaatgaat aataaaaacc attacgaagt gataaaaaag actcagtaat    780

ttatttcata tggaaattca gggcatgggg gggaaagggt gacgaactgg ccccccttcct    840

ccgtggattg ttctgtagca ttcttccaaa ataccaagga agtaatcctc cgataaagag    900

cttctacagc tgggacagca gttgaggagt accattccaa cggggtctga ttgctggtaa    960

tcagaatact gcgggccaaa aaaggtacag ttccaccttt agtctctaca gtcaatggat   1020

atcgatcaca cagtctcagt agatcatccc agggcagcca gccataaaag tcatcaataa   1080

caaccacttc ttcaccatgg taaccatccc accacttgtt tctaggtggt ttccagtatg   1140
```

-continued

```
tggtttccgg gtctgcaaaa ttagcagccc atttgctttt accacaccca ggtggcccca   1200

caatgacgtg tacattagtc ttccaatcac gcttctgcat tttcccgctc actttcaaaa   1260

gttcagccag cccgcggaaa tttctgacaa acgttacagg gtgctgctct gcaacggtca   1320

ccagactccc gctctccaac aaggtactca cagcagtaga caggtcactc cgttgtccct   1380

gagatctagg agctccacac tccatcagta agttgccttc tttactgcag tattctttat   1440

tctgctgatc tgttcctttc gctttctcga tgtggcagcg ggcacccaaa taccacttca   1500

ctttattaaa agtctgcttc ttcacaaaat tagcgaaccc ctggaggtga ggtgttcgtc   1560

cttcctcatt accctcctcg ccaacaataa aataatcaaa tagggatatt ggaagatccc   1620

gtattttctt gcgctcgtct tcggaaggat tattcagagt gaacacccac cttttatggg   1680

gttggggtcc gcttcttcca ttcttcttgc tgggcatgtt gctgctgagg tgctgccgag   1740

gtgctgccgc tgccgaagtg cgctggt                                        1767
```

<210> SEQ ID NO 20
<211> LENGTH: 567
<212> TYPE: PRT
<213> ORGANISM: Type B PWD circovirus

<400> SEQUENCE: 20

```
Gly Ala Cys Lys Pro Leu Pro Leu Val Glu Ala Ala Gly Cys Cys Cys
1               5                   10                  15

Ala Trp Cys Ser Ser His Phe Phe Arg Val Gly Val Gly Tyr Phe Thr
            20                  25                  30

Pro Thr Glu Ser Tyr Asp Lys Arg Leu Arg Ala Cys Ser Phe Val Pro
        35                  40                  45

Asp Glu Leu Ile Gly Ile Gln Asn Asn Gln Gln Arg Pro Pro Tyr His
    50                  55                  60

Pro Leu Val Phe Val Glu Gly Gly Pro Thr Arg Asn Gln Ser Ser Ala
65                  70                  75                  80

Ser Lys Tyr Leu Ser Thr Thr Asn Pro His Gly Ser Gly Cys Arg Ser
                85                  90                  95

Leu Ser Leu Phe Leu Asp Ala Ser Tyr Leu Ile Ser Cys Tyr Leu Leu
            100                 105                 110

Cys Ser Val Ser Pro Thr His Leu Glu Ile Glu Pro Val Val Ser His
        115                 120                 125

Gly Thr Gln Gln Ser Tyr Arg Thr Pro Ser Arg Ser Asp Pro Ser Arg
    130                 135                 140

Gln Leu Ala Ala Gly Gln Leu Thr Gln Phe Asn Gly Arg Ala Pro Gln
145                 150                 155                 160

Val Lys Ser Leu Ser Arg Ser Phe Ala Ser Ala His Asn Ser Ser His
                165                 170                 175

Val Arg Gln Pro Ala Val Gln Thr His Tyr Phe Cys Ile Pro Gln Asn
            180                 185                 190

Gln Leu Gly Pro Phe Trp Met Ser Ser Val Val Phe Cys Thr Thr Pro
        195                 200                 205

His Asn Gly His His Leu Leu Pro Gln Gln His Ser Lys His Ser Ala
    210                 215                 220

Ala Arg Pro His Asp Val Ser Val Thr His Asp Ile Asp Met Ser Gln
225                 230                 235                 240

Leu Ser Leu His Phe Gln Val Lys Lys Pro Gly Cys Tyr Glu Ser Trp
                245                 250                 255

Cys Asp Ser Gly Thr Pro Ile Thr Ser Arg Leu Gln Gln Gly Leu Gln
```

-continued

```
            260                 265                 270

Leu Leu Glu Lys Asp Ser Ser Lys Arg Pro Ile Lys Ser Ser His Leu
        275                 280                 285

Val Ile Trp Pro Pro Leu Pro Gly Thr Arg Gly Lys Gly Gly Met Gly
    290                 295                 300

Gln Ile Glu Met His Phe Leu Asn Ser Leu Arg Lys Lys Thr Ile Thr
305                 310                 315                 320

Lys Ile Ile Pro Asn Leu Pro Pro Asp Lys Phe Asn Phe Glu Arg Phe
                325                 330                 335

Gln Val Tyr Met Thr Val Arg Ile Asn Tyr Glu Gln Asp Tyr Ile Ser
            340                 345                 350

Asn Glu Phe Ala Thr Gly Leu Gly Val His Asp Val Asn Gly Ala Thr
        355                 360                 365

Gln Leu Arg Leu Trp Leu Gln Asn Arg Lys Asn Asn Pro Gln Phe Tyr
    370                 375                 380

Asp Ile Thr Phe Asp Leu Val Pro Lys Pro Thr Phe Tyr Arg Ser His
385                 390                 395                 400

Tyr Ser Phe Pro Gln Thr Ile Thr His Arg Ser Ser Tyr Asn Val Tyr
                405                 410                 415

Pro Asp Tyr Thr Leu Ala Thr Ala Lys Thr Val Pro Asn Asp Asp Leu
            420                 425                 430

Ile Val Ala Ser Ser Gly Val Gly Arg Asp Gly Gln Thr Ile Pro Ser
        435                 440                 445

Cys Pro Trp Phe Glu Val Lys Val Lys Arg Ile Arg Tyr Tyr Glu Phe
    450                 455                 460

Pro Val Ser Arg Pro Asn Ser Gly Gly Gly Pro Pro Leu Phe Asp Asn
465                 470                 475                 480

Ile Asn Phe Arg Met Met Asp Val Ala Trp Ser Pro Thr Arg Val Thr
                485                 490                 495

Thr Arg Lys Val Thr Tyr Gly Phe Thr Arg Ser Leu Arg Thr Asn Phe
            500                 505                 510

Ile Gly Asn Lys Arg Arg Trp Arg Tyr Arg His Arg Pro His Val Leu
        515                 520                 525

Trp Pro Arg Arg Arg Leu Ile Gln Gly Leu His Ser Arg Pro Arg His
    530                 535                 540

Arg Arg Arg Arg Tyr Arg Arg Arg Pro Tyr Thr Met Asp Ser Phe Ser
545                 550                 555                 560

Leu Leu Ala Ser Tyr Thr Asn
                565


<210> SEQ ID NO 21
<211> LENGTH: 566
<212> TYPE: PRT
<213> ORGANISM: Type B PWD circovirus

<400> SEQUENCE: 21

Trp Arg Val Glu Ala Ala Ala Ala Gly Arg Cys Cys Arg Leu Leu Leu
1               5                   10                  15

Met Gly Leu Leu Phe Phe Pro Leu Leu Pro Gly Trp Gly Trp Leu Leu
            20                  25                  30

His Thr Asn Val Arg Phe Leu Gly Glu Ser Ser Ser Arg Leu Phe Ile
        35                  40                  45

Arg Ser Arg Gly Ile Asp Arg Asn Ser Lys Ile Thr Pro Ser Ser Pro
    50                  55                  60
```

-continued

```
Leu Ser Ser Pro Arg Val Gly Arg Trp Pro Asn Ala Leu Lys Thr Phe
65                  70                  75                  80

Phe Cys Val Lys Leu Leu Thr Phe His Tyr Lys Pro Ala Arg Gln Trp
                85                  90                  95

Met Ser Phe Ala Phe Pro Val Ser Cys Phe Leu Ser Tyr Gln Leu Leu
            100                 105                 110

Ser Pro Leu Lys Ser Ile Ser His Pro Ala Gly Leu Asp Pro Cys Arg
        115                 120                 125

Leu Ser Arg Asp Val Ala Thr Leu Val Lys Asn Ser Leu Pro Leu Arg
    130                 135                 140

Thr Val Thr Ala Ser Cys Cys Gly Thr Val Asn Thr Leu Phe Lys Arg
145                 150                 155                 160

Pro Ser Ala Ser Ser Lys Phe Thr Leu Pro Phe Ile Cys Phe Arg Ser
                165                 170                 175

Gln Phe Val Leu Thr Cys Thr Met Thr Pro Gly Gly Pro His Pro Leu
            180                 185                 190

Leu Leu His Ala Ala Leu Lys Ala Ser Gly Ser Val Val Tyr Gln Phe
        195                 200                 205

Gly Gly Leu Phe Leu His His Ser Pro Trp Pro Ser Ser Thr Thr Thr
    210                 215                 220

Ile Ser Ser Lys Pro Gln Ser Gly Gln Ser Ser Arg Ser Leu Ser His
225                 230                 235                 240

Ser Arg Tyr Gly Asn Val Thr Ser Val Leu Pro Pro Val Thr Gly Lys
                245                 250                 255

Lys Ala Arg Leu Ile Arg Ile Val Leu Leu Val Gly Asn Ser His Tyr
            260                 265                 270

Glu Glu Val Ala Thr Gly Ala Thr Ser Ala Arg Arg Leu Ile Val Glu
        275                 280                 285

Lys Thr Asn Gln Phe Phe Ala Val Ser Cys Asp Val Ser Ser Pro Pro
    290                 295                 300

Trp Asn Thr Val Arg Glu Gly Gly His Gly Ser Asn Gly Tyr Ser Ile
305                 310                 315                 320

Phe Gln Thr Lys Lys Ile Val Glu Tyr His Asn Lys Asn Asn Met Leu
                325                 330                 335

Pro Thr Pro Pro Arg Phe Ile Arg Gln Ile Thr Cys Val His Asn Cys
            340                 345                 350

Pro Tyr Gln Ile Gly Pro Arg Ile Tyr Gln Lys Arg Val Cys His Arg
        355                 360                 365

Pro Arg Arg Pro Arg Cys Lys Trp Cys Asn Thr Thr Glu Ala Val Ala
    370                 375                 380

Pro Lys Lys Gln Gln Lys Thr Pro Leu Leu Tyr His Phe Arg Pro Cys
385                 390                 395                 400

Thr Gln Pro Tyr Leu Val Pro Leu Pro Leu Leu Leu Ala Pro Asn His
                405                 410                 415

Tyr Pro Pro Leu Leu Leu Lys Cys Leu Pro Leu His Pro Ser His Gly
            420                 425                 430

Lys Asn Cys Leu Arg Phe Tyr Cys Cys Gln Leu Gly Ser Gly Gln Gly
        435                 440                 445

Pro His Asp Pro Leu Leu Ala Leu Ile Gly Gly Lys Lys Asn Gln Leu
    450                 455                 460

Ile Leu Ala Cys Leu Pro Pro Lys Val Gly Arg Arg Pro Ser Ser Leu
465                 470                 475                 480

Tyr Gln Ile Glu Asp His Gly Gly Gly Leu Leu Ala Asn Gln Ser His
```

```
                485                 490                 495

Asn Ala Gln Cys Tyr Ile Arg Leu His Pro Leu Pro Pro His Gln Leu
            500                 505                 510

His Trp Lys Glu Lys Glu Leu Pro Leu Pro Pro Pro Pro Pro Arg Ala
        515                 520                 525

Leu Pro Pro Pro Pro Pro Asp Pro Trp Ser Pro Gln Pro Pro Pro Thr
    530                 535                 540

Lys Lys Lys Pro Leu Ala Glu Lys Ser Val Asp Tyr Arg Phe Val Phe
545                 550                 555                 560

Ser Thr Arg Gln Leu Tyr
                565


<210> SEQ ID NO 22
<211> LENGTH: 569
<212> TYPE: PRT
<213> ORGANISM: Type B PWD circovirus

<400> SEQUENCE: 22

Leu Ala Ser Arg Cys Arg Cys Cys Arg Pro Leu Val Glu Ala Ala Val
1               5                   10                  15

His Gly Ala Leu Leu Ile Ser Ser Ala Ser Gly Leu Gly Met Phe Pro
            20                  25                  30

Pro His Glu Ser Gln Ile Ile Arg Gly Phe Val Leu Ala Leu Phe Tyr
        35                  40                  45

Pro Ile Lys Trp Tyr Gly Lys Ile Ile Lys Asn Asn Ala Leu Leu Thr
    50                  55                  60

Ile Leu Phe Ser Ser Cys Arg Val Glu Leu Pro Glu Ser Ile Lys His
65                  70                  75                  80

Leu Leu Leu Ser Lys Ile Phe His Leu Pro Ile Gln Thr Gly Ala Ala
                85                  90                  95

Val Asp Leu Phe Arg Phe Ser Cys Ile Leu Leu Ile Phe Phe Val Ala
            100                 105                 110

Thr Phe Phe Ala Val Gln His Leu Thr Ser Ser Arg Ser Arg Leu Ser
        115                 120                 125

Leu Pro Thr Val Gln Arg Ser Ser His Thr Gly Gln Gln Leu Ala Pro
    130                 135                 140

Thr Gln His Gly Asn Cys Leu Leu Val Arg Tyr Arg Lys Asp Ser Ile
145                 150                 155                 160

Glu Ala Pro Gln Ser Phe Lys Gln Phe His Ala Pro Phe His Leu Leu
                165                 170                 175

Thr Ile Pro Leu Ser Ile Tyr Val Asp Asn His Pro Trp Arg Pro Thr
            180                 185                 190

Thr Phe Ala Phe Pro Ser Ser Ile Lys Cys Val Arg Phe Gly Cys Val
        195                 200                 205

Pro Phe Trp Arg Ser Val Leu Pro Pro Ile Thr Val Met Thr Phe Phe
    210                 215                 220

His Asn Asn Asn Ile Val Lys Ile Ala Pro Gln Gly Pro Ile Ile Gln
225                 230                 235                 240

Ser Gln Thr Ser Ser Ile Trp Gln Ser Tyr Leu Ser Phe Thr Ser Ser
                245                 250                 255

Tyr Arg Lys Gln Gly Ala Thr Asn Gln Asn Gly Ala Ile Leu Gly Arg
            260                 265                 270

Gln Phe Pro Val Gly Ser Ser Asp Trp Ser Tyr Phe Ser Lys Ile Pro
        275                 280                 285
```

-continued

```
Pro Asn Ser Gly Gln Tyr Lys Pro Leu Ile Ser Cys Phe Leu Gly Arg
    290                 295                 300

Leu Phe Pro Ala Leu Glu Asp Gly Lys Gly Gly Trp Ala Arg Phe Lys
305                 310                 315                 320

Trp Ile Phe Trp Ile Val Ser Asp Lys Lys Asp Ser Arg Leu Pro Lys
                325                 330                 335

Glu Asn Leu Thr Leu His Pro Thr Lys Leu Ile Leu Asn Glu Ser Asn
            340                 345                 350

Tyr Met Cys Pro Val Ser Ile Thr Asn Arg Thr Thr Tyr Val Thr Lys
        355                 360                 365

Ser Arg Leu Ala Ser Ala Thr Thr Met Glu Leu Leu Lys Tyr Asp Gly
    370                 375                 380

Cys Ser Thr Glu Lys Thr Thr Gln Asn Ser Thr Ile Leu Leu Ser Ile
385                 390                 395                 400

Ser Leu Asn Pro Pro Leu Thr Gly Pro Thr Thr Pro Ser Pro Ser Pro
                405                 410                 415

Pro Ile Ala Pro Pro Thr Thr Met Pro Thr Met Pro Ser Pro Gln Pro
            420                 425                 430

Arg Gln Leu Thr Ile Met Phe Leu Leu Val Pro Ala Trp Glu Gly Thr
        435                 440                 445

Val Arg Pro Ser Arg Pro Ala Pro Gly Ser Asn Leu Arg Leu Arg Glu
    450                 455                 460

Glu Thr Thr Asn Leu Pro Cys Leu Ala Pro Thr Gln Gly Gly Glu Gln
465                 470                 475                 480

Pro Phe Phe Thr Met Leu Ile Ser Asp Thr Trp Arg Gly Pro Pro Arg
                485                 490                 495

Glu Ser Gln Pro Glu Ser Ser Leu Ile Asp Ser Pro Ala Pro Ser Ala
            500                 505                 510

Pro Thr Ser Ser Ala Met Lys Gly Glu Gly Ala Thr Val Thr Ala Pro
        515                 520                 525

Thr Ser Ser Gly Pro Ala Ala Ala Ser Ser Arg Ala Leu Ile Ala Ala
    530                 535                 540

Pro Ala Thr Asp Glu Glu Glu Thr Val Gly Gly Gln Ile Arg Ile Gln
545                 550                 555                 560

Phe Arg Phe Phe His Ala Thr Leu Ile
                565


<210> SEQ ID NO 23
<211> LENGTH: 945
<212> TYPE: DNA
<213> ORGANISM: Type B PWD circovirus
<220> FEATURE:
<221> NAME/KEY: CDS
<222> LOCATION: (1)..(942)

<400> SEQUENCE: 23

atg ccc agc aag aag aat gga aga agc gga ccc caa ccc cat aaa agg       48
Met Pro Ser Lys Lys Asn Gly Arg Ser Gly Pro Gln Pro His Lys Arg
1               5                   10                  15

tgg gtg ttc act ctg aat aat cct tcc gaa gac gag cgc aag aaa ata       96
Trp Val Phe Thr Leu Asn Asn Pro Ser Glu Asp Glu Arg Lys Lys Ile
            20                  25                  30

cgg gat ctt cca ata tcc cta ttt gat tat ttt att gtt ggc gag gag      144
Arg Asp Leu Pro Ile Ser Leu Phe Asp Tyr Phe Ile Val Gly Glu Glu
        35                  40                  45

ggt aat gag gaa gga cga aca cct cac ctc cag ggg ttc gct aat ttt      192
Gly Asn Glu Glu Gly Arg Thr Pro His Leu Gln Gly Phe Ala Asn Phe
```

-continued

```
    50                  55                  60

gtg aag aag cag act ttt aat aaa gtg aag tgg tat ttg ggt gcc cgc      240
Val Lys Lys Gln Thr Phe Asn Lys Val Lys Trp Tyr Leu Gly Ala Arg
65                  70                  75                  80

tgc cac atc gag aaa gcg aaa gga aca gat cag cag aat aaa gaa tac      288
Cys His Ile Glu Lys Ala Lys Gly Thr Asp Gln Gln Asn Lys Glu Tyr
                85                  90                  95

tgc agt aaa gaa ggc aac tta ctg atg gag tgt gga gct cct aga tct      336
Cys Ser Lys Glu Gly Asn Leu Leu Met Glu Cys Gly Ala Pro Arg Ser
            100                 105                 110

cag gga caa cgg agt gac ctg tct act gct gtg agt acc ttg ttg gag      384
Gln Gly Gln Arg Ser Asp Leu Ser Thr Ala Val Ser Thr Leu Leu Glu
        115                 120                 125

agc ggg agt ctg gtg acc gtt gca gag cag cac cct gta acg ttt gtc      432
Ser Gly Ser Leu Val Thr Val Ala Glu Gln His Pro Val Thr Phe Val
    130                 135                 140

aga aat ttc cgc ggg ctg gct gaa ctt ttg aaa gtg agc ggg aaa atg      480
Arg Asn Phe Arg Gly Leu Ala Glu Leu Leu Lys Val Ser Gly Lys Met
145                 150                 155                 160

cag aag cgt gat tgg aag act aat gta cac gtc att gtg ggg cca cct      528
Gln Lys Arg Asp Trp Lys Thr Asn Val His Val Ile Val Gly Pro Pro
                165                 170                 175

ggg tgt ggt aaa agc aaa tgg gct gct aat ttt gca gac ccg gaa acc      576
Gly Cys Gly Lys Ser Lys Trp Ala Ala Asn Phe Ala Asp Pro Glu Thr
            180                 185                 190

aca tac tgg aaa cca cct aga aac aag tgg tgg gat ggt tac cat ggt      624
Thr Tyr Trp Lys Pro Pro Arg Asn Lys Trp Trp Asp Gly Tyr His Gly
        195                 200                 205

gaa gaa gtg gtt gtt att gat gac ttt tat ggc tgg ctg ccc tgg gat      672
Glu Glu Val Val Val Ile Asp Asp Phe Tyr Gly Trp Leu Pro Trp Asp
    210                 215                 220

gat cta ctg aga ctg tgt gat cga tat cca ttg act gta gag act aaa      720
Asp Leu Leu Arg Leu Cys Asp Arg Tyr Pro Leu Thr Val Glu Thr Lys
225                 230                 235                 240

ggt gga act gta cct ttt ttg gcc cgc agt att ctg att acc agc aat      768
Gly Gly Thr Val Pro Phe Leu Ala Arg Ser Ile Leu Ile Thr Ser Asn
                245                 250                 255

cag acc ccg ttg gaa tgg tac tcc tca act gct gtc cca gct gta gaa      816
Gln Thr Pro Leu Glu Trp Tyr Ser Ser Thr Ala Val Pro Ala Val Glu
            260                 265                 270

gct ctt tat cgg agg att act tcc ttg gta ttt tgg aag aat gct aca      864
Ala Leu Tyr Arg Arg Ile Thr Ser Leu Val Phe Trp Lys Asn Ala Thr
        275                 280                 285

gaa caa tcc acg gag gaa ggg ggc cag ttc gtc acc ctt tcc ccc cca      912
Glu Gln Ser Thr Glu Glu Gly Gly Gln Phe Val Thr Leu Ser Pro Pro
    290                 295                 300

tgc cct gaa ttt cca tat gaa ata aat tac tga                          945
Cys Pro Glu Phe Pro Tyr Glu Ile Asn Tyr
305                 310


<210> SEQ ID NO 24
<211> LENGTH: 314
<212> TYPE: PRT
<213> ORGANISM: Type B PWD circovirus

<400> SEQUENCE: 24

Met Pro Ser Lys Lys Asn Gly Arg Ser Gly Pro Gln Pro His Lys Arg
1               5                   10                  15

Trp Val Phe Thr Leu Asn Asn Pro Ser Glu Asp Glu Arg Lys Lys Ile
            20                  25                  30
```

```
Arg Asp Leu Pro Ile Ser Leu Phe Asp Tyr Phe Ile Val Gly Glu Glu
        35                  40                  45

Gly Asn Glu Glu Gly Arg Thr Pro His Leu Gln Gly Phe Ala Asn Phe
    50                  55                  60

Val Lys Lys Gln Thr Phe Asn Lys Val Lys Trp Tyr Leu Gly Ala Arg
65                  70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Met Glu Cys Gly Ala Pro Arg Ser
            100                 105                 110

Gln Gly Gln Arg Ser Asp Leu Ser Thr Ala Val Ser Thr Leu Leu Glu
        115                 120                 125

Ser Gly Ser Leu Val Thr Val Ala Glu Gln His Pro Val Thr Phe Val
    130                 135                 140

Arg Asn Phe Arg Gly Leu Ala Glu Leu Leu Lys Val Ser Gly Lys Met
145                 150                 155                 160

Gln Lys Arg Asp Trp Lys Thr Asn Val His Val Ile Val Gly Pro Pro
                165                 170                 175

Gly Cys Gly Lys Ser Lys Trp Ala Ala Asn Phe Ala Asp Pro Glu Thr
            180                 185                 190

Thr Tyr Trp Lys Pro Pro Arg Asn Lys Trp Trp Asp Gly Tyr His Gly
        195                 200                 205

Glu Glu Val Val Val Ile Asp Asp Phe Tyr Gly Trp Leu Pro Trp Asp
    210                 215                 220

Asp Leu Leu Arg Leu Cys Asp Arg Tyr Pro Leu Thr Val Glu Thr Lys
225                 230                 235                 240

Gly Gly Thr Val Pro Phe Leu Ala Arg Ser Ile Leu Ile Thr Ser Asn
                245                 250                 255

Gln Thr Pro Leu Glu Trp Tyr Ser Ser Thr Ala Val Pro Ala Val Glu
            260                 265                 270

Ala Leu Tyr Arg Arg Ile Thr Ser Leu Val Phe Trp Lys Asn Ala Thr
        275                 280                 285

Glu Gln Ser Thr Glu Glu Gly Gly Gln Phe Val Thr Leu Ser Pro Pro
    290                 295                 300

Cys Pro Glu Phe Pro Tyr Glu Ile Asn Tyr
305                 310


<210> SEQ ID NO 25
<211> LENGTH: 702
<212> TYPE: DNA
<213> ORGANISM: Type B PWD circovirus
<220> FEATURE:
<221> NAME/KEY: CDS
<222> LOCATION: (1)..(699)

<400> SEQUENCE: 25

atg acg tat cca agg agg cgt tac cga aga aga aga cac cgc ccc cgc       48
Met Thr Tyr Pro Arg Arg Arg Tyr Arg Arg Arg Arg His Arg Pro Arg
1               5                   10                  15

agc cat ctt ggc cag atc ctc cgc cgc cgc ccc tgg ctc gtc cac ccc       96
Ser His Leu Gly Gln Ile Leu Arg Arg Arg Pro Trp Leu Val His Pro
            20                  25                  30

cgc cac cgt tac cgc tgg aga agg aaa aat ggc atc ttc aac acc cgc      144
Arg His Arg Tyr Arg Trp Arg Arg Lys Asn Gly Ile Phe Asn Thr Arg
        35                  40                  45

ctc tcc cgc acc ttc gga tat act gtc aag cga acc aca gtc aga acg      192
```

-continued

```
Leu Ser Arg Thr Phe Gly Tyr Thr Val Lys Arg Thr Thr Val Arg Thr
    50                  55                  60

ccc tcc tgg gcg gtg gac atg atg aga ttc aat att aat gac ttt ctt      240
Pro Ser Trp Ala Val Asp Met Met Arg Phe Asn Ile Asn Asp Phe Leu
65                  70                  75                  80

ccc cca gga ggg ggg tca aac ccc cgc tct gtg ccc ttt gaa tac tac      288
Pro Pro Gly Gly Gly Ser Asn Pro Arg Ser Val Pro Phe Glu Tyr Tyr
                85                  90                  95

aga ata aga aag gtt aag gtt gaa ttc tgg ccc tgc tcc ccg atc acc      336
Arg Ile Arg Lys Val Lys Val Glu Phe Trp Pro Cys Ser Pro Ile Thr
            100                 105                 110

cag ggt gac agg gga gtg ggc tcc agt gct gtt att tta gat gat aac      384
Gln Gly Asp Arg Gly Val Gly Ser Ser Ala Val Ile Leu Asp Asp Asn
        115                 120                 125

ttt gta aca aag gcc aca gcc ctc acc tat gac ccc tat gta aac tac      432
Phe Val Thr Lys Ala Thr Ala Leu Thr Tyr Asp Pro Tyr Val Asn Tyr
    130                 135                 140

tcc tcc cgc cat acc ata acc cag ccc ttc tcc tac cac tcc cgg tac      480
Ser Ser Arg His Thr Ile Thr Gln Pro Phe Ser Tyr His Ser Arg Tyr
145                 150                 155                 160

ttt acc ccc aaa cct gtc cta gat ttc act att gat tac ttc caa cca      528
Phe Thr Pro Lys Pro Val Leu Asp Phe Thr Ile Asp Tyr Phe Gln Pro
                165                 170                 175

aac aac aaa aga aac cag ctg tgg ctg aga cta caa act gct gga aat      576
Asn Asn Lys Arg Asn Gln Leu Trp Leu Arg Leu Gln Thr Ala Gly Asn
            180                 185                 190

gta gac cac gta ggc ctc ggc act gcg ttc gaa aac agt ata tac gac      624
Val Asp His Val Gly Leu Gly Thr Ala Phe Glu Asn Ser Ile Tyr Asp
        195                 200                 205

cag gaa tac aat atc cgt gta acc atg tat gta caa ttc aga gaa ttt      672
Gln Glu Tyr Asn Ile Arg Val Thr Met Tyr Val Gln Phe Arg Glu Phe
    210                 215                 220

aat ttt aaa gac ccc cca ctt aac cct taa                              702
Asn Phe Lys Asp Pro Pro Leu Asn Pro
225                 230


<210> SEQ ID NO 26
<211> LENGTH: 233
<212> TYPE: PRT
<213> ORGANISM: Type B PWD circovirus

<400> SEQUENCE: 26

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Arg Thr Thr Val Arg Thr
    50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
        115                 120                 125
```

-continued

```
Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Phe Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220

Asn Phe Lys Asp Pro Pro Leu Asn Pro
225                 230


<210> SEQ ID NO 27
<211> LENGTH: 315
<212> TYPE: DNA
<213> ORGANISM: Type B PWD circovirus
<220> FEATURE:
<221> NAME/KEY: CDS
<222> LOCATION: (1)..(312)

<400> SEQUENCE: 27

atg gta acc atc cca cca ctt gtt tct agg tgg ttt cca gta tgt ggt       48
Met Val Thr Ile Pro Pro Leu Val Ser Arg Trp Phe Pro Val Cys Gly
1               5                   10                  15

ttc cgg gtc tgc aaa att agc agc cca ttt gct ttt acc aca ccc agg       96
Phe Arg Val Cys Lys Ile Ser Ser Pro Phe Ala Phe Thr Thr Pro Arg
            20                  25                  30

tgg ccc cac aat gac gtg tac att agt ctt cca atc acg ctt ctg cat      144
Trp Pro His Asn Asp Val Tyr Ile Ser Leu Pro Ile Thr Leu Leu His
        35                  40                  45

ttt ccc gct cac ttt caa aag ttc agc cag ccc gcg gaa att tct gac      192
Phe Pro Ala His Phe Gln Lys Phe Ser Gln Pro Ala Glu Ile Ser Asp
    50                  55                  60

aaa cgt tac agg gtg ctg ctc tgc aac ggt cac cag act ccc gct ctc      240
Lys Arg Tyr Arg Val Leu Leu Cys Asn Gly His Gln Thr Pro Ala Leu
65                  70                  75                  80

caa caa ggt act cac agc agt aga cag gtc act ccg ttg tcc ctg aga      288
Gln Gln Gly Thr His Ser Ser Arg Gln Val Thr Pro Leu Ser Leu Arg
                85                  90                  95

tct agg agc tcc aca ctc cat cag taa                                  315
Ser Arg Ser Ser Thr Leu His Gln
            100


<210> SEQ ID NO 28
<211> LENGTH: 104
<212> TYPE: PRT
<213> ORGANISM: Type B PWD circovirus

<400> SEQUENCE: 28

Met Val Thr Ile Pro Pro Leu Val Ser Arg Trp Phe Pro Val Cys Gly
1               5                   10                  15

Phe Arg Val Cys Lys Ile Ser Ser Pro Phe Ala Phe Thr Thr Pro Arg
            20                  25                  30

Trp Pro His Asn Asp Val Tyr Ile Ser Leu Pro Ile Thr Leu Leu His
        35                  40                  45

Phe Pro Ala His Phe Gln Lys Phe Ser Gln Pro Ala Glu Ile Ser Asp
    50                  55                  60
```

-continued

Lys Arg Tyr Arg Val Leu Leu Cys Asn Gly His Gln Thr Pro Ala Leu
65 70 75 80

Gln Gln Gly Thr His Ser Ser Arg Gln Val Thr Pro Leu Ser Leu Arg
85 90 95

Ser Arg Ser Ser Thr Leu His Gln
100

<210> SEQ ID NO 29
<211> LENGTH: 15
<212> TYPE: PRT
<213> ORGANISM: Type B PWD circovirus

<400> SEQUENCE: 29

Val Asp Met Met Arg Phe Asn Ile Asn Asp Phe Leu Pro Pro Gly
1 5 10 15

<210> SEQ ID NO 30
<211> LENGTH: 15
<212> TYPE: PRT
<213> ORGANISM: Type B PWD circovirus

<400> SEQUENCE: 30

Gln Gly Asp Arg Gly Val Gly Ser Ser Ala Val Ile Leu Asp Asp
1 5 10 15

<210> SEQ ID NO 31
<211> LENGTH: 15
<212> TYPE: PRT
<213> ORGANISM: Type B PWD circovirus

<400> SEQUENCE: 31

Gly Val Gly Ser Ser Ala Val Ile Leu Asp Asp Asn Phe Val Thr
1 5 10 15

<210> SEQ ID NO 32
<211> LENGTH: 15
<212> TYPE: PRT
<213> ORGANISM: Type B PWD circovirus

<400> SEQUENCE: 32

Val Asp His Val Gly Leu Gly Thr Ala Phe Glu Asn Ser Ile Tyr
1 5 10 15

<210> SEQ ID NO 33
<211> LENGTH: 8
<212> TYPE: DNA
<213> ORGANISM: Type A PWD circovirus

<400> SEQUENCE: 33 tgtggcga 8

<210> SEQ ID NO 34
<211> LENGTH: 8
<212> TYPE: DNA
<213> ORGANISM: Type A PWD circovirus

<400> SEQUENCE: 34 agtttcct 8

<210> SEQ ID NO 35
<211> LENGTH: 20
<212> TYPE: DNA
<213> ORGANISM: Type A PWD circovirus -continued

<400> SEQUENCE: 35
tcatttagag ggtctttcag 20

<210> SEQ ID NO 36
<211> LENGTH: 8
<212> TYPE: DNA
<213> ORGANISM: Type A PWD circovirus

<400> SEQUENCE: 36 gtcaacct 8

<210> SEQ ID NO 37
<211> LENGTH: 8
<212> TYPE: DNA
<213> ORGANISM: Type A PWD circovirus

<400> SEQUENCE: 37 gtggttgc 8

<210> SEQ ID NO 38
<211> LENGTH: 8
<212> TYPE: DNA
<213> ORGANISM: Type A PWD circovirus

<400> SEQUENCE: 38 agcccagg 8

<210> SEQ ID NO 39
<211> LENGTH: 8
<212> TYPE: DNA
<213> ORGANISM: Type A PWD circovirus

<400> SEQUENCE: 39 ttggctgg 8

<210> SEQ ID NO 40
<211> LENGTH: 12
<212> TYPE: DNA
<213> ORGANISM: Type A PWD circovirus

<400> SEQUENCE: 40
tctagctctg gt 12

<210> SEQ ID NO 41
<211> LENGTH: 12
<212> TYPE: DNA
<213> ORGANISM: Type A PWD circovirus

<400> SEQUENCE: 41
atctcagctc gt 12

<210> SEQ ID NO 42
<211> LENGTH: 12
<212> TYPE: DNA
<213> ORGANISM: Type A PWD circovirus

<400> SEQUENCE: 42
tgtcctcctc tt 12

<210> SEQ ID NO 43
<211> LENGTH: 8
<212> TYPE: DNA

-continued

<213> ORGANISM: Type A PWD circovirus

<400> SEQUENCE: 43 tctctaga 8

<210> SEQ ID NO 44
<211> LENGTH: 8
<212> TYPE: DNA
<213> ORGANISM: Type A PWD circovirus

<400> SEQUENCE: 44 tgtaccaa 8

<210> SEQ ID NO 45
<211> LENGTH: 8
<212> TYPE: DNA
<213> ORGANISM: Type A PWD circovirus

<400> SEQUENCE: 45 tccgtctt 8

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gtgtgctcga cattggtgtg 20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
tggaatgtta acgagctgag 20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ctcgcagcca tcttggaatg 20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
cgcgcgtaat acgactcact 20

<210> SEQ ID NO 50
<211> LENGTH: 26
<212> TYPE: DNA
<213> ORGANISM: Artificial Sequence -continued
<220> FEATURE:
<223> OTHER INFORMATION: Primer

<400> SEQUENCE: 50
cctgtctact gctgtgagta ccttgt 26

<210> SEQ ID NO 51
<211> LENGTH: 26
<212> TYPE: DNA
<213> ORGANISM: Artificial Sequence
<220> FEATURE:
<223> OTHER INFORMATION: Primer

<400> SEQUENCE: 51
gcagtagaca ggtcactccg ttgtcc 26

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tggaatgtta actacctcaa 20

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
ggcggcgcca tctgtaacgg ttt 23

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
gatggcgccg aaagacgggt atc 23

<210> SEQ ID NO 55
<211> LENGTH: 15
<212> TYPE: PRT
<213> ORGANISM: Type B PWD circovirus

<400> SEQUENCE: 55

Asn Val Asn Glu Leu Arg Phe Asn Ile Gly Gln Phe Leu Pro Pro
1 5 10 15

<210> SEQ ID NO 56
<211> LENGTH: 14
<212> TYPE: PRT
<213> ORGANISM: Type A PWD circovirus

<400> SEQUENCE: 56

Thr Ser Asn Gln Arg Gly Val Gly Ser Thr Val Val Ile Leu
1 5 10

<210> SEQ ID NO 57

-continued

<211> LENGTH: 15
<212> TYPE: PRT
<213> ORGANISM: Type A PWD circovirus

<400> SEQUENCE: 57

Arg Gly Val Gly Ser Thr Val Val Ile Leu Asp Ala Asn Phe Val
1 5 10 15

<210> SEQ ID NO 58
<211> LENGTH: 15
<212> TYPE: PRT
<213> ORGANISM: Type B PWD circovirus

<400> SEQUENCE: 58

Phe Thr Ile Asp Tyr Phe Gln Pro Asn Asn Lys Arg Asn Gln Leu
1 5 10 15

<210> SEQ ID NO 59
<211> LENGTH: 15
<212> TYPE: PRT
<213> ORGANISM: Type A PWD circovirus

<400> SEQUENCE: 59

Asp Gln Thr Ile Asp Trp Phe Gln Pro Asn Asn Lys Arg Asn Gln
1 5 10 15

<210> SEQ ID NO 60
<211> LENGTH: 15
<212> TYPE: PRT
<213> ORGANISM: Type A PWD circovirus

<400> SEQUENCE: 60

Asn Val Glu His Thr Gly Leu Gly Tyr Ala Leu Gln Asn Ala Thr
1 5 10 15

<210> SEQ ID NO 61
<211> LENGTH: 15
<212> TYPE: PRT
<213> ORGANISM: Type B PWD circovirus

<400> SEQUENCE: 61

His Arg Pro Arg Ser His Leu Gly Gln Ile Leu Arg Arg Arg Pro
1 5 10 15

<210> SEQ ID NO 62
<211> LENGTH: 15
<212> TYPE: PRT
<213> ORGANISM: Type B PWD circovirus

<400> SEQUENCE: 62

Ser His Leu Gly Gln Ile Leu Arg Arg Arg Pro Trp Leu Val His
1 5 10 15

<210> SEQ ID NO 63
<211> LENGTH: 15
<212> TYPE: PRT
<213> ORGANISM: Type B PWD circovirus

<400> SEQUENCE: 63

Gln Ile Leu Arg Arg Arg Pro Trp Leu Val His Pro Arg His Arg
1 5 10 15

<210> SEQ ID NO 64
<211> LENGTH: 15
<212> TYPE: PRT

-continued

<213> ORGANISM: Type B PWD circovirus

<400> SEQUENCE: 64

Arg Arg Pro Trp Leu Val His Pro Arg His Arg Tyr Arg Trp Arg
1 5 10 15

<210> SEQ ID NO 65
<211> LENGTH: 15
<212> TYPE: PRT
<213> ORGANISM: Type B PWD circovirus

<400> SEQUENCE: 65

Leu Val His Pro Arg His Arg Tyr Arg Trp Arg Arg Lys Asn Gly
1 5 10 15

<210> SEQ ID NO 66
<211> LENGTH: 15
<212> TYPE: PRT
<213> ORGANISM: Type B PWD circovirus

<400> SEQUENCE: 66

Arg His Arg Tyr Arg Trp Arg Arg Lys Asn Gly Ile Phe Asn Thr
1 5 10 15

<210> SEQ ID NO 67
<211> LENGTH: 15
<212> TYPE: PRT
<213> ORGANISM: Type B PWD circovirus

<400> SEQUENCE: 67

Arg Trp Arg Arg Lys Asn Gly Ile Phe Asn Thr Arg Leu Ser Arg
1 5 10 15

<210> SEQ ID NO 68
<211> LENGTH: 15
<212> TYPE: PRT
<213> ORGANISM: Type B PWD circovirus

<400> SEQUENCE: 68

Lys Asn Gly Ile Phe Asn Thr Arg Leu Ser Arg Thr Phe Gly Tyr
1 5 10 15

<210> SEQ ID NO 69
<211> LENGTH: 15
<212> TYPE: PRT
<213> ORGANISM: Type B PWD circovirus

<400> SEQUENCE: 69

Phe Asn Thr Arg Leu Ser Arg Thr Phe Gly Tyr Thr Val Lys Arg
1 5 10 15

<210> SEQ ID NO 70
<211> LENGTH: 15
<212> TYPE: PRT
<213> ORGANISM: Type B PWD circovirus

<400> SEQUENCE: 70

Leu Ser Arg Thr Phe Gly Tyr Thr Val Lys Arg Thr Thr Val Arg
1 5 10 15

<210> SEQ ID NO 71
<211> LENGTH: 15
<212> TYPE: PRT
<213> ORGANISM: Type B PWD circovirus -continued

<400> SEQUENCE: 71

Phe Gly Tyr Thr Val Lys Arg Thr Thr Val Arg Thr Pro Ser Trp
1 5 10 15

<210> SEQ ID NO 72
<211> LENGTH: 15
<212> TYPE: PRT
<213> ORGANISM: Type B PWD circovirus

<400> SEQUENCE: 72

Val Lys Arg Thr Thr Val Arg Thr Pro Ser Trp Ala Val Asp Met
1 5 10 15

<210> SEQ ID NO 73
<211> LENGTH: 15
<212> TYPE: PRT
<213> ORGANISM: Type B PWD circovirus

<400> SEQUENCE: 73

Thr Val Arg Thr Pro Ser Trp Ala Val Asp Met Met Arg Phe Asn
1 5 10 15

<210> SEQ ID NO 74
<211> LENGTH: 15
<212> TYPE: PRT
<213> ORGANISM: Type B PWD circovirus

<400> SEQUENCE: 74

Pro Ser Trp Ala Val Asp Met Met Arg Phe Asn Ile Asn Asp Phe
1 5 10 15

<210> SEQ ID NO 75
<211> LENGTH: 15
<212> TYPE: PRT
<213> ORGANISM: Type B PWD circovirus

<400> SEQUENCE: 75

Arg Phe Asn Ile Asn Asp Phe Leu Pro Pro Gly Gly Gly Ser Asn
1 5 10 15

<210> SEQ ID NO 76
<211> LENGTH: 15
<212> TYPE: PRT
<213> ORGANISM: Type B PWD circovirus

<400> SEQUENCE: 76

Asn Asp Phe Leu Pro Pro Gly Gly Gly Ser Asn Pro Arg Ser Val
1 5 10 15

<210> SEQ ID NO 77
<211> LENGTH: 15
<212> TYPE: PRT
<213> ORGANISM: Type B PWD circovirus

<400> SEQUENCE: 77

Pro Pro Gly Gly Gly Ser Asn Pro Arg Ser Val Pro Phe Glu Tyr
1 5 10 15

<210> SEQ ID NO 78
<211> LENGTH: 15
<212> TYPE: PRT
<213> ORGANISM: Type B PWD circovirus

<400> SEQUENCE: 78

-continued

```
Gly Ser Asn Pro Arg Ser Val Pro Phe Glu Tyr Tyr Arg Ile Arg
1               5                   10                  15


<210> SEQ ID NO 79
<211> LENGTH: 15
<212> TYPE: PRT
<213> ORGANISM: Type B PWD circovirus

<400> SEQUENCE: 79

Arg Ser Val Pro Phe Glu Tyr Tyr Arg Ile Arg Lys Val Lys Val
1               5                   10                  15


<210> SEQ ID NO 80
<211> LENGTH: 15
<212> TYPE: PRT
<213> ORGANISM: Type B PWD circovirus

<400> SEQUENCE: 80

Phe Glu Tyr Tyr Arg Ile Arg Lys Val Lys Val Glu Phe Trp Pro
1               5                   10                  15


<210> SEQ ID NO 81
<211> LENGTH: 15
<212> TYPE: PRT
<213> ORGANISM: Type B PWD circovirus

<400> SEQUENCE: 81

Arg Ile Arg Lys Val Lys Val Glu Phe Trp Pro Cys Ser Pro Ile
1               5                   10                  15


<210> SEQ ID NO 82
<211> LENGTH: 15
<212> TYPE: PRT
<213> ORGANISM: Type B PWD circovirus

<400> SEQUENCE: 82

Val Lys Val Glu Phe Trp Pro Cys Ser Pro Ile Thr Gln Gly Asp
1               5                   10                  15


<210> SEQ ID NO 83
<211> LENGTH: 15
<212> TYPE: PRT
<213> ORGANISM: Type B PWD circovirus

<400> SEQUENCE: 83

Phe Trp Pro Cys Ser Pro Ile Thr Gln Gly Asp Arg Gly Val Gly
1               5                   10                  15


<210> SEQ ID NO 84
<211> LENGTH: 15
<212> TYPE: PRT
<213> ORGANISM: Type A PWD circovirus

<400> SEQUENCE: 84

Thr Arg Pro Arg Ser His Leu Gly Asn Ile Leu Arg Arg Arg Pro
1               5                   10                  15


<210> SEQ ID NO 85
<211> LENGTH: 15
<212> TYPE: PRT
<213> ORGANISM: Type A PWD circovirus

<400> SEQUENCE: 85

Ser His Leu Gly Asn Ile Leu Arg Arg Arg Pro Tyr Leu Val His
1               5                   10                  15
```

-continued

<210> SEQ ID NO 86
<211> LENGTH: 15
<212> TYPE: PRT
<213> ORGANISM: Type A PWD circovirus

<400> SEQUENCE: 86

Asn Ile Leu Arg Arg Arg Pro Tyr Leu Val His Pro Ala Phe Arg
1 5 10 15

<210> SEQ ID NO 87
<211> LENGTH: 15
<212> TYPE: PRT
<213> ORGANISM: Type A PWD circovirus

<400> SEQUENCE: 87

Arg Arg Pro Tyr Leu Val His Pro Ala Phe Arg Asn Arg Tyr Arg
1 5 10 15

<210> SEQ ID NO 88
<211> LENGTH: 15
<212> TYPE: PRT
<213> ORGANISM: Type A PWD circovirus

<400> SEQUENCE: 88

Leu Val His Pro Ala Phe Arg Asn Arg Tyr Arg Trp Arg Arg Lys
1 5 10 15

<210> SEQ ID NO 89
<211> LENGTH: 15
<212> TYPE: PRT
<213> ORGANISM: Type A PWD circovirus

<400> SEQUENCE: 89

Ala Phe Arg Asn Arg Tyr Arg Trp Arg Arg Lys Thr Gly Ile Phe
1 5 10 15

<210> SEQ ID NO 90
<211> LENGTH: 15
<212> TYPE: PRT
<213> ORGANISM: Type A PWD circovirus

<400> SEQUENCE: 90

Arg Tyr Arg Trp Arg Arg Lys Thr Gly Ile Phe Asn Ser Arg Leu
1 5 10 15

<210> SEQ ID NO 91
<211> LENGTH: 15
<212> TYPE: PRT
<213> ORGANISM: Type A PWD circovirus

<400> SEQUENCE: 91

Arg Arg Lys Thr Gly Ile Phe Asn Ser Arg Leu Ser Arg Glu Phe
1 5 10 15

<210> SEQ ID NO 92
<211> LENGTH: 15
<212> TYPE: PRT
<213> ORGANISM: Type A PWD circovirus

<400> SEQUENCE: 92

Gly Ile Phe Asn Ser Arg Leu Ser Arg Glu Phe Val Leu Thr Ile
1 5 10 15

-continued

<210> SEQ ID NO 93
<211> LENGTH: 15
<212> TYPE: PRT
<213> ORGANISM: Type A PWD circovirus

<400> SEQUENCE: 93

Ser Arg Leu Ser Arg Glu Phe Val Leu Thr Ile Arg Gly Gly His
1 5 10 15

<210> SEQ ID NO 94
<211> LENGTH: 15
<212> TYPE: PRT
<213> ORGANISM: Type A PWD circovirus

<400> SEQUENCE: 94

Arg Glu Phe Val Leu Thr Ile Arg Gly Gly His Ser Gln Pro Ser
1 5 10 15

<210> SEQ ID NO 95
<211> LENGTH: 15
<212> TYPE: PRT
<213> ORGANISM: Type A PWD circovirus

<400> SEQUENCE: 95

Leu Thr Ile Arg Gly Gly His Ser Gln Pro Ser Trp Asn Val Asn
1 5 10 15

<210> SEQ ID NO 96
<211> LENGTH: 15
<212> TYPE: PRT
<213> ORGANISM: Type A PWD circovirus

<400> SEQUENCE: 96

Gly Gly His Ser Gln Pro Ser Trp Asn Val Asn Glu Leu Arg Phe
1 5 10 15

<210> SEQ ID NO 97
<211> LENGTH: 15
<212> TYPE: PRT
<213> ORGANISM: Type A PWD circovirus

<400> SEQUENCE: 97

Gln Pro Ser Trp Asn Val Asn Glu Leu Arg Phe Asn Ile Gly Gln
1 5 10 15

<210> SEQ ID NO 98
<211> LENGTH: 15
<212> TYPE: PRT
<213> ORGANISM: Type A PWD circovirus

<400> SEQUENCE: 98

Asn Val Asn Glu Leu Arg Phe Asn Ile Gly Gln Phe Leu Pro Pro
1 5 10 15

<210> SEQ ID NO 99
<211> LENGTH: 15
<212> TYPE: PRT
<213> ORGANISM: Type A PWD circovirus

<400> SEQUENCE: 99

Leu Arg Phe Asn Ile Gly Gln Phe Leu Pro Pro Ser Gly Gly Thr
1 5 10 15

<210> SEQ ID NO 100
<211> LENGTH: 15

-continued

<212> TYPE: PRT
<213> ORGANISM: Type A PWD circovirus

<400> SEQUENCE: 100

Ile Gly Gln Phe Leu Pro Pro Ser Gly Gly Thr Asn Pro Leu Pro
1 5 10 15

<210> SEQ ID NO 101
<211> LENGTH: 15
<212> TYPE: PRT
<213> ORGANISM: Type A PWD circovirus

<400> SEQUENCE: 101

Leu Pro Pro Ser Gly Gly Thr Asn Pro Leu Pro Leu Pro Phe Gln
1 5 10 15

<210> SEQ ID NO 102
<211> LENGTH: 15
<212> TYPE: PRT
<213> ORGANISM: Type A PWD circovirus

<400> SEQUENCE: 102

Gly Gly Thr Asn Pro Leu Pro Leu Pro Phe Gln Tyr Tyr Arg Ile
1 5 10 15

<210> SEQ ID NO 103
<211> LENGTH: 15
<212> TYPE: PRT
<213> ORGANISM: Type A PWD circovirus

<400> SEQUENCE: 103

Pro Leu Pro Leu Pro Phe Gln Tyr Tyr Arg Ile Arg Lys Ala Lys
1 5 10 15

<210> SEQ ID NO 104
<211> LENGTH: 15
<212> TYPE: PRT
<213> ORGANISM: Type A PWD circovirus

<400> SEQUENCE: 104

Pro Phe Gln Tyr Tyr Arg Ile Arg Lys Ala Lys Tyr Glu Phe Tyr
1 5 10 15

<210> SEQ ID NO 105
<211> LENGTH: 15
<212> TYPE: PRT
<213> ORGANISM: Type A PWD circovirus

<400> SEQUENCE: 105

Tyr Arg Ile Arg Lys Ala Lys Tyr Glu Phe Tyr Pro Arg Asp Pro
1 5 10 15

<210> SEQ ID NO 106
<211> LENGTH: 15
<212> TYPE: PRT
<213> ORGANISM: Type A PWD circovirus

<400> SEQUENCE: 106

Lys Ala Lys Tyr Glu Phe Tyr Pro Arg Asp Pro Ile Thr Ser Asn
1 5 10 15

<210> SEQ ID NO 107
<211> LENGTH: 15
<212> TYPE: PRT
<213> ORGANISM: Type A PWD circovirus -continued

<400> SEQUENCE: 107

Glu Phe Tyr Pro Arg Asp Pro Ile Thr Ser Asn Gln Arg Gly Val
1 5 10 15

<210> SEQ ID NO 108
<211> LENGTH: 15
<212> TYPE: PRT
<213> ORGANISM: Type A PWD circovirus

<400> SEQUENCE: 108

Arg Asp Pro Ile Thr Ser Asn Gln Arg Gly Val Gly Ser Thr Val
1 5 10 15

<210> SEQ ID NO 109
<211> LENGTH: 15
<212> TYPE: PRT
<213> ORGANISM: Type A PWD circovirus

<400> SEQUENCE: 109

Thr Ser Asn Gln Arg Gly Val Gly Ser Thr Val Val Ile Leu Asp
1 5 10 15

<210> SEQ ID NO 110
<211> LENGTH: 15
<212> TYPE: PRT
<213> ORGANISM: Type B PWD circovirus

<400> SEQUENCE: 110

Gly Val Gly Ser Ser Ala Val Ile Leu Asp Asp Asn Phe Val Thr
1 5 10 15

<210> SEQ ID NO 111
<211> LENGTH: 15
<212> TYPE: PRT
<213> ORGANISM: Type B PWD circovirus

<400> SEQUENCE: 111

Ser Ala Val Ile Leu Asp Asp Asn Phe Val Thr Lys Ala Thr Ala
1 5 10 15

<210> SEQ ID NO 112
<211> LENGTH: 15
<212> TYPE: PRT
<213> ORGANISM: Type B PWD circovirus

<400> SEQUENCE: 112

Leu Asp Asp Asn Phe Val Thr Lys Ala Thr Ala Leu Thr Tyr Asp
1 5 10 15

<210> SEQ ID NO 113
<211> LENGTH: 15
<212> TYPE: PRT
<213> ORGANISM: Type B PWD circovirus

<400> SEQUENCE: 113

Phe Val Thr Lys Ala Thr Ala Leu Thr Tyr Asp Pro Tyr Val Asn
1 5 10 15

<210> SEQ ID NO 114
<211> LENGTH: 15
<212> TYPE: PRT
<213> ORGANISM: Type B PWD circovirus

<400> SEQUENCE: 114

Ala Thr Ala Leu Thr Tyr Asp Pro Tyr Val Asn Tyr Ser Ser Arg
1 5 10 15

<210> SEQ ID NO 115
<211> LENGTH: 15
<212> TYPE: PRT
<213> ORGANISM: Type B PWD circovirus

<400> SEQUENCE: 115

Thr Tyr Asp Pro Tyr Val Asn Tyr Ser Ser Arg His Thr Ile Thr
1 5 10 15

<210> SEQ ID NO 116
<211> LENGTH: 15
<212> TYPE: PRT
<213> ORGANISM: Type B PWD circovirus

<400> SEQUENCE: 116

Tyr Val Asn Tyr Ser Ser Arg His Thr Ile Thr Gln Pro Phe Ser
1 5 10 15

<210> SEQ ID NO 117
<211> LENGTH: 15
<212> TYPE: PRT
<213> ORGANISM: Type B PWD circovirus

<400> SEQUENCE: 117

Ser Ser Arg His Thr Ile Thr Gln Pro Phe Ser Tyr His Ser Arg
1 5 10 15

<210> SEQ ID NO 118
<211> LENGTH: 15
<212> TYPE: PRT
<213> ORGANISM: Type B PWD circovirus

<400> SEQUENCE: 118

Thr Ile Thr Gln Pro Phe Ser Tyr His Ser Arg Tyr Phe Thr Pro
1 5 10 15

<210> SEQ ID NO 119
<211> LENGTH: 15
<212> TYPE: PRT
<213> ORGANISM: Type B PWD circovirus

<400> SEQUENCE: 119

Pro Phe Ser Tyr His Ser Arg Tyr Phe Thr Pro Lys Pro Val Leu
1 5 10 15

<210> SEQ ID NO 120
<211> LENGTH: 15
<212> TYPE: PRT
<213> ORGANISM: Type B PWD circovirus

<400> SEQUENCE: 120

His Ser Arg Tyr Phe Thr Pro Lys Pro Val Leu Asp Phe Thr Ile
1 5 10 15

<210> SEQ ID NO 121
<211> LENGTH: 15
<212> TYPE: PRT
<213> ORGANISM: Type B PWD circovirus

<400> SEQUENCE: 121

Phe Thr Pro Lys Pro Val Leu Asp Phe Thr Ile Asp Tyr Phe Gln

-continued 1 5 10 15

<210> SEQ ID NO 122
<211> LENGTH: 15
<212> TYPE: PRT
<213> ORGANISM: Type B PWD circovirus

<400> SEQUENCE: 122

Pro Val Leu Asp Phe Thr Ile Asp Tyr Phe Gln Pro Asn Asn Lys
1 5 10 15

<210> SEQ ID NO 123
<211> LENGTH: 15
<212> TYPE: PRT
<213> ORGANISM: Type B PWD circovirus

<400> SEQUENCE: 123

Phe Thr Ile Asp Tyr Phe Gln Pro Asn Asn Lys Arg Asn Gln Leu
1 5 10 15

<210> SEQ ID NO 124
<211> LENGTH: 15
<212> TYPE: PRT
<213> ORGANISM: Type B PWD circovirus

<400> SEQUENCE: 124

Tyr Phe Gln Pro Asn Asn Lys Arg Asn Gln Leu Trp Leu Arg Leu
1 5 10 15

<210> SEQ ID NO 125
<211> LENGTH: 15
<212> TYPE: PRT
<213> ORGANISM: Type B PWD circovirus

<400> SEQUENCE: 125

Asn Asn Lys Arg Asn Gln Leu Trp Leu Arg Leu Gln Thr Ala Gly
1 5 10 15

<210> SEQ ID NO 126
<211> LENGTH: 15
<212> TYPE: PRT
<213> ORGANISM: Type B PWD circovirus

<400> SEQUENCE: 126

Asn Gln Leu Trp Leu Arg Leu Gln Thr Ala Gly Asn Val Asp His
1 5 10 15

<210> SEQ ID NO 127
<211> LENGTH: 15
<212> TYPE: PRT
<213> ORGANISM: Type B PWD circovirus

<400> SEQUENCE: 127

Leu Arg Leu Gln Thr Ala Gly Asn Val Asp His Val Gly Leu Gly
1 5 10 15

<210> SEQ ID NO 128
<211> LENGTH: 15
<212> TYPE: PRT
<213> ORGANISM: Type B PWD circovirus

<400> SEQUENCE: 128

Thr Ala Gly Asn Val Asp His Val Gly Leu Gly Thr Ala Phe Glu
1 5 10 15

-continued

<210> SEQ ID NO 129
<211> LENGTH: 15
<212> TYPE: PRT
<213> ORGANISM: Type B PWD circovirus

<400> SEQUENCE: 129

Gly Leu Gly Thr Ala Phe Glu Asn Ser Ile Tyr Asp Gln Glu Tyr
1 5 10 15

<210> SEQ ID NO 130
<211> LENGTH: 15
<212> TYPE: PRT
<213> ORGANISM: Type B PWD circovirus

<400> SEQUENCE: 130

Ala Phe Glu Asn Ser Ile Tyr Asp Gln Glu Tyr Asn Ile Arg Val
1 5 10 15

<210> SEQ ID NO 131
<211> LENGTH: 15
<212> TYPE: PRT
<213> ORGANISM: Type B PWD circovirus

<400> SEQUENCE: 131

Ser Ile Tyr Asp Gln Glu Tyr Asn Ile Arg Val Thr Met Tyr Val
1 5 10 15

<210> SEQ ID NO 132
<211> LENGTH: 15
<212> TYPE: PRT
<213> ORGANISM: Type B PWD circovirus

<400> SEQUENCE: 132

Gln Glu Tyr Asn Ile Arg Val Thr Met Tyr Val Gln Phe Arg Glu
1 5 10 15

<210> SEQ ID NO 133
<211> LENGTH: 15
<212> TYPE: PRT
<213> ORGANISM: Type B PWD circovirus

<400> SEQUENCE: 133

Ile Arg Val Thr Met Tyr Val Gln Phe Arg Glu Phe Asn Phe Lys
1 5 10 15

<210> SEQ ID NO 134
<211> LENGTH: 15
<212> TYPE: PRT
<213> ORGANISM: Type B PWD circovirus

<400> SEQUENCE: 134

Met Tyr Val Gln Phe Arg Glu Phe Asn Phe Lys Asp Pro Pro Leu
1 5 10 15

<210> SEQ ID NO 135
<211> LENGTH: 15
<212> TYPE: PRT
<213> ORGANISM: Type B PWD circovirus

<400> SEQUENCE: 135

Val Gln Phe Arg Glu Phe Asn Phe Lys Asp Pro Pro Leu Asn Pro
1 5 10 15

<210> SEQ ID NO 136

-continued

<211> LENGTH: 15
<212> TYPE: PRT
<213> ORGANISM: Type A PWD circovirus

<400> SEQUENCE: 136

Arg Gly Val Gly Ser Thr Val Val Ile Leu Asp Ala Asn Phe Val
1 5 10 15

<210> SEQ ID NO 137
<211> LENGTH: 15
<212> TYPE: PRT
<213> ORGANISM: Type A PWD circovirus

<400> SEQUENCE: 137

Ser Thr Val Val Ile Leu Asp Ala Asn Phe Val Thr Pro Ser Thr
1 5 10 15

<210> SEQ ID NO 138
<211> LENGTH: 15
<212> TYPE: PRT
<213> ORGANISM: Type A PWD circovirus

<400> SEQUENCE: 138

Ile Leu Asp Ala Asn Phe Val Thr Pro Ser Thr Asn Leu Ala Tyr
1 5 10 15

<210> SEQ ID NO 139
<211> LENGTH: 15
<212> TYPE: PRT
<213> ORGANISM: Type A PWD circovirus

<400> SEQUENCE: 139

Asn Phe Val Thr Pro Ser Thr Asn Leu Ala Tyr Asp Pro Tyr Ile
1 5 10 15

<210> SEQ ID NO 140
<211> LENGTH: 15
<212> TYPE: PRT
<213> ORGANISM: Type A PWD circovirus

<400> SEQUENCE: 140

Pro Ser Thr Asn Leu Ala Tyr Asp Pro Tyr Ile Asn Tyr Ser Ser
1 5 10 15

<210> SEQ ID NO 141
<211> LENGTH: 15
<212> TYPE: PRT
<213> ORGANISM: Type A PWD circovirus

<400> SEQUENCE: 141

Leu Ala Tyr Asp Pro Tyr Ile Asn Tyr Ser Ser Arg His Thr Ile
1 5 10 15

<210> SEQ ID NO 142
<211> LENGTH: 15
<212> TYPE: PRT
<213> ORGANISM: Type A PWD circovirus

<400> SEQUENCE: 142

Pro Tyr Ile Asn Tyr Ser Ser Arg His Thr Ile Arg Gln Pro Phe
1 5 10 15

<210> SEQ ID NO 143
<211> LENGTH: 15
<212> TYPE: PRT

<213> ORGANISM: Type A PWD circovirus

<400> SEQUENCE: 143

Tyr Ser Ser Arg His Thr Ile Arg Gln Pro Phe Thr Tyr His Ser
1 5 10 15

<210> SEQ ID NO 144
<211> LENGTH: 15
<212> TYPE: PRT
<213> ORGANISM: Type A PWD circovirus

<400> SEQUENCE: 144

His Thr Ile Arg Gln Pro Phe Thr Tyr His Ser Arg Tyr Phe Thr
1 5 10 15

<210> SEQ ID NO 145
<211> LENGTH: 15
<212> TYPE: PRT
<213> ORGANISM: Type A PWD circovirus

<400> SEQUENCE: 145

Gln Pro Phe Thr Tyr His Ser Arg Tyr Phe Thr Pro Lys Pro Glu
1 5 10 15

<210> SEQ ID NO 146
<211> LENGTH: 15
<212> TYPE: PRT
<213> ORGANISM: Type A PWD circovirus

<400> SEQUENCE: 146

Tyr His Ser Arg Tyr Phe Thr Pro Lys Pro Glu Leu Asp Gln Thr
1 5 10 15

<210> SEQ ID NO 147
<211> LENGTH: 15
<212> TYPE: PRT
<213> ORGANISM: Type A PWD circovirus

<400> SEQUENCE: 147

Tyr Phe Thr Pro Lys Pro Glu Leu Asp Gln Thr Ile Asp Trp Phe
1 5 10 15

<210> SEQ ID NO 148
<211> LENGTH: 15
<212> TYPE: PRT
<213> ORGANISM: Type A PWD circovirus

<400> SEQUENCE: 148

Lys Pro Glu Leu Asp Gln Thr Ile Asp Trp Phe Gln Pro Asn Asn
1 5 10 15

<210> SEQ ID NO 149
<211> LENGTH: 15
<212> TYPE: PRT
<213> ORGANISM: Type A PWD circovirus

<400> SEQUENCE: 149

Asp Gln Thr Ile Asp Trp Phe Gln Pro Asn Asn Lys Arg Asn Gln
1 5 10 15

<210> SEQ ID NO 150
<211> LENGTH: 15
<212> TYPE: PRT
<213> ORGANISM: Type A PWD circovirus -continued

<400> SEQUENCE: 150

Asp Trp Phe Gln Pro Asn Asn Lys Arg Asn Gln Leu Trp Leu His
1 5 10 15

<210> SEQ ID NO 151
<211> LENGTH: 15
<212> TYPE: PRT
<213> ORGANISM: Type A PWD circovirus

<400> SEQUENCE: 151

Pro Asn Asn Lys Arg Asn Gln Leu Trp Leu His Leu Asn Thr His
1 5 10 15

<210> SEQ ID NO 152
<211> LENGTH: 15
<212> TYPE: PRT
<213> ORGANISM: Type A PWD circovirus

<400> SEQUENCE: 152

Arg Asn Gln Leu Trp Leu His Leu Asn Thr His Thr Asn Val Glu
1 5 10 15

<210> SEQ ID NO 153
<211> LENGTH: 15
<212> TYPE: PRT
<213> ORGANISM: Type A PWD circovirus

<400> SEQUENCE: 153

Trp Leu His Leu Asn Thr His Thr Asn Val Glu His Thr Gly Leu
1 5 10 15

<210> SEQ ID NO 154
<211> LENGTH: 15
<212> TYPE: PRT
<213> ORGANISM: Type A PWD circovirus

<400> SEQUENCE: 154

Asn Thr His Thr Asn Val Glu His Thr Gly Leu Gly Tyr Ala Leu
1 5 10 15

<210> SEQ ID NO 155
<211> LENGTH: 15
<212> TYPE: PRT
<213> ORGANISM: Type A PWD circovirus

<400> SEQUENCE: 155

Asn Val Glu His Thr Gly Leu Gly Tyr Ala Leu Gln Asn Ala Thr
1 5 10 15

<210> SEQ ID NO 156
<211> LENGTH: 15
<212> TYPE: PRT
<213> ORGANISM: Type A PWD circovirus

<400> SEQUENCE: 156

Thr Gly Leu Gly Tyr Ala Leu Gln Asn Ala Thr Thr Ala Gln Asn
1 5 10 15

<210> SEQ ID NO 157
<211> LENGTH: 15
<212> TYPE: PRT
<213> ORGANISM: Type A PWD circovirus

<400> SEQUENCE: 157

-continued

```
Tyr Ala Leu Gln Asn Ala Thr Thr Ala Gln Asn Tyr Val Val Arg
1               5                   10                  15


<210> SEQ ID NO 158
<211> LENGTH: 15
<212> TYPE: PRT
<213> ORGANISM: Type A PWD circovirus

<400> SEQUENCE: 158

Asn Ala Thr Thr Ala Gln Asn Tyr Val Val Arg Leu Thr Ile Tyr
1               5                   10                  15


<210> SEQ ID NO 159
<211> LENGTH: 15
<212> TYPE: PRT
<213> ORGANISM: Type A PWD circovirus

<400> SEQUENCE: 159

Ala Gln Asn Tyr Val Val Arg Leu Thr Ile Tyr Val Gln Phe Arg
1               5                   10                  15


<210> SEQ ID NO 160
<211> LENGTH: 15
<212> TYPE: PRT
<213> ORGANISM: Type A PWD circovirus

<400> SEQUENCE: 160

Val Val Arg Leu Thr Ile Tyr Val Gln Phe Arg Glu Phe Ile Leu
1               5                   10                  15


<210> SEQ ID NO 161
<211> LENGTH: 15
<212> TYPE: PRT
<213> ORGANISM: Type A PWD circovirus

<400> SEQUENCE: 161

Thr Ile Tyr Val Gln Phe Arg Glu Phe Ile Leu Lys Asp Pro Leu
1               5                   10                  15


<210> SEQ ID NO 162
<211> LENGTH: 15
<212> TYPE: PRT
<213> ORGANISM: Type A PWD circovirus

<400> SEQUENCE: 162

Tyr Val Gln Phe Arg Glu Phe Ile Leu Lys Asp Pro Leu Asn Glu
1               5                   10                  15


<210> SEQ ID NO 163
<211> LENGTH: 1759
<212> TYPE: DNA
<213> ORGANISM: Type A PWD circovirus

<400> SEQUENCE: 163

accagcgcac ttcggcagcg gcagcacctc ggcagcgtca gtgaaaatgc caagcaagaa     60

aagcggcccg caaccccata agaggtgggt gttcaccctt aataatcctt ccgaggagga    120

gaaaaacaaa atacgggagc ttccaatctc cctttttgat tattttgttt gcggagagga    180

aggtttggaa gagggtagaa ctcctcacct ccaggggttt gcgaattttg ctaagaagca    240

gacttttaac aaggtgaagt ggtattttgg tgcccgctgc cacatcgaga aagcgaaagg    300

aaccgaccag cagaataaag aatactgcag taaagaaggc cacatactta tcgagtgtgg    360

agctccgcgg aaccagggga agcgcagcga cctgtctact gctgtgagta ccctttttgga    420
```

-continued gacggggtct ttggtgactg tagccgagca gttccctgta acgtatgtga gaaatttccg 480
cgggctggct gaacttttga aagtgagcgg gaagatgcag aagcgtgatt ggaagacagc 540
tgtacacgtc atagtgggcc cgcccggttg tgggaagagc cagtgggccc gtaattttgc 600
tgagcctagg gacacctact ggaagcctag tagaaataag tggtgggatg gatatcatgg 660
agaagaagtt gttgttttgg atgattttta tggctggtta ccttgggatg atctactgag 720
actgtgtgac cggtatccat tgactgtaga gactaaaggg ggtactgttc ctttttggc 780 ccgcagtatt ttgattacca gcaatcaggc ccccaggaa tggtactcct caactgctgt 840
cccagctgta gaagctctct atcggaggat tactactttg caattttgga agactgctgg 900
agaacaatcc acggaggtac ccgaaggccg atttgaagca gtggacccac cctgtgccct 960
tttcccatat aaaataaatt actgagtctt ttttgttatc acatcgtaat ggtttttatt 1020
tttatttatt tagagggtct tttaggataa attctctgaa ttgtacataa atagtcagcc 1080
ttaccacata attttgggct gtggttgcat tttggagcgc atagcccagg cctgtgtgct 1140
cgacattggt gtgggtattt aaatggagcc acagctggtt tcttttatta tttgggtgga 1200
accaatcaat tgtttggtcc agctcaggtt tgggggtgaa gtacctggag tggtaggtaa 1260
agggctgcct tatggtgtgg cgggaggagt agttaatata ggggtcatag gccaagttgg 1320
tggagggggt tacaaagttg gcatccaaga taacaacagt ggacccaaca cctctttgat 1380
tagaggtgat ggggtctctg ggtaaaatt catatttagc ctttctaata cggtagtatt 1440
ggaaaggtag ggtagggggg ttggtgccgc ctgagggggg gaggaactgg ccgatgttga 1500
atttcagcta gttaacattc caagatggct gcgagtatcc tccttttatg gtgagtacaa 1560
attctgtaga aaggcgggaa ttgaagatac ccgtctttcg gcgccatctg taacggtttc 1620
tgaaggcggg gtgtgccaaa tatggtcttc tccggaggat gtttccaaga tggctgcggg 1680
ggcgggtcct tcttctgcgg taacgcctcc ttggccacgt catcctataa aagtgaaaga 1740
agtgcgctgc tgtagtatt 1759

<210> SEQ ID NO 164
<211> LENGTH: 1759
<212> TYPE: DNA
<213> ORGANISM: Type A PWD circovirus

<400> SEQUENCE: 164
accagcgcac ttcggcagcg gcagcacctc ggcagcgtca gtgaaaatgc caagcaagaa 60
aagcggcccg caaccccata agaggtgggt gttcaccctt aataatcctt ccgaggagga 120
gaaaaacaaa atacgggagc ttccaatctc cctttttgat tattttgttt gcggagagga 180
aggtttggaa gagggtagaa ctcctcacct ccaggggttt gctaattttg ctaagaagca 240
gacttttaac aaggtgaagt ggtattttgg tgcccgctgc cacatcgaga aagcgaaagg 300
aaccgaccag cagaataaag aatactgcag taaagaaggc cacatactta tcgagtgtgg 360
agctccgcgg aaccagggga agcgcagcga cctgtctact gctgtgagta cccttttgga 420
gacggggtct ttggtgactg tagccgagca gttccctgta acgtatgtga gaaatttccg 480
cgggctggct gaacttttga aagtgagcgg gaagatgcag aagcgtgatt ggaagacagc 540
tgtacacgtc atagtgggcc cgcccggttg tgggaagagc cagtgggccc gtaattttgc 600
tgagcctagc gacacctact ggaagcctag tagaaataag tggtgggatg gatatcatgg 660
agaagaagtt gttgttttgg atgattttta tggctggtta ccttgggatg atctactgag 720

-continued

```
actgtgtgac cggtatccat tgactgtaga gactaaaggc ggtactgttc ctttttggc     780

tcgcagtatt ttgattacca gcaatcaggc cccccaggaa tggtactcct caactgctgt     840

cccagctgta gaagctctct atcggaggat tactactttg caattttgga agactgctgg     900

agaacaatca acggaggtac ccgaaggccg atttgaagca gtggacccac cctgtgccct     960

tttcccatat aaaataaatt actgagtctt ttttgttatc acatcgtaat ggtttttatt    1020

tttatttatt tagagggtct tttaggataa attctctgaa ttgtacataa atagtcagcc    1080

ttaccacata attttgggct gtggttgcat tttggagcgc atagcccagg cctgtgtgct    1140

cgacattggt gtgggtattt aaatggagcc acagctggtt tcttttatta tttgggtgga    1200

accattcaat tgtttggtcc agctcaggtt tgggggtgaa gtacctggag tggtaggtaa    1260

agggctgcct tatggtgtgg cgggaggagt agttaatata ggggtcatag gccaagttgg    1320

tggagggggt tacaaagttg gcatccaaga taacaacagt ggacccaaca cctctttcat    1380

tagaggtgat ggggtctctg ggtaaaatt catatttagc ctttctaata cggtagtatt    1440

ggaaaggtag ggtagggggg ttggtgccgc ctgagggggg gaggaactgg ccgatgttga    1500

atctgaggtg gttaacatgc caagatggct gcgagtatcc tccttttatg gtgattacaa    1560

attctttaga aaggcggcaa ttgaagatac ccgtctttcg gcgccatctg taacggtttc    1620

tgaaggcggg gtgtgccaaa tatggtcttc tccggaggat gtttccaaga tggctgcggg    1680

ggcgggtcct tcttctgcgg taacgcctcc ttggccacgt catcctataa aagtgaaaga    1740

agtgcgctgc tgtagtatt                                                 1759


<210> SEQ ID NO 165
<211> LENGTH: 312
<212> TYPE: PRT
<213> ORGANISM: Type A PWD circovirus

<400> SEQUENCE: 165

Met Pro Ser Lys Lys Ser Gly Pro Gln Pro His Lys Arg Trp Val Phe
1               5                   10                  15

Thr Leu Asn Asn Pro Ser Gly Gly Gly Lys Asn Lys Ile Arg Gly Leu
            20                  25                  30

Pro Ile Ser Leu Phe Asp Tyr Phe Val Cys Gly Gly Gly Gly Leu Gly
        35                  40                  45

Gly Gly Arg Thr Pro His Leu Gln Gly Phe Ala Asn Phe Ala Lys Lys
    50                  55                  60

Gln Thr Phe Asn Lys Val Lys Trp Tyr Phe Gly Ala Arg Cys His Ile
65                  70                  75                  80

Gly Lys Ala Lys Gly Thr Asp Gln Gln Asn Lys Gly Tyr Cys Ser Lys
                85                  90                  95

Gly Gly His Ile Leu Ile Gly Cys Gly Ala Pro Arg Asn Gln Gly Lys
            100                 105                 110

Arg Ser Asp Leu Ser Thr Ala Val Ser Thr Leu Leu Gly Thr Gly Ser
        115                 120                 125

Leu Val Thr Val Ala Gly Gln Phe Pro Val Thr Tyr Val Arg Asn Phe
    130                 135                 140

Arg Gly Leu Ala Gly Leu Leu Lys Val Ser Gly Lys Met Gln Gln Arg
145                 150                 155                 160

Asp Trp Lys Thr Ala Val His Val Ile Val Gly Pro Pro Gly Cys Gly
                165                 170                 175

Lys Ser Gln Trp Ala Arg Asn Phe Ala Gly Pro Arg Asp Thr Tyr Trp
            180                 185                 190
```

```
Lys Pro Ser Arg Asn Lys Trp Trp Asp Gly Tyr His Gly Gly Gly Val
        195                 200                 205

Val Val Leu Asp Asp Phe Tyr Gly Trp Leu Pro Trp Asp Asp Leu Leu
    210                 215                 220

Arg Leu Cys Asp Arg Tyr Pro Leu Thr Val Gly Thr Lys Gly Gly Thr
225                 230                 235                 240

Val Pro Phe Leu Ala Arg Ser Ile Leu Ile Thr Ser Asn Gln Ala Pro
                245                 250                 255

Gln Gly Trp Tyr Ser Ser Thr Ala Val Pro Ala Val Gly Ala Leu Tyr
            260                 265                 270

Arg Arg Ile Thr Thr Leu Gln Phe Trp Lys Thr Ala Gly Gly Gln Ser
        275                 280                 285

Thr Gly Val Pro Gly Gly Arg Phe Gly Ala Val Asp Pro Pro Cys Ala
    290                 295                 300

Leu Phe Pro Tyr Lys Ile Asn Tyr
305                 310


<210> SEQ ID NO 166
<211> LENGTH: 312
<212> TYPE: PRT
<213> ORGANISM: Type A PWD circovirus

<400> SEQUENCE: 166

Met Pro Ser Lys Lys Ser Gly Pro Gln Pro His Lys Arg Trp Val Phe
1               5                   10                  15

Thr Leu Asn Asn Pro Ser Gly Gly Gly Lys Asn Lys Ile Arg Gly Leu
            20                  25                  30

Pro Ile Ser Leu Phe Asp Tyr Phe Val Cys Gly Gly Gly Gly Leu Gly
        35                  40                  45

Gly Gly Arg Thr Ala His Leu Gln Gly Phe Ala Asn Phe Ala Lys Lys
    50                  55                  60

Gln Thr Phe Asn Lys Val Lys Trp Tyr Phe Gly Ala Arg Cys His Ile
65                  70                  75                  80

Gly Lys Ala Lys Gly Thr Asp Gln Gln Asn Lys Gly Tyr Cys Ser Lys
                85                  90                  95

Gly Gly His Ile Leu Ile Gly Cys Gly Ala Pro Arg Asn Gln Gly Lys
            100                 105                 110

Arg Ser Asp Leu Ser Thr Ala Val Ser Thr Leu Leu Gly Thr Gly Ser
        115                 120                 125

Leu Val Thr Val Ala Gly Gln Phe Pro Val Thr Tyr Val Arg Asn Phe
    130                 135                 140

Arg Gly Leu Ala Gly Leu Leu Lys Val Ser Gly Lys Met Gln Gln Arg
145                 150                 155                 160

Asp Trp Lys Thr Ala Val His Val Ile Val Gly Pro Pro Gly Cys Gly
                165                 170                 175

Lys Ser Gln Trp Ala Arg Asn Phe Ala Gly Pro Ser Asp Thr Tyr Trp
            180                 185                 190

Lys Pro Ser Arg Asn Lys Trp Trp Asp Gly Tyr His Gly Gly Gly Val
        195                 200                 205

Val Val Leu Asp Asp Phe Tyr Gly Trp Leu Pro Trp Asp Asp Leu Leu
    210                 215                 220

Arg Leu Cys Asp Arg Tyr Pro Leu Thr Val Gly Thr Lys Gly Gly Thr
225                 230                 235                 240

Val Pro Phe Leu Ala Arg Ser Ile Leu Ile Thr Ser Asn Gln Ala Pro
```

-continued

```
            245                 250                 255

Gln Gly Trp Tyr Ser Ser Thr Ala Val Pro Ala Val Gly Ala Leu Tyr
            260                 265                 270

Arg Arg Ile Thr Thr Leu Gln Phe Trp Lys Thr Ala Gly Gly Gln Ser
        275                 280                 285

Thr Gly Val Pro Gly Gly Arg Phe Gly Ala Val Asp Pro Pro Cys Ala
    290                 295                 300

Leu Phe Pro Tyr Lys Ile Asn Tyr
305                 310


<210> SEQ ID NO 167
<211> LENGTH: 233
<212> TYPE: PRT
<213> ORGANISM: Type A PWD circovirus

<400> SEQUENCE: 167

Met Thr Trp Pro Arg Arg Arg Tyr Arg Arg Arg Arg Thr Arg Pro Arg
1               5                   10                  15

Ser His Leu Gly Asn Ile Leu Arg Arg Arg Pro Tyr Leu Ala His Pro
            20                  25                  30

Ala Phe Arg Asn Arg Tyr Arg Trp Arg Arg Lys Thr Gly Ile Phe Asn
        35                  40                  45

Ser Arg Leu Ser Thr Glu Phe Val Leu Thr Ile Arg Gly Gly His Ser
    50                  55                  60

Gln Pro Ser Trp Asn Val Asn Tyr Leu Lys Phe Asn Ile Gly Gln Phe
65                  70                  75                  80

Leu Pro Pro Ser Gly Gly Thr Asn Pro Leu Pro Leu Pro Phe Gln Tyr
                85                  90                  95

Tyr Arg Ile Arg Lys Ala Lys Tyr Glu Phe Tyr Pro Arg Asp Pro Ile
            100                 105                 110

Thr Ser Asn Gln Arg Gly Val Gly Ser Thr Val Val Ile Leu Asp Ala
        115                 120                 125

Asn Phe Val Thr Pro Ser Thr Asn Leu Ala Tyr Asp Pro Tyr Ile Asn
    130                 135                 140

Tyr Ser Ser Arg His Thr Ile Arg Gln Pro Phe Thr Tyr His Ser Arg
145                 150                 155                 160

Tyr Phe Thr Pro Lys Pro Glu Leu Asp Gln Thr Ile Asp Trp Phe His
                165                 170                 175

Pro Asn Asn Lys Arg Asn Gln Leu Trp Leu His Leu Asn Thr His Thr
            180                 185                 190

Asn Val Glu His Thr Gly Leu Gly Tyr Ala Leu Gln Asn Ala Ala Thr
        195                 200                 205

Ala Gln Asn Tyr Val Val Arg Leu Thr Ile Tyr Val Gln Phe Arg Glu
    210                 215                 220

Phe Ile Leu Lys Asp Pro Leu Asn Lys
225                 230


<210> SEQ ID NO 168
<211> LENGTH: 233
<212> TYPE: PRT
<213> ORGANISM: Type A PWD circovirus

<400> SEQUENCE: 168

Met Thr Trp Pro Arg Arg Arg Tyr Arg Arg Arg Arg Thr Arg Pro Arg
1               5                   10                  15

Ser His Leu Gly Asn Ile Leu Arg Arg Arg Pro Tyr Leu Val His Pro
```

-continued

```
            20                  25                  30

Ala Phe Arg Asn Arg Tyr Arg Trp Arg Arg Lys Thr Gly Ile Phe Asn
        35                  40                  45

Cys Arg Leu Ser Lys Glu Phe Val Ile Thr Ile Arg Gly Gly His Ser
    50                  55                  60

Gln Pro Ser Trp Ile Val Asn Ile Leu Arg Phe Asn Ile Gly Gln Phe
65                  70                  75                  80

Leu Pro Pro Ser Gly Gly Thr Asn Pro Leu Pro Leu Pro Phe Gln Tyr
                85                  90                  95

Tyr Arg Ile Arg Lys Ala Lys Tyr Glu Phe Tyr Pro Arg Asp Pro Ile
            100                 105                 110

Thr Ser Asn Glu Arg Gly Val Gly Ser Thr Val Val Ile Leu Asp Ala
        115                 120                 125

Asn Phe Val Thr Pro Ser Thr Asn Leu Ala Tyr Asp Pro Tyr Ile Asn
    130                 135                 140

Tyr Ser Ser Arg His Thr Ile Arg Gln Pro Phe Thr Tyr His Ser Arg
145                 150                 155                 160

Tyr Phe Thr Pro Lys Pro Glu Leu Asp Gln Thr Ile Glu Trp Phe His
                165                 170                 175

Pro Asn Asn Lys Arg Asn Gln Leu Trp Leu His Leu Asn Thr His Thr
            180                 185                 190

Asn Val Glu His Thr Gly Leu Gly Tyr Ala Leu Gln Asn Ala Ala Thr
        195                 200                 205

Ala Gln Asn Tyr Val Val Arg Leu Thr Ile Tyr Val Gln Phe Arg Glu
    210                 215                 220

Phe Ile Leu Lys Asp Pro Leu Asn Lys
225                 230


<210> SEQ ID NO 169
<211> LENGTH: 206
<212> TYPE: PRT
<213> ORGANISM: Type A PWD circovirus

<400> SEQUENCE: 169

Met Ile Ser Ile Pro Pro Leu Ile Ser Thr Arg Leu Pro Val Gly Val
1               5                   10                  15

Pro Arg Leu Ser Lys Ile Thr Gly Pro Leu Ala Leu Pro Thr Thr Gly
            20                  25                  30

Arg Ala His Tyr Asp Val Tyr Ser Cys Leu Pro Ile Thr Leu Leu His
        35                  40                  45

Leu Pro Ala His Phe Gln Lys Phe Ser Gln Pro Ala Glu Ile Ser His
    50                  55                  60

Ile Arg Tyr Arg Glu Leu Leu Gly Tyr Ser His Gln Arg Pro Arg Leu
65                  70                  75                  80

Gln Lys Gly Thr His Ser Ser Arg Gln Val Ala Ala Leu Pro Leu Val
                85                  90                  95

Pro Arg Ser Ser Thr Leu Asp Lys Tyr Val Ala Phe Phe Thr Ala Val
            100                 105                 110

Phe Phe Ile Leu Leu Val Gly Ser Phe Arg Phe Leu Asp Val Ala Ala
        115                 120                 125

Gly Thr Lys Ile Pro Leu His Leu Val Lys Ser Leu Leu Leu Ser Lys
    130                 135                 140

Ile Arg Lys Pro Leu Glu Val Arg Ser Ser Thr Leu Phe Gln Thr Phe
145                 150                 155                 160
```

-continued

```
Leu Ser Ala Asn Lys Ile Ile Lys Lys Gly Asp Trp Lys Leu Pro Tyr
                165                 170                 175

Phe Val Phe Leu Leu Leu Gly Arg Ile Ile Lys Gly Glu His Pro Pro
            180                 185                 190

Leu Met Gly Leu Arg Ala Ala Phe Leu Ala Trp His Phe His
        195                 200                 205
```

<210> SEQ ID NO 170
<211> LENGTH: 206
<212> TYPE: PRT
<213> ORGANISM: Type A PWD circovirus

<400> SEQUENCE: 170

```
Met Ile Ser Ile Pro Pro Leu Ile Ser Thr Arg Leu Pro Val Gly Val
1               5                   10                  15

Ala Arg Leu Ser Lys Ile Thr Gly Pro Leu Ala Leu Pro Thr Thr Gly
            20                  25                  30

Arg Ala His Tyr Asp Val Tyr Ser Cys Leu Pro Ile Thr Leu Leu His
        35                  40                  45

Leu Pro Ala His Phe Gln Lys Phe Ser Gln Pro Ala Glu Ile Ser His
    50                  55                  60

Ile Arg Tyr Arg Glu Leu Leu Gly Tyr Ser His Gln Arg Pro Arg Leu
65                  70                  75                  80

Gln Lys Gly Thr His Ser Ser Arg Gln Val Ala Ala Leu Pro Leu Val
                85                  90                  95

Pro Arg Ser Ser Thr Leu Asp Lys Tyr Val Ala Phe Phe Thr Ala Val
            100                 105                 110

Phe Phe Ile Leu Leu Val Gly Ser Phe Arg Phe Leu Asp Val Ala Ala
        115                 120                 125

Gly Thr Lys Ile Pro Leu His Leu Val Lys Ser Leu Leu Leu Ser Lys
    130                 135                 140

Ile Arg Lys Pro Leu Glu Val Ser Ser Ser Thr Leu Phe Gln Thr Phe
145                 150                 155                 160

Leu Ser Ala Asn Lys Ile Ile Lys Lys Gly Asp Trp Lys Leu Pro Tyr
                165                 170                 175

Phe Val Phe Leu Leu Leu Gly Arg Ile Ile Lys Gly Glu His Pro Pro
            180                 185                 190

Leu Met Gly Leu Arg Ala Ala Phe Leu Ala Trp His Phe His
        195                 200                 205
```

<210> SEQ ID NO 171
<211> LENGTH: 15
<212> TYPE: PRT
<213> ORGANISM: Type B PWD circovirus

<400> SEQUENCE: 171

```
Met Thr Tyr Pro Arg Arg Arg Tyr Arg Arg Arg Arg His Arg Pro
1               5                   10                  15
```

<210> SEQ ID NO 172
<211> LENGTH: 15
<212> TYPE: PRT
<213> ORGANISM: Type B PWD circovirus

<400> SEQUENCE: 172

```
Arg Arg Arg Tyr Arg Arg Arg Arg His Arg Pro Arg Ser His Leu
1               5                   10                  15
```

-continued

```
<210> SEQ ID NO 173
<211> LENGTH: 15
<212> TYPE: PRT
<213> ORGANISM: Type B PWD circovirus

<400> SEQUENCE: 173

Arg Arg Arg Arg His Arg Pro Arg Ser His Leu Gly Gln Ile Leu
1               5                   10                  15


<210> SEQ ID NO 174
<211> LENGTH: 15
<212> TYPE: PRT
<213> ORGANISM: Type B PWD circovirus

<400> SEQUENCE: 174

Ser Pro Ile Thr Gln Gly Asp Arg Gly Val Gly Ser Ser Ala Val
1               5                   10                  15


<210> SEQ ID NO 175
<211> LENGTH: 15
<212> TYPE: PRT
<213> ORGANISM: Type B PWD circovirus

<400> SEQUENCE: 175

Met Thr Trp Pro Arg Arg Arg Tyr Arg Arg Arg Arg Thr Arg Pro
1               5                   10                  15


<210> SEQ ID NO 176
<211> LENGTH: 15
<212> TYPE: PRT
<213> ORGANISM: Type B PWD circovirus

<400> SEQUENCE: 176

Arg Arg Arg Tyr Arg Arg Arg Arg Thr Arg Pro Arg Ser His Leu
1               5                   10                  15


<210> SEQ ID NO 177
<211> LENGTH: 15
<212> TYPE: PRT
<213> ORGANISM: Type B PWD circovirus

<400> SEQUENCE: 177

Arg Arg Arg Arg Thr Arg Pro Arg Ser His Leu Gly Asn Ile Leu
1               5                   10                  15
```

CIRCOVIRUS SEQUENCES ASSOCIATED WITH PIGLET WEIGHT LOSS DISEASE (PWD)

INFORMATION TO RELATED APPLICATIONS

This application is a continuation of U.S. patent application Ser. No. 11/488,904, filed Jul. 19, 2006, now U.S. Pat. No. 7,314,628, which is a continuation of U.S. application Ser. No. 10/682,420, filed Oct. 10, 2003, now abandoned, which is a continuation of U.S. application Ser. No. 10/637,011, filed Aug. 8, 2003, now U.S. Pat. No. 7,223,594, which is a continuation of U.S. application Ser. No. 09/514,245, filed Feb. 28, 2000, now U.S. Pat. No. 6,703,023, which is a 35 U.S.C. §120 continuation-in-part of International Application No. PCT/FR98/02634, filed Dec. 4, 1998, published in a non-English language, and now abandoned, which claims priority to French Application No. 97/15396, filed Dec. 5, 1997 each application which is incorporated herein by reference in their entireties for all purposes.

BACKGROUND OF THE INVENTION

The invention relates to the genomic sequence and nucleotide sequences coding for polypeptides of PWD circovirus, such as the structural and nonstructural polypeptides of said circovirus, as well as vectors including said sequences and cells or animals transformed by these vectors. The invention likewise relates to methods for detecting these nucleic acids or polypeptides and kits for diagnosing infection by the PWD circovirus. The invention is also directed to a method for selecting compounds capable of modulating the viral infection. The invention further comprises pharmaceutical compositions, including vaccines, for the prevention and/or the treatment of viral infections by PWD circovirus as well as the use of a vector according to the invention for the prevention and/or the treatment of diseases by gene therapy.

Piglet weight loss disease (PWD), alternatively called fatal piglet wasting (FPW) has been widely described in North America (Harding, J. C., 1997), and authors have reported the existence of a relationship between this pathology and the presence of porcine circovirus (Daft, B. et al., 1996; Clark, E. G., 1997; Harding, J. C., 1997; Harding, J. C. and Clark, E. G., 1997; Nayar, G. P. et al., 1997). A porcine circovirus has already been demonstrated in established lines of cell cultures derived from pigs and chronically infected (Tischer, I., 1986, 1988, 1995; Dulac, G. C., 1989; Edwards, S., 1994; Allan, G. M., 1995 and McNeilly, F., 1996). This virus, during experimental infection of piglets, does not prove pathogenic for pigs (Tischer, I., 1986, Horner, G. W., 1991) and its nucleotide sequence has been determined and characterized (Tischer, I., 1982; Meehan, B. M. et al., 1997; Mankertz., A., 1997). The porcine circovirus, called PCV virus, is part of the circovirus genus of the circoviridae family (Murphy, F. A. et al., 1995) whose virion has a circular DNA of size between 1.7 and 2.3 kb, which DNA comprises three open reading frames (ORF1 to ORF3), coding for a replication protein REP involved in the initiation and termination phase of rolling circular replication (RCR) (Heyraud-Nitschke, F., et al., 1995; Harding, M. R. et al., 1993; Hanson, S. F. et al., 1995; Fontes, E. P. B. et al., 1994), coding for a capsid protein (Boulton, L. H. et al., 1997; Hackland, A. F. et al., 1994; Chu, P. W. G. et al., 1993) and coding for a nonstructural protein called a dissemination protein (Lazarowitz., S. G. et al., 1989).

The authors of the present invention have noticed that the clinical signs perceptible in pigs and linked to infection by the PWD circovirus are very distinctive. These manifestations in general appear in pigs of 8 to 12 weeks of age, weaned for 4 to 8 weeks. The first signs are hypotonia without it being possible to speak of prostration. Rapidly (48 hours), the flanks hollow, the line of the spine becomes apparent, and the pigs "blanch." These signs are in general accompanied by hyperthermia, anorexia and most often by respiratory signs (coughing, dyspnea, polypnea). Transitory diarrhea can likewise appear. The disease state phase lasts approximately one month at the end of which the rate of mortality varies from 5 to 20%. To these mortalities, it is expedient to add a variable proportion (5-10%) of cadaveric animals which are no longer able to present an economic future. It is to be noted that outside of this critical stage of the end of post-weaning, no anomaly appears on the farms. In particular, the reproductive function is totally maintained.

On the epidemiological level, the first signs of this pathology appeared at the start of 1995 in the east of the Côtes d'Armor region in France, and the farms affected are especially confined to this area of the region. In December 1996, the number of farms concerned could not be evaluated with precision because of the absence of a specific laboratory diagnostic method or of an epidemiological surveillance system of the livestock. Based on the clinical facts as well as on results of postmortem examinations supplied by veterinarians, it is possible to estimate this number as several dozen (80-100). The contagiousness of the disease is weak to moderate. Cases are being reported outside the initial area and for the majority are following the transfer of animals coming from farms familiar with the problem. On the other hand, a characteristic of the condition is its strong remanence. Thus, farms which have been affected for a year are still affected in spite of the massive administration of therapeutics. Farms with clinical expression are drawn from various categories of specialization (breeders/fatteners, post-weaners/fatteners) and different economic structures are concerned. In addition, the disorders appear even in farms where the rules of animal husbandry are respected.

Numerous postmortem examinations have been carried out either on farms or in the laboratory. The elements of the lesional table are disparate. The most constant macroscopic lesions are pneumonia which sometimes appears in patchy form as well as hypertrophy of the lymphatic ganglia. The other lesions above all affect the thoracic viscera including, especially, pericarditis and pleurisy. However, arthritis and gastric ulcers are also observed. The lesions revealed in the histological examination are essentially situated at the pulmonary level (interstitial pneumonia), ganglionic level (lymphoid depletion of the lymph nodes, giant cells) and renal level (glomerulonephritis, vasculitis). The infectious agents have been the subject of wide research. It has been possible to exclude the intervention of pestiviruses and Aujeszky's disease. The disorders appear in the seropositive PDRS (Porcine Dysgenic and Respiratory Syndrome, an infection linked to an arteriovirus) herds, but it has not been possible to establish the role of the latter in the genesis of the disorders (the majority of the farms in Brittany are PDRS seropositive).

The authors of the present invention, with the aim of identifying the etiological agent responsible for PWD, have carried out "contact" tests between piglets which are obviously "ill" and SPF pigs (specific pathogen-free) from CNEVA (Centre National d'Etudes Vétérinaires et Alimentaires, France). These tests allow the development of signs comparable to those observed on the farm to be observed in protected animal houses. The discrete signs such as moderate hyperthermia, anorexia and intermittent diarrhea appeared after one week of contact. It must be noted that the PDRS virus only diffused subsequent to the clinical signs. In addition, inocculations of organ homogenates of sick animals to healthy pigs allowed signs related to those observed on the farms to be reproduced, although with a lower incidence, linked to the favorable conditions of upkeep of the animals in the experimental installations.

Thus, the authors of the present invention have been able to demonstrate that the pathological signs appear as a well-defined entity affecting the pig at a particular stage of its growth.

This pathology has never been described in France. However, sparse information, especially Canadian, relates to similar facts.

The disorders cannot be mastered with the existing therapeutics.

The data collected both on the farm and by experimentation have allowed the following points to be highlighted:

PWD is transmissible but its contagiousness is not very high, its etiological origin is of infectious and probably viral nature, PWD has a persistent character in the affected farms.

Considerable economic consequences ensue for the farms.

Thus, there is currently a significant need for a specific and sensitive diagnostic, whose production is practical and rapid, allowing the early detection of the infection.

A reliable, sensitive and practical test which allows the distinction between strains of porcine circovirus (PCV) is thus strongly desirable.

On the other hand, a need for efficient and well-tolerated treatment of infections with PWD circovirus likewise remains desirable, no vaccine currently being available against PWD circovirus.

Concerning PWD circovirus, it will probably be necessary to understand the role of the immune defense in the physiology and the pathology of the disease to develop satisfactory vaccines.

Fuller information concerning the biology of these strains, their interactions with their hosts, the associated infectivity phenomena and those of escape from the immune defenses of the host especially, and finally their implication in the development of associated pathologies, will allow a better understanding of these mechanisms. Taking into account the facts which have been mentioned above and which show in particular the limitations of combatting infection by the PWD circovirus, it is thus essential today on the one hand to develop molecular tools, especially starting from a better genetic knowledge of the PWD circovirus, and likewise to perfect novel preventive and therapeutic treatments, novel methods of diagnosis and specific, efficacious and tolerated novel vaccine strategies. This is precisely the subject of the present invention.

SUMMARY OF THE INVENTION

The present invention relates to vaccines comprising a nucleotide sequence of the genome of Porcine circovirus type B, or a homologue or fragment thereof, and an acceptable pharmaceutical or veterinary vehicle. In one embodiment of the invention, the nucleotide sequence is selected from SEQ ID No. 15, SEQ ID No. 19 SEQ ID No. 23, or SEQ ID No. 25, or a homologue or fragment thereof. In another embodiment of the invention, the homologue has at least 80% sequence identity to SEQ ID No. 15, SEQ ID No. 19, SEQ ID No. 23 or SEQ ID No. 25. In yet another embodiment, the vaccines further comprising an adjuvant The present invention also relates to vaccines comprising a polypeptide encoded by a nucleotide sequence of the genome of PCVB, or a homologue or fragment thereof, and an acceptable pharmaceutical or veterinary vehicle. In one embodiment, the homologue has at least 80% sequence identity to SEQ ID No. 15, SEQ ID No. 19, SEQ ID No. 23 or SEQ ID No. 25. In another embodiment of the invention, the nucleotide sequence is selected from SEQ ID No. 23 or SEQ ID No. 25, or a homologue or fragment thereof. In still another embodiment, the polypeptide has the amino acid sequence of SEQ ID No. 24 or SEQ ID No. 26. In yet another embodiment, the homologue has at least 80% sequence identity to SEQ ID No. 24 or SEQ ID No. 26. In another embodiment, the polypeptide has the amino acid sequence of SEQ ID No. 29, SEQ ID No. 30, SEQ ID No. 31, or SEQ ID No. 32.

A further aspect of the invention relates to vaccines comprising a vector and an acceptable pharmaceutical or veterinary vehicle, the vector comprising a nucleotide sequence of the genome of Porcine circovirus type B, or a homologue or fragment thereof. In one embodiment, the vaccine further comprises a gene coding for an expression product capable of inhibiting or retarding the establishment or development of a genetic or acquired disease.

The present invention also relates to vaccines comprising a cell and an acceptable pharmaceutical or veterinary vehicle, wherein the cell is transformed with a nucleotide sequence of the genome of Porcine circovirus type B, or a homologue or fragment thereof.

Still further, the present invention relates to vaccines comprising a pharmaceutically acceptable vehicle and a single polypetide, wherein the single polypeptide consists of SEQ ID No. 26.

Additionally, the present invention relates to methods of immunizing a mammal against piglet weight loss disease comprising administering to a mammal an effective amount of the vaccines described above.

These and other aspects of the invention will become apparent to the skilled artisan in view of the teachings contained herein.

Test 1: experimental reproduction of the PWD by inoculation of pig organ homogenates from farms affected by PWD;

Test 2: experimental reproduction of PWD.

Test 3: experimental reproduction of PWD.

Test 4: no experimental reproduction of PWD.

FIG. 2: Organization of the genome of the circovirus associated with PWD of type A (PCVA)

strand of (+) polarity (SEQ ID No. 1);

strand of (−) polarity (SEQ ID No. 5, represented according to the orientation 3'→5');

sequences of amino acids of proteins encoded by the two DNA strands in the three possible reading frames SEQ ID NOS: 2-4 and 6-8 respectively.

FIG. 3: Alignment of the nucleotide sequence SEQ ID No. 1 of the PWD circovirus of type A (PCVA) and of the MEEHAN SEQ ID No. 163 strain and MANKERTZ SEQ ID No. 164 strain circoviruses of the porcine cell lines.

FIG. 4: Alignment of the sequence of amino acids SEQ ID No. 10 of a polypeptide encoded by the nucleotide sequence SEQ ID No. 9 (ORF1) of the PWD circovirus of type A (PCVA) and of corresponding nucleotide sequences of the MEEHAN SEQ ID No. 165 strain and MANKERTZ SEQ ID No. 166 strain circoviruses of the porcine cell lines.

FIG. 5: Alignment of the sequence of amino acids SEQ ID No. 12 of a polypeptide encoded by the nucleotide sequence SEQ ID No. 11 (ORF2) of the PWD circovirus of type A (PCVA) and of corresponding nucleotide sequences of the MEEHAN SEQ ID No. 167 strain and MANKERTZ SEQ ID No. 168 strain circoviruses of the porcine cell lines.

FIG. 6: Alignment of the sequence of amino acids SEQ ID No. 14 of a polypeptide encoded by the nucleotide sequence SEQ ID No. 13 (ORF3) of the PWD circovirus of type A (PCVA) and of corresponding nucleotide sequences of the MEEHAN SEQ ID No. 169 strain and MANKERTZ SEQ ID No. 170 strain circoviruses of the porcine cell lines.

Figure 7:
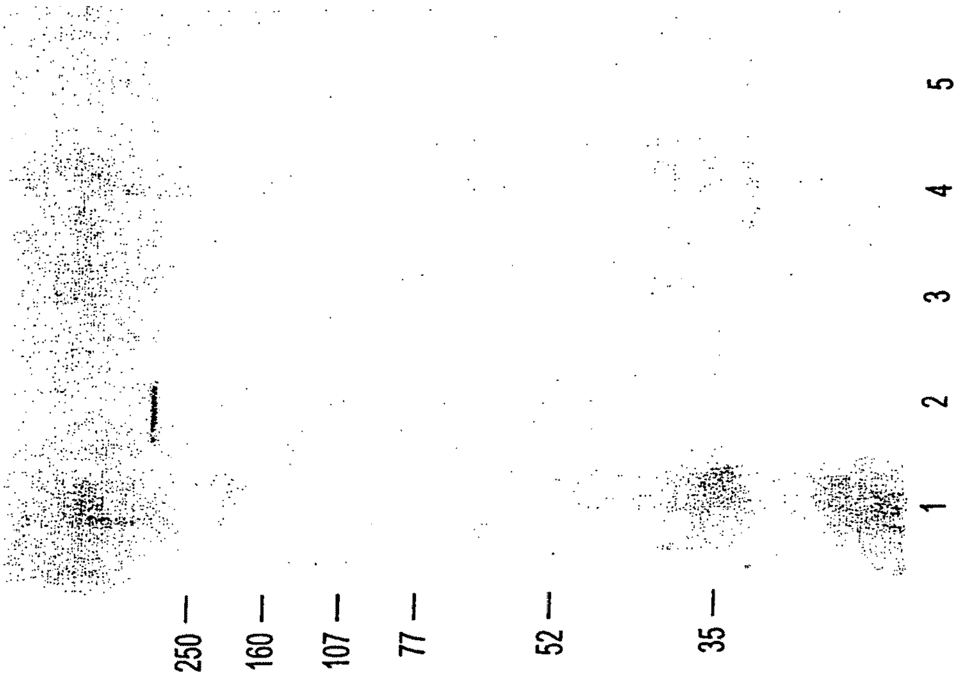

FIG. 7: Western blot analysis of recombinant proteins of the PWD circovirus of type A (PCVA).

The analyses were carried out on cell extracts of Sf9 cells obtained after infection with recombinant baculovirus PCF ORF 1.

FIG. 8: Organization of the genome of the circovirus associated with the PWD of type B (PCVB)

strand of (+) polarity (SEQ ID No. 15);

strand of (−) polarity (SEQ ID No. 19, represented according to the orientation 3'→5');

sequence of amino acids of proteins encoded by the two DNA strands in the three possible reading frames SEQ ID NOS: 16-18 and 20-22 respectively.

Figure 9:
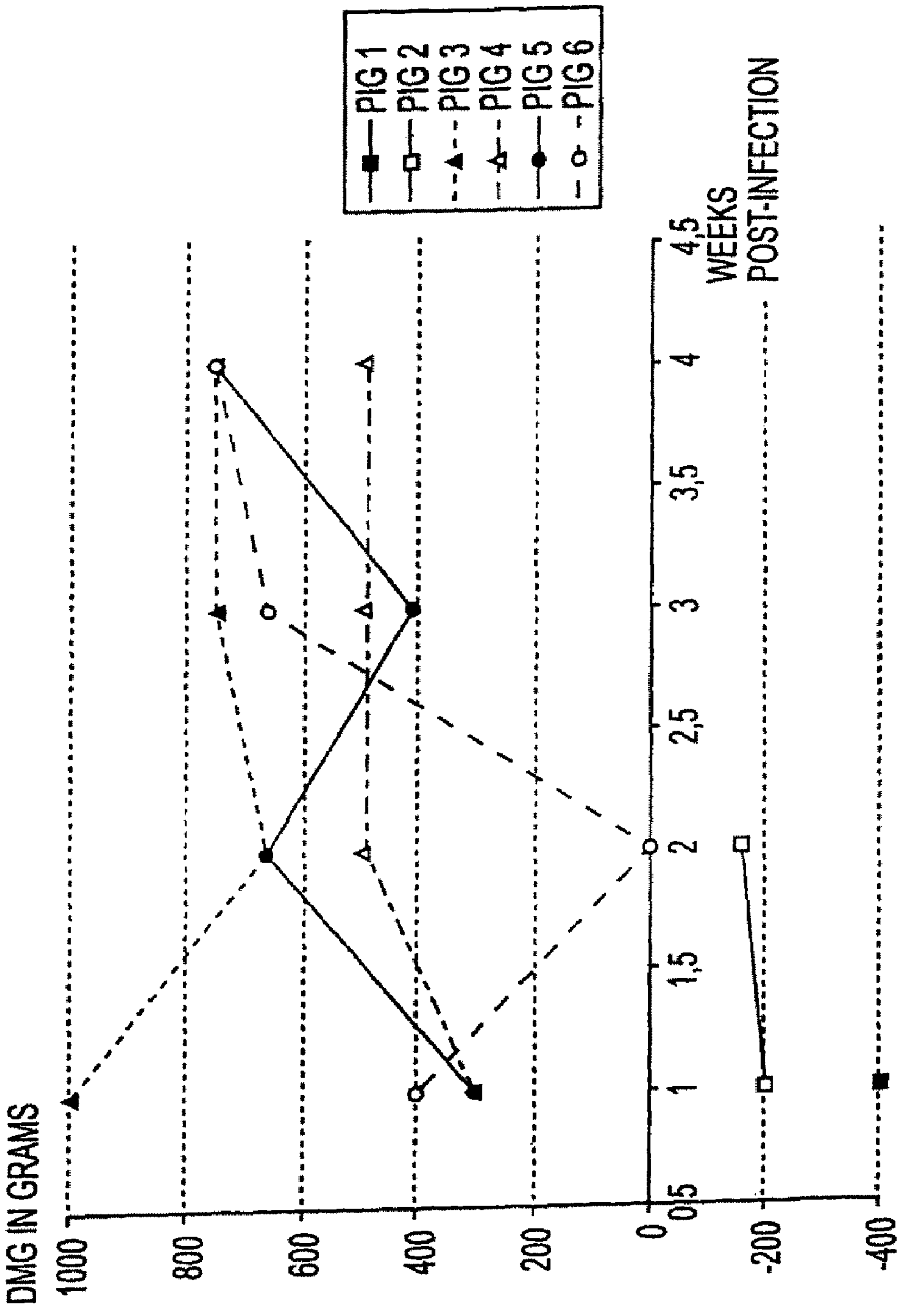

FIG. 9: Evolution of the daily mean gain (DMG) of pig farms affected by piglet weight loss disease (PWD), placed under experimental conditions.

Figure 10:
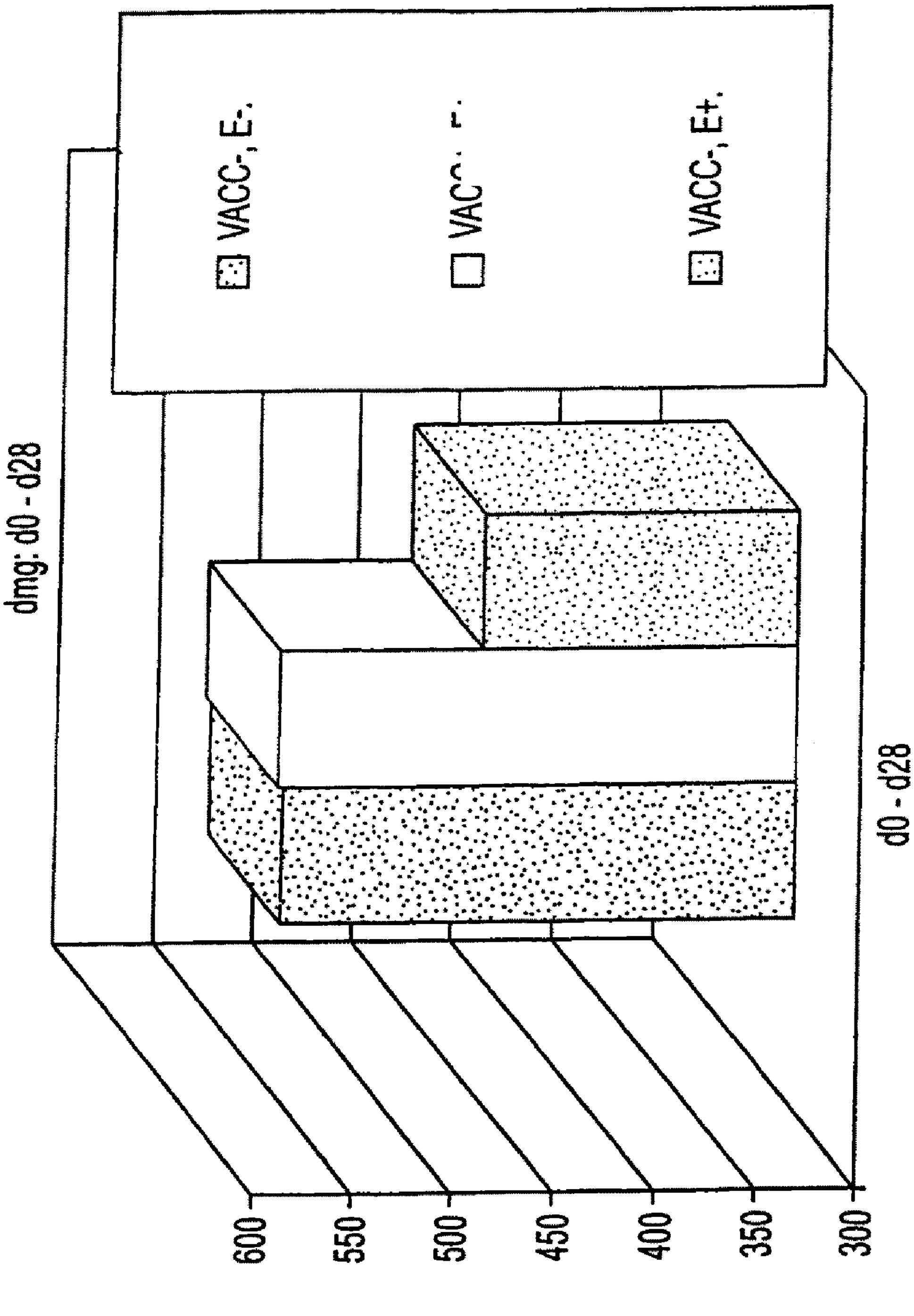

FIG. 10: DMG compared for the 3 batches of pigs (F1, F3 and F4) calculated over a period of 28 days, after vaccination test.

Figure 11:
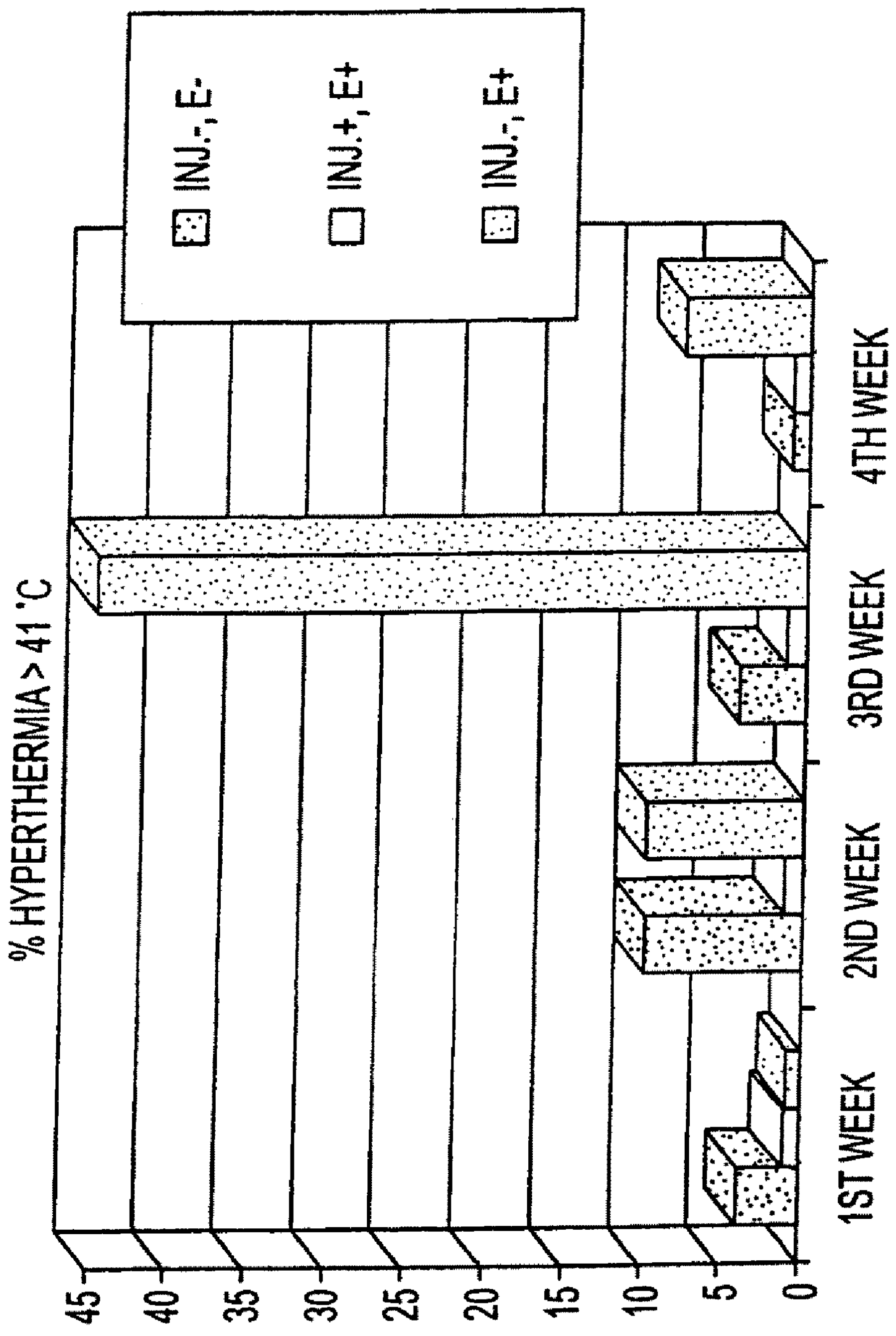

FIG. 11: Hyperthermia greater than 41° C., expressed as a percentage compared for the 3 batches of pigs (F1, F3 and F4) calculated per week over a period of 28 days, after vaccination test.

Figure 12:
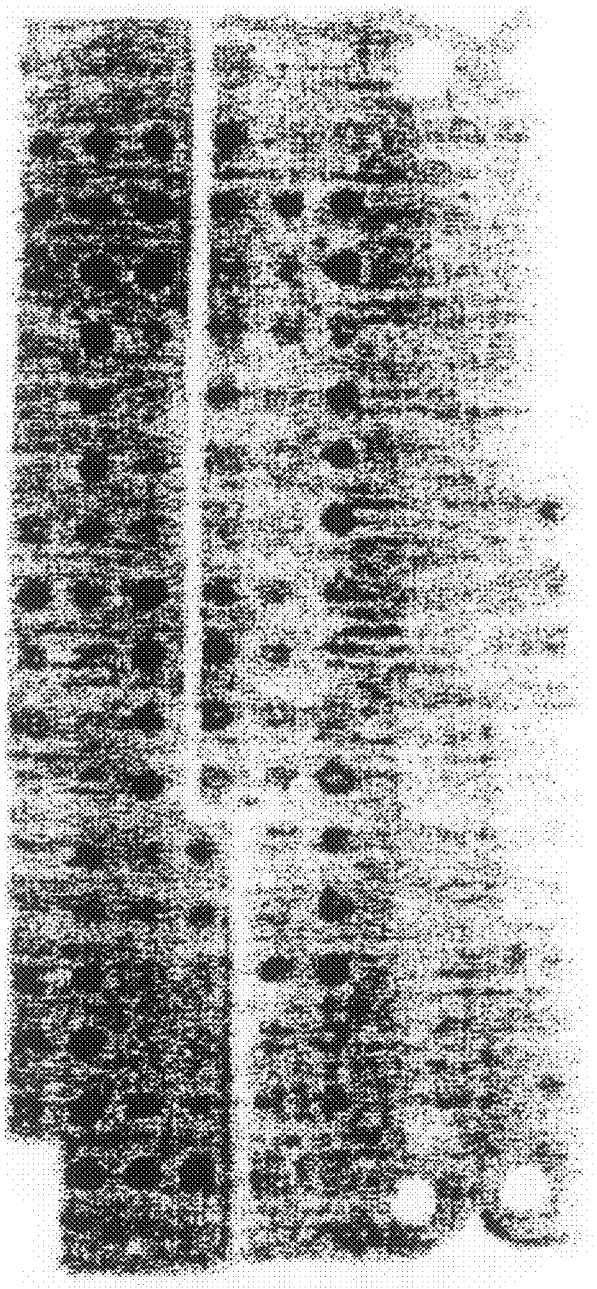

FIG. 12: Membranes of peptide spots corresponding to the ORF2s revealed with the aid of an infected pig serum, originating from a conventional farm.

The numbers of specific peptides of the circovirus of type B as well as their nonreactive homologs (type A) are indicated in bold.

The nonspecific immunogenic peptides are indicated in italics.

FIG. 13: Alignment of amino acid sequences of proteins encoded by the ORF2 of the PWD circovirus of type A SEQ ID No. 12 and by the ORF'2 of the PWD circovirus of type B SEQ ID No. 26. The position of 4 peptides corresponding to specific epitopes of the PWD circovirus of type B is indicated on the corresponding sequence by a bold line, their homolog on the sequence of the PWD circovirus of type A is likewise indicated by an ordinary line.

Figure 14:
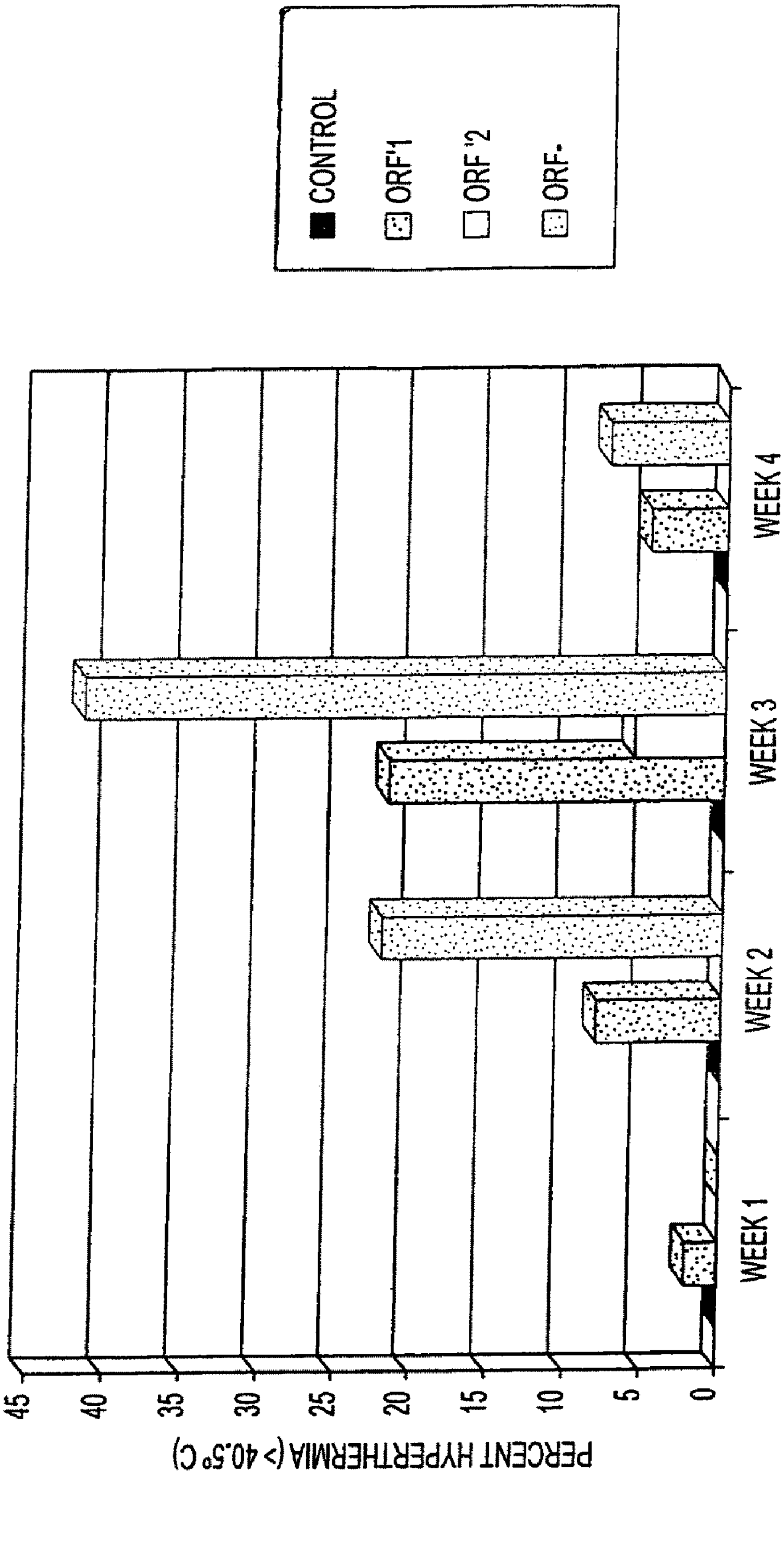

FIG. 14: Charts the results of experiments that demonstrate, in terms of percent hyperthermia, that vaccination with ORF'1 and ORF'2 of PCV-B enhances the level of protection in swine challenged with PCV-B.

Figure 15:
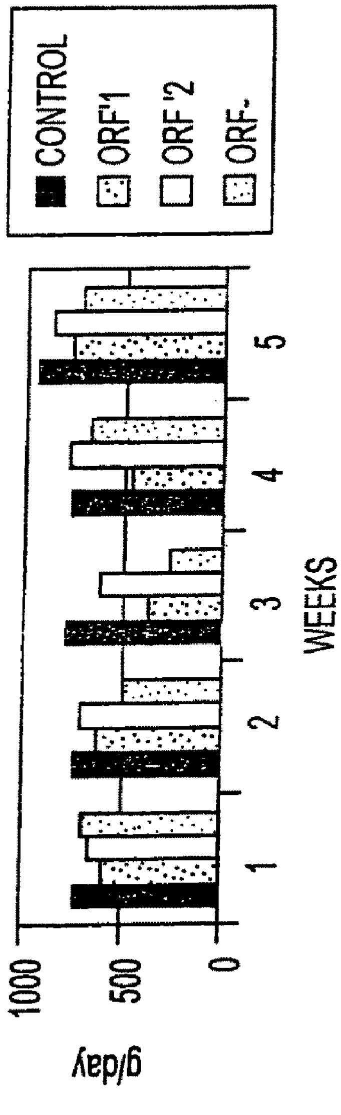

FIG. 15 Charts the results of experiments that demonstrate, in terms of animal growth, that vaccination with ORF'1 and ORF'2 of PCV-B enhances the level of protection in swine challeneged with PCV-B.

Figure 16:
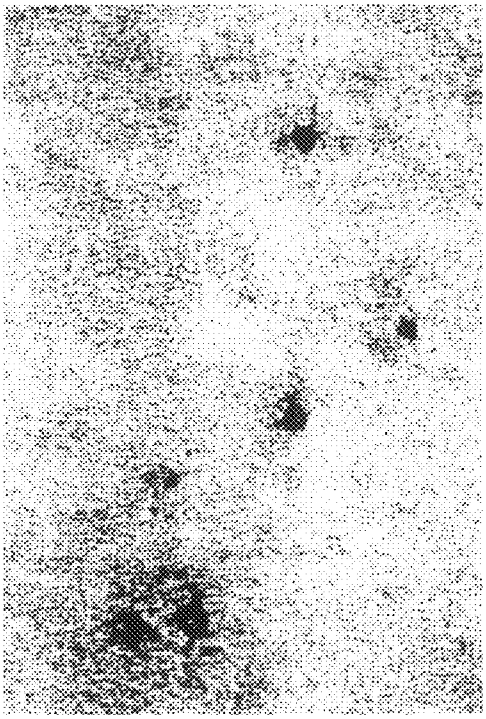

FIG. 16: Immunoperoxidase staining of PK15 cells at 24 h post-transfection with the pcDNA3/ORF'2 plasmid. Expression of PCVB ORF'2 was confirmed by IPMA following incubation in the presence of the swine anti-PCVB monospecific serum

DETAILED DESCRIPTION OF THE INVENTION

The present invention relates to nucleotide sequences of the genome of PWD circovirus selected from the sequences SEQ ID No. 1, SEQ ID No. 5, SEQ ID No. 15, SEQ ID No. 19 or one of their fragments.

The nucleotide sequences of sequences SEQ ID No. 1 and SEQ ID No. 5 correspond respectively to the genome sequence of the strand of (+) polarity and of the strand of (−) polarity of the PWD circovirus of type A (or PCVA), the sequence SEQ ID No. 5 being represented according to the orientation 5'→3'.

The nucleotide sequences of sequences SEQ ID No. 15 and SEQ ID No. 19 correspond respectively to the genome sequence of the strand of (+) polarity and of the strand of (−) polarity of the PWD circovirus of type B (or PCVB), the sequence SEQ ID No. 19 being represented according to the orientation 5'→3'.

The present invention likewise relates to nucleotide sequences, characterized in that they are selected from:

a) a nucleotide sequence of a specific fragment of the sequence SEQ ID No. 1, SEQ ID No. 5, SEQ ID No. 15, SEQ ID No. 19 or one of their fragments;

b) a nucleotide sequence homologous to a nucleotide sequence such as defined in a);

c) a nucleotide sequence complementary to a nucleotide sequence such as defined in a) or b), and a nucleotide sequence of their corresponding RNA;

d) a nucleotide sequence capable of hybridizing under stringent conditions with a sequence such as defined in a), b) or c);

e) a nucleotide sequence comprising a sequence such as defined in a), b), c) or d); and f) a nucleotide sequence modified by a nucleotide sequence such as defined in a), b), c), d) or e).

Nucleotide, polynucleotide or nucleic acid sequence will be understood according to the present invention as meaning both a double-stranded or single-stranded DNA in the monomeric and dimeric (so-called in tandem) forms and the transcription products of said DNAs.

It must be understood that the present invention does not relate to the genomic nucleotide sequences taken in their natural environment, that is to say in the natural state. It concerns sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the invention to be carried by vectors.

The nucleotide sequences SEQ ID No. 1 and SEQ ID No. 15 were obtained by sequencing of the genome by the Sanger method.

Nucleotide sequence fragment according to the invention will be understood as designating any nucleotide fragment of the PWD circovirus, type A or B, of length of at least 8 nucleotides, preferably at least 12 nucleotides, and even more preferentially at least 20 consecutive nucleotides of the sequence from which it originates.

Specific fragment of a nucleotide sequence according to the invention will be understood as designating any nucleotide fragment of the PWD circovirus, type A or B, having, after alignment and comparison with the corresponding fragments of known porcine circoviruses, at least one nucleotide or base of different nature. For example the specific nucleotide fragments of the PWD circovirus of type A can easily be determined by referring to FIG. 3 of the present invention in which the nucleotides or bases of the sequence SEQ ID No. 1 (circopordfp) are shown which are of different nature, after alignment of said sequence SEQ ID No. 1 with the other two sequences of known porcine circovirus (circopormeeh and circopormank).

Homologous nucleotide sequence in the sense of the present invention is understood as meaning a nucleotide sequence having at least a percentage identity with the bases of a nucleotide sequence according to the invention of at least 80%, preferably 90% or 95%, this percentage being purely statistical and it being possible to distribute the differences between the two nucleotide sequences at random and over the whole of their length.

Specific homologous nucleotide sequence in the sense of the present invention is understood as meaning a homologous nucleotide sequence having at least one nucleotide sequence of a specific fragment, such as defined above. Said "specific" homologous sequences can comprise, for example, the sequences corresponding to the genomic sequence or to the sequences of its fragments representative of variants of PWD circovirus of type A or B. These specific homologous sequences can thus correspond to variations linked to mutations within strains of PWD circovirus of type A and B, and especially correspond to truncations, substitutions, deletions and/or additions of at least one nucleotide. Said homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2: 482 (1981), by the homology alignment algorithm of Neddleman and Wunsch, *J. Mol. Biol.* 48: 443 (1970), by the search for similarity method of Pearson and Lipman, *Proc. Natl. Acad. Sci*. (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would use one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

In the BLAST N or BLAST P "BLAST 2 sequence", software which is available in the web site http://www.ncbi.nlm.nih.gov/gorf/bl2.html, and habitually used by the inventors and in general by the skilled man for comparing and determining the identity between two sequences, gap cost which depends on the sequence length to be compared is directly selected by the software (i.e. 11.2 for substitution matrix BLOSUM-62 for length>85).

In the present description, PWD circovirus will be understood as designating the circoviruses associated with piglet weight loss disease (PWD) of type A (PCVA) or type B (PCVB), defined below by their genomic sequence, as well as the circoviruses whose nucleic sequences are homologous to the sequences of PWD circoviruses of type A or B, such as in particular the circoviruses corresponding to variants of the type A or of the type B.

Complementary nucleotide sequence of a sequence of the invention is understood as meaning any DNA whose nucleotides are complementary to those of the sequence of the invention, and whose orientation is reversed (antiparallel sequence).

Hybridization under conditions of stringency with a nucleotide sequence according to the invention is understood as meaning a hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following:

2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by the person skilled in the art for oligonucleotides of greater or smaller size, according to the teaching of Sambrook et al., 1989.

Among the nucleotide sequences according to the invention, those are likewise preferred which can be used as a primer or probe in methods allowing the homologous sequences according to the invention to be obtained, these methods, such as the polymerase chain reaction (PCR), nucleic acid cloning and sequencing, being well known to the person skilled in the art.

Among said nucleotide sequences according to the invention, those are again preferred which can be used as a primer or probe in methods allowing the presence of PWD circovirus or one of its variants such as defined below to be diagnosed.

The nucleotide sequences according to the invention capable of modulating, of inhibiting or of inducing the expression of PWD circovirus gene, and/or capable of modulating the replication cycle of PWD circovirus in the host cell and/or organism are likewise preferred. Replication cycle will be understood as designating the invasion and the multiplication of PWD circovirus, and its propagation from host cell to host cell in the host organism.

Among said nucleotide sequences according to the invention, those corresponding to open reading frames, called ORF sequences, and coding for polypeptides, such as, for example, the sequences SEQ ID No. 9 (ORF1), SEQ ID No. 11 (ORF2) and SEQ ID No. 13 (ORF3) respectively corresponding to the nucleotide sequences between the positions 47 and 985 determined with respect to the position of the nucleotides on the sequence SEQ ID No. 1, the positions 1723 and 1022 and the positions 658 and 38 with respect to the position of the nucleotides on the sequence SEQ ID No. 5 (represented according to the orientation 3+-5'), the ends being included, or alternatively the sequences SEQ ID No. 23 (ORF'1), SEQ ID No. 25 (ORF'2) and SEQ ID No. 27 (ORF'3), respectively corresponding to the sequences between the positions 51 and 995 determined with respect to the position of the nucleotides on the sequence SEQ ID No. 15, the positions 1734 and 1033 and the positions 670 and 357, the positions being determined with respect to the position of the nucleotides on the sequence SEQ ID No. 19 (represented according to the orientation 3'→5'), the ends being included, are finally preferred.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Said representative fragments can likewise be obtained by chemical synthesis when their size is not very large and according to methods well known to persons skilled in the art.

Modified nucleotide sequence will be understood as meaning any nucleotide sequence obtained by mutagenesis according to techniques well known to the person skilled in the art, and containing modifications with respect to the normal sequences according to the invention, for example mutations in the regulatory and/or promoter sequences of polypeptide expression, especially leading to a modification of the rate of expression of said polypeptide or to a modulation of the replicative cycle.

Modified nucleotide sequence will likewise be understood as meaning any nucleotide sequence coding for a modified polypeptide such as defined below.

The present invention relates to nucleotide sequences of PWD circovirus according to the invention, characterized in that they are selected from the sequences SEQ ID No. 9, SEQ ID No. 11, SEQ ID No. 13, SEQ ID No. 23, SEQ ID No. 25, SEQ ID No. 27 or one of their fragments.

The invention likewise relates to nucleotide sequences characterized in that they comprise a nucleotide sequence selected from:

a) a nucleotide sequence SEQ ID No. 9, SEQ ID No. 11, SEQ ID No. 13, SEQ ID No. 23, SEQ ID No. 25, SEQ ID No. 27 or one of their fragments;

b) a nucleotide sequence of a specific fragment of a sequence such as defined in a), c) a homologous nucleotide sequence having at least 80% identity with a sequence such as defined in a) or b);

d) a complementary nucleotide sequence or sequence of RNA corresponding to a sequence such as defined in a), b) or c); and e) a nucleotide sequence modified by a sequence such as defined in a), b), c) or d).

As far as homology with the nucleotide sequences SEQ ID No. 9, SEQ ID No. 11, SEQ ID No. 13, SEQ ID No. 23, SEQ ID No. 25, SEQ ID No. 27 or one of their fragments is concerned, the homologous, especially specific, sequences having a percentage identity with one of the sequences SEQ ID No. 9, SEQ ID No. 11, SEQ ID No. 13, SEQ ID No. 23, SEQ ID No. 25, SEQ ID No. 27 or one of their fragments of at least 80%, preferably 90% or 95%, are preferred. Said specific homologous sequences can comprise, for example, the sequences corresponding to the sequences ORF1, ORF2, ORF3, ORF'1, ORF'2 and ORF'3 of PWD circovirus variants of type A or of type B. In the same manner, these specific homologous sequences can correspond to variations linked to mutations within strains of PWD circovirus of type A or of type B and especially correspond to truncations, substitutions, deletions and/or additions of at least one nucleotide.

Among nucleotide sequences according to the invention, the sequence SEQ ID No. 23 which has a homology having more than 80% identity with the sequence SEQ ID No. 9, as well as the sequence SEQ ID No. 25, are especially preferred.

Preferably, the invention relates to the nucleotide sequences according to the invention, characterized in that they comprise a nucleotide sequence selected from the following sequences:

a) SEQ ID No. 33 170 5'TGTGGCGA 3';

b) SEQ ID No. 34 450 5' AGTTTCCT 3';

c) SEQ ID No. 35 1026 5' TCATTTAGAGGGTCTTTCAG 3';

d) SEQ ID No. 36 1074 5' GTCAACCT 3';

e) SEQ ID No. 37 1101 5' GTGGTTGC 3';

f) SEQ ID No. 38 1123 5' AGCCCAGG 3';

g) SEQ ID No. 39 1192 5' TTGGCTGG 3';

h) SEQ ID No. 40 1218 5' TCTAGCTCTGGT 3';

i) SEQ ID No. 41 1501 5' ATCTCAGCTCGT 3';

j) SEQ ID No. 42 1536 5' TGTCCTCCTCTT 3';

k) SEQ ID No. 43 1563 5' TCTCTAGA 3';

l) SEQ ID No. 44 1623 5' TGTACCAA 3';

m) SEQ ID No. 45 1686 5' TCCGTCTT 3';

and their complementary sequences.

In the list of nucleotide sequences a)-m) above, the underlined nucleotides are mutated with respect to the two known sequences of circovirus which are nonpathogenic to pigs. The number preceding the nucleotide sequence represents the position of the first nucleotide of said sequence in the sequence SEQ ID No. 1.

The invention comprises the polypeptides encoded by a nucleotide sequence according to the invention, preferably a polypeptide whose sequence is represented by a fragment, especially a specific fragment, of one of the six sequences of amino acids represented in FIG. 2, these six amino acid sequences corresponding to the polypeptides which can be encoded according to one of the three possible reading frames of the sequence SEQ ID No. 1 or of the sequence SEQ ID No. 5, or a polypeptide whose sequence is represented by a fragment, especially a specific fragment, of one of the six sequences of amino acids shown in FIG. 8, these six sequences of amino acids corresponding to the polypeptides which can be encoded according to one of the three possible reading frames of the sequence SEQ ID No. 15 or of the sequence SEQ ID No. 19.

The invention likewise relates to the polypeptides, characterized in that they comprise a polypeptide selected from the amino acid sequences SEQ ID No. 10, SEQ ID No. 12, SEQ ID No. 14, SEQ ID No. 24, SEQ ID No. 26, SEQ ID No. 28 or one of their fragments.

Among the polypeptides according to the invention, the polypeptide of amino acid sequence SEQ ID No. 24 which has a homology having more than 80% identity with the sequence SEQ ID No. 10, as well as the polypeptide of sequence SEQ ID No. 26, are especially preferred.

The invention also relates to the polypeptides, characterized in that they comprise a polypeptide selected from:

a) a specific fragment of at least 5 amino acids of a polypeptide of an amino acid sequence according to the invention;

b) a polypeptide homologous to a polypeptide such as defined in a);

c) a specific biologically active fragment of a polypeptide such as defined in a) or b); and d) a polypeptide modified by a polypeptide such as defined in a), b) or c).

Among the polypeptides according to the invention, the polypeptides of amino acid sequences SEQ ID No. 29, SEQ ID No. 30, SEQ ID No. 31 and SEQ ID No. 32 are also preferred, these polypeptides being especially capable of specifically recognizing the antibodies produced during infection by the PWD circovirus of type B. These polypeptides thus have epitopes specific for the PWD circovirus of type B and can thus be used in particular in the diagnostic field or as immunogenic agent to confer protection in pigs against infection by PWD circovirus, especially of type B.

In the present description, the terms polypeptide, peptide and protein are interchangeable.

It must be understood that the invention does not relate to the polypeptides in natural form, that is to say that they are not taken in their natural environment but that they can be isolated or obtained by purification from natural sources, or else obtained by genetic recombination, or alternatively by chemical synthesis and that they can thus contain unnatural amino acids, as will be described below.

Polypeptide fragment according to the invention is understood as designating a polypeptide containing at least 5 consecutive amino acids, preferably 10 consecutive amino acids or 15 consecutive amino acids.

In the present invention, specific polypeptide fragment is understood as designating the consecutive polypeptide fragment encoded by a specific fragment nucleotide sequence according to the invention.

Homologous polypeptide will be understood as designating the polypeptides having, with respect to the natural polypeptide, certain modifications such as, in particular, a deletion, addition or substitution of at least one amino acid, a truncation, a prolongation, a chimeric fusion, and/or a mutation. Among the homologous polypeptides, those are preferred whose amino acid sequence has at least 80%, preferably 90%, homology with the sequences of amino acids of polypeptides according to the invention.

Specific homologous polypeptide will be understood as designating the homologous polypeptides such as defined above and having a specific fragment of polypeptide according to the invention.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following.

These equivalent amino acids can be determined either by depending on their structural homology with the amino acids which they substitute, or on results of comparative tests of biological activity between the different polypeptides, which are capable of being carried out.

By way of example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

The specific homologous polypeptides likewise correspond to polypeptides encoded by the specific homologous nucleotide sequences such as defined above and thus comprise in the present definition the polypeptides which are mutated or correspond to variants which can exist in PWD circovirus, and which especially correspond to truncations, substitutions, deletions and/or additions of at least one amino acid residue.

Specific biologically active fragment of a polypeptide according to the invention will be understood in particular as designating a specific polypeptide fragment, such as defined above, having at least one of the characteristics of polypeptides according to the invention, especially in that it is:

- capable of inducing an immunogenic reaction directed against a PWD circovirus; and/or
- capable of being recognized by a specific antibody of a polypeptide according to the invention; and/or
- capable of linking to a polypeptide or to a nucleotide sequence of PWD circovirus; and/or
- capable of exerting a physiological activity, even partial, such as, for example, a dissemination or structural (capsid) activity; and/or
- capable of modulating, of inducing or of inhibiting the expression of PWD circovirus gene or one of its variants, and/or capable of modulating the replication cycle of PWD circovirus in the cell and/or the host organism.

The polypeptide fragments according to the invention can correspond to isolated or purified fragments naturally present in a PWD circovirus or correspond to fragments which can be obtained by cleavage of said polypeptide by a proteolytic enzyme, such as trypsin or chymotrypsin or collagenase, or by a chemical reagent, such as cyanogen bromide (CNBr) or alternatively by placing said polypeptide in a very acidic environment, for example at pH 2.5. Such polypeptide fragments can likewise just as easily be prepared by chemical synthesis, from hosts transformed by an expression vector according to the invention containing a nucleic acid allowing the expression of said fragments, placed under the control of appropriate regulation and/or expression elements.

"Modified polypeptide" of a polypeptide according to the invention is understood as designating a polypeptide obtained by genetic recombination or by chemical synthesis as will be described below, having at least one modification with respect to the normal sequence. These modifications will especially be able to bear on amino acids at the origin of a specificity, of pathogenicity and/or of virulence, or at the origin of the structural conformation, and of the capacity of membrane insertion of the polypeptide according to the invention. It will thus be possible to create polypeptides of equivalent, increased or decreased activity, and of equivalent, narrower, or wider specificity. Among the modified polypeptides, it is necessary to mention the polypeptides in which up to 5 amino acids can be modified, truncated at the N- or C-terminal end, or even deleted or added.

As is indicated, the modifications of the polypeptide will especially have as objective:

to render it capable of modulating, of inhibiting or of inducing the expression of PWD circovirus gene and/or capable of modulating the replication cycle of PWD circovirus in the cell and/or the host organism, of allowing its incorporation into vaccine compositions, of modifying its bioavailability as a compound for therapeutic use.

The methods allowing said modulations on eukaryotic or prokaryotic cells to be demonstrated are well known to the person skilled in the art. It is likewise well understood that it will be possible to use the nucleotide sequences coding for said modified polypeptides for said modulations, for example through vectors according to the invention and described below, in order, for example, to prevent or to treat the pathologies linked to the infection.

The preceding modified polypeptides can be obtained by using combinatorial chemistry, in which it is possible to systematically vary parts of the polypeptide before testing them on models, cell cultures or microorganisms for example, to select the compounds which are most active or have the properties sought.

Chemical synthesis likewise has the advantage of being able to use:

unnatural amino acids, or nonpeptide bonds.

Thus, in order to improve the duration of life of the polypeptides according to the invention, it may be of interest to use unnatural amino acids, for example in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends compounds not recognized by the proteases.

The nucleotide sequences coding for a polypeptide according to the invention are likewise part of the invention.

The invention likewise relates to nucleotide sequences utilizable as a primer or probe, characterized in that said sequences are selected from the nucleotide sequences according to the invention.

Among the pairs of nucleotide sequences utilizable as a pair of primers according to the invention, the pairs of primers selected from the following pairs are Preferred:

```
a)    SEQ ID No. 46 5' GTG TGC TCG ACA TTG GTG TG 3',
and

      SEQ ID No. 47 5' TGG AAT GTT AAG GAG GTG AG 3';

b)    SEQ ID No. 46 5' GTG TGC TCG ACA TTG GTG TG 3',
and

      SEQ ID No. 48 5' GTG GGA GGC ATC TTG GAA TG 3';
```

-continued

```
c)    SEQ ID No. 49 5' CGC GCG TAA TAC GAC TCA CT 3',
and

      SEQ ID No. 46 5' GTG TGC TGG ACA TTG GTG TG 3';

d)    SEQ ID No. 49 5' CGC GGG TAA TAG GAG TGA CT 3',
and

      SEQ ID No. 48 5' CTC GCA GGG ATC TTG GAA TG 3';
and

e)    SEQ ID No. 50 5' CCT GTC TAG TGG TGT GAG TAG
                   CTT GT 3',
and

      SEQ ID No. 51 5' GCA GTA GAG AGG TGA GTG GGT
                   TGT CC 3'.
```

The cloning and the sequencing of the PWD circovirus, type A and B, has allowed it to be identified, after comparative analysis with the nucleotide sequences of other porcine circoviruses, that, among the sequences of fragments of these nucleic acids, were those which are strictly specific to the PWD circovirus of type A, of type B or of type A and B, and those which correspond to a consensus sequence of porcine circoviruses other than the PWD circoviruses of type A and/or B.

There is likewise a great need for nucleotide sequences utilizable as a primer or probe specific to the whole of the other known and nonpathogenic porcine circoviruses.

Said consensus nucleotide sequences specific to all circoviruses, other than PWD circovirus of type A and B, are easily identifiable from FIG. 3 and the sequence SEQ ID No. 15, and are part of the invention.

Among said consensus nucleotide sequences, that which is characterized in that it is part of the following pair of primers is preferred:

```
a) SEQ ID No. 46 5' GTG TGC TCG ACA TTG GTG TG 3',
and

   SEQ ID No. 52 5' TGG AAT GTT AAC TAC CTC AA 3'.
```

The invention likewise comprises a nucleotide sequence according to the invention, characterized in that said sequence is a specific consensus sequence of porcine circovirus other than PWD circovirus of type B and in that it is one of the primers of the following pairs of primers:

```
a)    SEQ ID No. 53   5' GGC GGC GCC ATC TGT AAC GGT
                      TT 3',
and

      SEQ ID No. 54   5' GAT GGC GCC GAA AGA CGG GTA
                      TC 3'.
```

It is well understood that the present invention likewise relates to specific polypeptides of known porcine circoviruses other than PWD circovirus, encoded by said consensus nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against said specific polypeptides encoded by said consensus nucleotide sequences are also part of the invention.

It will be possible to use said consensus nucleotide sequences, said corresponding polypeptides as well as said antibodies directed against said polypeptides in procedures or sets for detection and/or identification such as described below, in place of or in addition to nucleotide sequences, polypeptides or antibodies according to the invention, specific to PWD circovirus type A and/or B.

These protocols have been improved for the differential detection of the circular monomeric forms of specific replicative forms of the virion or of the DNA in replication and the dimeric forms found in so-called in-tandem molecular constructs.

The invention additionally relates to the use of a nucleotide sequence according to the invention as a primer or probe for the detection and/or the amplification of nucleic acid sequences.

The nucleotide sequences according to the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially at least 20 nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as:

- the TAS technique (Transcription-based Amplification System), described by Kwoh et al. in 1989;
- the 3SR technique (Self-Sustained Sequence Replication), described by Guatelli et al. in 1990;
- the NASBA technique (Nucleic Acid Sequence Based Amplification), described by Kievitis et al. in 1991;
- the SDA technique (Strand Displacement Amplification) (Walker et al., 1992);
- the TMA technique (Transcription Mediated Amplification).

The polynucleotides of the invention can also be employed in techniques of amplification or of modification of the nucleic acid serving as a probe, such as:

- the LCR technique (Ligase Chain Reaction), described by Landegren et al. in 1988 and improved by Barany et al. in 1991, which employs a thermostable ligase;
- the RCR technique (Repair Chain Reaction), described by Segev in 1992;
- the CPR technique (Cycling Probe Reaction), described by Duck et al. in 1990;
- the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

The invention also comprises the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive element ($^{32}$p, $^{35}$S, $^{3}$H, $^{125}$I) or with a nonradioactive molecule (biotin, acetylaminofluorene, digoxigenin, 5-bromodeoxyuridine, fluorescein) to obtain probes which are utilizable for numerous applications.

Examples of nonradioactive labeling of nucleotide sequences are described, for example, in French Patent No. 78.10975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called detection probe, labeled with an easily detectable element.

Another subject of the present invention is a vector for the cloning and/or expression of a sequence, characterized in that it contains a nucleotide sequence according to the invention.

The vectors according to the invention, characterized in that they contain the elements allowing the expression and/or the secretion of said nucleotide sequences in a determined host cell, are likewise part of the invention.

The vector must then contain a promoter, signals of initiation and termination of translation, as well as appropriate regions of regulation of transcription. It must be able to be maintained stably in the host cell and can optionally have particular signals specifying the secretion of the translated protein. These different elements are chosen as a function of the host cell used. To this end, the nucleotide sequences according to the invention can be inserted into autonomous replication vectors within the chosen host, or integrated vectors of the chosen host.

Such vectors will be prepared according to the methods currently used by the person skilled in the art, and it will be possible to introduce the clones resulting therefrom into an appropriate host by standard methods, such as, for example, lipofection, electroporation and thermal shock.

The vectors according to the invention are, for example, vectors of plasmid or viral origin.

A preferred vector for the expression of polypeptides of the invention is baculovirus.

The vector pBS KS in which is inserted the in-tandem DNA sequence of the PWD circovirus type A (or DFP) as deposited at the CNCM on 3 Jul. 1997, under the number I-1891, is likewise preferred.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of said cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as animal cells, in particular the cultures of mammalian cells (Edwards and Aruffo, 1993), and especially Chinese hamster ovary (CHO) cells, but likewise the cells of insects in which it is possible to use procedures employing baculoviruses, for example (Luckow, 1993).

The use of baculovirus vectors to express a wide variety of proteins in insect cells has increased dramatically in recent years. Compilations of many of the genes expressed in baculovirus-infected insect cells, along with extensive discussions of the biological properties of the recombinant proteins, can be found in several recent reviews [1. LUCKOW V A: Cloning and Expression of Heterologous Genes in Insect Cells with Baculovirus Vectors. In *Recombinant DNA Technology and Applications*. Edited by Prokop A, Bajpai R K, Ho C New York. McGraw-Hill; 1991:97-152; 2. O'REILLY D R, MILLER L K, LUCKOW V A: *Baculovirus Expression Vectors.: A Laboratory Manual*. New York: WH Freeman and Company; 1992: 1-347, This laboratory manual provides a comprehensive overview of baculovirus biology and genetics with particular emphasis on topics pertaining to the construction and use of baculovirus expression vectors. Maps of many widely used baculovirus transfer vectors and descriptions of the available parent viruses are included. Detailed methods for virus propagation in cultured cell lines and insect larvae are described. Practical suggestions for the production of cultured insect cells m large-scale bioreactors are also described; 4. LUCKOW V A: Protein Production and Processing from Baculovirus Expression Vectors. In *Insect Cell Cultures: Production of Improved Biopesticides and Proteins from Recombinant DNA*. Edited by Shuler M L, Wood H A, Granados R R, Hammer D A. New York: John Wiley & Sons; 1993: in press. A comprehensive review of recently described baculovirus transfer vectors and parent viruses. Includes an extensive discussion of post-translational processing of proteins expressed in baculovirusinfected insect cells. 5. LUCKOW V A, SUMMERS M D: Trends in the Development of Baculovirus Expression Vectors. *Biotechnology* 1988, 6:47-55. 6. MILLER L K: Baculoviruses as Gene Expression Vectors. *Annu Rev Microbiol* 1988, 42:177-199. 7. MAEDA S Expression of Foreign Genes in Insects using Baculovirus Vectors. *Annu Rev Entomol* 1989, 34:351-372. ]Baculovirus-infected insect cells perform many of the post-translational chemical modifications of higher eukaryotes including glycosylation, fatty acid acylation myristoylation, palmitylation, and isoprenylation), amino-terminal acetylation, carboxy-terminal a-amidation, and phosphorylation. In most cases, the recombinant proteins are targeted to their appropriate natural location within the cell, to the nucleus or to the cytoplasm. Those proteins containing signal peptides are recognized and properly cleaved within the endoplasmic reticulum before insertion into cellular membranes or secretion from the cell. Hetero- and homo-oligomeric assembly have been demonstrated for a wide variety of proteins in baciilovirus-infected cells, including structural and non-structural proteins from more than 20 families of viruses [2. O'Reilly, supra; 4. Luckow, 1993, supra; 40 SRIDHAR P, PANDA A K, PAL R, TALWAR G P, HASNAIN S E: Temporal Nature of the Promoter and Not Relative Strength Determines the expression of an Extensively Processed Protein in a Baculovirus System. *FEBS Lett* 1993, 315:282-286.]

A preferred host cell for the expression of the proteins of the invention is constituted by sf9 insect cells.

A more preferred host cell according to the invention is *E. coli*, such as deposited at the CNCM on 3 Jul. 1997, under the number I-1891.

The invention likewise relates to animals comprising one of said transformed cells according to the invention.

The obtainment of transgenic animals according to the invention overexpressing one or more of the genes of PWD circovirus or part of the genes will be preferably carried out in rats, mice or rabbits according to methods well known to the person skilled in the art, such as by viral or nonviral transfections. It will be possible to obtain the transgenic animals overexpressing one or more of said genes by transfection of multiple copies of said genes under the control of a strong promoter of ubiquitous nature, or selective for one type of tissue. It will likewise be possible to obtain the transgenic animals by homologous recombination in embryonic cell strains, transfer of these cell strains to embryos, selection of the affected chimeras at the level of the reproductive lines and growth of said chimeras.

The transformed cells as well as the transgenic animals according to the invention are utilizable in procedures for preparation of recombinant polypeptides.

It is today possible to produce recombinant polypeptides in relatively large quantity by genetic engineering using the cells transformed by expression vectors according to the invention or using transgenic animals according to the invention.

The procedures for preparation of a polypeptide of the invention in recombinant form, characterized in that they employ a vector and/or a cell transformed by a vector according to the invention and/or a transgenic animal comprising one of said transformed cells according to the invention, are themselves comprised in the present invention.

Among said procedures for preparation of a polypeptide of the invention in recombinant form, the preparation procedures employing a vector, and/or a cell transformed by said vector and/or a transgenic animal comprising one of said transformed cells, containing a nucleotide sequence according to the invention coding for a polypeptide of PWD circovirus, are preferred.

The recombinant polypeptides obtained as indicated above can just as well be present in glycosylated form as in nonglycosylated form and can or cannot have the natural tertiary structure.

A preferred variant consists in producing a recombinant polypeptide used to a "carrier" protein (chimeric protein). The advantage of this system is that it allows a stabilization of and a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps:

a) culture of transformed cells under conditions allowing the expression of a recombinant polypeptide of nucleotide sequence according to the invention;

b) if need be, recovery of said recombinant polypeptide.

When the procedure for preparation of a polypeptide of the invention employs a transgenic animal according to the invention, the recombinant polypeptide is then extracted from said animal.

The invention also relates to a polypeptide which is capable of being obtained by a procedure of the invention such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques which are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

According to another preferred technique of the invention, recourse will be made to the technique described by Merrifield.

To make a peptide chain according to the Merrifield procedure, recourse is made to a very porous polymoeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated form used with a view to obtaining immunogenic compositions capable of inducing the synthesis of antibodies directed against multiple epitopes. Said polypeptides or their glycosylated fragments are likewise part of the invention.

These hybrid molecules can be formed, in part, of a polypeptide carrier molecule or of fragments thereof according to the invention, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

Said hybrid nucleotide sequences coding for a hybrid polypeptide as well as the hybrid polypeptides according to the invention characterized in that they are recombinant polypeptides obtained by the expression of said hybrid nucleotide sequences are likewise part of the invention.

The invention likewise comprises the vectors characterized in that they contain one of said hybrid nucleotide sequences. The host cells transformed by said vectors, the transgenic animals comprising one of said transformed cells as well as the procedures for preparation of recombinant polypeptides using said vectors, said transformed cells and/or said transgenic animals are, of course, likewise part of the invention.

The polypeptides according to the invention, the antibodies according to the invention described below and the nucleotide sequences according to the invention can advantageously be employed in procedures for the detection and/or identification of PWD circovirus, or of porcine circovirus other than a PWD circovirus, in a biological sample (biological tissue or fluid) capable of containing them. These procedures, according to the specificity of the polypeptides, the antibodies and the nucleotide sequences according to the invention which will be used, will in particular be able to detect and/or to identify a PWD circovirus or a porcine circovirus other than a PWD circovirus or other than the PWD circovirus of type B.

The polypeptides according to the invention can advantageously be employed in a procedure for the detection and/or the identification of PWD circovirus of type A, of type B, of type A or B, or porcine circovirus other than the PWD circovirus of type B, or of porcine circovirus other than the PWD circovirus of type A or B, in a biological sample (biological tissue or fluid) capable of containing them, characterized in that it comprises the following steps:

a) contacting of this biological sample with a polypeptide or one of its fragments according to the invention (under conditions allowing an immunological reaction between said polypeptide and the antibodies possibly present in the biological sample);

b) demonstration of the antigen-antibody complexes possibly formed.

In the present description, PWD circovirus, except if a particular mention is indicated, will be understood as designating a PWD circovirus of type A or of type B, and porcine circovirus other than PWD, except if a particular mention is indicated, will be understood as designating a porcine circovirus other than a PWD circovirus of type A and B.

Preferably, the biological sample is formed by a fluid, for example a pig serum, whole blood or biopsies.

Any conventional procedure can be employed for carrying out such a detection of the antigen-antibody complexes possibly formed.

By way of example, a preferred method brings into play immunoenzymatic processes according to the ELISA technique, by immunofluorescence, or radioimmunological processes (RIA) or their equivalent.

Thus, the invention likewise relates to the polypeptides according to the invention, labeled with the aid of an adequate label such as of the enzymatic, fluorescent or radioactive type.

Such methods comprise, for example, the following steps:

deposition of determined quantities of a polypeptide composition according to the invention in the wells of a microtiter plate, introduction into said wells of increasing dilutions of serum, or of a biological sample other than that defined previously, having to be analyzed, incubation of the microplate, introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example at 550 nm, detection, by comparison with a control test, of the quantity of hydrolyzed substrate.

The invention likewise relates to a kit or set for the detection and/or identification of PWD circovirus, of porcine circovirus other than a PWD circovirus or of porcine circovirus other than the PWD circovirus of type B, characterized in that it comprises the following elements:

a polypeptide according to the invention, if need be, the reagents for the formation of the medium favorable to the immunological or specific reaction, if need be, the reagents allowing the detection of the antigen-antibody complexes produced by the immunological reaction between the polypeptide(s) of the invention and the antibodies possibly present in the biological sample, these reagents likewise being able to carry a label, or to be recognized in their turn by a labeled reagent, more particularly in the case where the polypeptide according to the invention is not labeled, if need be, a biological reference sample (negative control) devoid of antibodies recognized by a polypeptide according to the invention, if need be, a biological reference sample (positive control) containing a predetermined quantity of antibodies recognized by a polypeptide according to the invention.

The polypeptides according to the invention allow monoclonal or polyclonal antibodies to be prepared which are characterized in that they specifically recognize the polypeptides according to the invention. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide which has served as an antigen has previously been immobilized. The polyclonal antibodies according to the invention can also be prepared by purification, on an affinity column on which a polypeptide according to the invention has previously been immobilized, of the antibodies contained in the serum of pigs infected by a PWD circovirus.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of PWD circovirus, of porcine circovirus other than a PWD circovirus, or other than the PWD circovirus of type B, in a biological sample, characterized in that it comprises the following steps:

a) contacting of the biological sample (biological tissue or fluid) with a mono- or polyclonal antibody according to the invention (under conditions allowing an immunological reaction between said antibodies and the polypeptides of PWD circovirus, of porcine circovirus other than a PWD circovirus, of porcine circovirus other than the PWD circovirus of type B, possibly present in the biological sample);

b) demonstration of the antigen-antibody complex possibly formed.

Likewise within the scope of the invention is a kit or set for the detection and/or the identification of PWD circovirus, of porcine circovirus other than a PWD circovirus or of porcine circovirus other than the PWD circovirus of type B, characterized in that it comprises the following components:

a polyclonal or monoclonal antibody according to the invention, if need be labeled;

if need be, a reagent for the formation of the medium favorable to the carrying out of the immunological reaction;

if need be, a reagent allowing the detection of the antigen-antibody complexes produced by the immunological reaction, this reagent likewise being able to carry a label, or being capable of being recognized in its turn by a labeled reagent, more particularly in the case where said monoclonal or polyclonal antibody is not labeled;

if need be, reagents for carrying out the lysis of cells of the sample tested.

The present invention likewise relates to a procedure for the detection and/or the identification of PWD, of porcine circovirus other than a PWD circovirus or of porcine circovirus other than the PWD circovirus of type B, in a biological sample, characterized in that it employs a nucleotide sequence according to the invention.

More particularly, the invention relates to a procedure for the detection and/or the identification of PWD circovirus, of porcine circovirus other than a PWD circovirus or of porcine circovirus other than the PWD circovirus of type B, in a biological sample, characterized in that it contains the following steps:

a) if need be, isolation of the DNA from the biological sample to be analyzed;

b) specific amplification of the DNA of the sample with the aid of at least one primer, or a pair of primers, according to the invention;

c) demonstration of the amplification products.

These can be detected, for example, by the technique of molecular hybridization utilizing a nucleic probe according to the invention. This probe will advantageously be labeled with a nonradioactive (cold probe) or radioactive element.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in said biological sample.

Another aim of the present invention consists in a procedure according to the invention, characterized in that it comprises the following steps:

a) contacting of a nucleotide probe according to the invention with a biological sample, the DNA contained in the biological sample having, if need be, previously been made accessible to hybridization under conditions allowing the hybridization of the probe with the DNA of the sample;

b) demonstration of the hybrid formed between the nucleotide probe and the DNA of the biological sample.

The present invention also relates to a procedure according to the invention, characterized in that it comprises the following steps:

a) contacting of a nucleotide probe immobilized on a support according to the invention with a biological sample, the DNA of the sample having, if need be, previously been made accessible to hybridization, under conditions allowing the hybridization of the probe with the DNA of the sample;

b) contacting of the hybrid formed between the nucleotide probe immobilized on a support and the DNA contained in the biological sample, if need be after elimination of the DNA of the biological sample which has not hybridized with the probe, with a nucleotide probe labeled according to the invention;

c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the invention.

The invention is additionally directed at a kit or set for the detection and/or the identification of PWD circovirus, of porcine circovirus other than the PWD circovirus or of porcine circovirus other than the PWD circovirus of type B, characterized in that it comprises the following elements:

a) a nucleotide probe according to the invention;

b) if need be, the reagents necessary for the carrying out of a hybridization reaction;

c) if need be, at least one primer according to the invention as well as the reagents necessary for an amplification reaction of the DNA.

The invention likewise relates to a kit or set for the detection and/or the identification of PWD circovirus, of porcine circovirus other than a PWD circovirus or of porcine circovirus other than the PWD circovirus of type B, characterized in that it comprises the following components:

a) a nucleotide probe, called a capture probe, according to the invention;

b) an oligonucleotide probe, called a revealing probe, according to the invention, c) if need be, at least one primer according to the invention, as well as the reagents necessary for an amplification reaction of the DNA.

The invention also relates to a kit or set for the detection and/or identification of PWD circovirus, of porcine circovirus other than a PWD circovirus or of porcine circovirus other than the PWD circovirus of type B, characterized in that it comprises the following elements:

a) at least one primer according to the invention;

b) if need be, the reagents necessary for carrying out a DNA amplification reaction;

c) if need be, a component allowing the sequence of the amplified fragment to be verified, more particularly an oligonucleotide probe according to the invention.

The invention additionally relates to the use of a nucleotide sequence according to the invention, of a polypeptide according to the invention, of an antibody according to the invention, of a cell according to the invention, and/or of an animal transformed according to the invention, for the selection of an organic or inorganic compound capable of modulating, inducing or inhibiting the expression of genes, and/or of modifying the cellular replication of PWD circovirus or capable of inducing or of inhibiting the pathologies linked to an infection by a PWD circovirus.

The invention likewise comprises a method of selection of compounds capable of binding to a polypeptide or one of its fragments according to the invention, capable of binding to a nucleotide sequence according to the invention, or capable of recognizing an antibody according to the invention, and/or capable of modulating, inducing or inhibiting the expression of genes, and/or of modifying the cellular replication of PWD circovirus or capable of inducing or inhibiting the pathologies linked to an infection by a PWD circovirus, characterized in that it comprises the following steps:

a) contacting of said compound with said polypeptide, said nucleotide sequence, or with a cell transformed according to the invention and/or administration of said compound to an animal transformed according to the invention;

b) determination of the capacity of said compound to bind to said polypeptide or said nucleotide sequence, or to modulate, induce or inhibit the expression of genes, or to modulate the growth or the replication of PWD circovirus, or to induce or inhibit in said transformed animal the pathologies linked to an infection by PWD circovirus (designated activity of said compound).

The compounds capable of being selected can be organic compounds such as polypeptides or carbohydrates or any other organic or inorganic compounds already known, or novel organic compounds elaborated by molecular modelling techniques and obtained by chemical or biochemical synthesis, these techniques being known to the person skilled in the art.

It will be possible to use said selected compounds to modulate the cellular replication of PWD circovirus and thus to control infection by this virus, the methods allowing said modulations to be determined being well known to the person skilled in the art.

This modulation can be carried out, for example, by an agent capable of binding to a protein and thus of inhibiting or of potentiating its biological activity, or capable of binding to an envelope protein of the external surface of said virus and of blocking the penetration of said virus into the host cell or of favoring the action of the immune system of the infected organism directed against said virus. This modulation can likewise be carried out by an agent capable of binding to a nucleotide sequence of a DNA of said virus and of blocking, for example, the expression of a polypeptide whose biological or structural activity is necessary for the replication or for the proliferation of said virus host cells to host cells in the host animal.

The invention relates to the compounds capable of being selected by a selection method according to the invention.

The invention likewise relates to a pharmaceutical composition comprising a compound selected from the following compounds:

a) a nucleotide sequence according to the invention;

b) a polypeptide according to the invention;

c) a vector, a viral particle or a cell transformed according to the invention;

d) an antibody according to the invention;

e) a compound capable of being selected by a selection method according to the invention;

possibly in combination with a pharmaceutically acceptable vehicle and, if need be, with one or more adjuvants of the appropriate immunity.

The invention also relates to an immunogenic and/or vaccine composition, characterized in that it comprises a compound selected from the following compounds:

a) a nucleotide sequence according to the invention;

b) a polypeptide according to the invention;

c) a vector or a viral particle according to the invention; and d) a cell according to the invention.

In one embodiment, the vaccine composition according to the invention is characterized in that it comprises a mixture of at least two of said compounds a), b), c) and d) above and in that one of the two said compounds is related to the PWD circovirus of type A and the other is related to the PWD circovirus of type B.

In another embodiment of the invention, the vaccine composition is characterized in that it comprises at least one compound a), b), c), or d) above which is related to PWD circovirus of type B. In still another embodiment, the vaccine composition is characterized in that it comprises at least one compound a), b), c), or d) above which is related to PWD circovirus of type B ORF'2.

A compound related to the PWD circovirus of type A or of type B is understood here as respectively designating a compound obtained from the genomic sequence of the PWD circovirus of type A or of type B.

The invention is additionally aimed at an immunogenic and/or vaccine composition, characterized in that it comprises at least one of the following compounds:

a nucleotide sequence SEQ ID No. 23, SEQ ID No. 25, or one of their fragments or homologues;

a polypeptide of sequence SEQ ID No. 24, SEQ ID No. 26, or one of their fragments, or a modification thereof;

a vector or a viral particle comprising a nucleotide sequence SEQ ID No. 23, SEQ ID No. 25, or one of their fragments or homologues;

a transformed cell capable of expressing a polypeptide of sequence SEQ ID No. 24, SEQ ID No. 26, or one of their fragments, or a modification thereof; or a mixture of at least two of said compounds.

The invention also comprises an immunogenic and/or vaccine composition according to the invention, characterized in that it comprises said mixture of at least two of said compounds as a combination product for simultaneous, separate or protracted use for the prevention or the treatment of infection by a PWD circovirus, especially of type B.

In a preferred embodiment, the vaccine composition according to the invention comprises the mixture of the following compounds:

a pcDNA3 plasmid containing a nucleic acid of sequence SEQ ID No. 23;

a pcDNA3 plasmid containing a nucleic acid of sequence SEQ ID No. 25;

a pcDNA3 plasmid containing a nucleic acid coding for the GM-CSF protein;

a recombinant baculovirus containing a nucleic acid of sequence SEQ ID No. 23;

a recombinant baculovirus containing a nucleic acid of sequence SEQ ID No. 25; and if need be, an adjuvant of the appropriate immunity, especially the adjuvant AIF™.

The invention is likewise directed at a pharmaceutical composition according to the invention, for the prevention or the treatment of an infection by a PWD circovirus.

The invention is also directed at a pharmaceutical composition according to the invention for the prevention or the treatment of an infection by the PWD circovirus of type B.

The invention likewise concerns the use of a composition according to the invention, for the preparation of a medicament intended for the prevention or the treatment of infection by a PWD circovirus, preferably by the PWD circovirus of type B.

Under another aspect, the invention relates to a vector, a viral particle or a cell according to the invention, for the treatment and/or the prevention of a disease by gene therapy.

Finally, the invention comprises the use of a vector, of a viral particle or of a cell according to the invention for the preparation of a medicament intended for the treatment and/or the prevention of a disease by gene therapy.

The polypeptides of the invention entering into the immunogenic or vaccine compositions according to the invention can be selected by techniques known to the person skilled in the art such as, for example, depending on the capacity of said polypeptides to stimulate the T cells, which is translated, for example, by their proliferation or the secretion of interleukins, and which leads to the production of antibodies directed against said polypeptides.

In pigs, as in mice, in which a weight dose of the vaccine composition comparable to the dose used in man is administered, the antibody reaction is tested by taking of the serum followed by a study of the formation of a complex between the antibodies present in the serum and the antigen of the vaccine composition, according to the usual techniques.

The pharmaceutical compositions according to the invention will contain an effective quantity of the compounds of the invention, that is to say in sufficient quantity of said compound(s) allowing the desired effect to be obtained, such as, for example, the modulation of the cellular replication of PWD circovirus. The person skilled in the art will know how to determine this quantity, as a function, for example, of the age and of the weight of the individual to be treated, of the state of advancement of the pathology, of the possible secondary effects and by means of a test of evaluation of the effects obtained on a population range, these tests being known in these fields of application.

According to the invention, said vaccine combinations will preferably be combined with a pharmaceutically acceptable vehicle and, if need be, with one or more adjuvants of the appropriate immunity.

Today, various types of vaccines are available for protecting animals or man against infectious diseases: attenuated living microorganisms (*M. bovis*—BCG for tuberculosis), inactivated microorganisms (influenza virus), acellular extracts (*Bordetella pertussis* for whooping cough), recombined proteins (surface antigen of the hepatitis B virus), polysaccharides (pneumococcal). Vaccines prepared from synthetic peptides or genetically modified microorganisms expressing heterologous antigens are in the course of experimentation. More recently still, recombined plasmid DNAs carrying genes coding for protective antigens have been proposed as an alternative vaccine strategy. This type of vaccination is carried out with a particular plasmid originating from a plasmid of *E. coli* which does not replicate in vivo and which codes uniquely for the vaccinating protein. Animals have been immunized by simply injecting the naked plasmid DNA into the muscle. This technique leads to the pressin of the vaccine protein in situ and to an immune response of cellular type (CTL) and of humoral type (antibody). This double induction of the immune response is one of the principal advantages of the vaccination technique with naked DNA.

The vaccine compositions comprising nucleotide sequences or vectors into which are inserted said sequences are especially described in the international application No. WO 90/11092 and likewise in the international application No. WO 95/11307.

The constitutive nucleotide sequence of the vaccine composition according to the invention can be injected into the host after having been coupled to compounds which favor the penetration of this polynucleotide into the interior of the cell or its transport to the cell nucleus. The resultant conjugates can be encapsulated in polymeric microparticles, as described in the international application No. WO 94/27238 (Medisorb Technologies International).

According to another embodiment of the vaccine composition according to the invention, the nucleotide sequence, preferably a DNA, is complexed with DEAE-dextran (Pagano et al., 1967) or with nuclear proteins (Kaneda et al., 1989), with lipids (Felgner et al., 1987) or encapsulated in liposomes (Fraley et al., 1980) or else introduced in the form of a gel facilitating its transfection into the cells (Midoux et al., 1993, Pastore et al., 1994). The polynucleotide or the vector according to the invention can also be in suspension in a buffer solution or be combined with liposomes.

Advantageously, such a vaccine will be prepared according to the technique described by Tacson et al. or Huygen et al. in 1996 or alternatively according to the technique described by Davis et al. in the international application No. WO 95/11307.

Such a vaccine can likewise be prepared in the form of a composition containing a vector according to the invention, placed under the control of regulation elements allowing its expression in man or animal. It will be possible, for example, to use, by way of in vivo expression vector of the polypeptide antigen of interest, the plasmid pcDNA3 or the plasmid pcDNA1/neo, both marketed by Invitrogen (R&D Systems, Abingdon, United Kingdom). It is also possible to use the plasmid V1Jns.tPA, described by Shiver et al. in 1995. Such a vaccine will advantageously comprise, apart from the recombinant vector, a saline solution, for example a sodium chloride solution.

Pharmaceutically acceptable vehicle is understood as designating a compound or a combination of compounds entering into a pharmaceutical composition or vaccine which does not provoke secondary reactions and which allows, for example, the facilitation of the administration of the active compound, an increase in its duration of life and/or its efficacy in the body, an increase in its solubility in solution or alternatively an improvement in its conservation. These pharmaceutically acceptable vehicles are well known and will be adapted by the person skilled in the art as a function of the nature and of the mode of administration of the chosen active compound.

As far as the vaccine formulations are concerned, these can comprise adjuvants of the appropriate immunity which are known to the person skilled in the art, such as, for example, aluminum hydroxide, a representative of the family of muramyl peptides such as one of the peptide derivatives of N-acetyl muramyl, a bacterial lysate, or alternatively Freund's incomplete adjuvant.

These compounds can be administered by the systemic route, in particular by the intravenous route, by the intramuscular, intradermal or subcutaneous route, or by the oral route. In a more preferred manner, the vaccine composition comprising polypeptides according to the invention will be administered by the intramuscular route, through the food or by nebulization several times, staggered over time.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present invention is administered in an amount that is protective against piglet weight loss disease.

For example, in the case of a vaccine according to the present invention comprising a polypeptide encoded by a nucleotide sequence of the genome of PCV, or a homolgue or fragment thereof, the polypeptide will be administered one time or several times, spread out over time, directly or by means of a transformed cell capable of expressing the polypeptide, in an amount of about 0.1 to 10 μg per kilogram weight of the animal, prefereably about 0.2 to about 5 μg/kg, more preferably about 0.5 to about 2 μg/kg for a dose.

The present invention likewise relates to the use of nucleotide sequences of PWD circovirus according to the invention for the construction of autoreplicative retroviral vectors and the therapeutic applications of these, especially in the field of human gene therapy in vivo.

The feasibility of gene therapy applied to man no longer needs to be demonstrated and this relates to numerous therapeutic applications like genetic diseases, infectious diseases and cancers. Numerous documents of the prior art describe the means of employing gene therapy, especially through viral vectors. Generally speaking, the vectors are obtained by deletion of at least some of the viral genes which are replaced by the genes of therapeutic interest. Such vectors can be propagated in a complementation line which supplies in trans the deleted viral functions in order to generate a defective viral vector particle for replication but capable of infecting a host cell. To date, the retroviral vectors are amongst the most widely used and their mode of infection is widely described in the literature accessible to the person skilled in the art.

The principle of gene therapy is to deliver a functional gene, called a gene of interest, of which the RNA or the corresponding protein will produce the desired biochemical effect in the targeted cells or tissues. On the one hand, the insertion of genes allows the prolonged expression of complex and unstable molecules such as RNAs or proteins which can be extremely difficult or even impossible to obtain or to administer directly. On the other hand, the controlled insertion of the desired gene into the interior of targeted specific cells allows the expression product to be regulated in defined tissues. For this, it is necessary to be able to insert the desired therapeutic gene into the interior of chosen cells and thus to have available a method of insertion capable of specifically targeting the cells or the tissues chosen.

Among the methods of insertion of genes, such as, for example, microinjection, especially the injection of naked plasmid DNA (Derse, D. et al., 1995, and Zhao, T. M. et al., 1996), electroporation, homologous recombination, the use of viral particles, such as retroviruses, is widespread. However, applied in vivo, the gene transfer systems of recombinant retroviral type at the same time have a weak infectious power (insufficient concentration of viral particles) and a lack of specificity with regard to chosen target cells.

The production of cell-specific viral vectors, having a tissue-specific tropism, and whose gene of interest can be translated adequately by the target cells, is realizable, for example, by fusing a specific ligand of the target host cells to the N-terminal part of a surface protein of the envelope of PWD circovirus. It is possible to mention, for example, the construction of retroviral particles having the CD4 molecule on the surface of the envelope so as to target the human cells infected by the HIV virus (YOUNG, J. A. T. et al., Sciences 1990, 250, 1421-1423), viral particles having a peptide hormone fused to, an envelope protein to specifically infect the cells, expressing the corresponding receptor (KASAHARA, N. et al., Sciences 1994, 266, 1373-1376) or else alternatively viral particles having a fused polypeptide capable of immobilizing on the receptor of the epidermal growth factor (EGF) (COSSET, F. L. et al., J. of Virology 1995, 69, 10, 6314-6322). In another approach, single-chain fragments of antibodies directed against surface antigens of the target cells are inserted by fusion with the N-terminal part of the envelope protein (VALSESIA-WITTMAN, S. et al., J. of Virology 1996, 70, 3, 2059-2064; TEARINA CHU, T. H. et al., J. of Virology 1997, 71, 1, 720-725).

For the purposes of the present invention, a gene of interest in use in the invention can be obtained from a eukaryotic or prokaryotic organism or from a virus by any conventional technique. It is, preferably, capable of producing an expression product having a therapeutic effect and it can be a product homologous to the cell host or, alternatively, heterologous. In the scope of the present invention, a gene of interest can code for an (i) intracellular or (ii) membrane product present on the surface of the host cell or (iii) secreted outside the host cell. It can therefore comprise appropriate additional elements such as, for example, a sequence coding for a secretion signal. These signals are known to the person skilled in the art.

In accordance with the aims pursued by the present invention, a gene of interest can code for a protein corresponding to all or part of a native protein as found in nature. It can likewise be a chimeric protein, for example arising from the fusion of polypeptides of various origins or from a mutant having improved and/or modified biological properties. Such a mutant can be obtained, by conventional biological techniques, by substitution, deletion and/or addition of one or more amino acid residues.

It is very particularly preferred to employ a gene of therapeutic interest coding for an expression product capable of inhibiting or retarding the establishment and/or the development of a genetic or acquired disease. A vector according to the invention is in particular intended for the prevention or for the treatment of cystic fibrosis, of hemophilia A or B, of Duchenne's or Becker's myopathy, of cancer, of AIDS and of other bacteria or infectious diseases due to a pathogenic organism: virus, bacteria, parasite or prion. The genes of interest utilizable in the present invention are those which code, for example, for the following proteins:

- a cytokine and especially an interleukin, an interferon, a tissue necrosis factor and a growth factor and especially a hematopoietic growth factor (G-CSF, GM-CSF),
- a factor or cofactor involved in clotting and especially factor VIII, von Willebrand's factor, antithrombin III, protein C, thrombin and hirudin,
- an enzyme or an enzyme inhibitor such as the inhibitors of viral proteases,
- an expression product of a suicide gene such as thymidine kinase of the HSV virus (herpesvirus) of type 1,
- an activator or an inhibitor of ion channels,
- a protein of which the absence, the modification or the deregulation of expression is responsible for a genetic disease, such as the CFTR protein, dystrophin or minidystrophin, insulin, ADA (adenosine diaminose), glucocerebrosidase and phenylhydroxylase,
- a protein capable of inhibiting the initiation or the progression of cancers, such as the expression products of tumor suppressor genes, for example the P53 and Rb genes,
- a protein capable of stimulating an immune or an antibody response, and
- a protein capable of inhibiting a viral infection or its development, for example the antigenic epitopes of the virus in question or altered variants of viral proteins capable of entering into competition with the native viral proteins.

The invention thus relates to the vectors characterized in that they comprise a nucleotide sequence of PWD circovirus according to the invention, and in that they additionally comprise a gene of interest.

The present invention likewise relates to viral particles generated from said vector according to the invention. It additionally relates to methods for the preparation of viral particles according to the invention, characterized in that they employ a vector according to the invention, including viral pseudoparticles (VLP, virus-like particles).

The invention likewise relates to animal cells transfected by a vector according to the invention.

Likewise comprised in the invention are animal cells, especially mammalian, infected by a viral particle according to the invention.

The present invention likewise relates to a vector, a viral particle or a cell according to the invention, for the treatment and/or the prevention of a genetic disease or of an acquired disease such as cancer or an infectious disease. The invention is likewise directed at a pharmaceutical composition comprising, by way of therapeutic or prophylantic agent, a vector or a cell according to the invention, in combination with a vehicle acceptable from a pharmaceutical point of view.

Other characteristics and advantages of the invention appear in the examples and the figures.

The invention is described in more detail in the following illustrative examples. Although the examples may represent only selected embodiments of the invention, it should be understood that the following examples are illustrative and not limiting.

EXAMPLES

Example 1

Cloning, Sequencing and Characterization of the PWD Circovirus of Type A (PCVA)

1. Experimental Procedures

Figure 1:
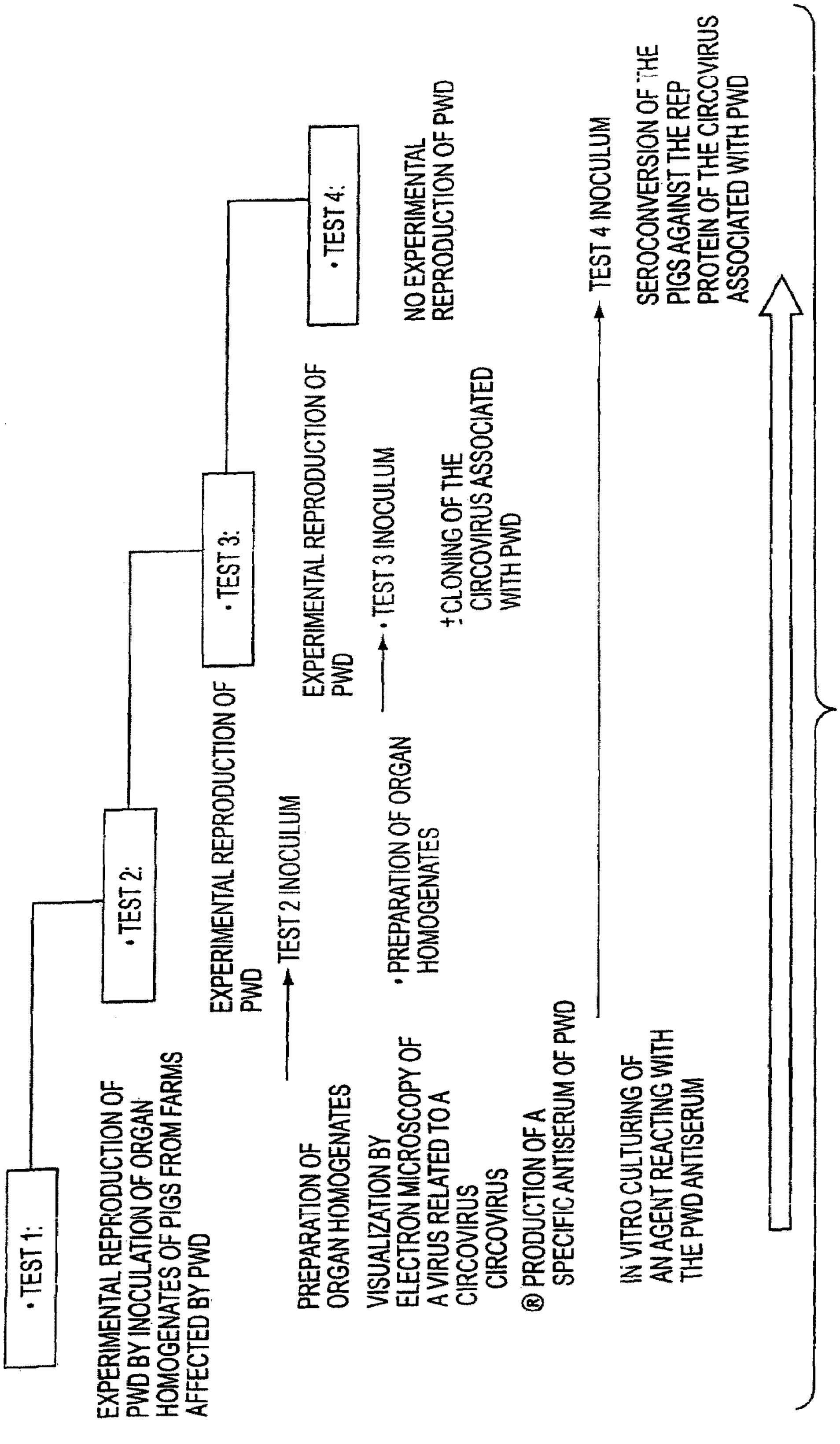
FIG. 1: Experimental scheme which has made it possible to bring about the isolation and the identification of the circovirus associated with PWD of type A and B.

Experimental reproduction of the infection and its syndrome (cf. FIG. 1).

A first test was carried out with pigs from a very well-kept farm, but affected by piglet weight loss disease (PWD), likewise called fatal piglet wasting (FPW). Tests carried out with SPF (specific pathogen-free) pigs showed a transfer of contaminant(s) finding expression in a complex pathology combining hyperthermia, retardation of growth, diarrhea and conjunctivitis. The PDRS (porcine dysgenic and respiratory syndrome) virus, an infectious disease due to an arteriovirus) was rapidly isolated from breeding pigs and contact pigs. It should have been possible to attribute all the clinical signs to the presence of the PDRS virus. However, two farm pigs presented signs of FPW without the PDRS virus being isolated. The histological analyses and blood formulas, however, showed that these pigs were suffering from an infectious process of viral origin.

In a second test, 8-week SPF pigs were inoculated by the intratracheal route with organ homogenates of two farm pigs suffering from FPW. The inoculated pigs exhibited hyperthermia 8 to 9 days post-infection, then their growth was retarded. Other SPF pigs, placed in contact, had similar, attenuated signs 30 days after the initial experiment. No seroconversion with respect to a European or Canadian strain of PDRS virus was recorded in these animals.

A third test allowed the syndrome to be reproduced from samples taken from the pigs of the second test.

Conclusion

The syndrome is reproduced under the experimental conditions. It is determined by at least one infectious agent, which is transmittable by direct contact. The clinical constants are a sometimes high hyperthermia (greater than or equal to 41.5° C.) which develops 8 to 10 days after infection. Retardation of the growth can be observed. The other signs are a reversal of the blood formula (reversal of the lymphocyte/polynuclear ratio from 70/30 to 30/70) and frequent lesions on the ganglia, especially those draining the respiratory apparatus (ganglionic hypertrophy, loss of structure with necrosis and infiltration by mononucleated or plurinucleated giant cells).

2. Laboratory Studies

Various cell supports including primary pig kidney cells or cell lines, pig testicle cells, monkey kidney cells, pig lymphocytes, pig alveolar macrophages and circulating blood monocytes were used to demonstrate the possible presence of a virus. No cytopathic effect was demonstrated in these cells. On the other hand, the use of a serum of a pig sick after experimental infection allowed an intracellular antigen to be revealed in the monocytes, the macrophages and approximately 10% of pig kidney (PK) cells infected with organ homogenates. This indirect revealing was carried out kinetically at different culture times. It is evident from this that the antigen initially appears in the nucleus of the infected cells before spreading into the cytoplasm. The successive passages in cell culture did not allow the signal to be amplified.

Under electron microscopy on organ homogenates, spherical particles labeled specifically by the serum of sick pigs, infected under the experimental conditions, were visualized. The size of these particles is estimated at 20 nm.

After two passages of these organ homogenates over pig lymphocytes and then three passages over pig kidney or testicle cells, a cytopathic effect developed and was amplified. An adenovirus was visualized in the electron microscope, which, under the experimental conditions, did not reproduce FPW (only a hyperthermia peak was noted 24 to 48 hours after infection, and then nothing more).

It has been possible to demonstrate DNA bands in certain samples of pigs infected under the experimental conditions and having exhibited signs of the disease (results not shown). A certain connection exists between the samples giving a positive result in cell culture and those having a DNA band.

Conclusion

At least two types of virus were demonstrated in the organ homogenates from pigs suffering from FPW. One is an adenovirus, but by itself alone it does not reproduce the disease. The other type of virus is a circovirus and is associated with FPW. This circovirus, of which two types have been isolated and sequenced, designated below PWD circovirus type A (or PCVA) and PWD circovirus of type B (or PCVB) have mutations with respect to the known sequences of circovirus which are nonpathogenic for the pig.

3. Cloning and Sequencing of the DNA of the PWD Circovirus of Type A

Extraction of the replicative form (RF) DNA, cleavage by the Kpn I enzyme and amplification by a pair of primers flanking the Kpn I restriction site. Sequencing of the two strands at least twice by the Sanger method.

The nucleic sequence of the strand of (+) polarity of the genome of the PWD circovirus of type A (or PCVA), strain FPW, is represented by the sequence SEQ ID No. 1 in the list of sequences, the nucleic sequence of the strand of (−) polarity of the genome of the PWD circovirus of type A (or PCVA) being represented by the nucleic sequence 3'→5' of FIG. 3 or by the sequence SEQ ID No. 5 (represented according to the orientation 5'→3') in the list of sequences.

The amino acid sequences SEQ ID No. 10, SEQ ID No. 12 and SEQ ID No. 14 of the list of sequences respectively represent the sequences of proteins encoded by the nucleic sequences of the 3 open reading frames SEQ ID No. 9 (ORF1), corresponding to the REP protein, SEQ ID No. 11 (ORF2) and SEQ ID No. 13 (ORF3), determined from the sequence SEQ ID No. 1 of the strand of (+) polarity or of the nucleic sequence SEQ ID No. 5 of the strand of (−) polarity of the genome of the PWD circovirus of type A.

4. Comparison of the Nucleotide Sequences and Amino Acids of the PWD Circovirus of Type A (or Associated with PWD) which are Obtained with the Corresponding Sequences of MEEHAN and MANKERTZ Circoviruses of Porcine Cell Lines Use of the DNA sequence analysis software, DNASIS.

Sequences of Olilonucleotides used as Primers or Probes in the Detection and/or Identification Procedures 1. Specific Detection of the PWD Circovirus of Type A:

```
                                      SEQ ID No. 46
primer PCV 5:    5' GTG TGC TCG ACA TTG GTG TG 3';

                                      SEQ ID No. 47
primer PCV 10:   5' TGG AAT GTT AAC GAG CTG AG 3';
```

2. Specific Detection of the Circovirus of the Cell Lines:

```
                                      SEQ ID No. 46
primer PCF 5:  5' GTG TGC TCG ACA TTG GTG TG 3';

                                      SEQ ID No. 52
primer MEE 1:  5' TGG AAT GTT AAC TAC CTC AA 3';
```

3. Differential Detection:

the pairs of primers used are those described, for example, in the paragraphs 1 and 2 above;

4. Detection of the Monomeric Circular Replicative forms RF:

```
                                      SEQ ID No. 46
primer PCV 5:  5' GTG TGC TCG ACA TTG GTG TG 3';

                                      SEQ ID No. 48
primer PCV 6:  5' CTC GCA GCC ATC TTG GAA TG 3';
```

5. Detection of the Vectors Carrying the Dimers in Tandem:

```
Nar dimer:
                                      SEQ ID No. 49
primer KS 620:   5' CGC GCG TAA TAC GAC TCA CT 3';

                                      SEQ ID No. 46
primer PCV 5:    5' GTG TGC TCG ACA TTG GTG TG 3';

Kpn dimer:
                                      SEQ ID No. 49
primer KS 620:   5' CGC GCG TAA TAC GAC TCA CT 3';

                                      SEQ ID No. 48
primer PCV 6:    5' CTC GCA GCC ATC TTG GAA TG 3';
```

6. Differential Detection:

The pairs of primers used are those described, for example, in paragraphs 4 and 5 above.

The procedures using the pairs or primers described in paragraphs 4 and 5 are of particular interest for differentially detecting the circular monomeric forms of specific replicative forms of the virion or of the DNA in replication and the dimeric forms found in the so-called in-tandem molecular constructs.

The in-tandem constructs of the viral genome (dimers) such as the constructs used for the preparation of the pBS KS+tandem PCV Kpn I vector, deposited at the CNCM under the number I-1891, 3 Jul. 1997 (*E. coli* transformed by said vector) are very interesting for their use in methods of production in sufficient quantity of an inoculum formed of DNA, intended for the virus production, this in the absence of a satisfactory virus production protocol in a cell system. These said methods of production using these in-tandem constructs of the viral genome will allow the virulence factors to be studied by mutation and by way of consequence will be able to be used for the production of a collection of viruses carrying the mutations indicated in the construction of vectors which will have the appropriate tropism and virulence. These vectors with autoreplicative structure have the sought gene transfer properties, especially for their applications in gene therapy, and in vaccinology.

Western-blot Analysis of Recombinant Proteins of the PWD Circovirus of Type A

The results were obtained using a specific antiserum of the PWD circovirus produced during test 1 (cf. FIG. 1).

Type of products analyzed.

The analyses were carried out on cell extracts of Sf9 cells obtained after infection by the recombinant baculovirus PCV ORF 1.

The culture of Sf9 cells was carried out in a 25 $cm^2$ Petri dish according to the standard culture methods for these cells. After centrifugation, the cell pellets are taken up with 300 μl of PBS buffer (phosphate saline buffer).

Electrophoresis (PAGE-SDS) The electrophoresis is carried out on the cell extracts of Sf9 cells obtained previously on 5 samples (cf. Table 1 below) under the following conditions:

% polyacrylamide gel: 8%; conditions: denaturing

Voltage: 80 V; duration: 135 mn.

TABLE 1

Nature of the samples subjected to electrophoresis

| Sample applied | Well No. 1 PM Rainbow | 2 Raoul 24 h | 3 Raoul 48 h | 4 Raoul 72 h | 5 Raoul 96 h |
|---|---|---|---|---|---|
| μl of sample | 10 | 15 | 15 | 15 | 15 |
| μl of Laemmli 4X | 0 | 5 | 5 | 5 | 5 |

Legends to Table 1:
Laemmli 4X: loading buffer
PM Rainbow: molecular-weight markers (35, 52, 77, 107, 160 and 250 kD)
Raoul 24 h, 48 h, 72 h and 96 h: expression products of the ORF1 of the PWD circovirus of type A.

Western Blot

After electrophoresis, the bands obtained in the different wells are transferred to nitrocellulose membrane for 1 h at 100 v in a TGM buffer (tris-glycine-methanol).

The Western blot is carried out under the following conditions:

1) Saturation with a solution containing 5% of skimmed milk; 0.05% of Tween 20 in a TBS 1X buffer (tris buffer saline) for 30 min.
2) 1st antibody:
   10 ml of PWD anticircovirus antibody of type A are added diluted to 1/100, then the reaction mixture is incubated for one night at 4° C. Three washes of 10 min in TBS 1X are carried out.
3) 2nd antibody:
   10 ml of pig rabbit P 164 antibody anti-immunoglobulins, coupled to peroxidase (Dakopath) are added diluted to 1/100, then the reaction medium is incubated for 3 hours at 37° C. Three washes of 10 min in TBS 1X are carried out.
4) Visualization
   The substrate 4-chloro-1-naphthol in the presence of oxygenated water is used for visualization.

Results

The results are shown in FIG. 7.

Kinetics of Appearance of Antibodies Specific for the REP recombinant Protein of the PWD Circovirus of Type A Expressed in Baculovirus after Infection of Pigs by the PWD Circovirus of Type A (Test 4. cf. FIG. 1)

After infection of the pigs, a sample of serum of each of the infected pigs is taken at different periods expressed in the table by the date of taking (carried out here in the same year) and is then analyzed by Western blot.

The visualization of the specific antibodies is carried out in the manner described previously.

The results obtained are shown by Table 2 below.

TABLE 2

Kinetics of appearance of specific antibodies

| Sample | Pigs | 10/6 | 16/06 | 23/06 | 01/07 | 08/07 | 15/07 | 21/07 |
|---|---|---|---|---|---|---|---|---|
| A3 | 1 | | | | | | Neg. | |
| Control | 2 | | | | | | Neg. | |
| B2 Infec. | 1 | Neg. | Neg. | Neg. | + | + | ++ | +++ |
| RP+ | 2 | Neg. | Neg. | Neg. | Neg. | Neg. | Neg. | Neg. |
| | 3 | Neg. | Neg. | Neg. | Neg. | + | + | + |
| | 4 | Neg. | Neg. | Neg. | Neg. | Neg. | Neg. | ++ |

Legends to Table 2:
A3 control: uninfected control animals;
B2 Infec. RP+: animals infected with pig kidney (PK) cells containing the circovirus;
Neg.: negative;
+, ++, +++: intensity scale of the positive reaction;
10/06, 16/06, 23/06, 01/07, 08/07, 15/07, 21/07: dates expressed in day/month on which the different withdrawals of serum were carried out.

Example 2

Cloning, Sequencing and Characterization of the Type B PWD Circovirus (PCVB)

The techniques used for cloning, sequencing and characterization of the type B PWD circovirus (PCVB) are those used in Example 1 above for the type A PWD circovirus (PCVA).

The nucleic sequence of the strand of (+) polarity of the genome of the PWD circovirus of type B (or PCVB) is represented by the sequence SEQ ID No. 15 in the sequence listing, the nucleic sequence of the strand of (−) polarity of the genome of the PWD circovirus of type B (or PCVB) being represented by the nucleic sequence 3→→5→ of FIG. 8 or by the sequence SEQ ID No. 19 (represented according to the orientation 5'→3') in the sequence listing.

The amino acid sequences SEQ ID No. 24, SEQ ID No. 26 and SEQ ID No. 28 of the sequence listing respectively represent the sequences of the proteins encoded by the nucleic sequences of the 3 open reading frames SEQ ID No. 23 (ORF'1), corresponding to the REP protein, SEQ ID No. 25 (ORF'2) and SEQ ID No. 27 (ORF'3), determined from the sequence SEQ ID No. 15 of the strand of (+) polarity or from the nucleic sequence SEQ ID No. 19 of the strand of (–) polarity of the genome of the PWD circovirus of type B.

Example 3

Comparative Analysis of Nucleotide Sequences (ORF1, ORF2 and Genomic) and Amino Acid Sequences Encoded by the ORF1 and the ORF2 of the PWD Circoviruses of Type A (PCVA) and of Type B (PCVB)

The results expressed in % of homology are shown in Tables 3 and 4 below.

TABLE 3

Compared analysis of the amino acid sequences

| % homology | ORF1 | ORF2 |
|---|---|---|
| PCVA/PCVB | 80.4 | 56.2 |

TABLE 4

Compared analysis of the nucleotide sequences

| % homology | Genomic | ORF1 | ORF2 | The remainder |
|---|---|---|---|---|
| PCVA/PCVB | 70.4 | 80.4 | 60.1 | 66.1 |

Example 4

Observation of the Disease and Reproduction of the Disease Under Experimental Conditions a) Test No. 1: Observation of the Disease The objective is to take breeding animals at the start of disease and to place them under experimental conditions to follow the progression of the pathology and describe all the clinical signs thereof. This first test was carried out on 3 breeding pigs aged 10 weeks of which 2 were already ill (suffering from wasting), and on 3 other pigs aged 13 weeks, not having signs of disease. The clinical observation was spread over a period of 37 days. Two pigs of 10 weeks wasted rapidly (pigs 1 and 2, FIG. 9) and had to be painlessly killed 5 and 6 days after their arrival. A single pig exhibited hyperthermia over 5 days and diarrhea. Two other pigs exhibited dyspnea and cough, of which one additionally had hyperthermia, greater than 41° C., for the two first days of its stay. Another pig had retarded growth in the second week (pig 6, FIG. 9), without any other clinical sign being recorded. On the lesional level, 5 pigs out of 6 exhibited macroscopic lesions of gray pneumonia, the sixth exhibited cicatricial lesions on the lung.

b) Test No. 2: Reproduction of the Disease from Inocula Prepared in Farm Pigs.

The two sick pigs in test 1 served to prepare inocula which were tested in test 2 on specific-pathogen-free (SPF) pigs. The SPF pigs were aged 9 weeks at the time of inoculation. The clinical and lesional results are shown in Table 5.

TABLE 5

Summary of the measurements carried out during experimental reproduction of PWD. (The values of the control animals are reported in brackets, the underlined values indicate a difference between infected animals and control animals)

| Test Measurement | 2 | 3 | 4 | 5 | 6 | 7 |
|---|---|---|---|---|---|---|
| Status of the pigs | SPF CNEVA | SPF field | SPF CNEVA | SPF CNEVA | Conventional | Conventional |
| Age | 9 weeks | 6 weeks | 5 weeks | 5 weeks | 5 weeks | 6-7 weeks |
| Number | 4 | 6 | 12 | 8 | 8 | 8 |
| Inoculation route | Intratracheal route | Intratracheal route | Intratracheal + intramuscular route | Intratracheal + intramuscular route | Intratracheal + intramuscular route | Intratracheal + intramuscular route |
| Inoculum titer per pig | ND* | ND* | $10^{4.53}$ $TCID_{50}$ per ml: 1 ml IM + 5 ml IT | $10^{4.53}$ $TCID_{50}$ per ml: 1 ml IM + 5 ml IT | $10^{4.53}$ $TCID_{50}$ per ml: 1 ml IM + 5 ml IT | $10^{4.53}$ $TCID_{50}$ per ml: 1 ml IM + 5 ml IT |
| Start of hyperthermia | 10 days post-infection | 9-13 days post-infection | 12-13 days post-infection | 9-14 days post-infection | 8-12 days post-infection | 12 days post-infection |
| % of pigs in hyperthermia** | 100% | 83% | 92% | 100% | 75% | 88% |
| Number of days of hyperthermia per pig** | 7 | 4.5 | 3.3 | 5.8 | 7.5 | 11.6 |
| Maximum temperatures*** | 40.4 to 41.7° C. | 40.6 to 42.3° C. | 40.2 to 41.6° C. | 40.3 to 40.8° C. | 40.6 to 42° C. | 40.2 to 41.9° C. |
| Hyperthermia**** % per week | | | | | | |
| W1 | 3.5 (3.5) | 17 (36) | 7 (5) | 37 (17) | 16 (17) | 20 (28) |
| W2 | <u>42 (3.5)</u> | 7 (13) | <u>13 (1)</u> | <u>21 (3)</u> | <u>52 (10)</u> | 37 (28) |
| W3 | <u>35 (3.5)</u> | <u>33 (10)</u> | <u>28 (7)</u> | <u>62 (2)</u> | <u>34 (12)</u> | <u>79 (17)</u> |
| W4 | <u>21 (3.5)</u> | <u>28 (7)</u> | 5 (0) | 6 (3) | 25 (22) | <u>55 (3)</u> |

TABLE 5-continued

Summary of the measurements carried out during experimental reproduction of PWD. (The values of the control animals are reported in brackets, the underlined values indicate a difference between infected animals and control animals)

| Test Measurement | 2 | 3 | 4 | 5 | 6 | 7 |
|---|---|---|---|---|---|---|
| DMG: | | | | | | |
| W1 | 928 (1053) | 417 (357) | 564 (620) | 650 (589) | 401 (407) | 509 (512) |
| W2 | 678 (1028) | 428 (617) | 503 (718) | 612 (584) | 294 (514) | 410 (310) |
| W3 | 661 (1000) | 771 (642) | 381 (657) | 520 (851) | 375 (586) | 435 (440) |
| W4 | 786 (1100) | 550 (657) | 764 (778) | 641 (696) | 473 (610) | 451 (681) |
| Contact pigs transmission | Yes to 100% | Yes to 75% | Not tested | Not tested | Not tested | Not tested |
| % of pulmonary lesions | 25 | 75 | 0 | 25 | 25 | 12 |
| % of ganglionic lesions | 17 | 33 | 67 | 25 | 50 | 12 |

*ND: not determined,
**hyperthermia when the temperature is greater than 40° C.,
***range of maximum temperatures recorded at the individual level,
****the percentage corresponds to the number of temperature recordings greater than 40° C. divided by the total number of temperature recordings in the week on all of the pigs.

In this test, there was no wasting, at the very most a retardation of the growth in the second, third or fourth week after infection. These data illustrate that certain breeding conditions probably favor the expression of the disease.

c) Tests No. 3 to No. 7: Reproduction of the Experimental Tests

The increase in the number of the experimental tests on pigs had the mastering and better characterization of the experimental model as an objective. All of the results are presented in Table 5.

Under the experimental conditions, PWD is thus characterized by a long incubation, of 8 to 14 days, true hyperthermia over 2 to 8 days, a decrease in food consumption and a retardation of the increase in weight on the second, third or fourth week post-infection. The lesional table associated with this clinical expression includes, in the main, ganglionic hypertrophy and lesions of pneumonia.

Conclusion

The perfection of this experimental model allows the direct etiological role of the PWD circovirus in the disease to be indisputably demonstrated. In addition, this model is an indispensable tool for the understanding of pathogenic mechanisms and the study of future vaccine candidates.

Example 5

Demonstration of the Vaccine Composition Protective Efficacy Produced from Nucleic Fragments of PWD Circovirus Sequence 1) Animals Used for the Study Piglets having the PWD disease, reproduced under experimental conditions described in paragraph c) of Example 4, were used in a protocol for evaluating the vaccine composition efficacy, comprising nucleic fragments of PWD circovirus sequence.

2) Tested Vaccine Composition and Vaccination Protocol a) Components Used for the Study The plasmids were obtained from the pcDNA3 plasmid of INVITROGENE pcDNA3ORF− plasmids These plasmids are plasmids which do not carry a PWD circovirus nucleic acid insert and are used as a negative control plasmid.

pcDNA3ORF1+ plasmid and pcDNA3O RF2+ plasmid

The pcDNA3ORF1+ and pcDNA3ORF2+ plasmids are plasmids which carry a nucleic acid insert of the sequence of the PWD circovirus of TYPE B, respectively an insert comprising the nucleic acid fragment SEQ ID No. 23 (ORF'1) coding for the Rep protein of sequence SEQ ID No. 24 and an insert comprising the nucleic acid fragment SEQ ID No. 25 (ORF'2) coding for the protein of sequence SEQ ID No. 26, probably corresponding to the capsid protein, these nucleic constructs comprising the ATG initiation codon of the coding sequence of the corresponding protein.

GMCSF+ plasmid

GM-CSF (granulocyte/macrophage colony stimulating factor) is a cytokine which occurs in the development, the maturation and the activation of macrophages, granulocytes and dendritic cells which present an antigen. The beneficial contribution of the GM-CSF in vaccination is considered to be a cellular activation with, especially, the recruitment and the differentiation of cells which present an antigen.

This pcDNA3-GMCSF+ plasmid carries a nucleic acid insert coding for the granulocyte/macrophage colony stimulation factor, the GM-CSF protein.

The gene coding for this GM-CSF protein was cloned and sequenced by Inumaru et al. (Immunol. Cell Biol., 1995, 73 (5), 474-476). The pcDNA3-GMCSF+ plasmid was obtained by Dr. B. Charley of INRA of Jouy-en-Josas (78, France).

Recombinant baculoviruses

The so-called ORF− baculoviruses are viruses not carrying any insert comprising a nucleic acid fragment capable of expressing a PWD circovirus protein.

The so-called ORF1+ (BAC ORF1+) or ORF2+ (BAC ORF2+) baculoviruses are recombinant baculoviruses respectively carrying an insert comprising a nucleic acid fragment SEQ ID No. 23 (ORF'1) and an insert comprising the nucleic acid fragment SEQ ID No. 25 (ORF'2).

Adjuvant

The adjuvant supplied by the Seppic Company, a subsidiary of AIR LIQUIDE, is the adjuvant corresponding to the reference AIF SEPPIC.

b) Vaccination Protocol

Weaned piglets aged 3 weeks are divided into four batches A, B, C and D each comprising 8 piglets.

Batches A, B and C, aged 3 weeks, each receive a first injection (injection M1) of 1 ml containing 200 micrograms of plasmids (naked DNA) in PBS, pH: 7.2, by the intramuscular route for each of the plasmids mentioned below for each batch, then, at the age of 5 weeks, a second injection (injection M2) comprising these same plasmids. A third injection is carried out simultaneously on the other side of the neck. This third injection comprises 1 ml of a suspension containing $5.10^6$ cells infected by recombinant baculoviruses and 1 ml of AIF SEPPIC adjuvant.

Batch A (F1) (Control Batch):

first injection pcDNA3O RF1− plasmid, pcDNA3ORF2− plasmid and GMCSF+ plasmid.

second and third injection (simultaneous)

pcDNA3ORF1− plasmid, pcDNA3ORF2− plasmid and GMCSF+ plasmid;

Cells transformed by baculoviruses not containing any nucleic acid insert coding for a PWD circovirus protein;

AIF SEPPIC adjuvant.

Batch B (F2) (control batch):

first injection pcDNA3ORF1− plasmid, pcDNA3ORF2− plasmid and GMCSF+ plasmid;

second and third injection (simultaneous)

pcDNA3ORF1− plasmid, pcDNA3ORF2− plasmid and GMCSF+ plasmid;

Cells transformed by baculoviruses not containing any nucleic acid insert coding for a PWD circovirus protein;

AIF SEPPIC adjuvant.

Batch C (F3):

first injection pcDNA3ORF1+ plasmid, pcDNA3ORF2+ plasmid and GMCSF+ plasmid;

second and third injection (simultaneous)

pcDNA3ORF1+ plasmid, pcDNA3ORF2+ plasmid and GMCSF+ plasmid;

Cells transformed by BAC ORF1+ and BAC ORF2+ recombinant baculoviruses capable of respectively expressing the Rep protein of sequence SEQ ID No. 24 and the protein of sequence SEQ ID No. 26 of the PWD circovirus of TYPE B.

Batch D (F4) (control batch): no injection

The batches of piglets B, C and D are infected (tested) at the age of 6 weeks although batch A is not subjected to the test.

3) Observation of the Batches counting of coughing/sneezing: 15 minutes/batch/day;

consistency of fecal matter: every day;

regular recordings: weekly taking of blood, weighing;

weighing of food refuse: 3 times per week;

calculation of the daily mean gain in weight (dmg);

The daily mean gains were calculated for each of the batches over a period of 28 days following testing (cf. FIG. 10), an intermediate calculation of the dmg was likewise carried out for each of the batches over the first and second periods of 14 days. The results obtained are reported below in Table 6.

TABLE 6

| | Daily mean gains | | | |
|---|---|---|---|---|
| | F1 | F2 | F3 | F4 |
| d0-d14 | 411 g | 450 g | 511 g | 461 g |
| d14-d28 | 623 g | 362 g | 601 g | 443 g |
| d0-d28 | 554 g | 406 g | 556 g | 452 g |

Measurement of Hyperthermia

The measurement of hyperthermia, of greater than 41° C. (cf. FIG. 11) and greater than 40.2° C., was carried out for each of the batches over a total period of 28 days following testing. The results obtained, corresponding to the ratio expressed as a percentage between the number of recordings of heat of greater than 41° C. (or greater than 40.2° C.) and the total number of recordings of heat carried out on all of the pigs per one-week period are reported below in Tables 7 and 8, respectively for the hyperthermia measurements of greater than 41° C. and greater than 40.2° C.

TABLE 7

| | Hyperthermia > 41° C. | | | |
|---|---|---|---|---|
| | F1 | F2 | F3 | F4 |
| W1 | 4.1 | 0. | 0. | 0. |
| W2 | 10.7 | 16. | 0. | 8.9 |
| W3 | 4.7 | 27. | 0. | 45. |
| W4 | 0. | 0. | 0. | 7.5 |

TABLE 8

| | Hyperthermia > 40.2 | | | |
|---|---|---|---|---|
| | F1 | F2 | F3 | F4 |
| W1 | 29.1 | 10.41 | 29.1 | 20.8 |
| W2 | 28.5 | 39.2 | 10.7 | 37.5 |
| W3 | 14.3 | 68.7 | 25.0 | 81.2 |
| W4 | 3.3 | 17.5 | 20.0 | 55 |

4) Conclusion

The recordings carried out clearly show that the animals which received the three injections of a vaccine composition comprising nucleic acid fragments of PWD circovirus according to the invention and/or capable of expressing recombinant proteins of PWD circovirus, in particular of type B, did not exhibit hyperthermia (cf. FIG. 10). These animals additionally did not experience a decline in their growth, the dmgs being comparable to those of uninfected control animals (cf. FIG. 9). They did not exhibit any particular clinical sign.

These results demonstrate the efficacious protection of the piglets against infection with a PWD circovirus of the invention, the primary agent responsible for PWD or FPW, provided by a vaccine composition prepared from a nucleic acid fragment of the nucleic sequence of PWD circovirus according to the invention, in particular of type B, and/or from recombinant proteins encoded by these nucleic acid fragments.

These results in particular show that the proteins encoded by the ORF1 and ORF2 of PWD circovirus according to the invention are immunogenic proteins inducing an efficacious protective response for the prevention of infection by a PWD circovirus.

Example 6

Serological Diagnosis of PWD Circovirus by Immunodetermination using Recombinant Proteins or Synthetic Peptides of PWD Circovirus A—Serological Diagnosis with Recombinant Proteins The identification and the sequencing of porcine PWD circovirus allow recombinant proteins of PWD circovirus to be produced by the techniques of genetic recombination well known to the person skilled in the art.

By these techniques, recombinant proteins encoded, in particular, by the ORF'2 of the PWD circovirus, type B, were expressed by transformed Sf9 insect cells and then isolated.

These recombinant proteins encoded by the ORF'2 are extracted, after culture of the transformed Sf9 cells, by thermal cell lysis by means of 3 cycles of freezing/thawing to −70° C./+37° C. Healthy Sf9 cells or nontransformed control Sf9 cells are also lyzed.

These two antigenic fractions originating from nontransformed control Sf9 cells and Sf9 cells expressing the ORF'2 are precipitated at 4° C. by a 60% plus or minus 5% saturated ammonium sulfate solution. Determination of total proteins is carried out with the aid of the Biorad kit. 500 ng of control Sf9 proteins and of semipurified Sf9 proteins expressing the ORF'2, in solution in 0.05 M bicarbonate buffer pH 9.6, are passively adsorbed at the bottom of 3 different cupules of a Nunc Maxisorp microplate by incubation for one night at +4° C.

The reactivity of with respect to each of these antigenic fractions is evaluated by an indirect ELISA reaction of which the experimental protocol is detailed below:

Saturation step: 200 μl/cupule of PBS1X/3% semi-skimmed milk, 1 h 30 incubation at 37° C.

Washing: 200 μl/cupule of PB1X/Tween 20: 0.05%, 3 rapid washes.

Serum incubation step: 100 μl/cupule of serum diluted to 1/100 in PBS1X/semi-skimmed milk, 1%/Tween 20: 0.05%, 1 h incubation at 37° C.

Washing: 200 μl/cupule of PBS1X/Tween 20: 0.05%, 2 rapid washes followed by 2 washes of 5 min.

Conjugate incubation step: 50 μl/cupule of rabbit anti-pig conjugate diluted to 1/1000 in PBS1X/semi-skimmed milk, 1%/Tween 20: 0.05%, 1 h incubation at 37° C.

Washing: 200 μl/cupule of PBS1X/Tween 20: 0.05%, 2 rapid washes followed by 2 washes of 5 min.

Visualization step: 100 μl/cupule of OPD substrate/citrate buffer/$H_2O_2$, 15 min incubation at 37° C.

Stopping of reaction: 50 μl/cupule of 1 N $H_2SO_4$.

Reading in a spectrophotometer at 490 nm.

Results

The results obtained are shown below in Table 9.

TABLE 9

| Antigens | Reactivity of Pig Serum not inoculated with Circovirus | Reactivity of Pig Serum inoculated with Circovirus |
|---|---|---|
| Purified Sf9 control | 0.076 | 0.088 |
| Sf9 expressing purified ORF'2 | 0.071 | 1.035 |

The results are expressed in optical density measured in a spectrophotometer at 490 nm during analysis by ELISA of the reactivity of pig sera which are or are not inoculated with the type B PWD circovirus according to the protocol indicated above.

B—Serological Diagnosis by Synthetic Peptide

The epitopic mapping of the proteins encoded, for example, by the nucleic sequences ORF1 and ORF2 of the two types of PWD circovirus (types A and B) additionally allowed immunogenic circoviral epitopes to be identified on the proteins encoded by the nucleic sequences ORF'1 and ORF'2 as well as the specific epitopes of the protein encoded by the nucleic sequence ORF'2 of the type B PWD circovirus. Four specific epitopes of the type B PWD circovirus and one epitope common to the two types of PWD circovirus situated on the protein encoded by the nucleic sequence ORF'2 were synthesized in peptide form. The equivalent peptides in the circovirus of type A were likewise synthesized. All these peptides were evaluated as diagnostic antigens within the context of carrying out a serological test.

Results

The results obtained are shown in Table 10 below.

TABLE 10

Results of the evaluation as a diagnostic antigen of synthetic peptides encoded by the nucleic sequences ORF2 and ORF'2 of PWD circovirus of type A and B.

| | | | | | Infected pig serum reactivity Circovirus B | | | |
|---|---|---|---|---|---|---|---|---|
| | Peptide | Type PWD circovirus | Position | AA sequence | SPF D0/D54 | Conventional 1 D0/D42 | Conventional 2 D0/D42 | Epitopic specificity |
| SEQ ID NO: 29 | 121 | B | 71-85 | VDMMRFNINDFLPPG | +/−, +++ | +/−, +++ | −, +++ | Circovirus B |
| SEQ ID NO: 55 | 177 | B | 70-84 | NVNELRFNIGQFLPP | +/−, + | +/−, +/− | +/−, − | |
| SEQ ID NO: 30 | 132 | B | 115-129 | QGDRGVGSSAVILDD | +/−, +/− | ++, ++ | +/−, + | Circovirus B |
| SEQ ID NO: 56 | 188 | A | 114-127 | TSNQRGVGSTVVIL | +/−, − | −, +/− | +/−, +/− | |
| SEQ ID NO: 31 | 133 | B | 119-134 | GVGSSAVILDDNVFTK | −, ++ | ++, +++ | +/−, ++ | |
| SEQ ID NO: 57 | 189 | A | 118-132 | RGVGSTVVILDANFV | +/−, − | −, +/− | +/−, +/− | |
| SEQ ID NO: 58 | 146 | B | 171-185 | FTIDYFQPNNKRNQL | −, +/− | −, ++ | −, ++ | Circovirus A&B |
| SEQ ID NO: 59 | 202 | A | 170-184 | DQTIDWFQPNNKRNQ | +++, +++ | +/−, ++ | +, ++ | |
| SEQ ID NO: 32 | 152 | B | 195-209 | VDHVGLGTAFENSIY | −, ++ | +++, +++ | +/−, + | Circovirus B |
| SEQ ID NO: 60 | 208 | A | 194-208 | NVEHTGLGYALQNAT | −, − | −, − | −, − | |

+/−, +, ++, +++. Increasing intensities of the reactivities observed in Spot peptides on a nitrocellulose membrane. The porcine sera tested are from animals experimentally infected with the circovirus of type B within the animal houses of the CNEVA. Samples are taken from the animals before inoculation on d 0 and 42 days or 54 days after inoculation, on d 42, d 54.

Example 7

Characterization of the Specific Epitopes of the PWD Circovirus of Type B

The proteins encoded by the ORF2 of the porcine circoviruses of type A and B were chosen for this study. For each of the ORF2 s (types A and B), 56 peptides of 15 amino acids which overlap every 4 amino acids were synthesized, thus covering the whole of the protein (cf. Table 11 below).

TABLE 11

Sequence of amino acids of the 56 peptides of 15 amino acids synthesized from the nucleic sequence ORF'2 (type B) and ORF2 (type A) of PWD circovirus with their corresponding spot number (cf. FIG. 12)

| Type B ORF'2 | | | Type A ORF2 | | |
|---|---|---|---|---|---|
| | Spot No. | Sequence | | Spot No. | Sequence |
| SEQ ID NO: 171 | 104 | MTYPRRRYRRRRHRP | SEQ ID NO: 175 | 160 | MTWPRRRYRRRRTRP |
| SEQ ID NO: 172 | 105 | RRRYRRRRHRPRSHL | SEQ ID NO: 176 | 161 | RRRYRRRRTRPRSHL |
| SEQ ID NO: 173 | 106 | RRRRHRPRSHLGOIL | SEQ ID NO: 177 | 162 | RRRRTRPRSHLGNIL |
| SEQ ID NO: 61 | 107 | HRPRSHLGQILRRRP | SEQ ID NO: 84 | 163 | TRPRSHLGNILRRRP |
| SEQ ID NO: 62 | 108 | SHLGQILRRRPWLVH | SEQ ID NO: 85 | 164 | SHLGNILRRRPYLVH |
| SEQ ID NO: 63 | 109 | QILRRRPWLVHPRHR | SEQ ID NO: 86 | 165 | NILRRRPYLVHPAFR |
| SEQ ID NO: 64 | 110 | RRPWLVHPRHRYRWR | SEQ ID NO: 87 | 166 | RRPYLVHPAFRNRYR |
| SEQ ID NO: 65 | 111 | LVHPRHRYRWRRKNG | SEQ ID NO: 88 | 167 | LVHPAFRNRYRWRRK |
| SEQ ID NO: 66 | 112 | RHRYRWRRKNGIFNT | SEQ ID NO: 89 | 168 | AFRNRYRWRRKTGIF |
| SEQ ID NO: 67 | 113 | RWRRKNGIFNTRLSR | SEQ ID NO: 90 | 169 | RYRWRRKTGIFNSRL |
| SEQ ID NO: 68 | 114 | KNGIFNTRLSRTFGY | SEQ ID NO: 91 | 170 | RRKTGIFNSRLSREF |
| SEQ ID NO: 69 | 115 | FNTRLSRTFQYTVKR | SEQ ID NO: 92 | 171 | GIFNSRLSREFVLTI |
| SEQ ID NO: 70 | 116 | LSRTFGYTVKRTTVR | SEQ ID NO: 93 | 172 | SRLSREFVLTIRGGH |
| SEQ ID NO: 71 | 117 | FGYTVKRTTVRTPSW | SEQ ID NO: 94 | 173 | REFVLTIRGGHSQPS |
| SEQ ID NO: 72 | 118 | VKRTTVRTPSWAVDM | SEQ ID NO: 95 | 174 | LTIRGGHSOPSWNVN |
| SEQ ID NO: 73 | 119 | TVRTPSWAVDMMRFN | SEQ ID NO: 96 | 175 | GGHSQPSWNVNELRF |
| SEQ ID NO: 74 | 120 | PSWAVDMMRFNINDF | SEQ ID NO: 97 | 176 | QPSWNVNELRFNIGO |
| SEQ ID NO: 29 | 121 | VDMMRFNINDFLPPG | SEQ ID NO: 98 | 177 | NVNELRFNIGQFLPP |
| SEQ ID NO: 75 | 122 | RFNINDFLPPGGGSN | SEQ ID NO: 99 | 178 | LRFNIGQFLPPSGGT |
| SEQ ID NO: 76 | 123 | NDFLPPGGGSNPRSV | SEQ ID NO: 100 | 179 | IGQFLPPSGGTNPLP |
| SEQ ID NO: 77 | 124 | PPGGGSNPRSVPFEY | SEQ ID NO: 101 | 180 | LPPSGGTNPLPLPFQ |
| SEQ ID NO: 78 | 125 | GSNPRSVPFEYYRIR | SEQ ID NO: 102 | 181 | GGTNPLPLPFQYYRI |
| SEQ ID NO: 79 | 126 | RSVPFEYYRIRKVKV | SEQ ID NO: 103 | 182 | PLPLPFQYYRIRKAK |
| SEQ ID NO: 80 | 127 | FEYYRIRKVKVEFWP | SEQ ID NO: 104 | 183 | PFQYYRIRKAKYEFY |
| SEQ ID NO: 81 | 128 | RIRKVKVEFWPCSPI | SEQ ID NO: 105 | 184 | YRIRKAKYEFYPRDP |
| SEQ ID NO: 82 | 129 | VKVEFWPCSPITQGD | SEQ ID NO: 106 | 185 | KAKYEFYPRDPITSN |
| SEQ ID NO: 83 | 130 | FWPCSPITQGDRGVG | SEQ ID NO: 107 | 186 | EFYPRDPITSNQRGV |
| SEQ ID NO: 30 | 131 | SPITQGDRGVGSSAV | SEQ ID NO: 108 | 187 | RDPITSNQRGVGSTV |
| SEQ ID NO: 31 | 132 | QGDRGVGSSAVILDD | SEQ ID NO: 109 | 188 | TSNQRGVGSTVVILD |
| SEQ ID NO: 110 | 133 | GVGSSAVILDDNFVT | SEQ ID NO: 136 | 189 | RGVGSTVVILDANFV |
| SEQ ID NO: 111 | 134 | SAVILDDNFVTKATA | SEQ ID NO: 137 | 190 | STVVILDANFVTPST |
| SEQ ID NO: 112 | 135 | LDDNFVTKATALTYD | SEQ ID NO: 138 | 191 | ILDANFVTPSTNLAY |
| SEQ ID NO: 113 | 136 | FVTKATALTYDPYVN | SEQ ID NO: 139 | 192 | NFVTPSTNLAYDPYI |
| SEQ ID NO: 114 | 137 | ATALTYDPYVNYSSR | SEQ ID NO: 140 | 193 | PSTNLAYDPYINYSS |
| SEQ ID NO: 115 | 138 | TYDPYVNYSSRIITIT | SEQ ID NO: 141 | 194 | LAYDPYINYSSRHTI |
| SEQ ID NO: 116 | 139 | YVNYSSRHTITQPFS | SEQ ID NO: 142 | 195 | PYINYSSRHTIRQPF |

TABLE 11-continued

Sequence of amino acids of the 56 peptides of 15 amino acids synthesized from the nucleic sequence ORF'2 (type B) and ORF2 (type A) of PWD circovirus with their corresponding spot number (cf. FIG. 12)

| Type B ORF'2 | | | Type A ORF2 | | |
|---|---|---|---|---|---|
| | Spot No. | Sequence | | Spot No. | Sequence |
| SFQ ID NO: 117 | 140 | SSRHTITOPFSYHSR | SEQ ID NO: 143 | 196 | YSSRIITIRQPFTYHS |
| SEQ ID NO: 118 | 141 | TITQPFSYHSRYFTP | SEQ ID NQ: 144 | 197 | HTIRQPFTYHSRYFT |
| SEQ ID NQ: 119 | 142 | PFSYHSRYFTPKPVL | SEQ ID NO: 145 | 198 | QPFTYHSRYFTPKPE |
| SEQ ID NO: 120 | 143 | HSRYFTPKPVLDFTI | SEQ ID NO: 146 | 199 | YHSRYFTPKPELDQT |
| SEQ ID NO: 121 | 144 | FTPKPVLDFTIDYYFQ | SEQ ID NO: 147 | 200 | YFTPKPELDQTIDWF |
| SEQ ID NO: 122 | 145 | PVLDFTIDYFQPNNK | SEQ ID NO: 148 | 201 | KPELDQTIDWFQPNN |
| SEQ ID NO: 123 | 146 | FTIDYFQPNNKRNQL | SEQ ID NO: 149 | 202 | DQTIDWFQPNNKRNQ |
| SEQ ID NO: 124 | 147 | YFQPNNKRNQLWLRL | SEQ ID NO: 150 | 203 | DWFQPNNKRNQLWLH |
| SEQ ID NO: 125 | 148 | NNKRNQLWLRLQTAG | SEQ ID NO: 151 | 204 | PNNKRNQLWLHLNTH |
| SEQ ID NO: 126 | 149 | NQLWLRLQTAGNVDH | SEQ ID NO: 152 | 205 | RNQLWLHLNTHTNVE |
| SEQ ID NO: 127 | 150 | LRLQTAGNVDHVGLG | SEQ ID NO: 153 | 206 | WLHLNTHTNVEHTGL |
| SEQ ID NO: 128 | 151 | TAGNVDHVGLGTAFE | SEQ ID NO: 154 | 207 | NTHTNVEHTGLGYAL |
| SEQ ID NO: 32 | 152 | VDHVGLGTAFENSIY | SEQ ID NO: 155 | 208 | NVEHTGLGYALQNAT |
| SEQ ID NO: 129 | 153 | GLGTAFENSIYDQEY | SEQ ID NO: 156 | 209 | TGLGYALQNATTAQN |
| SEQ ID NO: 130 | 154 | AFENSIYDQEYNIRV | SEQ ID NO: 157 | 210 | YALQNATTAQNYVVR |
| SEQ ID NO: 131 | 155 | SIYDQEYNIRVTMYV | SEQ ID NO: 158 | 211 | NATTAQNYVVRLTIY |
| SEQ ID NO: 132 | 156 | QEYNIRVTMYVQFRE | SEQ ID NO: 159 | 212 | AQNYVVRLTIYVQFR |
| SEQ ID NO: 133 | 157 | IRVTMYVQFREFNFK | SEQ ID NO: 160 | 213 | VVRLTIYVQFREFIL |
| SEQ ID NO: 134 | 158 | MYVQFREFNFKDPPL | SEQ ID NO: 161 | 214 | TIYVQFREFILKDPL |
| SEQ ID NO: 135 | 159 | VQFREFNFKDPPLNP | SEQ ID NO: 162 | 215 | YVQFREFILKDPLNE |

These peptides were synthesized according to the "spot" method which consists in simultaneous synthesis of a large number of peptides on a cellulose solid support, each site of synthesis of a peptide constituting a spot (Synt:em,.NIMES). This method involves orientation of the peptides on the plate, these being fixed covalently by the carboxy-terminal end. A spot represents approximately 50 nmol of peptide.

The reference of the spots and corresponding peptide sequences is given in Table 11.

These membranes were used for immunoreactivity tests with respect to serum of SPF pigs which were or were not infected experimentally with the type B PWD circoviral strain as well as with respect to sera of infected pigs from conventional farms (conventional farms 1 or 2). This study allowed specific immunoreactive peptides of the circovirus of type B corresponding to the spots No. 121, No. 132, No. 133 and No. 152 (respectively of amino acid sequences SEQ ID No. 29, SEQ ID No. 30, SEQ ID No. 31 and SEQ ID No. 32) to be demonstrated. An illustration is shown in FIG. 12 where the membranes are visualized with an infected pig serum coming from a conventional farm. Nonspecific immunoreactive peptides of type [lacuna] were likewise demonstrated, among which we shall keep the peptide No. 146 SEQ ID No. 123 which is strongly immunogenic.

A comparison between the peptide sequences of circoviruses of type A and B (FIG. 13) indicates a divergence ranging from 20 to 60% for the specific immunoreactive peptides of the type B, and a weaker divergence (13%) between the nonspecific peptides.

Example 8

Protection of Swine From Post-Weaning Multisystemic Wasting Syndrome (PMWS) Conferred by Procine Circovirus TypeB (PCV-B) ORF'2 Protein The ORF'1-encoded protein (REP) and ORF'2-encoded putative capsid protein of PCV-B were expressed, either in insect cells by recombinant baculovirus vectors, or in mammalian cell lines by transfection with plasmidic expression vectors. These two circovirus-derived-proteins were detectable in both expression system. As evaluated by weight gains, hyperthermia and absence of lesions following challenge, the pigs were protected against a virulent circovirus challenge after one first DNA immunization with plasmids directing ORF'2 protein and GM-CSF expression and a second injection, 15 days later, with the same plasmid preparation plus the ORF'2 recombinant protein. A lower level of protection was observed when the pigs were vaccinated with ORF'1 protein, as opposed to pigs vaccinated with ORF'2 protein.

A. Development of an Experimental Model of PMWS in Swine:

Eight 3 week-old SPF pigs were inoculated intratracheally (5 ml) and intramuscularly (1 ml).

B. Production and Control of PCV-B Plasmids:

PCV-B ORF'1 and ORF'2 genes, isolated from PCV-B challenge strain, have been cloned into vector plasmid pcDNA3.1.

All constructs have been validated through a partial sequencing of the PCV-B genes in the final plasmids and expression control by immunoperoxidase on PK15 cells respectively transfected with each plasmid, using swine polyclonal antibodies. Plasmid encoding GM-CSF has been co-administered.

C. Construction of Recombinant Baculoviruses:

ORF'1 and ORF'2 proteins were expressed under polyhedrin promoter control. Recombinant proteins were detected by western-blot using swine polyclonal antibodies.

D. Vaccination and Challenge:

Four groups of 7 pigs were vaccinated intramuscularly at day 0 (Do), two weeks later, they received the same plasmid preparation plus the recombinant baculovirus.

E. Monitoring:

All groups of pigs were housed in isolated experimental units with air filtration and low air pressure. Clinical observations and rectal temperatures were recorded every day. The pigs were weighed weekly.

F. Conclusions

Expression of PCV-B ORF'2 or PCV-B ORF'1 in swine resulted in a significantly enhanced level of protection as evaluated by weight evolution and body temperature evolution following challenge with PCV-B circovirus. These results are summarized in FIGS. 14 and 15.

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications and patent applications cited above and below, including International Patent Application No. PCT/FR98/02634, filed Dec. 4, 1998, and published as International Publication No. WO 99/29871 on Jun. 17, 1999, are expressly incorporated herein by reference in their entireties to the same extent as if each were incorporated by reference individually.

BIBLIOGRAPHIC REFERENCES

Allan, G. M. et al., 1995, Vet. Microbiol., 44: 49-64.
Barany, F., 1911, PNAS. USA, 88: 189-193.
Boulton, L. H. et al., 1997, J. Gen. Virol., 78 (Pt 6), 1265-1270.
Buckholz, R. G., 1993, Yeast systems for the expression of heterologous gene products. Curr. Op. Biotechnology 4: 538-542.
Burg, J. L. et al., 1996, Mol. and Cell. Probes, 10: 257-271.
Chu, B. C. F. et al., 1986, NAR, 14: 5591-5603.
Chu, P. W. G. et al., 1993, Virus Research, 27: 161-171.
Clark, E. G., 1997, American Association of Swine Practitioners, 499-501.
Daft, B. et al., 1996, American Association of Veterinary Laboratory Diagnosticians, 32.
Derse, D. et al., 1995, J. Virol., 69(3): 1907-1912.
Duck, P. et al., 1990, Biotechniques, 9: 142-147.
Dulac, G. C. et al., 1989, Can. J. Vet. Res., 53: 431-433.
Edwards, C. P., and Aruffo, A., 1993, Current applications of COS cell based transient expression systems. Curr. Op. Biotechnology 4: 558-563.
Edwards, S. et al., 1994, Vet. Rec., 134: 680-681.
Erlich, H. A., 1989, In PCR Technology. Principles and Applications for DNA Amplification. New York: Stockton Press.
Felgner, et al., 1987, Proc. Natl. Acad. Sci., 84: 7413.
Fontes, E. P. B. et al., 1994, J. Biol. Chem., Vol. 269, No. 11: 8459-8465.
Fraley et al., 1980, J. Biol. Chem., 255: 10431.
Guateli, J. C. et al., 1990, PNAS. USA, 87: 1874-1878.
Hackland, A. F. et al., 1994, Arch. Virol., 139: 1-22.
Hanson, S. F. et al., 1995, Virology, 211: 1-9.
Harding, J. C., 1997, American Association of Swine Practitioners, 503.
Harding, R. M. et al., 1993, Journal of General Virology, 74: 323-328.
Harding, J. C. and Clark, E. G., 1997, Swine Health and Production, Vol. 5, No. 5: 201-203.
Heyraud-Nitschke, F. et al., 1995, Nucleic Acids Research, Vol. 23, No. 6.
Homer, G. W., 1991, Surveillance 18(5): 23.
Houben-Weyl, 1974, in Methode der Organischen Chemie, E. Wunsch Ed., Volume 15-I and 15-II, Thieme, Stuttgart.
Huygen, K. et al., 1996, Nature Medicine, 2(8): 893-898.
Innis, M. A. et al., 1990, in PCR Protocols. A guide to Methods and Applications, San Diego, Academic Press.
Kaneda, et al., 1989, Science, 243: 375.
Kievitis, T. et al., 1991, J. Virol. Methods, 35: 273-286.
Kohler, G. et al., 1975, Nature, 256(5517): 495-497.
Kwoh, D. Y. et al., 1989, PNAS. USA, 86:1173-1177.
Ladany, S. et al., 1989, J. Clin. Microbiol. 27: 2778-2783.
Lazarowitz, S. G. et al., 1989, The EMBO Journal, Vol. 8 No. 4: 1023-1032.
Luckow, V. A., 1993, Baculovirus systems for the expression of human gene products. Curr. Op. Biotechnology 4: 564-572.
Mankertz, A. et al., 1997, J. Virol., 71: 2562-2566.
Matthews, J. A. et al., 1988, Anal. Biochem., 169: 1-25.
McNeilly, F. et al., 1996, Vet. Immunol. Immunopathol., 49: 295-306.
Meehan, B. M. et al., 1997, J. Gen. Virol. 78: 221-227.
Merrifield, R. D., 1966, J. Am. Chem. Soc., 88(21): 5051-5052.
Midoux, 1993, Nucleic Acids Research, 21: 871-878.
Miele, E. A. etal., 1983, J. Mol. Biol., 171:281-295.
Murphy, F. A. et al., 1995, Sixth Report of the International Committee on Taxonomy of Viruses. Springer-Verlag Wien New York.
Nayar, G. P. et al., 1997, Can. Vet. J. 38(6): 385-386.
Olnis, P. O., and Lee, S. C. 1993, Recent advances in heterologous gene expression in *E.coli*. Curr. Op. Biotechnology 4: 520-525.
Pagano et al., 1967, J. Virol., 1: 891.
Rolfs, A. et al., 1991, In PCR Topics. Usage of Polymerase Chain reaction in Genetic and Infectious Disease. Berlin: Springer-Verlag.
Sambrook, J. et al., 1989, In Molecular cloning: A Laboratory Manual. Cold Spring Harbor, N.Y.: Cold Spring Harbor Laboratory Press.
Sanchez-Pescador, R., 1988, J. Clin. Microbiol., 26(10): 1934-1938.

Segev D., 1992, in “Non-radioactive Labeling and Detection of Biomolecules”. Kessler C. Springer Verlag, Berlin, N.Y.: 197-205.

Shiver, J. W., 1995, in Vaccines 1995, eds Chanock, R. M. Brown, F. Ginsberg, H. S. & Norrby, E., pp. 95-98, Cold Spring Harbor Laboratory Press, Cold Spring Harbor, N.Y.

Tascon, R. E. et al., 1996, Nature Medicine, 2(8): 888-892.

Tischer, I. et al., 1982, Nature, 295: 64-66.

Tischer, I. et al., 1986, Arch. Virol., 91: 271-276.

Tischer, I. et al., 1988, Zentralbl Bakteriol Mikrobiol Hyg [A] 270: 280-287.

Tischer, I. et al., 1995, Arch. Virol., 140: 737-743.

Urdea, M. S., 1988, Nucleic Acids Research, II: 4937-4957.

Walker, G. T. et al., 1992, NAR 20: 1691-1696.

Walker, G. T. et al., 1992, PNAS. USA, 89: 392-396.

White, B. A. et al., 1997, Methods in Molecular Biology, 67, Humana Press, Towota.

Zhao, T. M. et al., 1996, Proc. Natl. Acad. Sci., USA 93(13): 6653-6648.

We claim:

1. A method of recovering recombinant protein expressed by open reading frame 2 (ORF'2) of PCVB comprising the steps of: A) cloning said recombinant ORF'2 from PCVB into a transfer vector; B) transferring the portion of said transfer vector containing said recombinant ORF'2 into a virus; C) infecting cells in media with said virus; D) causing said virus to express the protein from said ORF'2 and the cells to secrete said protein into the media; E) separating the cells from the media; and F) recovering said expressed ORF'2 protein from the media.

2. The method of claim 1, wherein said method further includes the step of amplifying said ORF'2 from a strain of PCVB prior to cloning said ORF'2 into said transfer vector.

3. The method of claim 1, wherein said PCVB ORF'2 comprises SEQ ID NO:25.

4. The method of claim 1, wherein said cells comprise SF+ cells.

5. The method of claim 1, wherein said virus comprises baculovirus.

6. A method of preparing a composition for inducing an immune response against PCVB, wherein said method comprises the steps of: a) transferring a recombinant DNA from ORF'2 of PCVB into a virus; b) infecting cells with said virus, said cells being in a growth media; c) causing said virus to express the protein from said ORF'2 and the cells to secrete said protein into the media; d) separating the cells from the media; e) recovering said recombinant protein from the media; and f) combining said recovered protein with a suitable adjuvant or other pharmaceutically acceptable carrier or excipient.

7. The method of claim 6, wherein said method further includes the step of obtaining said DNA from a transfer vector.

8. The method of claim 6, wherein said method further includes the step of amplifying said ORF'2 from a strain of PGVB prior to cloning said ORF'2 into said transfer vector.

9. The method of claim 6, wherein said PCVB ORF'2 comprises SEQ ID NO:25.

10. The method of claim 6, wherein said cells comprise SF+ cells.

11. The method of claim 6, wherein said virus comprises baculovirus.

12. A method of recovering protein expressed by ORF'2 from PCVB, wherein said method includes the steps of: a) infecting cells in growth media with a recombinant viral vector containing said ORF'2; b) causing said virus to express the protein from said ORF'2 and the cells to secrete said protein into the media; and c) recovering said expressed protein from the media.

13. A method of recovering recombinant protein expressed by open reading frame 2 (ORF'2) of PCVB comprising the steps of: A) cloning said recombinant ORF'2 from PCVB into a transfer vector; B) transferring the portion of said transfer vector containing said recombinant ORF'2 into a virus; C) infecting cells in media with said virus; D) causing said virus to express the protein from said ORF'2; and E) recovering said expressed ORF'2 protein.

14. The method of claim 13, wherein said method further includes the step of amplifying said ORF'2 from a strain of PCVB prior to cloning said ORF'2 into said transfer vector.

15. The method of claim 13, wherein said PCVB ORF'2 comprises SEQ ID NO:25.

16. The method of claim 13, wherein said cells comprise SF+ cells.

17. The method of claim 13, wherein said virus comprises baculovirus.

18. A method of recovering protein expressed by ORF'2 from PCVB, wherein said method includes the steps of: a) infecting cells in growth media with a recombinant viral vector containing said ORF'2; b) causing said virus to express the protein from said ORF'2; and c) recovering said expressed protein.

19. The method of claim 18, wherein said PCVB ORF'2 comprises SEQ ID NO:25.

20. The method of claim 18, wherein said cells comprise SF+ cells.

21. The method of claim 18, wherein said virus comprises baculovirus.

22. A method of preparing a composition for inducing an immune response against PCVB, wherein said method comprises the steps of: a) transferring a recombinant DNA from ORF'2 of PCVB into a virus; b) infecting cells with said virus, said cells being in a growth media; c) causing said virus to express the protein from said ORF'2; d) recovering said recombinant protein; and e) combining said recovered protein with a suitable adjuvant or other pharmaceutically acceptable carrier or excipient.

23. The method of claim 22, wherein said method further includes the step of obtaining said DNA from a transfer vector.

24. The method of claim 22, wherein said method further includes the step of amplifying said ORF'2 from a strain of PCVB prior to cloning said ORF'2 into said transfer vector.

25. The method of claim 22, wherein said PCVB ORF'2 comprises SEQ ID NO:25.

26. The method of claim 22, wherein said cells comprise SF+ cells.

27. The method of claim 22, wherein said virus comprises baculovirus.

* * * * *